US012428631B2

(12) United States Patent
Gersbach et al.

(10) Patent No.: US 12,428,631 B2
(45) Date of Patent: Sep. 30, 2025

(54) CRISPR/CAS9-BASED REPRESSORS FOR SILENCING GENE TARGETS IN VIVO AND METHODS OF USE

(71) Applicant: Duke University, Durham, NC (US)

(72) Inventors: Charles A. Gersbach, Chapel Hill, NC (US); Pratiksha I. Thakore, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 18/405,995

(22) Filed: Jan. 5, 2024

(65) Prior Publication Data

US 2024/0279628 A1 Aug. 22, 2024

Related U.S. Application Data

(63) Continuation of application No. 16/093,272, filed as application No. PCT/US2017/027490 on Apr. 13, 2017, now abandoned.

(60) Provisional application No. 62/369,248, filed on Aug. 1, 2016, provisional application No. 62/321,947, filed on Apr. 13, 2016.

(51) Int. Cl.

| | |
|---|---|
| ***C12N 9/22*** | (2006.01) |
| ***A61K 9/00*** | (2006.01) |
| ***A61K 48/00*** | (2006.01) |
| ***A61P 9/00*** | (2006.01) |
| ***C07K 14/47*** | (2006.01) |
| ***C12N 7/00*** | (2006.01) |
| ***C12N 15/11*** | (2006.01) |
| ***C12N 15/113*** | (2010.01) |
| ***C12N 15/52*** | (2006.01) |
| ***C12N 15/63*** | (2006.01) |
| ***C12N 15/86*** | (2006.01) |

(52) U.S. Cl.
CPC .............. *C12N 9/22* (2013.01); *A61K 9/0019* (2013.01); *A61K 48/0058* (2013.01); *A61P 9/00* (2018.01); *C07K 14/4703* (2013.01); *C12N 7/00* (2013.01); *C12N 15/11* (2013.01); *C12N 15/111* (2013.01); *C12N 15/113* (2013.01); *C12N 15/52* (2013.01); *C12N 15/63* (2013.01); *C12N 15/86* (2013.01); *A61K 48/00* (2013.01); *C07K 2319/09* (2013.01); *C07K 2319/71* (2013.01); *C07K 2319/80* (2013.01); *C12N 2310/20* (2017.05); *C12N 2320/32* (2013.01); *C12N 2750/14143* (2013.01); *C12N 2800/80* (2013.01)

(58) Field of Classification Search
CPC . C12N 9/22; C12N 7/00; C12N 15/11; C12N 15/111; C12N 15/113; C12N 15/52; C12N 15/63; C12N 15/86; C12N 2310/20; C12N 2320/32; C12N 2750/14143; C12N 2800/80; A61K 9/0019; A61K 48/0058; A61K 48/00; A61P 9/00; C07K 14/4703; C07K 2319/09; C07K 2319/71; C07K 2319/80
See application file for complete search history.

(56) References Cited

U.S. PATENT DOCUMENTS

| | | | |
|---|---|---|---|
| 3,687,808 | A | 8/1972 | Merigan, Jr. |
| 4,469,863 | A | 9/1984 | Ts'o et al. |
| 4,476,301 | A | 10/1984 | Imbach et al. |
| 4,501,729 | A | 2/1985 | Boucher et al. |
| 4,554,101 | A | 11/1985 | Hopp |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,737,323 | A | 4/1988 | Martin et al. |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohsuka et al. |
| 5,023,243 | A | 6/1991 | Tullis |
| 5,034,506 | A | 7/1991 | Summerton et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,139,941 | A | 8/1992 | Muzyczka et al. |

(Continued)

FOREIGN PATENT DOCUMENTS

| | | | |
|---|---|---|---|
| AU | 2022318664 | A1 | 2/2024 |
| CA | 2749305 | A1 | 7/2010 |

(Continued)

OTHER PUBLICATIONS

US 11,898,176 B2, 02/2024, Gersbach et al. (withdrawn)

(Continued)

*Primary Examiner* — Fereydoun G Sajjadi
*Assistant Examiner* — Alexander W Nicol
(74) *Attorney, Agent, or Firm* — Michael Best & Friedrich LLP

(57) ABSTRACT

The present disclosure provides Crispr/cas9-based repressors for silencing gene targets in vivo and methods of use.

19 Claims, 21 Drawing Sheets

Specification includes a Sequence Listing.

(56) References Cited

U.S. PATENT DOCUMENTS 5,149,797 A 9/1992 Pederson et al.
5,166,315 A 11/1992 Summerton et al.
5,175,273 A 12/1992 Bischofberger et al.
5,177,196 A 1/1993 Meyer et al.
5,185,444 A 2/1993 Summerton et al.
5,188,897 A 2/1993 Suhadolnik et al.
5,214,134 A 5/1993 Weis et al.
5,214,136 A 5/1993 Lin et al.
5,216,141 A 6/1993 Benner
5,218,105 A 6/1993 Cook et al.
5,219,740 A 6/1993 Miller et al.
5,220,007 A 6/1993 Pederson et al.
5,235,033 A 8/1993 Summerton et al.
5,245,022 A 9/1993 Weis et al.
5,254,469 A 10/1993 Warren, III
5,256,775 A 10/1993 Froehler
5,258,506 A 11/1993 Urdea et al.
5,262,536 A 11/1993 Hobbs, Jr.
5,264,423 A 11/1993 Cohen et al.
5,264,562 A 11/1993 Matteucci
5,264,564 A 11/1993 Matteucci
5,272,250 A 12/1993 Spielvogel et al.
5,276,019 A 1/1994 Cohen et al.
5,278,302 A 1/1994 Caruthers et al.
5,286,717 A 2/1994 Cohen et al.
5,292,873 A 3/1994 Rokita et al.
5,317,098 A 5/1994 Shizuya et al.
5,321,131 A 6/1994 Agrawal et al.
5,366,878 A 11/1994 Pederson et al.
5,367,066 A 11/1994 Urdea et al.
5,371,241 A 12/1994 Brush
5,391,723 A 2/1995 Priest
5,399,676 A 3/1995 Froehler
5,403,711 A 4/1995 Walder et al.
5,405,938 A 4/1995 Summerton et al.
5,405,939 A 4/1995 Suhadolnik et al.
5,414,077 A 5/1995 Lin et al.
5,416,203 A 5/1995 Letsinger
5,432,272 A 7/1995 Benner
5,434,257 A 7/1995 Matteucci et al.
5,451,463 A 9/1995 Nelson et al.
5,453,496 A 9/1995 Caruthers et al.
5,455,233 A 10/1995 Spielvogel et al.
5,457,187 A 10/1995 Gmeiner et al.
5,459,255 A 10/1995 Cook et al.
5,466,677 A 11/1995 Baxter et al.
5,470,967 A 11/1995 Huie et al.
5,476,925 A 12/1995 Letsinger et al.
5,478,745 A 12/1995 Samulski et al.
5,484,908 A 1/1996 Froehler et al.
5,486,603 A 1/1996 Buhr
5,489,677 A 2/1996 Sanghvi et al.
5,491,133 A 2/1996 Walder et al.
5,502,177 A 3/1996 Matteucci et al.
5,510,473 A 4/1996 Camerini-otero et al.
5,510,475 A 4/1996 Agrawal et al.
5,512,439 A 4/1996 Horner et al.
5,512,667 A 4/1996 Reed et al.
5,514,785 A 5/1996 Van Ness et al.
5,519,126 A 5/1996 Hecht
5,525,465 A 6/1996 Haralambidis et al.
5,525,711 A 6/1996 Hawkins et al.
5,536,821 A 7/1996 Agrawal et al.
5,541,306 A 7/1996 Agrawal et al.
5,541,307 A 7/1996 Cook et al.
5,541,313 A 7/1996 Ruth
5,545,730 A 8/1996 Urdea et al.
5,550,111 A 8/1996 Suhadolnik et al.
5,552,538 A 9/1996 Urdea et al.
5,552,540 A 9/1996 Haralambidis
5,561,225 A 10/1996 Maddry et al.
5,563,253 A 10/1996 Agrawal et al.
5,565,350 A 10/1996 Kmiec
5,565,552 A 10/1996 Magda et al.
5,567,810 A 10/1996 Weis et al.
5,571,799 A 11/1996 Tkachuk et al.
5,574,142 A 11/1996 Meyer et al.
5,578,717 A 11/1996 Urdea et al.
5,578,718 A 11/1996 Cook et al.
5,580,731 A 12/1996 Chang et al.
5,585,481 A 12/1996 Arnold, Jr. et al.
5,587,361 A 12/1996 Cook et al.
5,587,371 A 12/1996 Sessler et al.
5,587,469 A 12/1996 Cook et al.
5,591,584 A 1/1997 Chang et al.
5,593,972 A 1/1997 Weiner et al.
5,595,726 A 1/1997 Magda et al.
5,596,086 A 1/1997 Matteucci et al.
5,596,091 A 1/1997 Switzer
5,597,696 A 1/1997 Linn et al.
5,599,923 A 2/1997 Sessler et al.
5,599,928 A 2/1997 Hemmi et al.
5,602,240 A 2/1997 De Mesmaeker et al.
5,608,046 A 3/1997 Cook et al.
5,610,289 A 3/1997 Cook et al.
5,614,617 A 3/1997 Cook et al.
5,618,704 A 4/1997 Sanghvi et al.
5,623,065 A 4/1997 Cook et al.
5,623,070 A 4/1997 Cook et al.
5,625,050 A 4/1997 Beaton et al.
5,633,360 A 5/1997 Bischofberger et al.
5,652,355 A 7/1997 Metelev et al.
5,652,356 A 7/1997 Agrawal
5,658,784 A 8/1997 Eckner et al.
5,663,312 A 9/1997 Chaturvedula et al.
5,677,437 A 10/1997 Teng et al.
5,677,439 A 10/1997 Weis et al.
5,681,941 A 10/1997 Cook et al.
5,688,941 A 11/1997 Cook et al.
5,700,922 A 12/1997 Cook et al.
5,714,331 A 2/1998 Buchardt et al.
5,719,262 A 2/1998 Buchardt et al.
5,741,683 A 4/1998 Zhou et al.
5,750,692 A 5/1998 Cook et al.
5,773,700 A 6/1998 Van Grinsven et al.
5,962,428 A 10/1999 Carrano et al.
6,057,152 A 5/2000 Samulski et al.
6,140,081 A 10/2000 Barbas
6,204,059 B1 3/2001 Samulski et al.
6,207,453 B1 3/2001 Maass et al.
6,268,213 B1 7/2001 Samulski et al.
6,268,490 B1 7/2001 Imanishi et al.
6,287,860 B1 9/2001 Monia et al.
6,453,242 B1 9/2002 Eisenberg et al.
6,462,254 B1 10/2002 Vernachio et al.
6,491,907 B1 12/2002 Rabinowitz et al.
6,534,261 B1 3/2003 Cox, III et al.
6,596,535 B1 7/2003 Carter
6,660,514 B1 12/2003 Zolotukhin et al.
6,734,291 B2 5/2004 Kochkine et al.
6,770,748 B2 8/2004 Imanishi et al.
6,794,499 B2 9/2004 Wengel et al.
6,951,753 B2 10/2005 Shenk et al.
7,034,133 B2 4/2006 Wengel et al.
7,053,207 B2 5/2006 Wengel
7,060,809 B2 6/2006 Wengel et al.
7,074,596 B2 7/2006 Darzynkiewicz et al.
7,084,125 B2 8/2006 Wengel
7,094,604 B2 8/2006 Snyder et al.
7,125,717 B2 10/2006 Carter
7,172,893 B2 2/2007 Rabinowitz et al.
7,201,898 B2 4/2007 Monahan et al.
7,229,823 B2 6/2007 Samulski et al.
7,282,199 B2 10/2007 Gao et al.
7,439,065 B2 10/2008 Ferrari et al.
7,449,561 B1 11/2008 Sommer et al.
7,456,683 B2 11/2008 Takano et al.
7,572,582 B2 8/2009 Wengel et al.
7,588,772 B2 9/2009 Kay et al.
7,728,118 B2 6/2010 Wood et al.
7,745,651 B2 6/2010 Heyes et al.
7,790,449 B2 9/2010 Gao et al.
7,799,565 B2 9/2010 Maclachlan et al.
7,906,111 B2 3/2011 Wilson et al.

(56) References Cited

U.S. PATENT DOCUMENTS 8,278,036 B2 10/2012 Kariko et al.
8,450,107 B1 5/2013 Zhang et al.
8,586,526 B2 11/2013 Gregory et al.
8,697,359 B1 4/2014 Zhang et al.
8,889,356 B2 11/2014 Zhang
8,993,233 B2 3/2015 Zhang et al.
9,139,554 B2 9/2015 Hope et al.
9,458,205 B2 10/2016 Gregory et al.
9,738,879 B2 8/2017 Gersbach et al.
9,828,582 B2 11/2017 Perez-Pinera et al.
9,834,791 B2 12/2017 Zhang et al.
9,890,364 B2 2/2018 Joung et al.
10,011,850 B2 7/2018 Joung et al.
10,190,106 B2 1/2019 Wolfe et al.
10,266,850 B2 4/2019 Doudna et al.
10,676,726 B2 6/2020 Gersbach et al.
10,676,735 B2 6/2020 Gersbach et al.
10,704,060 B2 7/2020 Gersbach et al.
10,711,256 B2 7/2020 Gersbach et al.
10,745,714 B2 8/2020 Gersbach et al.
11,155,796 B2 10/2021 Gersbach et al.
11,421,251 B2 8/2022 Gersbach et al.
11,427,817 B2 8/2022 Josephs et al.
11,970,710 B2 4/2024 Gersbach et al.
11,976,307 B2 5/2024 Gersbach et al.
12,214,054 B2 2/2025 Gersbach et al.
12,214,056 B2 2/2025 Gersbach et al.
12,215,345 B2 2/2025 Perez-Pinera et al.
12,215,366 B2 2/2025 Gersbach et al.
2002/0160940 A1 10/2002 Case et al.
2003/0124102 A1 7/2003 Rudnicki et al.
2004/0142025 A1 7/2004 Maclachlan et al.
2004/0175727 A1 9/2004 Draghia-Akli et al.
2004/0192593 A1 9/2004 Draghia-Akli et al.
2004/0204345 A1 10/2004 Case et al.
2005/0079512 A1 4/2005 Emerson et al.
2006/0068395 A1 3/2006 Wood et al.
2006/0171924 A1 8/2006 Luo et al.
2006/0211647 A1 9/2006 Khan
2006/0270595 A1 11/2006 Jullien et al.
2007/0042031 A1 2/2007 Maclachlan et al.
2007/0042462 A1 2/2007 Hildinger
2007/0059795 A1 3/2007 Moore et al.
2007/0185042 A1 8/2007 Tsai et al.
2007/0192880 A1 8/2007 Muyan et al.
2008/0070299 A1 3/2008 Wood et al.
2008/0090291 A1 4/2008 Wood et al.
2008/0200409 A1 8/2008 Wilson et al.
2009/0018031 A1 1/2009 Trinklein et al.
2010/0035968 A1 2/2010 Rasmussen et al.
2010/0076057 A1 3/2010 Sontheimer et al.
2010/0261175 A1 10/2010 Rasmussen et al.
2010/0267018 A1 10/2010 Wengel et al.
2011/0145940 A1 6/2011 Voytas et al.
2011/0197290 A1 8/2011 Fahrenkrug et al.
2011/0236353 A1 9/2011 Wilson et al.
2011/0263682 A1 10/2011 De Kimpe et al.
2011/0286957 A1 11/2011 Prieve et al.
2011/0301073 A1 12/2011 Gregory et al.
2011/0301218 A1 12/2011 Bozzoni et al.
2012/0195917 A1 8/2012 Sahin et al.
2012/0207744 A1 8/2012 Mendlein et al.
2013/0274129 A1 10/2013 Katzen et al.
2013/0323001 A1 12/2013 Ueki et al.
2014/0068797 A1 3/2014 Doudna et al.
2014/0140969 A1 5/2014 Beausejour et al.
2014/0170753 A1 6/2014 Zhang
2014/0179006 A1 6/2014 Zhang
2014/0186958 A1 7/2014 Zhang et al.
2014/0234975 A1 8/2014 Silva et al.
2014/0295557 A1* 10/2014 Joung ...................... C12N 9/96
536/23.1
2014/0309177 A1 10/2014 Perez-Pinera et al.
2014/0315862 A1 10/2014 Kaye
2014/0356956 A1 12/2014 Church et al.
2014/0357530 A1 12/2014 Zhang et al.
2014/0377868 A1 12/2014 Joung et al.
2015/0024499 A1 1/2015 Brouns et al.
2015/0031089 A1 1/2015 Lindstrom
2015/0044772 A1 2/2015 Zhao
2015/0045413 A1 2/2015 De Visser et al.
2015/0056705 A1 2/2015 Conway et al.
2015/0079064 A1 3/2015 Gersbach et al.
2015/0159178 A1 6/2015 Green et al.
2015/0166980 A1 6/2015 Liu et al.
2015/0225717 A1 8/2015 Lee et al.
2015/0252358 A1 9/2015 Maeder et al.
2016/0002634 A1 1/2016 Sazani et al.
2016/0040189 A1 2/2016 Kennedy et al.
2016/0058889 A1 3/2016 Olson et al.
2016/0177278 A1 6/2016 Wolfe et al.
2016/0199419 A1 7/2016 Miura
2016/0201089 A1 7/2016 Gersbach et al.
2016/0281166 A1 9/2016 Bhattacharjee et al.
2016/0354487 A1 12/2016 Zhang et al.
2017/0002316 A1 1/2017 Gascón Jiménez et al.
2017/0198308 A1 7/2017 Qi et al.
2017/0204407 A1 7/2017 Gilbert et al.
2017/0283831 A1 10/2017 Zhang et al.
2017/0298331 A1 10/2017 Gersbach et al.
2017/0327806 A1 11/2017 Joung et al.
2017/0362635 A1 12/2017 Chamberlain et al.
2018/0023064 A1 1/2018 Gersbach et al.
2018/0073012 A1 3/2018 Liu et al.
2018/0094238 A1 4/2018 Perez-Pinera et al.
2018/0127780 A1 5/2018 Liu et al.
2018/0135023 A1 5/2018 Wang et al.
2018/0135109 A1 5/2018 Jayaram et al.
2018/0201951 A1 7/2018 Guilak et al.
2018/0237771 A1 8/2018 Kim et al.
2018/0251735 A1 9/2018 Ko
2018/0271069 A1 9/2018 Min et al.
2018/0280539 A1 10/2018 Debs et al.
2018/0291370 A1 10/2018 Gersbach et al.
2018/0305689 A1 10/2018 Sætrom et al.
2018/0305704 A1 10/2018 Zhang
2018/0305719 A1 10/2018 Perez-Pinera et al.
2018/0319850 A1 11/2018 Payne et al.
2018/0320197 A1 11/2018 Gersbach et al.
2018/0327740 A1 11/2018 Gifford et al.
2018/0334685 A1 11/2018 Yeo et al.
2018/0334688 A1 11/2018 Gersbach et al.
2018/0353615 A1 12/2018 Gersbach et al.
2018/0355332 A1 12/2018 Steinberg et al.
2019/0032049 A1 1/2019 Naldini et al.
2019/0038776 A1 2/2019 Pyle et al.
2019/0048337 A1 2/2019 Hsu et al.
2019/0062790 A1 2/2019 Doudna et al.
2019/0078119 A1 3/2019 Wilson et al.
2019/0106710 A1 4/2019 Zhang et al.
2019/0127713 A1* 5/2019 Gersbach ............... C12N 15/63
2019/0134221 A1 5/2019 Bumcrot et al.
2019/0136229 A1 5/2019 Josephs et al.
2019/0151476 A1 5/2019 Gersbach et al.
2019/0167815 A1 6/2019 Holmes et al.
2019/0183932 A1 6/2019 Mackall et al.
2019/0192691 A1 6/2019 Barrett et al.
2019/0194633 A1 6/2019 Gersbach et al.
2019/0201402 A1 7/2019 Jiang et al.
2019/0225955 A1 7/2019 Liu et al.
2019/0248854 A1 8/2019 Tremblay et al.
2019/0264232 A1 8/2019 Hou et al.
2019/0351074 A1 11/2019 Ahituv et al.
2019/0359959 A1 11/2019 Jaenisch et al.
2019/0374655 A1 12/2019 Kabadi et al.
2020/0002731 A1 1/2020 Frendewey et al.
2020/0056206 A1 2/2020 Tremblay et al.
2020/0063105 A1 2/2020 Ng et al.
2020/0080108 A1 3/2020 Jaskula-Ranga et al.
2020/0080112 A1 3/2020 Zhang et al.
2020/0109406 A1 4/2020 Miller et al.
2020/0123533 A1 4/2020 Wang et al.
2020/0216549 A1 7/2020 Fukumura et al.
2020/0216810 A1 7/2020 Metelitsa et al.

(56) References Cited

U.S. PATENT DOCUMENTS

| | | | |
|---|---|---|---|
| 2020/0260698 | A1 | 8/2020 | Kyrychenko et al. |
| 2020/0275641 | A1 | 9/2020 | Min et al. |
| 2020/0318139 | A1 | 10/2020 | Gersbach et al. |
| 2020/0332307 | A1 | 10/2020 | Hummel et al. |
| 2020/0347105 | A1 | 11/2020 | Gersbach et al. |
| 2020/0361877 | A1 | 11/2020 | Mahajan et al. |
| 2020/0385695 | A1 | 12/2020 | Gersbach et al. |
| 2021/0002665 | A1 | 1/2021 | Gersbach et al. |
| 2021/0024895 | A1 | 1/2021 | Kariko et al. |
| 2021/0032654 | A1 | 2/2021 | Gersbach et al. |
| 2021/0040460 | A1 | 2/2021 | Gersbach et al. |
| 2021/0054448 | A1 | 2/2021 | Ng et al. |
| 2021/0277379 | A1 | 9/2021 | Gaudelli et al. |
| 2021/0322577 | A1 | 10/2021 | Lande et al. |
| 2021/0363525 | A1 | 11/2021 | Sætrom et al. |
| 2022/0098561 | A1 | 3/2022 | Gersbach et al. |
| 2022/0177879 | A1 | 6/2022 | Gersbach et al. |
| 2022/0184229 | A1 | 6/2022 | Gersbach et al. |
| 2022/0186199 | A1 | 6/2022 | Cotta-Ramusino et al. |
| 2022/0195406 | A1 | 6/2022 | Gersbach et al. |
| 2022/0244244 | A1 | 8/2022 | Schmedt et al. |
| 2022/0249626 | A1 | 8/2022 | Kmiec et al. |
| 2022/0305141 | A1 | 9/2022 | Gersbach et al. |
| 2022/0307015 | A1 | 9/2022 | Gersbach et al. |
| 2022/0364124 | A1 | 11/2022 | Gersbach et al. |
| 2022/0396790 | A1 | 12/2022 | Gersbach et al. |
| 2023/0032846 | A1 | 2/2023 | Gersbach et al. |
| 2023/0047669 | A1 | 2/2023 | Josephs et al. |
| 2023/0159927 | A1 | 5/2023 | Gersbach et al. |
| 2023/0201375 | A1 | 6/2023 | Gersbach et al. |
| 2023/0257723 | A1 | 8/2023 | Gersbach et al. |
| 2023/0304000 | A1 | 9/2023 | Josephs et al. |
| 2023/0348870 | A1 | 11/2023 | Gersbach et al. |
| 2023/0349888 | A1 | 11/2023 | Gersbach et al. |
| 2023/0383270 | A1 | 11/2023 | Gersbach et al. |
| 2023/0383297 | A1 | 11/2023 | Gersbach et al. |
| 2023/0392132 | A1 | 12/2023 | Gersbach et al. |
| 2024/0026352 | A1 | 1/2024 | Gersbach et al. |
| 2024/0052328 | A1 | 2/2024 | Kwon et al. |
| 2024/0058425 | A1 | 2/2024 | Gersbach et al. |
| 2024/0067968 | A1 | 2/2024 | Cosgrove et al. |
| 2024/0141341 | A1 | 5/2024 | Gersbach et al. |
| 2025/0114482 | A1 | 4/2025 | Gersbach et al. |

FOREIGN PATENT DOCUMENTS

| | | | |
|---|---|---|---|
| CA | 2981508 | A1 | 10/2016 |
| CA | 3086885 | A1 | 7/2019 |
| CA | 3101477 | A1 | 12/2019 |
| EP | 2620161 | A1 | 7/2013 |
| EP | 3009511 | A2 | 4/2016 |
| EP | 3199632 | A1 | 8/2017 |
| EP | 3712272 | A1 | 9/2020 |
| EP | 3209783 | B1 | 11/2021 |
| EP | 3995584 | A1 | 5/2022 |
| JP | 2013-509159 | A | 3/2013 |
| JP | 2015-534817 | A | 12/2015 |
| JP | 2016-521452 | A | 7/2016 |
| JP | 2016-521452 | A2 | 7/2016 |
| JP | 2016-521975 | A | 7/2016 |
| JP | 2016-523082 | A | 8/2016 |
| JP | 2018-011546 | A | 1/2018 |
| JP | 2019-103393 | A | 6/2019 |
| JP | 2020-517247 | A | 6/2020 |
| KR | 20190134673 | A | 12/2019 |
| WO | WO1991/18114 | A1 | 11/1991 |
| WO | WO1992/000387 | A1 | 1/1992 |
| WO | WO1993/007883 | A1 | 4/1993 |
| WO | WO1993/024640 | A2 | 12/1993 |
| WO | WO1994/016737 | A1 | 8/1994 |
| WO | WO1998/053058 | A1 | 11/1998 |
| WO | WO1998/053059 | A1 | 11/1998 |
| WO | WO1998/053060 | A1 | 11/1998 |
| WO | WO 2000/028004 | A1 | 5/2000 |
| WO | WO2001/083783 | A2 | 11/2001 |
| WO | WO2001/083793 | A2 | 11/2001 |
| WO | WO 2001/092551 | A2 | 12/2001 |
| WO | WO2002/016536 | A1 | 2/2002 |
| WO | WO2003/016496 | A2 | 2/2003 |
| WO | WO2003/042397 | A2 | 5/2003 |
| WO | WO2003/072788 | A1 | 9/2003 |
| WO | WO2005/033321 | A2 | 4/2005 |
| WO | WO2006/110689 | A2 | 10/2006 |
| WO | WO2007/019301 | A2 | 2/2007 |
| WO | WO2008/006028 | A2 | 1/2008 |
| WO | WO2008/070859 | A2 | 6/2008 |
| WO | WO2010/053572 | A2 | 5/2010 |
| WO | WO2010/075424 | A2 | 7/2010 |
| WO | WO2010/144740 | A1 | 12/2010 |
| WO | WO2011/036640 | A2 | 3/2011 |
| WO | WO2011/126808 | A2 | 10/2011 |
| WO | 2011/146121 | A1 | 11/2011 |
| WO | WO2011/141820 | A1 | 11/2011 |
| WO | WO2011/154427 | A1 | 12/2011 |
| WO | WO2012/136476 | A1 | 10/2012 |
| WO | WO2012/170930 | A1 | 12/2012 |
| WO | WO2013/049493 | A1 | 4/2013 |
| WO | WO2013/098244 | A1 | 7/2013 |
| WO | WO2013/143555 | A1 | 10/2013 |
| WO | WO2013/163628 | A2 | 10/2013 |
| WO | WO2013/176772 | A1 | 11/2013 |
| WO | WO2013/182683 | A1 | 12/2013 |
| WO | WO2014/018423 | A2 | 1/2014 |
| WO | WO2014/059255 | A1 | 4/2014 |
| WO | WO2014/065596 | A1 | 5/2014 |
| WO | WO2014/081855 | A1 | 5/2014 |
| WO | 2014/099744 | A1 | 6/2014 |
| WO | WO2014/089290 | A1 | 6/2014 |
| WO | WO2014/093479 | A1 | 6/2014 |
| WO | WO2014/093595 | A1 | 6/2014 |
| WO | WO2014/093622 | A2 | 6/2014 |
| WO | WO2014/093655 | A2 | 6/2014 |
| WO | WO2014/093661 | A2 | 6/2014 |
| WO | WO2014/093709 | A1 | 6/2014 |
| WO | WO2014/093712 | A1 | 6/2014 |
| WO | WO2014/144288 | A1 | 9/2014 |
| WO | WO2014/144592 | A2 | 9/2014 |
| WO | WO2014/152432 | A2 | 9/2014 |
| WO | WO2014/172470 | A2 | 10/2014 |
| WO | WO2014/186585 | A2 | 11/2014 |
| WO | 2014/197568 | A2 | 12/2014 |
| WO | WO2014/191128 | A1 | 12/2014 |
| WO | WO2014/197748 | A2 | 12/2014 |
| WO | WO2014/204726 | A1 | 12/2014 |
| WO | WO2014/204728 | A1 | 12/2014 |
| WO | WO2015/006747 | A2 | 1/2015 |
| WO | 2015/021457 | A2 | 2/2015 |
| WO | WO2015/017519 | A1 | 2/2015 |
| WO | 2015/035139 | A2 | 3/2015 |
| WO | WO2015/035136 | A2 | 3/2015 |
| WO | WO2015/048690 | A1 | 4/2015 |
| WO | WO2015/070083 | A1 | 5/2015 |
| WO | 2015/089462 | A1 | 6/2015 |
| WO | WO2015/089419 | A2 | 6/2015 |
| WO | WO2015/089427 | A1 | 6/2015 |
| WO | WO2015/089465 | A1 | 6/2015 |
| WO | WO2015/089486 | A2 | 6/2015 |
| WO | WO2015/126927 | A2 | 8/2015 |
| WO | WO2015/155686 | A2 | 10/2015 |
| WO | WO2015/161276 | A2 | 10/2015 |
| WO | 2015/195621 | A1 | 12/2015 |
| WO | WO2016/011070 | A2 | 1/2016 |
| WO | WO2016/011080 | A2 | 1/2016 |
| WO | WO2016/049258 | A2 | 3/2016 |
| WO | WO 2016/054326 | A1 | 4/2016 |
| WO | WO2016/063264 | A1 | 4/2016 |
| WO | WO2016/070070 | A1 | 5/2016 |
| WO | WO2016/081924 | A1 | 5/2016 |
| WO | WO2016/094880 | A1 | 6/2016 |
| WO | WO2016/114972 | A1 | 7/2016 |
| WO | WO2016/123578 | A1 | 8/2016 |
| WO | WO2016/130600 | A2 | 8/2016 |
| WO | WO2016/161380 | A1 | 10/2016 |
| WO | 2016/182893 | A1 | 11/2016 |

(56) References Cited

FOREIGN PATENT DOCUMENTS

| | | | |
|---|---|---|---|
| WO | 2016/205613 | A1 | 12/2016 |
| WO | WO2016/187717 | A1 | 12/2016 |
| WO | WO2017/015637 | A1 | 1/2017 |
| WO | 2017/016915 | A1 | 2/2017 |
| WO | WO2017/035416 | A2 | 3/2017 |
| WO | WO2017/049266 | A2 | 3/2017 |
| WO | WO2017/049407 | A1 | 3/2017 |
| WO | WO2017/066497 | A2 | 4/2017 |
| WO | WO2017/070632 | A2 | 4/2017 |
| WO | WO2017/072590 | A1 | 5/2017 |
| WO | WO2017/075478 | A2 | 5/2017 |
| WO | WO2017/095967 | A2 | 6/2017 |
| WO | WO2017/139505 | A2 | 8/2017 |
| WO | WO2017/165859 | A1 | 9/2017 |
| WO | WO2017/180915 | A2 | 10/2017 |
| WO | WO2017/180976 | A1 | 10/2017 |
| WO | WO2017/193029 | A2 | 11/2017 |
| WO | 2018/002812 | A1 | 1/2018 |
| WO | 2018/005805 | A1 | 1/2018 |
| WO | 2018/017483 | A1 | 1/2018 |
| WO | WO 2018/013932 | A1 | 1/2018 |
| WO | WO2018/017751 | A1 | 1/2018 |
| WO | WO2018/017754 | A1 | 1/2018 |
| WO | WO2018/031762 | A1 | 2/2018 |
| WO | WO2018/035388 | A1 | 2/2018 |
| WO | WO2018/035495 | A1 | 2/2018 |
| WO | 2018/039145 | A1 | 3/2018 |
| WO | WO2018/081504 | A1 | 5/2018 |
| WO | WO2018/098480 | A1 | 5/2018 |
| WO | 2018/107003 | A1 | 6/2018 |
| WO | 2018/129486 | A2 | 7/2018 |
| WO | WO2018/129296 | A1 | 7/2018 |
| WO | 2018/162702 | A1 | 9/2018 |
| WO | 2018/195073 | A2 | 10/2018 |
| WO | WO2018/179578 | A1 | 10/2018 |
| WO | WO2018/191388 | A1 | 10/2018 |
| WO | 2019/009682 | A2 | 1/2019 |
| WO | 2019/023291 | A2 | 1/2019 |
| WO | WO2019/002590 | A1 | 1/2019 |
| WO | WO 2019/014230 | A1 | 1/2019 |
| WO | WO 2019/036599 | A1 | 2/2019 |
| WO | WO 2019/038776 | A1 | 2/2019 |
| WO | 2019/046755 | A1 | 3/2019 |
| WO | WO2019/067786 | A1 | 4/2019 |
| WO | WO2019/077001 | A1 | 4/2019 |
| WO | WO2019/079514 | A1 | 4/2019 |
| WO | 2019/084050 | A1 | 5/2019 |
| WO | WO2019/092505 | A1 | 5/2019 |
| WO | 2019/123014 | A1 | 6/2019 |
| WO | WO2019/113472 | A1 | 6/2019 |
| WO | 2019/136216 | A1 | 7/2019 |
| WO | WO2019/144061 | A1 | 7/2019 |
| WO | 2019/152609 | A1 | 8/2019 |
| WO | WO2019/204750 | A1 | 10/2019 |
| WO | 2019/213626 | A1 | 11/2019 |
| WO | WO2019/232069 | A1 | 12/2019 |
| WO | 2020/018918 | A1 | 1/2020 |
| WO | 2020/101042 | A1 | 5/2020 |
| WO | WO2020/124257 | A1 | 6/2020 |
| WO | WO 2020/132226 | A1 | 6/2020 |
| WO | 2020/168133 | A1 | 8/2020 |
| WO | WO2020/163396 | A1 | 8/2020 |
| WO | WO2020/210776 | A1 | 10/2020 |
| WO | WO2020/214609 | A1 | 10/2020 |
| WO | WO2020/214613 | A1 | 10/2020 |
| WO | WO2020/257665 | A1 | 12/2020 |
| WO | WO2021/026516 | A1 | 2/2021 |
| WO | WO2021/034984 | A2 | 2/2021 |
| WO | WO2021/034987 | A1 | 2/2021 |
| WO | WO2021/055956 | A1 | 3/2021 |
| WO | 2021/076744 | A1 | 4/2021 |
| WO | WO2021/067878 | A1 | 4/2021 |
| WO | WO2021/113536 | A1 | 6/2021 |
| WO | WO2021/222268 | A1 | 11/2021 |
| WO | WO2021/222314 | A1 | 11/2021 |
| WO | WO2021/222327 | A1 | 11/2021 |
| WO | WO2021/222328 | A1 | 11/2021 |
| WO | WO2021/226555 | A2 | 11/2021 |
| WO | WO2022/038264 | A1 | 2/2022 |
| WO | 2022/055946 | A1 | 3/2022 |
| WO | WO2022/087321 | A1 | 4/2022 |
| WO | WO 2022/103935 | A1 | 5/2022 |
| WO | WO2022/104159 | A1 | 5/2022 |
| WO | WO2022/133062 | A1 | 6/2022 |
| WO | WO2022/187288 | A2 | 9/2022 |
| WO | 2023/283631 | A2 | 1/2023 |
| WO | WO 2023/010133 | A2 | 2/2023 |
| WO | WO 2023/137471 | A1 | 7/2023 |
| WO | WO 2023/137472 | A2 | 7/2023 |
| WO | WO2023/164670 | A2 | 8/2023 |
| WO | WO2023/164671 | A2 | 8/2023 |
| WO | WO2023/200998 | A2 | 10/2023 |
| WO | WO 2024/015881 | A2 | 1/2024 |
| WO | 2024/040253 | A1 | 2/2024 |
| WO | WO 2024/064642 | A2 | 3/2024 |
| WO | 2024/081937 | A1 | 4/2024 |
| WO | 2024/092258 | A2 | 5/2024 |
| WO | WO 2024/040254 | A3 | 5/2024 |
| WO | WO 2024/220947 | A2 | 10/2024 |
| WO | WO 2025/038982 | A2 | 2/2025 |
| WO | WO 2025/049903 | A2 | 3/2025 |

OTHER PUBLICATIONS

Ran et al. "In vivo genome editing using *Staphylococcus aureus* Cas9." Nature 520.7546 (2015): 186-191 (Year: 2015).*

Vojta et al. "Repurposing the CRISPR-Cas9 system for targeted DNA methylation." Nucleic acids research 44.12 (2016): 5615-5628 (Year: 2016).*

'T Hoen et al., "Generation and characterization of transgenic mice with the full-length human DMD gene," J. Biol. Chem., 2008, 283: 5899-5907.

Aartsma-Rus et al., "Antisense-mediated exon skipping: a versatile tool with therapeutic and research applications," RNA 13, 2007, 1609-1624.

Aartsma-Rus et al., "Exploring the frontiers of therapeutic exon skipping for Duchenne muscular dystrophy by double targeting within one or multiple exons," Mol Ther, 2006, 14:401-407.

Aartsma-Rus et al., "Theoretic applicability of antisense-mediated exon skipping for Duchenne muscular dystrophy mutations," Hum Mutat, 2009, 30:293-299.

Acosta et al., "Use of two gRNAs for CRISPR/Cas9 improves bi-allelic homologous recombination efficiency in mouse embryonic stem cells," Genesis, 2018, 56(5): 1-8.

Adamson et al., "A Multiplexed Single-Cell CRISPR Screening Platform Enables Systematic Dissection of the Unfolded Protein Response," Cell, 2016, 167: 1867-1882 e1821.

Adamson et al., "A Multiplexed Single-Cell CRISPR Screening Platform Enables Systematic Dissection of the Unfolded Protein Response," Cell, 2016, 167: 1867-1882.e21.

Adikusuma et al., "Versatile single-step-assembly CRISPR/Cas9 vectors for dual gRNA expression," 2017, 12(12): e0187236.

Adler et al., "Nonviral direct conversion of primary mouse embryonic fibroblasts to neuronal cells," Molecular therapy, 2012 Nucleic acids 1, e32.

Aguilar et al., "Transcriptional and Chromatin Dynamics of Muscle Regeneration after Severe Trauma," Stem Cell Rep, 2016, 7: 983-997.

Ahlenius et al., "FoxO3 regulates neuronal reprogramming of cells from postnatal and aging mice," Proc Natl Acad Sci U S A, 2016, 113: 8514-8519.

Aiuti et al., "Lentiviral hematopoietic stem cell gene therapy in patients with Wiskott-Aldrich syndrome," Science, 2013, 341(6148): p. 1233151.

Albuquerque et al., "Mammalian nicotinic acetylcholine receptors: from structure to function," Physiol Rev, 2009, 89: 73-120.

Aloia, "Epigenetic Regulation of Cell-Fate Changes That Determine Adult Liver Regeneration After Injury," Front. Cell Dev. Biol., 2021, 9: 643055.

(56) References Cited

OTHER PUBLICATIONS

Amabile et al., “Inheritable Silencing of Endogenous Genes by Hit-and-Run Targeted Epigenetic Editing,” Cell, 2016, 167(1): 219-232.e14.
Amabile et al., “Permanent Epigenetic Silencing of Human Genes With Artificial Transcriptional Repressors,”, Molecular Therapy, 2015, 23(Suppl. 1): S275.
Amoasii et al., “Gene editing restores dystrophin expression in a canine model of Duchenne muscular dystrophy,” Science, 2018, 362: 86-91.
Amoasii et al., “Single-cut genome editing restores dystrophin expression in a new mouse model of muscular dystrophy,” Sci Transl Med, Nov. 2017, 9(418): eaan8081.
Anders et al., “Differential expression analysis for sequence count data,” Genome biology 11, 2010, R106.
Anders et al., “Structural basis of PAM-dependent target DNA recognition by the Cas9 endonuclease,” Nature (2014) 513: 569-73.
Andersen et al., “Dual role of delta-like 1 homolog (DLK1) in skeletal muscle development and adult muscle regeneration,” Development, 2013, 140: 3743-3753.
Anguela et al., “Robust ZFN-mediated genome editing in adult hemophilic mice,” Blood, 2013, 122:3283-3287.
Aoki et al., “Bodywide skipping of exons 45-55 in dystrophic mdx52 mice by systemic antisense delivery,” Proc Natl Acad Sci USA, 2012, 109:13763-13768.
Arechavala-Gomeza et al., “Comparative analysis of antisense oligonucleotide sequences for targeted skipping of exon 51 during dystrophin pre-mRNA splicing in human muscle,” Human Gene Therapy, 2007, 18: 798-810.
Arnett et al., “Adeno-associated viral vectors do not efficiently target muscle satellite cells,” Molecular Therapy Methods & Clinical Development, 2014, 1: 14038.
Arnold et al., “Genome-wide quantitative enhancer activity maps identified by STARR-seq,” Science, 2013, 339(6123):1074-7.
Asokan et al., “Reengineering a receptor footprint of adeno-associated virus enables selective and systemic gene transfer to muscle,” Nat Biotechnol, 2010, 28: 79-82.
Asokan et al., “The AAV Vector Toolkit: Poised at the Clinical Crossroads,” Mol Ther, 2012, 20, 699-708.
Asrani et al., “Burden of liver diseases in the world,” J Hepatol, 2019, 70(1): 151-171.
Ayyanathan et al., “Regulated recruitment of HP1 to a euchromatic gene induces mitotically heritable, epigenetic gene silencing: a mammalian cell culture model of gene variegation,” Genes Dev, 2003, 17, 1855-1869.
Bae et al., “Cas-OFFinder: a fast and versatile algorithm that searches for potential off-target sites of Cas9 RNA-guided endonucleases,” Bioinformatics, 2014, 30: 1473-1475.
Balboa et al., “Conditionally Stabilized dCas9 Activator for Controlling Gene Expression in Human Cell Reprogramming and Differentiation,” Stem Cell Rep, 2015, 5: 448-459.
Baratta et al., “Cellular organization of normal mouse liver: a histological, quantitative immunocytochemical, and fine structural analysis,” Histochem Cell Biol, 2009, 131(6): 713-726.
Barberi et al., “Derivation of engraftable skeletal myoblasts from human embryonic stem cells,” Nat Med, 2007, 13: 642-648.
Barr et al., “Predominant Expression of Alternative PAX3 and PAX7 Forms in Myogenic and Neural Tumor Cell Lines,” Cancer Res, 1999, 59: 5443-5448.
Barrangou et al., “CRISPR provides acquired resistance against viruses in prokaryotes,” Science, 2007, 315(5819): 1709-1712.
Bartel et al., “Isolation of new ribozymes from a large pool of random sequences,” Science, 1993, 261(5127): 1411-1418.
Bartsevich et al., “Engineered zinc finger proteins for controlling stem cell fate,” Stem Cells 21, 2003, 632-637.
Bauer et al., “An erythroid enhancer of BCL11A subject to genetic variation determines fetal hemoglobin level,” Science 342, 2013, 253-257.
Beaudry et al., “Directed evolution of an RNA enzyme,” Science, 1992, 257(5070): 635-641.
Beerli et al., “Chemically regulated zinc finger transcription factors,” J Biol Chem, 2000, 275(42):32617-27.
Beerli et al., “Engineering polydactyl zinc-finger transcription factors,” Nat Biotechnol 20, 2002, 135-141.
Beerli et al., “Positive and negative regulation of endogenous genes by designed transcription factors,” Proc Natl Acad Sci U S A 97, 2000, 1495-1500.
Beerli et al., “Toward controlling gene expression at will: specific regulation of the erbB-2/HER-2 promoter by using polydactyl zinc finger proteins constructed from modular building blocks,” Proc Natl Acad Sci U S A 95, 1998, 14628-14633.
Beltran et al., “Re-activation of a dormant tumor suppressor gene maspin by designed transcription factors,” Oncogene 26, 2007, 2791-2798.
Bender et al., “Independent formation of DnaseI hypersensitive sites in the murine beta-globin locus control region,” Blood, 2000, 95, 3600-3604.
Benedetti et al., “Repair or Replace? Exploiting Novel Gene and Cell Therapy Strategies for Muscular Dystrophies,” FEBS Journal, 2013, 280:4263-4280.
Bengtsson et al., “Muscle-specific CRISPR/Cas9 dystrophin gene editing ameliorates pathophysiology in a mouse model for Duchenne muscular dystrophy,” Nat Commun, 2017, 8: 1-10.
Berghella et al., “Reversible immortalization of human myogenic cells by site-specific excision of a retrovirally transferred oncogene,” Human gene therapy 10, 1999, 1607-1617.
Bernstein et al., “An integrated encyclopedia of DNA elements in the human genome,” Nature, 2012, 489: 57-74.
Bernstein et al., “The NIH Roadmap Epigenomics Mapping Consortium,” Nat Biotechnol, 2010, 28, 1045-1048.
Beverley, “Primer: making sense of T-cell memory,” Nat. Clin. Pract. Rheumatol. 2008, 4, 43-49.
Bhakta et al., “Highly active zinc-finger nucleases by extended modular assembly,” Genome Res, 2013, 530-538.
Bidou et al., “Sense from nonsense: therapies for premature stop codon diseases,” Trends in Molecular Medicine 18, 2012, 679-688.
Bieth et al., “Highly restricted deletion of the SNORD116 region is implicated in Prader-Willi Syndrome,” Eur J Hum Genet, 2015, 23: 252-255.
Bittel et al., “Prader-Willi syndrome: clinical genetics, cytogenetics and molecular biology,” Expert Rev Mol Med, 2005, 7(14): 1-20.
Black et al., “Targeted Epigenetic Remodeling of Endogenous Loci by CRISPR/Cas9-Based Transcriptional Activators Directly Converts Fibroblasts to Neuronal Cells,” Cell Stem Cell, 2016, 19: 406-414.1
Bladen et al., “The TREAT-NMD DMD Global Database: analysis of more than 7,000 Duchenne muscular dystrophy mutations,” Human Mutation, 2015, 36(4):395-402.
Blakemore et al., “Editing of Human Genes May Begin by Year's End in the U.S.” Smithsonian.com, <https://www.smithsonianmag.com/smart-news/editing-human-genes-may-begin-years-end-US-180959532/?no-ist> 2016.
Blancafort et al., “Scanning the human genome with combinatorial transcription factor libraries,” Nat Biotechnol 21, 2003, 269-274.
Blancafort et al., “Writing and rewriting the epigenetic code of cancer cells: from engineered proteins to small molecules,” Mol. Pharmacol., 2013, 83(3): 563-576.
Boch et al., “Breaking the code of DNA binding specificity of TAL-type III effectors,” Science 326, 2009, 1509.
Boldrin et al., “Donor satellite cell engraftment is significantly augmented when the host niche is preserved and endogenous satellite cells are incapacitated,” Stem Cells, 2012, 30: 1971-1984.
Boshart et al., “A very strong enhancer is located upstream of an immediate early gene of human cytomegalovirus,” Cell, 1985, 41:521-530.
Bowles et al., “Phase 1 Gene Therapy for Duchenne Muscular Dystrophy Using a Translation Optimized AAV Vector,” Molecular Therapy 20, 2012, 443-455.
Boyle et al., “High-resolution mapping and characterization of open chromatin across the genome,” Cell, 2008. 132(2):311-22.
Braasch et al., “Novel Antisense and Peptide Nucleic Acid Strategies for Controlling Gene Expression,” Biochemistry, 2002, 41: 4503-4510.

(56) References Cited

OTHER PUBLICATIONS

Breaker et al., "Inventing and improving ribozyme function rational design versus iterative selection methods," TIBTECH, 1994, 12: 268-274.
Breaker, "Are engineered proteins getting competition from RNA?," Curr. Op. Biotech., 1996, 7(4): 442-448.
Briguet et al., "Histological parameters for the quantitative assessment of muscular dystrophy in the mdx-mouse," Neuromuscul. Disord., 2004, 14: 675-682.
Briner et al., "Guide RNA Functional Modules Direct Cas9 Activity and Orthogonality," Molecular Cell, 2014, 56(2): 333-339.
Briner et al., "Lactobacillus buchneri genotyping on the basis of clustered regularly interspaced short palindromic repeat (CRISPR) locus diversity," Appl. Environ. Microbiol., 2014, 80: 994-1001.
Brummelkamp et al., "A system for stable expression of short interfering RNAs in mammalian cells," Science, 2002, 296(5567): 550-553.
Brunet et al., "Chromosomal translocations induced at specific loci in human stem cells," Proc Natl Acad Sci USA, 2009, 106:10620-10625.
Brunger et al., "CRISPR/Cas9 Editing of Murine Induced Pluripotent Stem Cells for Engineering Inflammation-Resistant Tissues," Arthritis Rheumatol, 2017, 69: 1111-1121.
Brunger et al., "Genome Engineering of Stem Cells for Autonomously Regulated, Closed-Loop Delivery of Biologic Drugs," Stem Cell Reports, 2017, 8: 1202-1213.
Buenrostro et al., "Transposition of native chromatin for fast and sensitive epigenomic profiling of open chromatin, DNA-binding proteins and nucleosome position," Nat Methods, 2013, 10: 1213-1218.
Buiting, "Prader-Willi syndrome and Angelman syndrome," Am J Med Genet C Semin Med Genet, 2010, 154C(3): 365-376.
Buler et al., "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, Jan. 13, 2012, vol. 287, No. 3, pp. 1847-1860.
Bultmann et al., "Targeted transcriptional activation of silent oct4 pluripotency gene by combining designer TALEs and inhibition of epigenetic modifiers," Nucleic Acids Res 40, 2012, 5368-5377.
Burnett et al., "Deficiency in prohormone convertase PC1 impairs prohormone processing in Prader-Willi syndrome," J Clin Invest, 2017, 127: 293-305.
Busskamp et al., "Rapid neurogenesis through transcriptional activation in human stem cells," Mol Syst Biol, 2014, 10: 760.
Cano-Rodriguez et al., "Writing of H3K4Me3 overcomes epigenetic silencing in a sustained but context-dependent manner," Nat Commun, 2016, 7: 12284.
Carcagno et al., "Neurogenin3 Restricts Serotonergic Neuron Differentiation to the Hindbrain," The Journal of Neuroscience, 2014, 34(46): 15223-15233.
Carrillo et al., "The Multiple Sequence Alignment Problem in Biology" SIAM J. Applied Math., 1988, 48, 1073.
Carroll, "A CRISPR approach to gene targeting," Molecular Therapy, 2012, 20: 1658-1660.
Carter et al., "Long-range chromatin regulatory interactions in vivo," Nat Genet, 2002, 32, 623-626.
Cassidy et al., "Prader-Willi syndrome," Eur J Hum Genet, 2009, 17(1): 3-13.
Cassidy et al., "Prader-Willi syndrome," Genet Med, 2012, 14: 10-26.
Cencic et al., "Protospacer adjacent motif (PAM)-distal sequences engage CRISPR Cas9 DNA target cleavage," PLoS one, 2014, 9, e109213, 13 pages.
Cerletti et al., "Highly efficient, functional engraftment of skeletal muscle stem cells in dystrophic muscles," Cell 134, 2008, 37-47.
Cermak et al., "Efficient design and assembly of custom TALEN and other TAL effector-based constructs for DNA targeting," Nucleic Acids Res 30, 2011, pp. 1-11.
Chakraborty et al., "A CRISPR/Cas9-Based System for Reprogramming Cell Lineage Specification," Stem cell reports 3, 2014, 940-947.
Chal et al., "Differentiation of pluripotent stem cells to muscle fiber to model Duchenne muscular dystrophy," Nat Biotechnol, 2015, 33: 962-969.
Chamberlain et al., "Progress toward Gene Therapy for Duchenne Muscular Dystrophy," Mol. Ther., 2017, 25: 1125-1131.
Chanda et al., "Generation of induced neuronal cells by the single reprogramming factor ASCL1," Stem Cell Reports, 2014, 3: 282-296.
Chang et al., "Integrating Combinatorial Lipid Nanoparticle and Chemically Modified Protein for Intracellular Delivery and Genome Editing," Acc. Chem. Res., 2019, 52: 665-675.
Chapdelaine et al., "Meganucleases can restore the reading frame of a mutual dystrophin," Gene therapy 17, 2010, 846-858.
Chavez et al., "Comparison of Cas9 activators in multiple species," Nat Methods, 2016, 13: 563-67.
Chavez et al., "Highly efficient Cas9-mediated transcriptional programming," Nat Methods 12, 2015, 326-328.
Cheloufi et al., "The histone chaperone CAF-1 safeguards somatic cell identity," Nature, 2015, 528: 218-224.
Chen et al., "Acetylation of RelA at discrete sites regulates distinct nuclear functions of NF-kB," The EMBO Journal, 2002, 21(23): 6539-6548.
Chen et al., "Dynamic imaging of genomic loci in living human cells by an optimized CRISPR/Cas system," Cell, 2013, 155: 1479-1491.
Chen et al., "Enrichr: interactive and collaborative HTML5 gene list enrichment analysis tool," BMC Bioinformatics, 2013, 14: 128.
Chen et al., "Expanding the CRISPR imaging toolset with Staphylococcus aureus Cas9 for simultaneous imaging of multiple genomic loci," Nucleic Acids Research, 2016, 44(8):e75, 13 pages.
Chen et al., "Genome-wide CRISPR screen in a mouse model of tumor growth and metastasis," Cell, 2015, 160: 1246-1260.
Chen et al., "Life and death of transcriptional co-activator p300," Epigenetics 6, 2011, 957-961.
Chen et al., "microRNA-1 and microRNA-206 regulate skeletal muscle satellite cell proliferation and differentiation by repressing Pax7," J Cell Biol, 2010, 190: 867-879.
Chen et al., "Targeted activation of diverse CRISPR-Cas systems for mammalian genome editing via proximal CRISPR targeting," Nature Communications, 2017, 8: 14958.
Chen et al., "Two upstream enhancers collaborate to regulate the spatial patterning and timing of MyoD transcription during mouse development," Dev Dyn, 2001, 221, 274-288.
Chen et al., "Vitamin D receptor suppresses proliferation and metastasis in renal cell carcinoma cell lines via regulating the expression of the epithelial Ca2+ channel TRPV5," PloS One, 2018, 13: e0195844.
Cheng et al., "Multiplexed activation of endogenous genes by CRISPR-on, an RNA-guided transcriptional activator system," Cell Res, 2013, 23(10):1163-1171.
Chew et al., "A multifunctional AAV-CRISPR-Cas9 and its host response," Nat Methods, 2016; 13:868-74.
Chhatwal et al., "Identification of cell-type-specific promoters within the brain using lentiviral vectors," Gene Therapy, 2007, 14(7): 575-583.
Childers et al., "Gene therapy prolongs survival and restores function in murine and canine models of myotubular myopathy," Sci Transl Med, 2014, 6: 220ra210.
Cho et al., "Analysis of off-target effects of CRISPR/Cas-derived RNA-guided endonucleases and nickases," Genome Res, 2014, 24:132-141.
Cho et al., "Targeted genome engineering in human cells with the Cas9 RNA-guided endonuclease," Nat Biotechnol 31, 2013, 230-232.
Choy et al., "Eukaryotic activators function during multiple steps of preinitiation complex assembly," Nature 366, 1993, 531-536.
Christian et al., "Targeting DNA double-strand breaks with TAL effector nucleases," Genetics 186, 2010, 757-761.
Christoffersen et al., "Ribozymes as human therapeutic agents," J. Med. Chem., 1995, 38(12): 2023-2037.

(56) References Cited

OTHER PUBLICATIONS

Chronis et al., "Cooperative Binding of Transcription Factors Orchestrates Reprogramming," Cell, 2017, 168: 442-459 e420.
Chu et al., "SV40 DNA transfection of cells in suspension: analysis of efficiency of transcription and translation of T-antigen," Gene, 1981, 13:197.
Cirak et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.
Concise Encyclopedia of Polymer Science And Engineering, 1990, pp. 858-859.
Cong et al., "Comprehensive interrogation of natural TALE DNA-binding modules and transcriptional repressor domains," Nat Commun 3, 2012, 968.
Cong et al., "Multiplex Genome Engineering Using CRISPR/Cas Systems," Science 339, 2013, 819-823.
Consortium, "An integrated encyclopedia of DNA elements in the human genome," Nature 489, 2012, 57-74.
Cooper et al., "Improved induction of immune tolerance to factor IX by hepatic AAV-8 gene transfer," Hum Gene Ther, 2009, 20: 767-776.
Corces et al., "The chromatin accessibility landscape of primary human cancers," Science, 2018, 362(6413): eaav1898.
Cordier et al., "Muscle-specific promoters may be necessary for adeno-associated virus- mediated gene transfer in the treatment of muscular dystrophies," Hum. Gene Ther., 2001, 12: 205-215.
Cornu et al., "DNA-binding specificity is a major determinant of the activity and toxicity of zinc-finger nucleases," Mol Ther, 2008, 16:352-358.
Cornu et al., "Quantification of zinc finger nuclease-associated toxicity," Meth Mol Biol, 2010, 649:237-245.
Cradick et al., "CRISPR/Cas9 systems targeting beta-globin and CCR5 genes have substantial off-target activity," Nucleic Acids Res, 2013, 41(20):9584-92.
Crawford et al., "Genome-wide mapping of DNase hypersensitive sites using massively parallel signature sequencing (MPSS)," Genome Res. 2006, 16, 123-131.
Crocker et al., "TALE-mediated modulation of transcriptional enhancers in vivo," Nature methods 10, 2013, 762-767.
Crooke et al., "Pharmacokinetic properties of several novel oligonucleotide analogs in mice," J. Pharmacol. Exp. Ther., 1996, 277(2): 923-937.
Cruvinel et al., "Reactivation of maternal SNORD116 cluster via SETDB1 knockdown in Prader- Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
D'Alessio et al., "A Systematic Approach to Identify Candidate Transcription Factors that Control Cell Identity," Stem Cell Reports, 2015, 5: 763-775.
Daley et al., "CRISPhieRmix: a hierarchical mixture model for CRISPR pooled screens," Genome Biol, 2018, 19: 159.
Darabi et al., "Functional skeletal muscle regeneration from differentiating embryonic stem cells," Nat Med, 2008, 14: 134-143.
Darabi et al., "Human ES- and iPS-derived myogenic progenitors restore dystrophin and improve contractility upon transplantation in dystrophic mice," Cell Stem Cell 10, 2012, 610-619.
Darmanis et al., "A survey of human brain transcriptome diversity at the single cell level," Proc Natl Acad Sci U S A, 2015, 112: 7285-7290.
Datlinger et al., "Pooled CRISPR screening with single-cell transcriptome readout," Nat. Methods, 2017, 14: 297-301.
De Groote et al., "Epigenetic Editing: targeted rewriting of epigenetic marks to modulate expression of selected target genes," Nucleic Acids Res, 2012, vol. 40, No. 21, pp. 10596-10613.
De Mesmaeker et al., "Antisense Oligonucleotides," Ace. Chem. Res., 1995, 28: 366-374.
De Smith et al., "A deletion of the HBII-85 class of small nucleolar RNAs (snoRNAs) is associated with hyperphagia, obesity and hypogonadism," Hum Mol Genet, 2009, 18: 3257-3265.
Dean et al., "Inducible transcription of five globin genes in K562 human leukemia cells," Proceedings of the National Academy of Sciences of the United States of America 80, 1983, 5515-5519.
Deconinck et al., "Utrophin-Dystrophin-Deficient Mice as a Model for Duchenne Muscular Dystrophy," Cell, 1997, 90(4): 717-727.
Deltcheva et al., "CRISPR RNA maturation by trans-encoded small RNA and host factor RNase III," Nature, 2011, 471(7340):602-7.
Delvecchio et al., "Structure of the p300 catalytic core and implications for chromatin targeting and HAT regulation," Nat Struct Mol Biol 20, 2013, 1040-1046.
Dempster et al., "Extracting Biological Insights from the Project Achilles Genome-Scale CRISPR Screens in Cancer Cell Lines," Cold Spring Harbor Laboratory, 2019, 35 pages.
Deng et al., "Reactivation of developmentally silenced globin genes by forced chromatin looping," Cell 158, 2014, 849-860.
Dezawa et al., "Bone marrow stromal cells generate muscle cells and repair muscle degeneration," Science Signaling 309, 2005, 314-317.
Diao et al., "A new class of temporarily phenotypic enhancers identified by CRISPR/Cas9-mediated genetic screening," Genome Res, 2016, 26: 397-405.
Dijkema et al., "Cloning and expression of the chromosomal immune interferon gene of the rat," EMBO J., 1985, 4:761.
Ding et al., "A TALEN Genome-Editing System for Generating Human Stem Cell-Based Disease Models," 2013, Cell Stem Cell 12, 238-251.
Ding et al., "Enhanced efficiency of human pluripotent stem cell genome editing through replacing TALENs with CRISPRs," Cell Stem Cell, 2013, 12:393-394.
Ding et al., "Permanent Alteration of PCSK9 With In Vivo CRISPR-Cas9 Genome Editing," Circulation Research, 2014, vol. 115, No. 5, pp. 488-492.
Dirks et al., "Triggered amplification by hybridization chain reaction," Proceedings of the National Academy of Sciences of the United States of America, 2004, 101(43): 15275-15278.
Dixit et al., "Perturb-Seq: Dissecting Molecular Circuits with Scalable Single-Cell RNA Profiling of Pooled Genetic Screens," Cell, 2016, 167: 1853-1866.e17.
Doench et al., "Optimized sgRNA design to maximize activity and minimize off-target effects of CRISPR-Cas9," Nat Biotechnol. (2016) 34:184-91.
Doench et al., "Rational design of highly active sgRNAs for CRISPR-Cas9-mediated gene inactivation," Nat Biotechnol. (2014) 32:1262-7.
Dostie et al., "Chromosome Conformation Capture Carbon Copy (5C): a massively parallel solution for mapping interactions between genomic elements," Genome research 16, 2006, 1299-1309.
Doudna et al., "Genome editing. The new frontier of genome engineering with CRISPR-Cas9," Science 346, 2014, 1258096.
Doyle et al., "TAL Effector-Nucleotide Targeter (TALE-NT) 2.0: tools for TAL effector design and target prediction," Nucleic Acids Res 40, 2012, W117-122.
Doyon et al., "Enhancing zinc-finger-nuclease activity with improved obligate heterodimeric architectures," Nat Methods 8, 2010, 74-79.
Du et al., "Genetic interaction mapping in mammalian cells using CRISPR interference," Nat Methods, 2017, 14: 577-580.
Duan et al., "Expanding AAV packaging capacity with transsplicing or overlapping vectors: a quantitative comparison," Molecular Therapy, 2001, 4: 383-391.
Duan et al., "Genome-wide identification of CRISPR/Cas9 off-targets in human genome," Cell research, 2014, 24(8): 1009-12.
Duan, "Systemic AAV Micro-dystrophin Gene Therapy for Duchenne Muscular Dystrophy," Molecular Therapy, 2018, 26(10): 2337-2356.
Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
Dumont et al., "Dystrophin expression in muscle stem cells regulates their polarity and asymmetric division," Nat Med, 2015, 21: 1455-1463.

(56) References Cited

OTHER PUBLICATIONS

Dumont et al., "Intrinsic and extrinsic mechanisms regulating satellite cell function," Development, 2015, 142: 1572-1581.
Dunbar et al., "Gene therapy comes of age," Science, 2018, 359: eaan4672.
Dykeman, "An implementation of the Gillespie algorithm for RNA kinetics with logarithmic time update," Nucleic Acids Research, 2015, 45(12): 5708-5715.
EBI Accession No. GSP: BCJ39961 (2016).
Edelstein et al., "Gene therapy clinical trials worldwide 1989-2004—an overview," J. Gene Med., 2004, vol. 6, pp. 597-602.
Egger et al., "Epigenetics in human disease and prospects for epigenetic therapy," Nature 429, 2004, 457-463.
Eguchi et al., "Reprogramming cell fate with a genome-scale library of artificial transcription factors," Proc Natl Acad Sci U S A, 2016, 113: E8257-E8266.
Englisch et al., Chemically Modified Oligonucleotides as Probes and Inhibitors, Angewandle Chemie, International Edition, 1991, 30(6): 613-629.
Eraslan et al., "Deep learning: new computational modelling techniques for genomics, " Nat. Rev. Genet., 2019, 20: 389-403.
Ernsberger, "Role of neurotrophin signalling in the differentiation of neurons from dorsal root ganglia and sympathetic ganglia," Cell Tissue Res, 2009, 336: 349-384.
Erwin et al., "Synthetic transcription elongation factors license transcription across repressive chromatin," Science, 2017, 358: 1617-1622.
Esvelt et al., "Orthogonal Cas9 proteins for RNA-guided gene regulation and editing," Nature Methods 2013, 10(11):1116-21.
Fagerlund et al., "The Cpf1 CRISPR-Cas protein expands genome-editing tools," Genome Biology, 2015, 16:251.
Fairclough et al., "Therapy for Duchenne muscular dystrophy: renewed optimism from genetic approaches," Nat. Rev. Genet., 2013, 14: 373-378.
Farasat et al., "A Biophysical Model of CRISPR/Cas9 Activity for Rational Design of Genome Editing and Gene Regulation," PLOS Computational Biology, 2016, 12(1):e1004724.
Farasat, "Sequence-to-Function Models for Efficient Optimization of Metabolic Pathways and Genetic Circuits," Ph. D. Thesis, 2015, 254 pages.
Farinelli et al., "Lentiviral vectors for the treatment of primary immunodeficiencies," J Inherit Metab Dis, 2014, 37:525-533.
Farzadfard et al., "Tunable and Multifunctional Eukaryotic Transcription Factors Based on CRISPR/Cas," ACS Synth Biol, 2013, 604-613.
FDA approval brings first gene therapy to the United States, <https://www.fda.gov/newsevents/newsroom/pressannouncements/ucm574058.htm> (Aug. 30, 2017).
FDA approves first drug for spinal muscular atrophy, <https://www.fda.gov/newsevents/newsroom/pressannouncements/ucm534611.htm> (Dec. 23, 2016).
FDA approves first-of-its kind targeted RNA-based therapy to treat a rare disease, <https://www.fda.gov/newsevents/newsroom/pressannouncements/ucm616518.htm> (Aug. 10, 2018).
FDA approves novel gene therapy to treat patients with a rare form of inherited vision loss, <https://www.fda.gov/newsevents/newsroom/pressannouncements/ucm589467.htm> (Dec. 18, 2017).
FDA grants accelerated approval to first drug for Duchenne muscular dystrophy, <https://www.fda.gov/newsevents/newsroom/pressannouncements/ucm521263.htm> (Sep. 19, 2016).
Ferretti et al., "Complete genome sequence of an M1 strain of *Streptococcus pyogenes*," Proc Natl Acad Sci U S A, 2001, 98(8): 4658-63.
Fine et al., "Trans-spliced Cas9 allows cleavage of HBB and CCR5 genes in human cells using compact expression cassettes," Sci Rep. 2015;5:10777.
Flamm et al., "RNA folding at elementary step resolution," Rna, 2000, 6: 325-338.
Flandin et al., "Lhx6 and Lhx8 coordinately induce neuronal expression of Shh that controls the generation of interneuron progenitors," Neuron, 2011, 70: 939-950.
Flanigan et al., "Mutational spectrum of DMD mutations in dystrophinopathy patients: application of modern diagnostic techniques to a large cohort," Human mutation 30, 2009, 1657-1666.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5: 838-843.
Fonfara et al., "Phylogeny of Cas9 determines functional exchangeability of dual-RNA and Cas9 among orthologous type II CRISPR-Cas systems," Nucleic Acids Res, 2013, 42(4):2577-2590.
Fontenot et al., "Regulatory T cell lineage specification by the forkhead transcription factor foxp3," Immunity, 2005, 22, 329-341.
Forget, "Molecular basis of hereditary persistence of fetal hemoglobin," Ann N Y Acad Sci, 1998, 850, 38-44.
Frank et al., "HDAC inhibitors cause site-specific chromatin remodeling at PU.1-bound enhancers in K562 cells," Epigenetics Chromatin, 2016, 9: 15.
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Molecular Therapy, 2015, 23(Suppl. 1):S224.
Friedland et al., "*Staphyloccocus aureus* Cas9: An Alternative Cas9 for Genome Editing Applications," Retrieved from the Internet: <http://www.editasmedicine.com/data/documents/ASGCT%20poster 2015 Ari.pdf> Retrieved on Feb. 28, 2018.
Fu et al., "High-frequency off-target mutagenesis induced by CRISPR-Cas nucleases in human cells," Nat Biotechnol, 2013, 31(9):822-6.
Fu et al., "Improving CRISPR-Cas nuclease specificity using truncated guide RNAs," Nat Biotechnol 32, 2014, 279-284.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gaj et al., "Structure-Guided Reprogramming of Serine Recombinase DNA Sequence Specificity," Proc Natl Acad Sci U S A, 2011, 108(2): 498-503.
Gaj et al., "Targeted gene knockout by direct delivery of zinc-finger nuclease proteins," Nature Methods, 2012, 9(8):805-807.
Gaj et al., "ZFN, TALEN, and CRISPR/Cas-based methods for genome engineering," Trends Biotechnol, 2013, 31:397-405.
Gao et al., "Comparison of TALE designer transcription factors and the CRISPR/dCas9 in regulation of gene expression by targeting enhancers," Nucleic Acids Res 42, 2014, e155.
Gao et al., "Complex transcriptional modulation with orthogonal and inducible dCas9 regulators," Nat Methods, 2016, 13: 1043-1049.
Gao et al., "Reprogramming to Pluripotency Using Designer TALE Transcription Factors Targeting Enhancers," Stem Cell Reports, 2013, 1(2):183-97.
Garg et al., "Engineering synthetic TAL effectors with orthogonal target sites," Nucleic Acids Res 40, 2012, 7584-7595.
Garriga-Canut et al., "Synthetic zinc finger repressors reduce mutant huntingtin expression in the brain of R6/2 mice," Proceedings of the National Academy of Sciences of the United States of America 109, 2012, E3136-3145.

(56) References Cited

OTHER PUBLICATIONS

Gascon et al., "Direct Neuronal Reprogramming: Achievements, Hurdles, and New Roads to Success," Cell Stem Cell, 2017, 21: 18-34.
Gasiunas et al., "Cas9-crRNA ribonucleoprotein complex mediates specific DNA cleavage for adaptive immunity in bacteria," Proc. Natl. Acad. Sci., 2012, 109: E2579-E2586.
Gasperini et al., "A Genome-wide Framework for Mapping Gene Regulation via Cellular Genetic Screens," Cell, 2018, 176(1-2); 377-390.e19.
Gaudelli et al., "Directed evolution of adenine base editors with increased activity and therapeutic application," Nat Biotechnol, Jul. 2020, 38(7): 892-900.
Gaudelli et al., "Programmable base editing of A•T to G•C in genomic DNA without DNA cleavage," Nature, Nov. 2017, 551(7681): 464-471.
Gebeyehu et al., "Novel biotinylated nucleotide—analogs for labeling and colorimetric detection of DNA," Nucl. Acids Res., 1987, 15(11): 4513-4534.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974.
Genbank Accenssion AP006627.1 (2016).
Genbank Accenssion BA000004.3 (2016).
Genbank Accenssion BAB04055.1 (2016).
GenBank Accession AF214528.1 (2000).
GenBank Accession No. AAC75803.1 (2018).
GenBank Accession No. AIN33136.1 (2014).
GenBank Accession No. BAB04055.1 (2017).
GenBank Accession No. EOT14076.1 (2013).
GenBank Accession No. AK019325 (2010).
GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
GenBank Accession X51934.1 (1997).
GenBank P38036.2 (2013).
Gersbach et al., "Activating human genes with zinc finger proteins, transcription activator-like effectors and CRISPR/Cas9 for gene therapy and regenerative medicine," Expert Opin Ther Targets, 2014, 18(8):835-9.
Gersbach et al., "Targeted plasmid integration into the human genome by an engineered zinc-finger recombinase," Nucleic Acids Res, 2011, 39: 7868-7878.
Gersbach, "Genome engineering: the next genomic revolution," Nat Methods 11, 2014, 1009-1011.
Gerstein et al., "Architecture of the human regulatory network derived from ENCODE data," Nature 489, 2012, 91-100.
Gertz et al., "Transposase mediated construction of RNA-seq libraries," Genome Res 22, 2012, 134-141.
Ghisletti et al., "Identification and characterization of enhancers controlling the inflammatory gene expression program in macrophages," Immunity, 2010, 32: 317-328.
Gibson et al., "Enzymatic assembly of DNA molecules up to several hundred kilobases," Nature Methods, 2009, 6(5): 343-345.
Gilbert et al., "CRISPR-mediated modular RNA-guided regulation of transcription in eukaryotes," Cell 154, 2013, 442-451.
Gilbert et al., "Genome-Scale CRISPR-Mediated Control of Gene Repression and Activation," Cell 159, 2014, 647-661.
Gillespie, "A general method for numerically simulating the stochastic time evolution of coupled chemical reactions," Journal of computational physics, 1976, 22: 403-434.
Gilman et al., "Distal CCAAT box deletion in the A gamma globin gene of two black adolescents with elevated fetal A gamma globin," Nucleic Acids Res 16, 1988, 10635-10642.
Goemans et al., "Systemic administration of PRO051 in Duchenne's muscular dystrophy," The New England journal of medicine 364, 2011, 1513-1522.
Goldstein et al., "In Situ Modification of Tissue Stem and Progenitor Cell Genomes," Cell Reports, 2019, 27: 1254-1264.e7.
Gomaa et al., "Programmable Removal of Bacterial Strains by Use of Genome-Targeting CRISPR-Cas Systems," 2014, mBio 5(1): e00928-13.
Gonda "Aerosols for delivery of therapeutic and diagnostic agents to the respiratory tract," Critical Reviews in Therapeutic Drug Carrier Systems, 1990 6:273-313.
Gong et al., "Molecular insights into DNA interference by CRISPR-associated nuclease-helicase Cas3," Proc Natl Acad Sci U S A, 2014, 111(46):16359-64.
Gorman et al., "The Rous sarcoma virus long terminal repeat is a strong promoter when introduced into a variety of eukaryotic cells by DNA-mediated transfection," Proc. Natl. Acad. Sci. U.S.A., 1982, 79:6777.
Gou et al., "A novel approach for the construction of multiple shRNA expression vectors," J Gene Med, 2007, 9(9):751-63.
Graham et al., "A new technique for the assay of infectivity of human adenovirus 5 DNA," Virol., 1973, 52:456-467.
Graslund et al., "Exploring strategies for the design of artificial transcription factors: targeting sites proximal to known regulatory regions for the induction of gamma-globin expression and the treatment of sickle cell disease," J Biol Chem 280, 2005, 3707-3714.
Gray et al., "G quadruplexes are genomewide targets of transcriptional helicases XPB and XPD," Nat. Chem. Biol, 2014, 10: 313-318.
Gregorevic et al., "Systemic delivery of genes to striated muscles using adeno-associated viral vectors," Nat Med, 2004, 10:828-834.
Gregorevic et al., "Systemic microdystrophin gene delivery improves skeletal muscle structure and function in old dystrophic mdx mice," Mol Ther, 2008, 16: 657-664.
Grimmer et al., "Analysis of an artificial zinc finger epigenetic modulator: widespread binding but limited regulation," Nucleic acids research 42, 2014, 10856-10868.
Grissa et al., "CRISPRFinder: a web tool to identify clustered regularly interspaced short palindromic repeats," Nucleic Acids Res., 2007, 35(Web Server issue):W52-57.
Groner et al., "KRAB-zinc finger proteins and KAP1 can mediate long-range transcriptional repression through heterochromatin spreading," PLoS Genet 6, 2010, e1000869.
Guo et al., "Directed evolution of an enhanced and highly efficient Fokl cleavage domain for zinc finger nucleases," J Mol Biol, 2010, 400:96-107.
Guo et al., "Harnessing accurate non-homologous end joining for efficient prease deletion in CRISPR/Cas9-mediated genome editing," Genome Biology, 2018, 19: 170, 20 pages.
Guo, J. et al., "Directed evolution of an enhanced and highly efficient Fokl cleavage domain for zinc finger nucleases," J Mol Biol, 2010, 400(1): 96-107.
Guschin et al., "A rapid and general assay for monitoring endogenous gene modification," Methods Mol Biol 649, 2010, 247-256.
Hacein-Bey-Abina et al., "LMO2-associated clonal T cell proliferation in two patients after gene therapy for SCID-X1," Science, 2003, 302: 415-419.
Hakim et al., "Evaluation of Muscle Function of the Extensor Digitorum Longus Muscle Ex vivo and Tibialis Anterior Muscle In situ in Mice," J. Vis. Exp., 2013, 1-8.
Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.
Hall et al., "Prevention of Muscle Aging by Myofiber-Associated Satellite Cell Transplantation," Sci Transl Med, 2010, 2: 57ra83.
Hamar et al., "Small interfering RNA targeting Fas protects mice against renal ischemia- reperfusion injury," PNAS, 2004, 101:14883-8.
Hardison et al., "Locus control regions of mammalian beta-globin gene clusters: combining phylogenetic analyses and experimental results to gain functional insights," Gene 205, 1997, 73-94.

(56) References Cited

OTHER PUBLICATIONS

Hardy et al., "Comparative Study of Injury Models for Studying Muscle Regeneration in Mice," PLoS ONE, 2016, 11: e0147198.
Harper et al., "Modular flexibility of dystrophin: implications for gene therapy of Duchenne muscular dystrophy," Nat. Med., 2002, 8: 253-261.
Harrow et al., "GENCODE: The reference human genome annotation for the ENCODE Project," Genome Res, 2012, 22: 1760-1774.
Hart et al., "High-Resolution CRISPR Screens Reveal Fitness Genes and Genotype-Specific Cancer Liabilities," Cell, 2015, 163: 1515-1526.
Hathaway et al., "Dynamics and memory of heterochromatin in living cells," Cell 149, 2012, 1447-1460.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Heagerty et al., "Time-dependent ROC curves for censored survival data and a diagnostic marker," Biometrics, 2000, 56(2): 337-344.
Heasman, "Morpholino oligos: making sense of antisense?," Dev. Biol., 2002, 243(2): 209-214.
Heintzman et al., "Distinct and predictive chromatin signatures of transcriptional promoters and enhancers in the human genome," Nat Genet 39, 2007, 311-318.
Henikoff et al., "Amino acid substitution matrices from protein blocks," Proc. Natl. Acad. Sci. USA, 1992, 89: 10915-9.
Henning et al., "Epigenetic control of CD8 + T cell differentiation," Nat Rev Immunol, 2018, 18(5): 340-356.
Hilton et al., "Enabling functional genomics with genome engineering," Genome Research, 2015, 25(10):1442-1455.
Hilton et al., "Epigenome editing by a CRISPR-Cas9-based acetyltransferase activates genes from promoters and enhancers," Nature biotechnology, 2015, vol. 33, No. 5, pp. 510-519.
Himeda et al., "Design and Testing of Regulatory Cassettes for Optimal Activity in Skeletal and Cardiac Muscles," Methods Mol Biol, 2011, 709: 3-19 (Published Online Dec. 2010).
Hockemeyer et al., "Efficient targeting of expressed and silent genes in human ESCs and iPSCs using zinc-finger nucleases," Nat Biotechnol, 2009, 27(9):851-7.
Hockemeyer et al., "Genetic engineering of human pluripotent cells using TALE nucleases," Nat Biotechnol 29, 2011, 731-734.
Hoffman et al., "Dystrophin: the protein product of the Duchenne muscular dystrophy locus," Cell, 1987, 51:919.
Hori et al., "Simple and reproducible hepatectomy in the mouse using the clip technique, " World J Gastroenterol, 2012, 18(22): 2767-2774.
Hotta et al., "Isolation of human iPS cells using EOS lentiviral vectors to select for pluripotency," Nat Methods 6, 2009, 370-376.
Hou et al., "Efficient genome engineering in human pluripotent stem cells using Cas9 from Neisseria meningitidis," Proc Natl Acad Sci USA, 2013, 110:15644-15649.
Howarth et al., "A monovalent streptavidin with a single femtomolar biotin binding site," Nature methods, 2006, 3(4): 267-273.
Hsu et al., "Development and applications of CRISPR-Cas9 for genome engineering," Cell, 2014, 157, 1262-1278.
Hsu et al., "Dissecting Neural Function Using Targeted Genome Engineering Technologies," ACS Chem. Neurosci., 2012, pp. 603-610.
Hsu et al., "DNA targeting specificity of RNA-guided Cas9 nucleases," Nature Biotechnology 31, 2013, 827-832.
Hu et al., "Direct activation of human and mouse Oct4 genes using engineered TALE and Cas9 transcription factors," Nucleic Acids Res 42, 2014, 4375-4390.
Huang et al., "Generation and comparison of CRISPR-Cas9 and Cre-mediated genetically engineered mouse models of sarcoma," Nature Communications, 2017, 8(15999): 1-11.
Huang et al., "Impaired respiratory function in mdx and mdx/utrn+/− mice," Muscle & Nerve, 2011, 43(2): 263-267.
Humbert et al., "Targeted gene therapies: tools, applications, optimization", Critical Reviews in Biochemistry and Molecular Biology, CRC Press, vol. 47, No. 3, Apr. 2012, pp. 264-281.
Huntriss et al., "Imprinted expression of SNRPN in human preimplantation embryos," Am J Hum Genet, 1998, 63: 1009-1014.
Hwang et al., "Efficient genome editing in zebrafish using CRISPR-Cas system," Nat Biotechnol, 2013, 31(3):227-9.
Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.
Ikonomi et al., "Levels of GATA-1/GATA-2 transcription factors modulate expression of embryonic and fetal hemoglobins," Gene 261, 2000, 277-287.
Inoue et al., "Runx transcription factors in neuronal development," Neural Dev, 2008, 3: 20.
Isaac et al., "Dystrophin and utrophin "double knockout" dystrophic mice exhibit a spectrum of degenerative musculoskeletal abnormalities," Journal of Orthopaedic Research, 2013, 31(3): 343-349.
Lyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.
Jansen et al., "Identification of genes that are associated with DNA repeats in prokaryotes, " Mol Microbiol, 2002, 43(6): 1565-1575.
Jeltsch et al., "Application of DNA methyltransferases in targeted DNA methylation," Appl. Microbiol. Biotechnol., 2007, 75(6): 1233-1240.
Jepsen et al., "Locked nucleic acid: a potent nucleic acid analog in therapeutics and biotechnology," Oligonucleotides, 2004, 14(2): 130-146.
Ji et al., "Engineered zinc-finger transcription factors activate OCT4 (POUSFI ), SOX2, KLF4, c-MYC (MYC) and miR302/367," Nucleic Acids Res 42, 2014, 6158-6167.
Jiang et al., "A Cas9-guide RNA complex preorganized for target DNA recognition," Science, 2015, 348, 1477-1481.
Jiang et al., "Notch signaling deficiency underlies age-dependent depletion of satellite cells in muscular dystrophy," Disease Models & Mechanisms, 2014, 7: 997-1004.
Jiang et al., "RNA-guided editing of bacterial genomes using CRISPR-Cas systems," Nat. Biotechnol., 2013, 31:233-239.
Jimenez et al., "Activation of the beta-globin locus control region precedes commitment to the erythroid lineage," Proceedings of the National Academy of Sciences, 1992, 89: 10618-10622.
Jinek et al., "A programmable dual-RNA-guided DNA endonuclease in adaptive bacterial immunity," Science 337, 2012, 816-821.
Jinek et al., "RNA-programmed genome editing in human cells," eLife 2, 2013, e00471.
Jinek et al., "Structures of Cas9 endonucleases reveal RNA-mediated conformational activation," Science, 2014, 343: 1247997.
Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.
Jobling et al., "Chitayat-Hall and Schaaf-Yang syndromes:a common aetiology: expanding the phenotype of MAGEL2-related disorders," J Med Genet, 2018, 55: 316-321.
Jooss et al., "Transduction of dendritic cells by DNA viral vectors directs the immune response to transgene products in muscle fibers," J. Virol., 1998, 72: 4212-4223.
Jörg, "Engineering of the epigenome: synthetic biology to define functional causality and develop innovative therapies," Epigenomics, 2016, 8(2):153-156.
Josephs et al., "Structure and specificity of the RNA-guided endonuclease Cas9 during DNA interrogation, target binding and cleavage," Nucleic Acids Research, 2015, 43(18): 8924-8941.
Joung et al., "TALENs: a widely applicable technology for targeted genome editing," Nature Reviews Molecular Cell Biology 14, 2013, 49-55.
Joyce, "Amplification, mutation and selection of catalytic RNA," Gene, 1989, 82(1): 83-87.
Joyce, "Directed molecular evolution," Scientific American, 1992, 267(6): 90-97.

(56) References Cited

OTHER PUBLICATIONS

Jurkowska and Jeltsch, "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197.
Kabadi et al., "Multiplex CRISPR/Cas9-based genome engineering from a single lentiviral vector," Nucleic Acids Res, 2014, 42(19):e147.
Kabanov et al., "A new class of antivirals: antisense oligonucleotides combined with a hydrophobic substituent effectively inhibit influenza virus reproduction and synthesis of virus- specific proteins in MDCK cells," FEBS Lett., 1990, 259: 327-330.
Kalsner et al., "Prader-Willi, Angelman, and 15q11-q13 Duplication Syndromes," Pediatric Clinics of North America United States, 2015, 62(3): 587-606.
Karlin et al., "Applications and statistics for multiple high-scoring segments in molecular sequences," Proc. Natl. Acad. Sci. USA, 1993, 90: 5873-77.
Kauppinen et al., "Locked nucleic acid (LNA): High affinity targeting of RNA for diagnostics and therapeutics," Drug Discov Today Technol, 2005, 2(3): 287-290.
Kayali et al., "Site-directed gene repair of the dystrophin gene mediated by PNA-ssODNs," Human Molecular Genetics, vol. 19, No. 16, Aug. 15, 2010, pp. 3266-3281.
Kearns et al., "Cas9 effector-mediated regulation of transcription and differentiation in human pluripotent stem cells," Development, 2014, 141(1):219-23.
Kearns et al., "Functional annotation of native enhancers with a Cas9-histone demethylase fusion," Nat Methods, 2015, 12(5):401-403.
Keefe et al., "Muscle stem cells contribute to myofibers in sedentary adult mice," Nat Commun, 2015, 6: 7087.
Keil et al., "Brain transcriptome databases: a user's guide," J Neurosci, 2018, 38(10): 2399-2412.
Kempfer et al., "Methods for mapping 3D chromosome architecture," Nat. Rev. Genet., 2020, 21: 207-226.
Keung et al., "Using targeted chromatin regulators to engineer combinatorial and spatial transcriptional regulation," Cell 158, 2014, 110-120.
Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.
Khambata-Ford et al., "Identification of Promoter Regions in the Human Genome by Using a Retroviral Plasmid Library-Based Functional Reporter Gene Assay," Genome Research, 2003, 13: 1765-1774.
Khodakov et al., "Protected DNA strand displacement for enhanced single nucleotide discrimination in double-stranded DNA," Scientific reports, 2015, 5: 8721.
Khoury et al., "Efficient new cationic liposome formulation for systemic delivery of small interfering RNA silencing tumor necrosis factor a in experimental arthritis," Arthritis Rheumatol, 2006, 54: 1867-77.
Khurana et al., "Role of non-coding sequence variants in cancer," Nat. Rev. Genet., 2016, 17: 93-108.
Kim et al., "A Histone acetylation contributes to chromatin looping between the locus control region and globin gene by influencing hypersensitive site formation," Biochim Biophys Acta, 2013, 1829: 963-969.
Kim et al., "Epigenetic therapy of Prader-Willi Syndrome," Transl Res, 2019, 208: 105-118.
Kim et al., "Expansion and Purification Are Critical for the Therapeutic Application of Pluripotent Stem Cell-Derived Myogenic Progenitors," Stem Cell Rep, 2017, 9: 12-22.
Kim et al., "Histone acetylation contributes to chromatin looping between the locus control region and globin gene by influencing hypersensitive site formation," Biochim Biophys Acta, 2013, 1829: 963-969.
Kim et al., "Surrogate reporters for enrichment of cells with nuclease-induced mutations," Nat Methods, 2011, 8:941-943.
Kim et al., "TALENs and ZFNs are associated with different mutation signatures," Nat Methods, 2013, 10(3):185.
Kim et al., "Targeting the histone methyltransferase G9a activates imprinted genes and improves survival of a mouse model of Prader-Willi syndrome," Nat Med, 2017, 23: 213-222.
Kim et al., "Use of the human elongation factor 1α promoter as a versatile and efficient expression system," Gene, 1990, 91:217.
Kim et al., "Engineering and Application of Zinc Finger Proteins and TALEs for Biomedical Research," Mol Cells, 2017, 40(8): 533-541.
Kimura et al., "Cell-lineage regulated myogenesis for dystrophin replacement: a novel therapeutic approach for treatment of muscular dystrophy," Hum Mol Genet 17, 2008, 2507-2517.
Klann et al., "CRISPR-based methods for high-throughput annotation of regulatory DNA," Curr Opin Biotechnol, 2018, 52: 32-41.
Klann et al., "Genome-wide annotation of gene regulatory elements linked to cell fitness," bioRxiv doi: 10.1101/2021.03.08.434470. Preprint posted Mar. 9, 2021, 42 pages.
Kleinstiver et al., "Broadening the targeting range of *Staphylococcus aureus* CRISPR-Cas9 by modifying PAM recognition," Nature Biotechnology, 2015, 33(12): 1293-1298.
Kleinstiver et al., "Engineered CRISPR-Cas9 nucleases with altered PAM specificities," Nature, 2015, 523(7561): 481-485.
Kleinstiver et al., "Genome-wide specificities of CRISPR-Cas Cpf1 nucleases in human cells," Nature Biotechnology, 2016, 34(8):869-874.
Koblan et al., "Improving cytidine and adenine base editors by expression optimization and ancestral reconstruction," Oct. 2018, 36(9): 843-846.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.
Kocher et al., "Phylogenetic Analysis of the SNORD116 Locus," Genes, 2017, 8(12): 358.
Kodaka et al., "Skeletal Muscle Cell Induction from Pluripotent Stem Cells," Stem Cells Int, Apr. 2017, Article ID 1376151, 16 pages.
Koerber et al., "DNA shuffling of adeno-associated virus yields functionally diverse viral progeny," Mol Ther, 2008, 16: 1703-1709.
Komor et al., "Programmable editing of a target base in genomic DNA without double-stranded DNA cleavage," Nature, 2016, 533(7603): 420-424.
Konermann et al., "Genome-scale transcriptional activation by an engineered CRISPRCas9 complex," Nature, 2015, 517: 583-588.
Konermann et al., "Optical control of mammalian endogenous transcription and epigenetic states," Nature, 2013, 500(7463): 472-6.
Konieczny et al., "Gene and cell-mediated therapies for muscular dystrophy," Muscle Nerve, 2013, 47:649-663.
Koo et al., "Functional Rescue of Dystrophin Deficiency in Mice Caused by Frameshift Mutations Using Campylobacter jejuni Cas9," Molecular Therapy, 2018 26(6): 1529-1538.
Koopmans et al., "SynGO: An Evidence-Based, Expert-Curated Knowledge Base for the Synapse," Neuron, 2019, 103: 217-234 e214.
Koppanati et al., "Improvement of the mdx mouse dystrophic phenotype by systemic in utero AAV8 delivery of a minidystrophin gene," Gene Ther, 2010, 17: 1355-1362.
Kornberg et al., "DNA Replication," 1980, pp. 75-77.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.
Kotin, "Prospects for the use of adeno-associated virus as a vector for human gene therapy," Hum. Gene Ther., 1994, 5:793-801.
Kreis et al., "The Multifaceted p21 (Cip1/Waf1/CDKN1A) in Cell Differentiation, Migration and Cancer Therapy," Cancers (Basel), 2019, 11(9): 1220.

(56) References Cited

OTHER PUBLICATIONS

Kubokawa et al., "Molecular characterization of the 5'-UTR of retinal dystrophin reveals a cryptic intron that regulates translational activity," Molecular Vision, 2010, vol. 16, pp. 2590-2597.
Kuhnel et al., "Tumor-specific adenoviral gene therapy: Transcriptional repression of gene expression by utilizing p53-signal transduction pathways," Cancer Gene Ther., 2004, 11: 28-40.
Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kuscu et al., "Genome-wide analysis reveals characteristics of off-target sites bound by the Cas9 endonuclease," Nat Biotechnol, 2014, 32(7): 677-83.
Kwa et al., "Chromatin modifying agents—the cutting edge of anticancer therapy," Drug Discovery Today, 2011, 16(13/14):543-547.
Kwon et al., "Myogenic Progenitor Cell Lineage Specification by CRISPR/Cas9-Based Transcriptional Activators," Stem cell reports, 2020, 14: 755-769.
Kyte et al., "A Simple Method for Displaying the Hydropathic Character of a Protein," J. Mol. Biol., 1982, 157:105-132.
La Russa et al., "The New State of the Art: Cas9 for Gene Activation and Repression," Molecular and Cellular Biology, 2015, 35(22):3800-3809.
Lacerra et al., "Restoration of hemoglobin A synthesis in erythroid cells from peripheral blood of thalassemic patients," Proc. Natl. Acad. Sci., 2000, 97(17): 9591-9596.
Lai et al., "Partial restoration of cardiac function with ΔPDZ nNOS in aged mdx model of Duchenne cardiomyopathy," Hum Mol Genet., 2014, 23(12): 3189-3199.
Lake et al., "Integrative single-cell analysis of transcriptional and epigenetic states in the human adult brain," Nat Biotechnol, 2018, 36: 70-80.
Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.
Lambert et al., "The Human Transcription Factors," Cell, 2018, 172: 650-665.
Lamey et al., "Pax genes in myogenesis: alternate transcripts add complexity," Histol Histopathol, 2004, 19: 1289-1300.
Landen et al., "Intraperitoneal delivery of liposomal siRNA for therapy of advanced ovarian cancer," Cancer Biol. Ther, 2006, 5(12):1708-13.
Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.
Langmead et al., "Fast gapped-read alignment with Bowtie 2," Nature methods, 2012, 9: 357-359.
Langmead et al., "Ultrafast and memory-efficient alignment of short DNA sequences to the human genome," Genome biology 10, 2009, R25.
Langouet et al., "Zinc finger protein 274 regulates imprinted expression of transcripts in Prader-Willi syndrome neurons," Hum Mol Genet, 2018, 27: 505-515.
Larson et al., "CRISPR interference (CRISPRi) for sequence-editing control of gene expression," Nat Protoc, 2013, 8(11): 2180-96.
Latta-Mahieu et al., "Gene transfer of a chimeric trans-activator is immunogenic and results in short-lived transgene expression," Human Gene Therapy, Sep. 2002, vol. 13, No. 13, pp. 1611-1620.
Lattanzi et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.
Laumont et al., "Noncoding regions are the main source of targetable tumor-specific antigens," Sci. Transl. Med., 2018, 10(470): eaau5516, 11 pages.
Lawrence et al., "Discovery and saturation analysis of cancer genes across 21 tumour types," Nature, 2014, 505: 495-501.
Lee et al., "Activation of innate immunity is required for efficient nuclear reprogramming," Cell, 2012, 151: 547-558.
Lee et al., "Expression of small interfering RNAs targeted against HIV-1 rev transcripts in human cells," Nature Biotechnol, 2002, 20(5): 500-505.
Lee et al., "Nanoparticle delivery of Cas9 ribonucleoprotein and donor DNA in vivo induces homology-directed DNA repair," Nat Biomed Eng, 2017, 1: 889-901.
Lee et al., "Role of satellite cells versus myofibers in muscle hypertrophy induced by inhibition of the myostatin/activin signaling pathway," Proc Natl Acad Sci U S A, 2012, 109(35):E2353-60.
Lee et al., "Targeted chromosomal deletions in human cells using zinc finger nucleases," Genome research 20, 2010, 81-89.
Lee, "Regulation of muscle mass by myostatin," Annu Rev Cell Dev Biol, 2004, 20: 61-86.
Lenoir et al., "PICKLES: the database of pooled in-vitro CRISPR knockout library essentiality screens," Nucleic Acids Res, 2018, 46: D776-D780.
Lesnik et al., "Relative thermodynamic stability of DNA, RNA, and DNA: RNA hybrid duplexes: relationship with base composition and structure," Biochemistry, 1995, 34(34): 10807-10815.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.
Levin et al., "Position-dependent effects of locked nucleic acid (LNA) on DNA sequencing and PCR primers," Nuc. Acids. Res., 2006, 34: e142.
Levskaya et al., "Synthetic biology: engineering *Escherichia coli* to see light," Nature, 2005, 438:441-442.
Li et al., "In vivo genome editing restores haemostasis in a mouse model of haemophilia," Nature 475, 2011, 217-221.
Li et al., "Chimeric DNA methyltransferases target DNA methylation to specific DNA sequences and repress expression of target genes," Nucleic Acids Res., 2007, 35(1): 100-112.
Li et al., "Engineering and selection of shuffled AAV genomes: a new strategy for producing targeted biological nanoparticles," Mol Ther, 2008, 16: 1252-1260.
Li et al., "Ex vivo cell-based CRISPR/Cas9 genome editing for therapeutic applications," Biomaterials, 2020, 234: 119711.
Li et al., "Extensive promoter-centered chromatin interactions provide a topological basis for transcription regulation," Cell, 2012, 148: 84-98.
Li et al., "Locus control regions," Blood, 2002, 100: 3077-3086.
Li et al., "Marginal level dystrophin expression improves clinical outcome in a strain of dystrophin/utrophin double knockout mice," PLoS One, 2010, 5:e15286.
Li et al., "Modularly assembled designer TAL effector nucleases for targeted gene knockout and gene replacement in eukaryotes," Nucleic Acids Research, 2011, vol. 39, No. 14, pp. 6315-6325.
Li et al., "Precise correction of the dystrophin gene in duchenne muscular dystrophy patient induced pluripotent stem cells by TALEN and CRISPR-Cas9," Stem Cell Reports, 2015, 4: 143-154.
Li et al., "Preservation of muscle force in Mdx3cv mice correlates with low-level expression of a near full-length dystrophin protein," Am. J. Pathol., 2008, 172: 1332-1341.
Li et al., "RSEM: accurate transcript quantification from RNA-Seq data with or without a reference genome," BMC Bioinformatics, 2011, 12: 323.
Li et al., "Synthetic muscle promoters: activities exceeding naturally occurring regulatory sequences," Nature Biotechnology, 1999, 17: 241-245.
Li et al., "The autism-related gene SNRPN regulates cortical and spine development via controlling nuclear receptor Nr4a1," Sci Rep, 2016, 6: 29878.
Li et al., "The role of chromatin during transcription," Cell, 2007, 128: 707-719.

(56) References Cited

OTHER PUBLICATIONS

Li et al., "The Sequence Alignment/Map format and SAMtools," Bioinformatics, 2009, 25: 2078-2079.
Li et al., "Transcription activator-like effector hybrids for conditional control and rewiring of chromosomal transgene expression," Scientific reports 2, 2012, 897.
Lian et al., "Robust cardiomyocyte differentiation from human pluripotent stem cells via temporal modulation of canonical Wnt signaling," Proc Natl Acad Sci, 2012, 109: E1848-E1857.
Liang et al., "Engineering biological systems with synthetic RNA molecules," Mol Cell 43, 2011, 915-926.
Liao et al., "In Vivo Target Gene Activation via CRISPR/Cas9-Mediated Trans-epigenetic Modulation," Cell, 2017, 171: 1495-1507.
Liao et al., "The Subread aligner: fast, accurate and scalable read mapping by seed-and-vote," Nucleic Acids Res, 2013, 41: e108.
Lim et al., "Application of CRISPR/Cas9 for the Treatment of Duchenne Muscular Dystrophy," Journal of Personalized Medicine, 2018, 8(4): 1-20.
Limberis et al., "Transduction efficiencies of novel AAV vectors in mouse airway epithelium in vivo and human ciliated airway epithelium in vitro," Molecular therapy: the journal of the American Society of Gene Therapy, 2009, 17: 294-301.
Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.
Liu et al., "Adeno-associated virus-mediated microdystrophin expression protects young mdx muscle from contraction-induced injury," Mol. Ther., 2005, 11: 245-256.
Liu et al., "CRISPR Activation Screens Systematically Identify Factors that Drive Neuronal Fate and Reprogramming," Cell Stem Cell, 2018, 23: 758-771 e758.
Liu et al., "CRISPR-Based Chromatin Remodeling of the Endogenous Oct4 or Sox2 Locus Enables Reprogramming to Pluripotency," Cell Stem Cell, 2018, 22: 252-261 e254.
Liu et al., "Editing DNA Methylation in the Mammalian Genome," Cell, Sep. 2016, 167(1): 233-247.
Liu et al., "Monte Carlo simulation for single RNA unfolding by force," Biophysical journal, 2005, 88(1): 76-84.
Lohmueller et al., "A tunable zinc finger-based framework for Boolean logic computation in mammalian cells," Nucleic Acids Res 40, 2012, 5180-5187.
Long et al., "Postnatal genome editing partially restores dystrophin expression in a mouse model of muscular dystrophy," Science, 2016, 351(6271):400-403.
Love et al., "Moderated estimation of fold change and dispersion for RNA-seq data with DESeq2," Genome biology, 2014, 15: 550.
Lovric et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu et al., "The status of exon skipping as a therapeutic approach to duchenne muscular dystrophy," Molecular Therapy 19, 2011, 9-15.
Lund et al., "Promoter-targeted phage display selections with preassembled synthetic zinc finger libraries for endogenous gene regulation," Journal of Molecular Biology, 2004, vol. 340, pp. 599-613.
Luo et al., "Repurposing endogenous type I CRISPR-Cas systems for programmable gene repression," Nucleic Acids Research, 2014, 43(1): 674-681.
Luo et al., "Synthetic DNA delivery systems," Nature Biotechnology, 2000, vol. 18, pp. 33-37.
Ma et al., "Targeted gene suppression by inducing de novo DNA methylation in the gene promoter," Epigenetics Chromatin, 2014, 7: 20.
Machinek et al., "Programmable energy landscapes for kinetic control of DNA strand displacement," Nature communications, 2014, 5: 5324, 9 pages.
Macpherson et al., "Flexible guide-RNA design for CRISPR applications using Protospacer Workbench," Nature biotechnology, 2015, 33(8): 805-806.
Mader et al., "CRISPR RNA-guided activation of endogenous human genes," Nature Methods, 2013, 10(10): 977-979.
Madigan et al., "Engineering AAV receptor footprints for gene therapy," Curr Opin Virol, 2016, 18: 89-96.
Madisen et al., "A robust and high-throughput Cre reporting and characterization system for the whole mouse brain," Nat Neurosci, 2010, 13: 133-140.
Maeder et al., "CRISPR RNA-guided activation of endogenous human genes," Nat Methods, 2013, 10: 977-979.
Maeder et al., "Robust, synergistic regulation of human gene expression using TALE activators," Nat Methods, 2013, 10(3): 243-245.
Maeder et al., "Robust, synergistic regulation of human gene expression using TALE activators," Nature Methods, vol. 10, No. 3, pp. 243-246, Feb. 10, 2013, including pp. 1/14-14/14 of Supplementary Material.
Maeder, "Targeted DNA demethylation and activation of endogenous genes using programmable TALE-TET1 fusion proteins," Nat Biotechnol, 2013, 31(12): 1137-42.
Magli et al., "PAX7 Targets, CD54, Integrin α9β1, and SDC2, Allow Isolation of Human ESC/iPSC-Derived Myogenic Progenitors," Cell Rep, 2017, 19: 2867-2877.
Magnenat et al., "In vivo selection of combinatorial libraries and designed affinity maturation of polydactyl zinc finger transcription factors for ICAM-1 provides new insights into gene regulation," J Mol Biol, 2004, 341: 635-649.
Maheshri et al., "Directed evolution of adeno-associated virus yields enhanced gene delivery vectors," Nat Biotechnol, 2006, 24: 198-204.
Majzner et al., "Clinical lessons learned from the first leg of the CAR T cell journey," Nature Medicine, 2019, 25(9): 1341-1355.
Makarova et al., "An updated evolutionary classification of CRISPR-Cas systems," Nature Reviews Microbiology, 2015, 13:722-736.
Makarova et al., "Evolution and classification of the CRISPR-Cas systems," Nature Reviews Microbiology, 2011, pp. 467-477.
Mali et al., "Cas9 as a versatile tool for engineering biology," Nat Methods, 2013, 10(10): 957-63.
Mali et al., "CAS9 transcriptional activators for target specificity screening and paired nickases for cooperative genome engineering," Nat Biotechnol, 2013, 31(9): 833-8.
Mali et al., "RNA-Guided Human Genome Engineering via Cas9," Science 339, 2013, 823-826.
Mamchaoui et al., "Immortalized pathological human myoblasts: towards a universal tool for the study of neuromuscular disorders," Skelet Muscle 1, 2011, 1-11.
Maniatis et al., "Regulation of inducible and tissue-specific gene expression," Science, 1987, 236:1237.
Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease?," Journal of Muscle Research and Cell Motility, 2015, 36: 155-167.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.
Manoharan et al., "Lipidic Nucleic Acids," Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al., "A New Access to 2'-O-Alkylated Ribonucleosides and Properties of 2'-O-Alkylated Oligoribonucleotides," Helv. Chim. Acta, 1995, 78: 486-504.

(56) References Cited

OTHER PUBLICATIONS

Maruyama et al., "Epigenetic Regulation of Cell Type-Specific Expression Patterns in the Human Mammary Epithelium," PLoS Genetics, 2011, 7(4): e1001369, 15 pages.
Mastellos et al., "Inducing and characterizing liver regeneration in mice: Reliable models, essential "readouts" and critical perspectives," Curr Protoc Mouse Biol., 2013, 3(3): 141-170.
Mathews et al., "Expanded sequence dependence of thermodynamic parameters improves prediction of RNA secondary structure," Journal of Molecular Biology, 1999, 288(5): 911-940.
Matsushita et al., "Adeno-associated virus vectors can be efficiently produced without helper virus," Gene Therapy, 1998, 5:938.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.
McCarthy et al., "Schaaf-Yang syndrome overview: Report of 78 individuals," Am J Med Genet A, 2018, 176(12): 2564-2574.
McCarty et al., "Self-complementary recombinant adeno-associated virus (scAAV) vectors promote efficient transduction independently of DNA synthesis," Gene Ther. 2001, 8:1248-54.
McDowell et al., "Structural and functional cross-talk between a distant enhancer and the epsilon-globin gene promoter shows interdependence of the two elements in chromatin," Molecular and cellular biology, 1999, 19: 7600-7609.
McFadden et al., "The Hand1 and Hand2 transcription factors regulate expansion of the embryonic cardiac ventricles in a gene dosage-dependent manner," Development, 2005, 132: 189-201.
McGreevy et al., "Animal models of Duchenne muscular dystrophy: from basic mechanisms to gene therapy," Disease Models Mechanisms, 2015, 8(3): 195-213.
McTigue et al., "Sequence-dependent thermodynamic parameters for locked nucleic acid (LNA)-DNA duplex formation," Biochemistry, 2004, 43(18): 5388-5405.
Memedula et al., "Sequential recruitment of HAT and SWI/SNF components to condensed chromatin by VP16," Curr Biol, 2003, 13, 241-246.
Mendell et al., "Dystrophin immunity in Duchenne's muscular dystrophy," New England Journal of Medicine 363, 2010, 1429-1437.
Mendenhall et al., "Locus-specific editing of histone modification at endogenous enhancers," Nat Biotechnol, 2013, 31(12): 1133-6.
Mercer et al., "Regulation of Endogenous Human Gene Expression by Ligand-Inducible TALE Transcription Factors," ACS Synth Biol, 2013.
Mertens et al., "Evaluating cell reprogramming, differentiation and conversion technologies in neuroscience," Nat Rev Neurosci, 2016, 17: 424-437.
Mevissen et al., "Molecular basis of Lys11-polyubiquitin specificity in the deubiquitinase Cezanne," Nature, 2016, 538(7625): 402-405.
Meyers et al., "Computational correction of copy No. effect improves specificity of CRISPR-Cas9 essentiality screens in cancer cells," Nat. Genet., 2017, 49: 1779-1784.
Miller et al., "A TALE nuclease architecture for efficient genome editing," Nat Biotechnol 29, 2011, 143-148.
Miller et al., "Transcriptional landscape of the prenatal human brain," Nature, 2014, 508: 199-206.
Min et al., "CRISPR Correction of Duchene Muscular Dystrophy Exon 44 Deletion Mutations in Mice and Human Cells," Science Advances, 2019, 5: eaav4324.
Min et al., "CRISPR Correction of Duchene Muscular Dystrophy," Annual Review of Medicine, Epub Oct. 2018, 70: 239-255.
Mishra et al., "Improved leishmanicidal effect of phosphorotioate antisense oligonucleotides by LDL-mediated delivery," Biochim. Biophys. Acta, 1995, 1264(2): 229-237.
Mittler et al., "A novel docking site on Mediator is critical for activation by VP 16 in mammalian cells," EMBO J, 2003, 22: 6494-6504.
Miyagishi et al., "U6 promoter-driven siRNAs with four uridine 3' overhangs efficiently suppress targeted gene expression in mammalian cells," Nature Biotechnol, 2002, 20(5): 497-500.
Mizushima et al., "pEF-BOS, a powerful mammalian expression vector," Nucl. Acids. Res., 1990, 18:5322.
Mojica et al., "Intervening sequences of regularly spaced prokaryotic repeats derive from foreign genetic elements," J Molec Evolution, 2005, 60(2): 174-182.
Mojica et al., "Short motif sequences determine the targets of the prokaryotic CRISPR defence system," Microbiology, 2009, 155: 733-740.
Montalbano et al., "High-Throughput Approaches to Pinpoint Function within the Noncoding Genome," Mol. Cell, 2017, 68: 44-59.
Montarras, "Direct Isolation of Satellite Cells for Skeletal Muscle Regeneration," Science, 2005, 309: 2064-2067.
Moore et al., "Transcription Activator-like Effectors: A Toolkit for Synthetic Biology," ACS Synth Biol, 2014, 3(10): 708-716.
Morris et al., "Dissecting engineered cell types and enhancing cell fate conversion via CellNet," Cell, 2014, 158: 889-902.
Morrissey et al., "Activity of stabilized short interfering RNA in a mouse model of hepatitis B virus replication," Hepatol. (2005) 41: 1349-56.
Moscou et al., "A simple cipher governs DNA recognition by TAL effectors," Science 326, 2009, 1501.
Muir et al., "Engraftment potential of dermal fibroblasts following in vivo myogenic conversion in immunocompetent dystrophic skeletal muscle," Mol. Ther. Methods Clin. Dev., 2014, 1:14025.
Murphy et al., "The in vitro transcription of the 7SK RNA gene by RNA polymerase III is dependable only on the presence of an upstream promoter," Cell, 1987, 51:81-87.
Murray et al., "Codon usage in plant genes," Nucl. Acids Res., 1989, 17:477-498.
Mussolino et al., "A novel TALE nuclease scaffold enables high genome editing activity in combination with low toxicity," Nucleic Acids Res 39, 2011, 9283-9293.
Muzycka, "Use of adeno-associated virus as a general transduction vector for mammalian cells," Curr. Top. Microbiol. Immunol., 1992, 158:97-129.
Myslinski et al., "An unusually compact external promoter for RNA polymerase III transcription of the human H1RNA gene," Nucleic Acids Res, 2001, 29:2502-2509.
Naguibneva et al., "An LNA-based loss-of-function assay for micro-RNAs," Biomed Pharmacother, 2006, 60: 633-638.
Najm et al., "Orthologous CRISPR-Cas9 enzymes for combinatorial genetic screens," Nat Biotechnol, 2018, 36: 179-189.
Naldini, "Gene therapy returns to centre stage," Nature, 2015, 526: 351-360.
Nam et al., "Cas5d protein processes pre-crRNA and assembles into a Cascade-like interference complex in Subtype I-C/Dvulg CRISPR-Cas system," Structure, 2012, 20:1574-1584.
Nance et al., "AAV9 Edits Muscle Stem Cells in Normal and Dystrophic Adult Mice," Molecular Therapy, 2019, 27: 1568-1585.
Nasevicius et al., "Effective targeted gene 'knockdown' in zebrafish," Nat. Genet., 2000, 26(2): 216-220.
NCBI Reference Sequence NG_028016.2 (2013).
NCBI Reference Sequence NM_004020.2 (2010).
NCBI Reference Sequence XM011532698.1 (2015).
Negroni et al., "In Vivo Myogenic Potential of Human CD133+ Muscle-derived Stem Cells: A Quantitative Study," Molecular Therapy 17, 2009, 1771-1778.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Nelson et al., "In vivo genome editing improves muscle function in a mouse model of Duchenne muscular dystrophy," Science, 2016, 351, 403-7.
Nelson et al., "Local and Systemic Gene Editing in a Mouse Model of Duchenne Muscular Dystrophy," Molecular Therapy, 2016, 24(Supp 1):S191.

(56) References Cited

OTHER PUBLICATIONS

Nelson et al., "Long-term evaluation of AAV-CRISPR genome editing for Duchenne muscular dystrophy," Nature Medicine, 2019, 25(3): 427-432.
Nguyen et al., "Transcriptional Enhancers in the Regulation of T Cell Differentiation," Front. Immunol., 2015, 6: 462.
Nielsen et al., "Sequence-selective recognition of DNA by strand displacement with a thymine-substituted polyamide," Science, 1991, 254: 1497-1500.
Nikfarjam et al., "A Model of Partial Hepatectomy in Mice," Journal of Investigative Surgery, 2004, 17(5): 291-294.
Nishimasu et al., "Crystal structure of Cas9 in complex with guide RNA and target DNA," Cell, 2014, 156:935-49.
Nissim et al., "Multiplexed and Programmable Regulation of Gene Networks with an Integrated RNA and CRISPR/Cas Toolkit in Human Cells," Mol Cell, 2014, 54: 698-710.
Nordhoff et al., "Comparative analysis of human, bovine, and murine Oct-4 upstream promoter sequences," Mamm Genome, 2001, 12: 309-317.
Nowotny et al., "Crystal structures of RNase H bound to an RNA/DNA hybrid: substrate specificity and metal-dependent catalysis," Cell, 2005, 121(7): 1005-1016.
Nuñez et al., "Genome-wide programmable transcriptional memory by CRISPR-based epigenome editing," Cell, 2021, 184(9): p. 2503-2519.
O'Brien et al., "GT-Scan: identifying unique genomic targets," Bioinformatics, 2014, 30: 2673-2675.
Oberhauser et al., "Effective incorporation of 2'-O-methyl-oligoribonucleotides into liposomes and enhanced cell association through modification with thiocholesterol," Nucl. Acids Res., 1992, 20(3): 533-538.
Obika et al., "Stability and structural features of the duplexes containing nucleoside analogues with a fixed N-type conformation, 2'-O,4'-C-methyleneribonucleosides," Tetrahedron Lett. 1998, 39(30): 5401-5404.
O'Connell et al., "Programmable RNA recognition and cleavage by CRISPR/Cas9," Nature, 2014, 516: 263-266.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.
O'Geen et al., "dCas9-based epigenome editing suggests acquisition of histone methylation is not sufficient for target gene repression," Nucleic Acids Res, 2017, 45: 9901-9916.
O'Geen et al., "Ezh2-dCas9 and KRAB-dCas9 enable engineering of epigenetic memory in a context-dependent manner," Epigenetics Chromatin, 2019, 12: 26.
Ogryzko et al., "The transcriptional coactivators p300 and CBP are histone acetyltransferases," Cell, 1996, 87: 953-959.
Ohshima et al., "Nucleotide sequence of mouse genomic loci including a gene or pseudogene for U6 (4.85) nuclear RNA," Nucleic Acids Res, 1981, 9:5145-5158.
Ohta et al., "Imprinting-Mutation Mechanisms in Prader-Willi Syndrome," The American Journal of Human Genetics, 1999,64(2): 397-413.
Okkenhaug et al., "PI3K in lymphocyte development, differentiation and activation," Nat. Rev. Immunol., 2003, 3(4): 317-330.
Olguin et al., "Pax-7 up-regulation inhibits myogenesis and cell cycle progression in satellite cells: a potential mechanism for self-renewal," Dev Biol, 2004, 275: 375-388.
Ong et al., "Enhancer function: new insights into the regulation of tissuespecific gene expression," Nature reviews. Genetics, 2011, 12: 283-293.
Orgel, "Selection in vitro," Proc. R. Soc. B, 1979, 205: 435-442.
Orlando et al., "Promoter capture Hi-C-based identification of recurrent noncoding mutations in colorectal cancer," Nat. Genet., 2018, 50: 1375-1380.
Orom et al., "LNA-modified oligonucleotides mediate specific inhibition of microRNA function," Gene, 2006, 372: 137-141.
Osakabe et al., "FLAG-NLS-SpCas9-2A-GFBSD2 [Binary vector pEgP526-2A-GFBSD2]," National Center for Biotechnology Information, Genbank Entry, Retrieved from the Internet on Sep. 18, 2017 <https://www.ncbi.nlm.nih.gov/protein/BAV01234>.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Genetic Correction of Duchenne Muscular Dystrophy Using Zinc Finger Nucleases," Mol. Ther., 2013, vol. 21, Supplement 1, 292, p. S111-S112.
Ousterout et al., "Multiplex CRISPR/Cas9-based genome editing for correction of dystrophin mutations that cause Duchenne muscular dystrophy," Nature Communications, 2015, 6:6244.
Ousterout et al., "Reading frame correction by targeted genome editing restores dystrophin expression in cells from Duchenne muscular dystrophy patients," Mol Ther, 2013, 21:1718-1726.
Ousterout, "Genetic Correction of Duchenne Muscular Dystrophy using Engineered Nucleases," Dept. of Biomedical Engineering Duke University (Dissertation), 2014, pp. 1-204.
Paddison et al., "Short hairpin RNAs (shRNAs) induce sequence-specific silencing in mammalian cells," Genes & Dev, 2002, 16(8): 948-958.
Paez-Espino et al., "CRISPR immunity drives rapid phage genome evolution in *Streptococcus thermophilus,*" mBio, 2015, 6(2): e00262-15.
Palu et al., "In pursuit of new developments for gene therapy of human diseases," J. Biotechnol, 1999, vol. 68, pp. 1-13.
Pang et al., "Induction of human neuronal cells by defined transcription factors," Nature, 2011, 476: 220-223.
Papapetrou, "Induced pluripotent stem cells, past and future," Science, 2016, 353: 991-992.
Papayannakos et al., "Understanding lentiviral vector chromatin targeting: working to reduce insertional mutagenic potential for gene therapy," Gene Ther, 2013, 20(6): 581-8.
Parekh et al., "Mapping Cellular Reprogramming via Pooled Overexpression Screens with Paired Fitness and Single-Cell RNA-Sequencing Readout," Cell Systems, 2018, 7: 548-555.e548.
Park et al., "Cas-Designer: a web-based tool for choice of CRISPR-Cas9 target sites," Bioinformatics, 2015, 31(24): 4014-4016.
Park et al., "Multi-Parametric MRI at 14T for Muscular Dystrophy Mice Treated with AAV Vector-Mediated Gene Therapy," PLoS ONE, 2015, 10(4): e0124914.
Park et al., "Phenotypic alteration of eukaryotic cells using randomized libraries of artificial transcription factors," Nat Biotechnol 21, 2003, 1208-1214.
Pattanayak et al., "High-throughput profiling of off-target DNA cleavage reveals RNA-programmed Cas9 nuclease specificity," Nat Biotechnol, 2013, 31(9): 839-43.
Paul et al., "Effective expression of small interfering RNA in human cells," Nature Biotechnol, 2002, 20(5): 505-508.
Pawlikowski et al., "Regulation of skeletal muscle stem cells by fibroblast growth factors," Dev Dyn, 2017, 246: 359-367.
Peault et al., "Stem and progenitor cells in skeletal muscle development, maintenance, and therapy," Molecular Therapy 15, 2007, 867-877.
Penczek et al., "Three-dimensional reconstruction of single particles embedded in ice," Ultramicroscopy, 1992, 40, 33-53.
Perez et al., "Establishment of HIV-1 resistance in CD4+ T cells by genome editing using zinc-finger nucleases," Nature biotechnology 26, 2008, 808-816.
Perez-Pinera et al., "Advances in targeted genome editing," Current Opinion in Chemical Biology 16, 2012, 268-277.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera et al., "Synergistic and tunable human gene activation by combinations of synthetic transcription factors," Nat Methods, 2013, 10: 239-242.
Perez-Pinera et al., "Synergistic and tunable human gene activation by combinations of synthetic transcription factors," Nature Meth-

(56) References Cited

OTHER PUBLICATIONS ods, vol. 10, No. 3, pp. 239-244, Feb. 3, 2013, including pp. 1/12-12-12 of Supplementary Material.
Perez-Pinera et al., "Synergistic Transcriptional Activation by Combinations of Engineered TALEs" was publicly presented at the American Society of Gene & Cell Therapy's 15th Annual Meeting in Philadelphia, Pennsylvania during the Late Abstracts Poster Session III: Saturday, May 19, 2012. Abstract 855.
Persons, "Lentiviral vector gene therapy: effective and safe?" Mol Ther, 2010, 18(5): 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant et al., "Current status of pharmaceutical and genetic therapeutic approaches to treat DMD," Molecular Therapy 19, 2011, 830-840.
Pigozzo et al., "Revertant Fibers in the mdx Murine Model of Duchenne Muscular Dystrophy: An Age- and Muscle-Related Reappraisal," PLoS One, 2013, 8(8): e72147.
Pinello et al., "Analyzing CRISPR genome-editing experiments with CRISPResso," Nat Biotechnol, 2016, 34(7):695-697.
Polstein et al., "A light-inducible CRISPR-Cas9 system for control of endogenous gene activation," Nature Chemical Biology, 2015, 11: 198-200.
Polstein et al., "Genome-wide specificity of DNA-binding, gene regulation, and chromatin remodeling by TALE- and CRISPR/Cas9-based transcriptional activators," Genome Res, 2015, 25:1158-1169.
Polstein et al., "Light-inducible spatiotemporal control of gene activation by customizable zinc finger transcription factors," J Am Chem Soc, 2012, 134(40): 16480-3.
Ponting et al., "Evolution and functions of long noncoding RNAs," Cell, 2009, 136(4): 629-641.
Popplewell et al., "Gene correction of a duchenne muscular dystrophy mutation by meganuclease-enhanced exon knock-in," Hum Gene Ther, 2013, 24:692-701.
Povero et al., "Lipid-induced toxicity stimulates hepatocytes to release angiogenic microparticles that require Vanin-1 for uptake by endothelial cells," Sci Signal, 2013, 6(296): ra88.
Powell et al., "A Prader-Willi locus IncRNA cloud modulates diurnal genes and energy expenditure," Hum Molec Genet, 2013, 22: 4318-4328.
Prykhozhij et al., "CRISPR MultiTargeter: A Web Tool to Find Common and Unique CRISPR Single Guide RNA Targets in a Set of Similar Sequences," PLoS One, 2015, 10(3): e0119372.
Puccini et al., "Colorectal cancer: epigenetic alterations and their clinical implications", Biochim Biophys Acta, 2017, vol. 1868, No. 2, pp. 439-448.
Qi et al., "Repurposing CRISPR as an RNA-guided platform for sequence-specific control of gene expression," Cell 152, 2013, 1173-1183.
Quinlan et al., "BEDTools: a flexible suite of utilities for comparing genomic features," Bioinformatics 26, 2010, 841-842.
Rackham et al., "A predictive computational framework for direct reprogramming between human cell types," Nature Genetics, 2016, 48: 331-335.
Rada-Iglesias et al., "A unique chromatin signature uncovers early developmental enhancers in humans," Nature 470, 2011, 279-283.
Raeburn et al., "Techniques for drug delivery to the airways, and the assessment of lung function in animal models," J. Pharmacol. Toxicol. Meth., 1992, 27:143-159.
Rahdar et al., "Synthetic CRISPR RNA-Cas9-Guided Genome Editing in Human Cells," Proceedings to the National Academy of Sciences of USA, 2015, vol. 112, No. 51, pp. E7110-E7117.
Rajagopal et al., "High-throughput mapping of regulatory DNA," Nat. Biotechnol, 2016, 34: 167-174.
Ramachandran et al., "Nitric Oxide Signaling Pathway in Duchenne Muscular Dystrophy Mice: Upregulation of L-arginine Transport," Biochem. J., 2012, 449: 133-142.
Ran et al., "Double nicking by RNA-guided CRISPR Cas9 for enhanced genome editing specificity," Cell, 2013, 154(6): 1380-9.
Ran et al., "Genome engineering using the CRISPR-Cas9 system," Nature Protocols, 2013, 8(11): 2281-2308.
Ran et al., "In vivo genome editing using *Staphylococcus aureus* Cas9," Nature 520, 2015, 186-91.
Rao et al., "Engineering human pluripotent stem cells into a functional skeletal muscle tissue," Nat Commun, 2018, 9: 126.
Ratcliff et al., "A novel single-molecule study to determine protein-protein-protein association constants," Journal of the American Chemical Society, 2001, 123(24): 5632-5635.
Rauscher et al., "GenomeCRISPR—a database for high-throughput CRISPR/Cas9 screens," Nucleic Acids Res, 2017, 45: D679-D686.
Rebar et al., "Induction of angiogenesis in a mouse model using engineered transcription factors," Nat Med 8, 2002, 1427-1432.
Reynolds et al., "NuRD-mediated deacetylation of H3K27 facilitates recruitment of Polycomb Repressive Complex 2 to direct gene repression," The EMBO Journal 31, 2012, 593- 605.
Reyon et al., "FLASH assembly of TALENs for high-throughput genome editing," Nat Biotechnol 30, 2012, 460-465.
Rheinbay et al., "Analyses of non-coding somatic drivers in 2,658 cancer whole genomes," Nature, 2020, 578: 102-111.
Rhodes et al., "G-quadruplexes and their regulatory roles in biology," Nucleic Acids Res, 2015, 43: 8627-8637.
Richter et al., "Phage-assisted evolution of an adenine base editor with improved Cas domain compatibility and activity," Nat Biotechnol, Jul. 2020, 38(7): 883-891.
Riley, "PD-1 signaling in primary T cells," Immunological Reviews, 2009, 229: 114-125.
Riordan et al., "Application of CRISPR/Cas9 for biomedical discoveries," Cell & Bioscience, 2015, 5(1):11 pages.
Rivenbark et al., "Epigenetic reprogramming of cancer cells via targeted DNA methylation," Epigenetics 7, 2012, 350-360.
Rmilah et al., "Understanding the marvels behind liver regeneration," Wiley Interdiscip Rev Dev Biol., 2019, 8(3): e340.
Roadmap Epigenomics Consortium, "Integrative analysis of 111 reference human epigenomes," Nature, 2015, 518: 317-330.
Robinson-Hamm et al., "Gene therapies that restore dystrophin expression for the treatment of Duchenne muscular dystrophy," Human Genetics, 2016, 135(9): 1029-1040.
Rodriguez et al., "Clustering by fast search and find of density peaks," Science, 2014, 344(6191): 1492-1496.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.
Rousseau et al., "Endonucleases: tools to correct the dystrophin gene" The Journal of Gene Medicine, 2011, vol. 13, pp. 522-537.
Rousseau et al., "New TALENs To Correct the Reading Frame of Exon 54 of the Dystrophin Gene," Mol. Ther., 2013, vol. 21, Supplement 1, 293, p. S112.
Russa et al. "The New State of the Art: Cas9 for Gene Activation and Repression," Molecular and Cellular Biology, 2015, 35(22):3800-3809.
Rutkauskas et al., "Directional R-loop formation by the CRISPR-Cas surveillance complex cascade provides efficient off-target site rejection," Cell reports, 2015, 10, 1534-1543.
Sacco et al., "Short Telomeres and Stem Cell Exhaustion Model Duchenne Muscular Dystrophy in mdx/mTR Mice," Cell, 2010, 143: 1059-1071.
Sagal et al., "Proneural transcription factor Atoh1 drives highly efficient differentiation of human pluripotent stem cells into dopaminergic neurons," Stem Cells Transl Med, 2014, 3: 888-898.
Sahoo et al., "Prader-Willi phenotype caused by paternal deficiency for the HBII-85 C/D box small nucleolar RNA cluster," Nat Genet, 2008, 40: 719-721.
Saito et al., "Specific activation of microRNA-127 with downregulation of the proto-oncogene BCL6 by chromatin-modifying drugs in human cancer cells," Cancer Cell, 2006, vol. 9, pp. 435-443.
Saitoh et al., "Parent-of-Origin Histone Acetylation and Reactivation of a Key Imprinted Gene Locus in Prader-Willi Syndrome," Am J Hum Genet, 2000, 66: 1958-1962.

(56) References Cited

OTHER PUBLICATIONS

Salmon et al., "Production and titration of lentiviral vectors," Curr Protoc Neurosci, 2006, Chapter 4: Unit 4 21.
Salmon et al., "Production and titration of lentiviral vectors," Curr Protoc Hum Genet Chapter, 2007, 12: Unit 12 10, 24 pages.
Salva et al., "Design of tissue-specific regulatory cassettes for high-level rAAV-mediated expression in skeletal and cardiac muscle," Mol. Ther., 2007, 15:320-329.
Sambasivan et al., "Embryonic founders of adult muscle stem cells are primed by the determination gene Mrf4," Developmental Biology, 2013, 381: 241-255.
Sambrook et al., Molecular Cloning and Laboratory manual, Second Ed., Cold Spring Harbor, 1989, pp. 16.7-16.8.
Sanghvi et al., "Heterocyclic Base Modifications in Nucleic Acids and their Applications in Antisense Oligonucleotides," 1993, Antisense Research and Applications, Chapter 15, pp. 274-285.
Sanjana et al., "High-resolution interrogation of functional elements in the noncoding genome," Science, 2016, 353: 1545-1549.
Sanson et al., "Optimized libraries for CRISPR-Cas9 genetic screens with multiple modalities," Nat Commun, 2018, 9: 5416.
Santalucia et al., "Improved nearest-neighbor parameters for predicting DNA duplex stability," Biochemistry, 1996, 35(11): 3555-3562.
Schaaf et al., "Truncating mutations of MAGEL2 cause Prader-Willi phenotypes and autism," Nat Genet, 2013, 45(11): 1405-1408.
Schifrut et al., "Genome-wide CRISPR Screens in Primary Human T Cells Reveal Key Regulators of Immune Function," Cell, 2018, 175(7): 1958-1971.e15.
Schmid-Burgk et al., "A ligation-independent cloning technique for high-throughput of transcription activator-like effector genes," Nat Biotechnol 31, 2012, 76-81.
Schmidt et al., "GenomeRNAi: a database for cell-based and in vivo RNAi phenotypes, 2013 update," Nucleic Acids Res, 2013, 41: D1021-6.
Schmittgen et al., "Analyzing real-time PCR data by the comparative CT method," Nature Protocols, 2008, 3(6): 1101-1108.
Scholze et al., "TAL effectors are remote controls for gene activation," Current Opinion in Microbiology, Jan. 2011, vol. 14, pp. 47-53.
Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than inhibiting hybridization," 2014, arXiv preprint arXiv: 1408.4401.
Schultz et al., "Recombinant adeno-associated virus transduction and integration," Molecular Therapy 16, 2008, 1189-1199.
Schultz et al., "Recombinant adeno-associated virus transduction and integration," Molecular Therapy, 2008, 16: 1189-1199.
Schultz et al., "SETDB1: a novel KAP-1-associated histone H3, lysine 9-specific methyltransferase that contributes to HP1-mediated silencing of euchromatic genes by KRAB zinc-finger proteins," Genes & development 16, 2002, 919-932.
Schultz et al., "SETDBI: a novel KAP-I-associated histone H3, lysine 9-specific methyltransferase that contributes to HPI-mediated silencing of euchromatic genes by KRAB zinc-finger proteins," Genes & Development, 2002, 16: 919-932.
Sebastiano et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Segal and Meckler, "Genome Engineering at the Dawn of the Golden Age," Annu. Rev. Genomics Hum. Genet., 2013, 14: 135-158.
Seidel et al., "Chromatin-modifygin agents in anti-cancer therapy," Biochimie, 2012, vol. 94, pp. 2264-2279.
Semenova et al., "The Cas6e ribonuclease is not required for interference and adaptation by the *E. coli* type I-E CRISPR-Cas system," Nucleic Acids Res, 2015, 43(12):6049-61.
Sengupta et al., "Super-Enhancer-Driven Transcriptional Dependencies in Cancer," Trends Cancer Res, 2017, 3: 269-281.
Sentmanat et al., "A Survey of Validation Strategies for CRISPR-Cas9 Editing," Scientific Reports, 2018, 8: 888.
Sequence alignment: SEQ ID No. 102920 (2019). Reference cited in U.S. Appl. No. 15/779,633, U.S. Patent and Trademark Office action dated Aug. 31, 2021.
Sequence alignment: SEQ ID No. 102921 (2019). Reference cited in U.S. Appl. No. 15/779,633, U.S. Patent and Trademark Office action dated Aug. 31, 2021.
Sequence alignment: SEQ ID No. 103735 (2019). Reference cited in U.S. Appl. No. 15/779,633, U.S. Patent and Trademark Office action dated Aug. 31, 2021.
Sequence alignment: SEQ ID No. 103736 (2019). Reference cited in U.S. Appl. No. 15/779,633, U.S. Patent and Trademark Office action dated Aug. 31, 2021.
Serra et al., "Predicting thermodynamic properties of RNA," Methods in Enzymology, 1995, 259: 242-261.
Seto et al., "Gene Replacement Therapies for Duchenne Muscular Dystrophy Using Adeno-Associated Viral Vectors," Current Gene Therapy, 2012, 12:139-151.
Shalem et al., "Genome-scale CRISPR-Cas9 knockout screening in human cells," Science, 2014, 343: 84-87.
Sharma et al., "Efficiency of nonhomologous DNA and joining varies among somatic tissues, despite similarity in mechanism," Cellular and Molecular Life Science 68, 2011, 661-676.
Sharma et al., "In vivo genome editing of the albumin locus as a platform for protein replacement therapy," Blood, 2015, 126: 1777-1784.
Shea et al., "Synthesis, hybridization properties and antiviral activity of lipid-oligodeoxynucleotide conjugates, " Nucl. Acids Res, 1990, 18: 3777-3783.
Shelton et al., "Derivation and Expansion of PAX7-Positive Muscle Progenitors from Human and Mouse Embryonic Stem Cells," Stem Cell Rep, 2014, 3: 516-529.
Shen et al., "Combinatorial CRISPR-Cas9 screens for de novo mapping of genetic interactions," Nat Methods, 2017, 14: 573-576.
Shen et al., "Engraftment of a galactose receptor footprint onto adeno-associated viral capsids improves transduction efficiency," J Biol Chem, 2013, 288(40): 28814-28823.
Shen et al., "Massively parallel cis-regulatory analysis in the mammalian central nervous system," Genome Research, 2015, 26(2): 238-255.
Shin et al., "Microdystrophin Ameliorates Muscular Dystrophy in the Canine Model of Duchenne Muscular Dystrophy," Mol. Ther., 2013, 21: 750-757.
Shlyakhtenko et al., "Silatrane-based surface chemistry for immobilization of DNA, protein-DNA complexes and other biological materials," Ultramicroscopy, 2003, 97: 279-287.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.
Silva et al., "Meganucleases and other tools for targeted genome engineering: perspective and challenges for gene therapy," Current gene therapy, 2011, 11:11-27.
Simpson, "Contacts between *Escherichia coli* RNA polymerase and thymines in the lac UV5 promoter," Proc. Natl. Acad. Sci. USA, 1979, 76: 3233-3237.
Singh et al. "Protein Engineering Approaches in the Post-Genomic Era," Current Protein and Peptide Science, 2017, 18: 1-11.
Skene et al., "Genetic identification of brain cell types underlying schizophrenia," Nat Genet, 2018, 50: 825-833.
Smith et al., "Myostatin inhibitors as therapies for muscle wasting associated with cancer and other disorders," Curr Opin Support Palliat Care, 2013, 7, 352-60.
Snowden et al., "Gene-specific targeting of H3K9 methylation is sufficient for initiating repression in vivo," Curr Biol 12, 2002, 2159-2166.
Soejima et al., "Imprinting centers, chromatin structure, and disease," J Cell Biochem, 2005, 95(2): 226-233.

(56) References Cited

OTHER PUBLICATIONS

Şöllü et al., "Autonomous zinc-finger nuclease pairs for targeted chromosomal deletion," Nucleic acids research 38, 2010, 8269-8276.
Song et al., "Dnase-seq: a high-resolution technique for mapping active gene regulatory elements across the genome from mammalian cells," Cold Spring Harbor protocols 2010, 2010(2):11.
Song et al., "Non-immunogenic utrophin gene therapy for the treatment of muscular dystrophy animal models," Nature Medicine, 2019, 25(10): 1505-1511.
Song et al., "Open chromatin defined by DNaseI and FAIRE identifies regulatory elements that shape cell-type identify," Genome Res 21, 2011, 1757-1767.
Soutschek et al., "Therapeutic silencing of an endogenous gene by systemic administration of modified siRNAs," Nature (2004) 432: 173-8.
Spitz et al., "Transcription factors: from enhancer binding to developmental control," Nat. Rev. Genet. 2012, 13, 613-626.
Sripathy et al., "The KAP1 corepressor functions to coordinate the assembly of de novo HP1-demarcated microenvironments of heterochromatin required for KRAB zinc finger protein-mediated transcriptional repression," Molecular and cellular biology 26, 2006, 8623-8638.
Stanton et al., "Chemical modification study of antisense gapmers," Nucleic Acid Ther., 2012, 22(5): 344-359.
Stemmer et al., "CCTop: An Intuitive, Flexible and Reliable CRISPR/Cas9 Target Prediction Tool," PLoS One, 2015, 10(4): e0124633.
Stephens, "False discovery rates: a new deal," Biostatistics, 2017, 18: 275-294.
Stepper et al., "Efficient targeted DNA methylation with chimeric dCas9-Dnmt3a-Dnmt3L methyltransferase," Nucleic Acids Res., 2017, 45(4): 1703-1713.
Sternberg et al., "Conformational Control of DNA Target Cleavage by CRISPR-Cas9," Nature, 2015, vol. 527, No. 7576, pp. 110-113.
Sternberg et al., "DNA interrogation by the CRISPR RNA-guided endonuclease Cas9," Nature, 2014, 507, 62-67.
Stolzenburg et al., "Targeted silencing of the oncogenic transcription factor SOX2 in breast cancer," Nucleic Acids Res., 2012, 40(14): 6725-6740.
Stuelsatz et al., "A Contemporary Atlas of the Mouse Diaphragm: Myogenicity, Vascularity, and the Pax3 Connection" J Histochem Cytochem, 2012, 60(9): 638-657.
Su et al., "Identification of biologically relevant enhancers in human erythroid cells," J Biol Chem 288, 2013, 8433-8444.
Su et al., "In vitro and in vivo mRNA delivery using lipid-enveloped pH-responsive polymer nanoparticles," Mol. Pharmaceutics, 2011, 8, 774-787.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sui et al., "A DNA vector-based RNAi technology to suppress gene expression in mammalian cells," PNAS, 2002, 99(8): 5515-5520.
Sun et al., "Optimized TAL effector nucleases (TALENs) for use in treatment of sickle cell disease," Molecular bioSystems 8, 2012, 1255-1263.
Sun et al., "Phage mutations in response to CRISPR diversification in a bacterial population," Environmental microbiology, 2013, 15(2): 463-470.
Sur et al., "The role of enhancers in cancer," Nat. Rev. Cancer., 2016, 16: 483-493.
Sutcliffe et al., "Deletions of a differentially methylated CpG island at the SNRPN gene define a putative imprinting control region," Nature Genetics, 1994, 8: 52-58.
Suzuki et al., "In vivo genome editing via CRISPR/Cas9 mediated homology-independent targeted integration," Nature, 2016, 540: 144-149.
Svinarchuk et al., "Inhibition of HIV proliferation in MT-4 cells by antisense oligonucleotide conjugated to lipophilic groups," Biochimie, 1993, 75: 49-54.
Szczelkun et al., "Direct observation of R-loop formation by single RNA-guided Cas9 and Cascade effector complexes," Proceedings of the National Academy of Sciences, 2014, 6 pages.
Szostak, "in Vitro Genes," TIBS, 1993, 17: 89-93.
Szyf, "Epigenetics, DNA methylation, and chromatin modifying drugs," Annual Review of Pharmacology and Toxicology, 2009, vol. 49, pp. 243-263.
Szymczak et al., "Correction of multi-gene deficiency in vivo using a single 'self-cleaving' 2A peptide-based retroviral vector," Nature Biotechnology, 2004, 22(5): 589-594.
Tabebordbar et al., "In vivo gene editing in dystrophic mouse muscle and muscle stem cells," Science, 2016, 351, 407-11.
Takahashi et al., "A decade of transcription factor-mediated reprogramming to pluripotency," Nature Reviews, 2016, 17: 183-193.
Takahashi et al., "Induction of pluripotent stem cells from adult human fibroblasts by defined factors," Cell 1131, 2007, 861-872.
Takahashi et al., "Induction of pluripotent stem cells from mouse embryonic and adult fibroblast cultures by defined factors," Cell, 2006, 126: 663-676.
Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.
Takeshima et al., "Mutation spectrum of the dystrophin gene in 442 Duchene/Becker muscular dystrophy cases from one Japanese referral center," Journal of Human Genetics, 2010, 55: 379-388.
Tam et al., "Benefits and limitations of genome-wide association studies," Nat. Rev. Genet., 2019, 20: 467-484.
Tan et al., "Efficient derivation of lateral plate and paraxial mesoderm subtypes from human embryonic stem cells through GSKi-mediated differentiation," Stem Cells Dev, 2013, 22: 1893-1906.
Tan et al., "Rationally engineered Staphylococcus aureus Cas9 nucleases with high genome-wide specificity," Proc. Nat. Acad. Sci. USA, 2019, 116(46): 20969-20976.
Tanenbaum et al., "A Protein-Tagging System for Signal Amplification in Gene Expression and Fluorescence Imaging," Cell, 2014, pp. 635-646.
Taniguchi-Ikeda et al., "Pathogenic exon-trapping by SVA retrotransposon and rescue in Fukuyama muscular dystrophy," Nature 478, 2011, 127-131.
Tebas et al., "Gene editing of CCR5 in autologous CD4 T cells of persons infected with HIV," N Engl J Med, 2014, 370:901-910.
Tedesco et al., "Repairing skeletal muscle: regenerative potential of skeletal muscle stem cells," J Clin Invest, 2010, 120:11-19.
Tedesco et al., "Stem Cell-Mediated Transfer of a Human Artificial Chromosome Ameliorates Musculat Dystrophy," Science Translational Medicine 3, 2011, 96ra78-96ra78.
Tedesco et al., "Transplantation of Genetically Corrected Human iPSC-Derived Progenitors in Mice with Limb-Girdle Muscular Dystrophy," Science Translational Medicine 4, 2012, 140ra189.
Teratani-Ota et al., "Induction of specific neuron types by overexpression of single transcription factors," In Vitro Cell Dev Biol Anim, 2016, 52(9): 961-973.
Thakore et al., "Editing the epigenome: technologies for programmable transcription and epigenetic modulation," Nat Methods. 2016, 13:127-37.
Thakore et al., "Highly specific epigenome editing by CRISPR-Cas9 repressors for silencing of distal regulatory elements," Nat Methods, 2015, 12, 1143-9.
Thakore et al., "RNA-guided transcriptional silencing in vivo with *S. aureus* CRISPR-Cas9 repressors," Nature Communications, 2018, 9(1):1674, 9 pages.
Theodorou et al., "A high throughput embryonic stem cell screen identifies Oct-2 as a bifunctional regulator of neuronal differentiation," Genes Dev, 2009, 23: 575-588.
Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression, " Virol., 1994, 204:304-311.

(56) References Cited

OTHER PUBLICATIONS

Thorgeirsson et al., "A variant associated with nicotine dependence, lung cancer and peripheral arterial disease," Nature, 2008, 452: 638-642.
Thurman et al., "The accessible chromatin landscape of the human genome," Nature 489, 2012, 75-82.
Tian et al., "CRISPR Interference-Based Platform for Multimodal Genetic Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.
Tone et al., "Smad3 and NFAT cooperate to induce Foxp3 expression through its enhancer," Nat. Immunol., 2008, 9, 194-202.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Trinklein et al., "Identification and functional analysis of human transcriptional promoters," Genome Research, 2003, 13(2): 308-312.
Truong et al., "Development of an intein-mediated split-Cas9 system for gene therapy," Nucleic Acids Res. 2015; 43: 6450-6458.
Tsai et al., "GUIDE-seq enables genome-wide profiling of off-target cleavage by CRISPR-Cas nucleases," Nature biotechnology, 2015, 33(2): 187-197.
Tsuchiya et al., "The "Spanning Protocol": A new DNA extraction method for efficient single-cell genetic diagnosis," Journal of Assisted Reproduction Genetics, 2005, 22(11-12):407-14.
Tsunemoto et al., "Diverse reprogramming codes for neuronal identity," Nature, 2018, 557: 375-380.
Tuan et al., "Transcription of the hypersensitive site HS2 enhancer in erythroid cells," Proceedings of the National Academy of Sciences of the United States of America 89, 1992, 11219-11223.
Tycko et al., "Screening *S. aureus* CRISPR-Cas9 Paired Guide RNAs for Efficient Targeted Deletion in Duchenne Muscular Dystrophy," Editas, Poster presented on May 5, 2016.
Tyle, "Iontophoretic Devices for Drug Delivery," Pharm. Res., 1986, 3: 318-326.
Uchida et al., "In Vivo Messenger RNA Introduction into the Central Nervous System Using Polyplex Nanomicelle," PLoS ONE, 2013, 8: e56220.
Uetsuki et al., "Isolation and characterization of the human chromosomal gene for polypeptide chain elongation factor-1 alpha," J. Biol. Chem., 1989, 264:5791.
Urnov et al., "Highly efficient endogenous human gene correction using designed zinc-finger nucleases," Nature 435, 2005, 646-651.
Urrutia, "KRAB-containing zinc-finger repressor proteins," Genome Biol., 2003, 4(10): 231.
Usman et al., "Catalytic RNA (Ribozymes) as Drugs," Ann. Rep. Med. Chem., 1995, Chapter 30, pp. 285-294.
Vakoc et al., "Proximity among distant regulatory elements at the beta-globin locus requires GATA-1 and FOG-1," Molecular cell 17, 2005, 453-462.
Van Arensbergen et al., "Genome-wide mapping autonomous promoter activity in human cells," Nature Biotechnology, 2017, 35(2): 145-153.
Van der Oost et al., "Unravelling the structural and mechanistic basis of CRISPR-Cas systems," Nature Reviews Microbiology, 2014, 12: 479-492.
Van Deutekom et al., "Advances in Duchenne muscular dystrophy gene therapy," Nat. Rev. Genet., 2003, 4: 774-783.
Van Putten et al., "Low dystrophin levels in heart can delay heart failure in mdx mice," J Mol Cell Cardiol, 2014, 69C:17-23.
Van Putten et al., "Low dystrophin levels increase survival and improve muscle pathology and function in dystrophin/utrophin double-knockout mice," FASEB J, 2013, 27:2484-2495.
Vaquerizas et al., "A census of human transcription factors: function, expression and evolution," Nat Rev Genet, 2009, 10: 252-263.
Veltrop et al., "A dystrophic Duchenne mouse model for testing human antisense oligonucleotides," PLoS One, 2018, 13(2): e0193289, 18 pages.
Verkhusha et al., "GFP-like flourescent proteins and chromoproteins of the class Anthozoa," Protein Structures: Kaleidoscope of Structural Properties and Functions, 2003, 405-439.
Verma et al., "Gene Therapy: Twenty-first century medicine," Annual Review of Biochemistry, 2005, vol. 74, pp. 711-738.
Verma et al., "Gene therapy—promises, problems and prospects," Nature, 1997, vol. 389, pp. 239-242.
Vierbuchen et al., "Direct conversion of fibroblasts to functional neurons by defined factors," Nature 463, 2010, 1035-1041.
Vierbuchen et al., "Direct lineage conversions: unnatural but useful?," Nat Biotechnol, 2011, 29: 892-907.
Vierbuchen et al., "Molecular roadblocks for cellular reprogramming," Mol Cell, 2012, 47: 827- 838.
Visel et al., "ChIP-seq accurately predicts tissue-specific activity of enhancers," Nature 457, 2009, 854-858.
Vorobyov et al., "Expression of two protein isoforms of PAX7 is controlled by competing cleavage-polyadenylation and splicing," Gene, 2004, 342: 107-112.
Voss et al., "The role of enhancers in the regulation of cell-type-specific transcriptional control," Trends Biochem. Sci., 1986, 11:287.
Wada et al., "Codon usage tabulated from the GenBank genetic sequence data," Nucl. Acids Res., 1990, 18: 2367-2411.
Waddell et al., "DIk1 Is Necessary for Proper Skeletal Muscle Development and Regeneration," PLoS ONE, 2010, 5(11): e15055.
Wagner et al., "A phase I/IItrial of MYO-029 in adult subjects with muscular dystrophy," Ann Neurol 63, 2008, 561-71.
Waldrop et al., "Update in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Wang et al., "Adeno-associated virus vector carrying human minidystrophin genes effectively ameliorates muscular dystrophy in mdx mouse model," Proc Natl Acad Sci US A., 2000, 97(25):13714-13719.
Wang et al., "Construction and analysis of compact muscle-specific promoters for AAV vectors," Gene Ther, 2008, 15: 1489-1499.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.
Wang et al., "Efficient delivery of genome-editing proteins using bioreducible lipid nanoparticles," Proc Natl Acad Sci USA, 2016, 113(11): 2868-2873.
Wang et al., "Epstein-Barr virus nuclear protein 2 interacts with p300, CBP, and PCAF histone acetyltransferases in activation of the LMPI promoter," Proc Natl Acad Sci U S A 97, 2000, 430-435.
Wang et al., "Gene Essentiality Profiling Reveals Gene Networks and Synthetic Lethal Interactions with Oncogenic Ras," Cell, 2017, 168: 890-903.e15.
Wang et al., "Genetic screens in human cells using the CRISPR-Cas9 system," Science, 2014, 343: 80-84.
Wang et al., "Genome-wide mapping of HATs and HDACs reveals distinct functions in active and inactive genes," Cell 138, 2009, 1019-1031.
Wang et al., "Identification and characterization of essential genes in the human genome," Science, 2015, 350: 1096-1101.
Wang et al., "One-Step Generation of Mice Carrying Mutations in Multiple Genes by CRISPR-Cas-Mediated Genome Engineering," Cell, 2013, 153(4): 910-8.
Wang et al., "Potential of Epigenetic Therapy for Pader-Willi Syndrome," Trends in Pharmacological Sciences, 2019, 40(9): 605-608.
Wang et al., "Systemic human minidystrophin gene transfer improves functions and life span of dystrophin and dystrophin/utrophin-deficient mice," J. Orthop. Res., 2009, 27: 421-426.
Wang et al., "Unbiased detection of off-target cleavage by CRISPR-Cas9 and TALENs using integrase-defective lentiviral vectors," Nature biotechnology, 2015, 33(2): 175-8.
Wapinski et al., "Hierarchical mechanisms for direct reprogramming of fibroblasts to neurons," Cell, 2013, 155: 621-635.

(56) References Cited

OTHER PUBLICATIONS

Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wei et al., "Targeting Regnase-1 programs long-lived effector T cells for cancer therapy," Nature, 2019, 576(7787): 471-476.
Wein et al., "Efficient bypass of mutations in dysferlin deficient patient cells by antisense-induced exon skipping," Hum Mutat 31, 2010, 136-142.
Welch et al., "PTC124 targets genetic disorders caused by nonsense mutations," Nature 447, 2007, 87-91.
Weltner et al., "Human pluripotent reprogramming with CRISPR activators," Nat Commun Lond, 2018, 9: 1-12.
Westendorp et al., "E2F7 represses a network of oscillating cell cycle genes to control S-phase progression," Nucleic Acids Res, 2012, 40: 3511-3523.
Wherry, "T cell exhaustion," Nat. Immunology, 2011, 12: 492-499.
Whisstock et al., "Prediction of protein function from protein sequence," Q. Rev. Biophysics., 2003, 36(3): 307-340.
Wienert et al., "Editing the genome to introduce a beneficial naturally occurring mutation associated with increased fetal globin," Nat Commun 6, 2015, 7085.
Wiggins et al., "High flexibility of DNA on short length scales probed by atomic force microscopy," Nature nanotechnology, 2006, 1(2): 137-141.
Wilbie et al., "Delivery Aspects of CRISPR/Cas for in Vivo Genome Editing," Acc Chem Res, 2019, 52(6): 1555-1564.
Wiles et al., "CRISPR-Cas9_mediated genome editing and guide RNA design, " Mammalian Genome, 2015, 26(9): 501-510.
Willmann et al., "Mammalian animal models for Duchenne muscular dystrophy," Neuromuscular Disorders, 2009, 19(4): 241-249.
Wood, "Neuromuscular disease: CRISPR/Cas9 gene-editing platform corrects mutations associated with Duchenne muscular dystrophy," Nature Reviews Neurology, 2015, 11(4):184.
Wu et al., "A Myogenic Double-Reporter Human Pluripotent Stem Cell Line Allows Prospective Isolation of Skeletal Muscle Progenitors," Cell Rep, 2018, 25: 1966-1981.e4.
Wu et al., "Genome-wide binding of the CRISPR endonuclease Cas9 in mammalian cells," Nat Biotechnol 32, 2014, 670-676.
Wu et al., "Induction of anion exchanger-1 translation and its opposite roles in the carcinogenesis of gastric cancer cells and differentiation of K562 cells," Oncogene, 2010, 29: 1987-1996.
Wu et al., "Unusual Processing Generates SPA LncRNAs that Sequester Multiple RNA Binding Proteins," Mol Cell, 2016, 64: 534-548.
Wu et al., "Genome-wide binding of the CRISPR endonuclease Cas9 in mammalian cells," Nat Biotechnol, 2014, 32: 670-676.
Wüst et al., "Metabolic Maturation during Muscle Stem Cell Differentiation Is Achieved by miR-1/133a-Mediated Inhibition of the Dlk1-Dio3 Mega Gene Cluster," Cell Metab, 2018, 27: 1026-1039.e6.
Wylie et al., "Distinct transcriptomes define rostral and caudal serotonin neurons," J Neurosci, 2010, 30: 670-684.
Xie et al., "Multiplexed Engineering and Analysis of Combinatorial Enhancer Activity in Single Cells," Mol. Cell, 2017, 66: 285-299.e5.
Xie et al., "sgRNAcas9: a software package for designing CRISPR sgRNA and evaluating potential off-target cleavage sites," PLoS One, 2014, 9(6): e100448.
Xu et al., "CRISPR-mediated Genome Editing Restores Dystrophin Expression and Function in mdx Mice," Molecular Therapy: The Journal of the American Society of Gene Therapy, 2016, 24(3):564-569.
Xu et al., "Direct lineage reprogramming: strategies, mechanisms, and applications," Cell Stem Cell, 2015, 16: 119-134.
Xu et al., "Human Satellite Cell Transplantation and Regeneration from Diverse Skeletal Muscles," Stem Cell Rep, 2015, 5: 419-434.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yan et al., "Drugging the undruggable: Transcription therapy for cancer," Biochimica et Biophysica Acta (BBA)—Reviews on Cancer, Jan. 2013, vol. 1835, No. 1, pp. 76-85.
Yang et al., "A dual AAV system enables the Cas9-mediated correction of a metabolic liver disease in newborn mice," Nature Biotechnology, 2016, 34(3): 334-338.
Yang et al., "Determination of protein-DNA binding constants and specificities from statistical analyses of single molecules: MutS-DNA interactions," Nucleic acids research, 2005, 33(13): 4322-4334.
Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.
Yang et al., "Generation of pure GABAergic neurons by transcription factor programming," Nat Methods, 2017, 14: 621-628.
Yang, "Optimization of scarless human stem cell genome editing," Nucleic Acids Res, 2013, 41:9049-9061.
Yin et al., "Long noncoding RNAs with snoRNA ends," Mol Cell, 2012, 48(2): 219-230.
Yin et al., "Programming biomolecular self-assembly pathways," Nature, 2008, 451(7176): 318-323.
You et al., "Design of LNA probes that improve mismatch discrimination," Nuc. Acids. Res., 2006, 34(8): e60.
Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.
Young et al., "Creation of a Novel Humanized Dystrophic Mouse Model of Duchenne Muscular Dystrophy and Application of a CRISPR/Cas9 Gene Editing Therapy," Journal of Neuronuscular Diseases, 2017, 4(2): 139-145.
Youngblood et al., "Chronic virus infection enforces demethylation of the locus that encodes PD-1 in antigen-specific CD8+ T cells," Immunity, 2011, 35: 400-412.
Younossi et al., "Epidemiology of chronic liver diseases in the USA in the past three decades," Gut, 2020, 69(3): 564-568.
Yu et al., "Dystrophin-deficient large animal models: translational research and exon skipping," Am J Transl Res, 2015, 7(8): 1314-1331.
Yu et al., "RNA interference by expression of short-interfering RNAs and hairpin RNAs in mammalian cells," PNAS, 2002, 99(9): 6047-6052.
Yusa et al., "Targeted gene correction of a1-antitrypsin deficiency in induced pluripotent stem cells," Nature 478, 2011, 391-394.
Zenser et al., "A new TAP system for isolation of plant protein complexes and subsequent mass-spec analysis," <https://www.sigmaaldrich.com/deepweb/assets/sigmaaldrich/product/documents/388/028/flag_ha_tap_poster.pdf> published 2008, printed as pp. 1/4-4/4.
Zetsche et al., "Cpf1 Is a Single RNA-Guided Endonuclease of a Class 2 CRISPR-Cas System," Cell, 2015, 163(3):759-71.
Zhang et al. "Efficient construction of sequence-specific TAL effectors for modulating mammalian transcription," Nat Biotechnol 29, 2011, 149-153.
Zhang et al., "Adenovirus—Adeno-Associated Virus Hybrid for Large-Scale Recombinant Adeno-Associated Virus Production," Hum Gene Ther. 2009, 20:922-9.
Zhang et al., "Comprehensive Structure-Function Study of Neurogenin3 Disease-Causing Alleles during Human Pancreas and Intestinal Organoid Development," Dev Cell, 2019, 50(3): 367-380.e7.
Zhang et al., "Efficient precise knockin with a double cute HDR donor after CRISPR/Cas9-mediated double-stranded DNA cleavage," Genome Biol, 2017 18(35): 18 pages.
Zhang et al., "Gene activation in human cells using CRISPR/Cpf1-p300 and CRISPR/Cpf1-SunTag systems," Protein Cell, 2018, 9: 380-383.
Zhang et al., "Model-based analysis of ChIP-Seq (MACS)," Genome biology 9, 2008, R137.

(56) References Cited

OTHER PUBLICATIONS

Zhang et al., "Myoediting: Toward Prevention of Muscular Dystrophy by Therapeutic Genome Editing," Physiological Reviews, 2018, 98(3): 1205-1240.
Zhang et al., "Propagated Perturbations from a Peripheral Mutation Show Interactions Supporting WW Domain Thermostability," Structure, 2018, 26: 1474-1485.
Zhang et al., "Rapid single-step induction of functional neurons from human pluripotent stem cells," Neuron, 2013, 78: 785-798.
Zhao et al., "High-efficiency transfection of primary human and mouse T lymphocytes using RNA electroporation, " Mol. Ther., 2006, 13: 151-159.
Zhao et al., "Intracellular delivery of artificial transcription factors fused to the protein transduction domain of HIV-1 Tat," Protein Expr Purif, 2013, 90(1): 27-33.
Zhao et al., "The LIM-homeobox gene Lhx8 is required for the development of many cholinergic neurons in the mouse forebrain," Proc Natl Acad Sci U S A, 2003, 100: 9005-9010.
Zheng et al., "Foxp3 in control of the regulatory T cell lineage," Nat. Immunol. 2007, 8, 457-462.
Zheng et al., "Role of conserved non-coding DNA elements in the Foxp3 gene in regulatory T-cell fate," Nature, 2010, 463, 808-812.
Zhou et al., "Haploinsufficiency of utrophin gene worsens skeletal muscle inflammation and fibrosis in mdx mice," Journal of the Neurological Sciences, 2008, 264(1): 106-111.
Zhou et al., "High-throughput screening of a CRISPR/Cas9 library for functional genomics in human cells," Nature, 2014, 509(7501): 487-491.
Zhu et al., "Cellular senescence in human telomerase reverse transcriptase and cyclin—dependent kinase 4: consequences in aging muscle and therapeutic strategies for muscular dystrophies," Aging cell 6, 2007, 515-523.
Zhu et al., "The role of histone deacetylase 7 (HDAC7) in cancer cell proliferation: regulation on c-Myc," J. Mol. Med, 2011, 89: 279-289.
Zincarelli et al., "Analysis of AAV serotypes 1-9 mediated gene expression and tropism in mice after systemic injection," Mol Ther 16, 1073-80 (2008).
Zou et al., "Site-specific gene correction of a point mutation in human iPS cells derived from an adult patient with sickle cell disease," Blood 118, 2011, 4599-4608.
Buckingham, M. et al. "The role of Pax genes in the development of tissues and organs: Pax3 and Pax7 regulate muscle progenitor cell functions." Annu. Rev. Cell Dev. Biol. 23 (2007): 645-673.
International Search Report and Written Opinion for Application No. PCT/US14/41190 dated Dec. 17, 2014 (14 pages).
International Search Report and Written Opinion for Application No. PCT/US14/17221 dated Oct. 26, 2016 (11 pages).
International Search Report and Written Opinion for Application No. PCT/US2017/027490 dated Sep. 28, 2017 (34 pages).
International Search Report and Written Opinion for Application No. PCT/US2017/046282 dated Jan. 12, 2018 (20 pages).
International Search Report and Written Opinion for Application No. PCT/US2020/027867 dated Jul. 27, 2020 (18 pages).
International Search Report and Written Opinion for Application No. PCT/US2020/054160 dated Mar. 8, 2021 (21 pages).
International Search Report and Written Opinion for Application No. PCT/US2021/029500 dated Sep. 2, 2021 (10 pages).
International Search Report and Written Opinion for Application No. PCT/US2021/031436 dated Nov. 5, 2021 (11 pages).
International Search Report and Written Opinion for Application No. PCT/US2020/047080 dated Feb. 12, 2021 (14 pages).
International Search Report and Written Opinion for Application No. PCT/US2021/054292 dated Mar. 17, 2022.
International Search Report and Written Opinion for Application No. PCT/US2021/054636 dated Mar. 22, 2022 (18 pages).
International Search Report and Witten Opinion for Application No. PCT/US2021/059270 dated Apr. 19, 2022 (20 pages).
International Search Report and Written Opinion for Application No. PCT/US2022/018400 dated Sep. 1, 2022 (18 pages).
International Search Report and Written Opinion for Application No. PCT/US2023/018559 dated Sep. 29, 2023 (11 pages).
International Search Report and Written Opinion for Application No. PCT/US2023/063296 dated Oct. 19, 2023 (12 pages).
International Search Report and Written Opinion for Application No. PCT/US2023/063297 dated Oct. 18, 2023 (12 pages).
European Patent Office Extended Search Report for Application No. 17783164.1 dated Oct. 2, 2019 (8 pages).
European Patent Office Action for Application No. 17783164.1 dated Mar. 7, 2022 (5 pages).
European Patent Office Action for Application No. 17783164.1 dated Oct. 17, 2023 (6 pages).
United States Patent Office Action for U.S. Appl. No. 15/549,842 dated May 17, 2019 (29 pages).
United States Patent Office Action for U.S. Appl. No. 15/549,842 dated Oct. 10, 2019 (14 pages).
United States Patent Office Notice of Allowance for U.S. Appl. No. 15/549,842 dated Jan. 30, 2020 (7 pages).
United States Patent Office Action for U.S. Appl. No. 15/746,653 dated Jun. 28, 2019 (22 pages).
United States Patent Office Notice of Allowance for U.S. Appl. No. 15/746,653 dated Jan. 10, 2020 (5 pages).
United States Patent Office Notice of Allowance for U.S. Appl. No. 16/865,151 dated Mar. 18, 2021 (7 pages).
United States Patent Office Notice of Allowance for U.S. Appl. No. 16/865,151 dated Jun. 10, 2021 (7 pages).
United States Patent Office Action for U.S. Appl. No. 16/093,272 dated Nov. 22, 2021 (11 pages).
United States Patent Office Action for U.S. Appl. No. 16/322,234 dated Mar. 1, 2022 (24 pages).
United States Patent Office Action for U.S. Appl. No. 16/093,272 dated Jun. 9, 2022 (10 pages).
United States Patent Office Action for U.S. Appl. No. 16/322,234 dated Nov. 7, 2022 (26 pages).
United States Patent Office Action for U.S. Appl. No. 16/322,234 dated Apr. 19, 2023 (25 pages).
United States Patent Office Action for U.S. Appl. No. 16/093,272 dated Mar. 14, 2023 (9 pages).
United States Patent Office Action for U.S. Appl. No. 17/471,935 dated Jun. 2, 2023 (24 pages).
United States Patent Office Notice of Allowance for U.S. Appl. No. 17/471,935 dated Nov. 1, 2023 (9 pages).
European Patent Office Exam Report for Application No. 17840274.9 dated Jan. 4, 2024 (4 pages).
United States Patent Office Action for U.S. Appl. No. 16/322,234 dated Dec. 1, 2023 (29 pages).
United States Patent Office Action for U.S. Appl. No. 16/093,272 dated Dec. 29, 2023 (12 pages).
Abaandou et al., "Affecting HEK293 Cell Growth and Production Performance by Modifying the Expression of Specific Genes," Cells, 2021, 10: 1667, 21 pages.
Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/IIrg-/-mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "Familial hypercholesterolemia," Cardiol. Clin., 2015, 33(2): 169-179.
Braliou et al., "The v-ErbA oncoprotein quenches the activity of an erythroid-specific enhancer," Oncogene, 2001, 20(7): 775-87.

(56) References Cited

OTHER PUBLICATIONS

Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 6(12): 1468-1471.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep, 2016, 4: 170-179.
Carlens et al., "Ex vivo T lymphocyte expansion for retroviral transduction: influence of serum- free media on variations in cell expansion rates and lymphocyte subset distribution," Exp Hematol, 2000, 28(10): 1137-46.
Cavalieri et al., "Human T lymphocytes transduced by lentiviral vectors in the absence of TCR activation maintain an intact immune competence," Blood, 2003, 102(2): 497-505.
Chakraborty et al. "553. AAV-fVlediated Delivery of HSV-.Specific Homing Endonucleases to Neurons of the Trigeminal Ganglia for HSV-1 Inhibition." Molecular Therapy 22 (2014).
Chen et al., "Fusion protein linkers: property, design and functionality," Adv. Drug Deliv. Rev., 2013, 65(10): 1357-1369.
Chicaybam et al., "An efficient low cost method for gene transfer to T lymphocytes," PLoS ONE, 2013, 8(3): e60298, 11 pages.
Chylinski et al., "The tracrRNA and Cas9 families of type II CRISPR-Cas immunity systems," RNA Biol., 2013, 10(5): 726-737.
Cooper et al., "T-cell clones can be rendered specific for CD19: toward the selective augmentation of the graft-versus-B-lineage leukemia effect," Blood, 2003, 101(4): 1637-1644.
Cortes-Mancera et al., "Gene-Targeted DNA Methylation: Towards Long-Lasting Reprogramming of Gene Expression?" Adv Exp Med Biol., 2022, 1389: 515-533.
Das et al., "Tet-On Systems For Doxycycline-inducible Gene Expression," Current Gene Therapy, 2016, 16: 156-167.
Defesche et al., "Familial hypercholesterolaemia," Nat. Rev. Dis. Primers, 2017, 3: 17093, 20 pages.
Deng et al., "Highly sensitive electrochemical methyltransferase activity assay," Anal Chem., 2014, 86: 2117-2123.
Fuks, "DNA methylation and histone modifications: teaming up to silence genes," Current Opinion in Genetics & Development, 2005, 15(5): 490-495.
Gersbach et al., "Synthetic zinc finger proteins: the advent of targeted gene regulation and genome modification technologies," Acc. Chem. Res., 2014, 47(8): 2309-18.
Gowher et al., "Molecular enzymology of the catalytic domains of the Dnmt3a and Dnmt3b DNA methyltransferases," J. Biol. Chem., 2002, 277(23): 20409-20414.
Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.
Hochstrasser et al., "CasA mediates Cas3-catalyzed target degradation during CRISPR RNA-guided interference," PNAS, 2014, 111(18): 6618-23.
Huang et al., "Ch 9: DNA transposons for modification of human primary T lymphocytes," Methods Mol Biol, 2009, 506: 115-126.
Jia et al., "Structure of Dnmt3a bound to Dnmt3L suggests a model for de novo DNA methylation," Nature, 2007, 449(7159): 248-251.
Johnston, "Biolistic transformation: microbes to mice," Nature, 1990, 346: 776-777.
Kao et al., "Ectopic DNMT3L triggers assembly of a repressive complex for retroviral silencing in somatic cells," J Virol., 2014, 88(18): 10680-95.
Kim et al., "Zinc-fingers and homeoboxes 1 (ZHX1) binds DNA methyltransferase (DNMT) 3B to enhance DNMT3B-mediated transcriptional repression," Biochemical and Biophysical Research Communications, 2007, 355(2): 318-323.
Koste et al., "T-cell receptor transfer into human T cells with ecotropic retroviral vectors," Gene Ther, 2014, 21(5): 533-538.
Lagace, "PCSK9 and LDLR degradation: regulatory mechanisms in circulation and in cells," Curr. Opin. Lipidol., 2014, 25(5): 387-393.
Lei et al., "Targeted DNA methylation in vivo using an engineered dCas9-MQ1 fusion protein," Nat. Commun, 2017, 8: 16026, 10 pages.
Li et al., "The histone methyltransferase SETDB1 and the DNA methyltransferase DNMT3A interact directly and localize to promoters silenced in cancer cells," J. Biol. Chem., 2006, 281(28): 19489-19500.
Li et al., "Development of fluorescent methods for DNA methyltransferase assay," Methods Appl. Fluoresc., 2017, 5: 012002, 8 pages.
Liu et al., "Design of polydactyl zinc-finger proteins for unique addressing within complex genomes," PNAS, 1997, 94(11): 5525-5530.
Ma et al., "Pol III Promoters to Express Small RNAs: Delineation of Transcription Initiation," Molecular Therapy-Nucleic Acids, 2014, 3: e161, 11 pages.
Makarova et al., "Annotation and Classification of CRISPR-Cas Systems," Methods Mol. Biol, 2015, 1311: 47-75.
Manuri et al., "piggyBac transposon/transposase system to generate CD19-specific T cells for the treatment of B-lineage malignancies," Hum Gene Ther, 2010, 21(4): 427-437.
Mavrothalassitis et al., "Proteins of the ETS family with transcriptional repressor activity," Oncogene, 2000, 19: 6524-6532.
Miller et al., "Improved retroviral vectors for gene transfer and expression, " BioTechniques, 1989, 7(9): 980-990.
Miller, "Retrovirus packaging cells," Human Gene Therapy, 1990, 1: 5-14.
Milone et al., "Clinical use of lentiviral vectors," Leukemia, 2018, 32(7): 1529-1541.
Mok et al., "Stabilized plasmid-lipid particles: factors influencing plasmid entrapment and transfection properties," Biochimica et Biophysica Acta, 1999, 1419(2): 137-150.
Moon et al., "Recent advances in the CRISPR genome editing tool set," Exp. Mol. Med., 2019, 51(11): 130, 11 pages.
Moussa et al., "Here to stay: Writing lasting epigenetic memories," Cell, 2021, 184(9): 2281-2283.
Murphy et al., "The Transcriptional Repressive Activity of KRAB Zinc Finger Proteins Does Not Correlate with Their Ability to Recruit TRIM28," PLoS ONE, 2016, 11(9): e0163555, 19 pages.
O'Geen et al., "Determinants of heritable gene silencing for KRAB-dCas9 + DNMT3 and Ezh2-dCas9 + DNMT3 hit-and-run epigenome editing," Nucleic Acids Res, 2022, 50(6): 3239-3253.
Orth et al., "Structural basis of gene regulation by the tetracycline inducible Tet repressor- operator system," natural structural biology, 2000, 7(3): 215-219.
Park et al., "Treating cancer with genetically engineered T cells," Trends Biotechnol, 2011, 29(11): 550-557.
Peterson et al., "PCSK9 function and physiology," J. Lipid Res., 2008, 49(6): 1152-1156.
Pickar-Oliver et al., "The next generation of CRISPR-Cas technologies and applications," Nature Reviews Molecular Cell Biology, 2019, 20(8): 490-507.
Poh et al., "DNA Methyltransferase Activity Assays: Advances and Challenges," Theranostics, 2016, 6(3): 369-391.
Poirier et al., "The proprotein convertase PCSK9 induces the degradation of low density lipoprotein receptor (LDLR) and its closest family members VLDLR and ApoER2"J. Biol. Chem., 2008, 283: 2363-2372.
Policarpi et al., "Epigenetic editing: Dissecting chromatin function in context," Bioessays, 2021, 43(5): e2000316, 16 pages.
Saha et al., "The NIH Somatic Cell Genome Editing program," Nature, 2021, 592: 195-204.
Scarpa et al., "Characterization of recombinant helper retroviruses from moloney-based vectors in ecotropic and amphotropic packaging cell lines," Virology, 1991, 180: 849-852.
Schellenberger et al., "A recombinant polypeptide extends the in vivo half-life of peptides and proteins in a tunable manner," Nature Biotechnology, 2009, 27(12): 1186-1190.

(56) References Cited

OTHER PUBLICATIONS

Sharma et al., "Efficient Sleeping Beauty DNA Transposition From DNA Minicircles," Molec Ther Nucl Acids, 2013, 2(2): e74, 10 pages.
Stepper, "Dissertation: CRISPR-Cas9 fusions for synthetic epigenetics," Von der Fakultat 4: Energie-, Verfahrens-und Biotechnik, Institut für Biochemie und Technische Biochemie der Universität Stuttgart, 2020, 148 pages.
Thakore et al., "385. Inhibiting the Myostatin Signaling Pathway using CRISPR/Cas9-Based Repressors." Molecular Therapy 2016, 24: S153.
Tycko et al., "High-Throughput Discovery and Characterization of Human Transcriptional Effectors," Cell, 2020, 183(7): 2020-2035.
Van Tedeloo et al., "High-level transgene expression in primary human T lymphocytes and adult bone marrow CD34+ cells via electroporation-mediated gene delivery," Gene Therapy, 2000, 7(16): 1431-1437.
Verhoeyen et al., "Ch 8: Lentiviral vector gene transfer into human T cells," Methods Mol Biol, 2009, 506: 97-114.
Wang et al., "Phenotypic and functional attributes of lentivirus modified CD19-specific human CD8+ central memory T cells manufactured at clinical scale," J. Immunother, 2012, 35(9): 689-701.
Wright et al., "Standardized reagents and protocols for engineering zinc finger nucleases by modular assembly," Nat. Protoc., 2006, 1(3): 1637-1652.
Wright et al., "Rational design of a split-Cas9 enzyme complex," PNAS, 2015, 112(10): 2984-2989.
Zetsche et al., "A split-Cas9 architecture for inducible genome editing and transcription modulation," Nat. Biotechnol, 2015, 33(2): 139-142.
Echevarria et al., "Exon-skipping advances for Duchenne muscular dystrophy," Human Molecular Genetics, 2018, 27 (R2): R163-R172.
Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.
Ryu et al., "Adenine base editing in mouse embryos and an adult mouse model of Duchenne muscular dystrophy," Nature Biotechnology, 2018, 36(6): 536-539.
Rees et al., "Base editing: precision chemistry on the genome and transcriptome of living cells," Nature Reviews Genetics, 2018, 19(12): 770-788.
Nelson et al., "Long-term evaluation of genome editing for Duchenne muscular dystrophy," Duke Presentation, 2019, 123 pages. Retrieved from the Internet: <https://static.seekingalpha.com/uploads/sa_presentations/453/41453/original.pdf>.
Young, "Development of a Therapeutic CRISPR/Cas9 Plataform for Duchenne Muscular Dystrophy," UCLA Electronic Theses and Dissertations, Jan. 1, 2018, 136 pages.
Kwon et al., "In Vivo Gene Editing of Muscle Stem Cells with Adeno-Associated Viral Vectors in a Mouse Model of Duchenne Muscular Dystrophy," Molecular Therapy, 2020, 19: 320-329.
International Search Report and Written Opinion for Application No. PCT/US2023/072524 dated Jan. 12, 2024 (10 pages).
Chao et al., "Several log increase in therapeutic transgene delivery by distinct adeno-associated viral serotype vectors," (2000) Molecular Therapy 2:619.
Chen et al., "In vivo CD8+ T cell CRISPR screening reveals control by Fli1 in infection and cancer," Cell, 2021, 184(5): 1262-1280.
Corces et al., "An improved ATAC-seq protocol reduces background and enables interrogation of frozen tissues," Nature Methods. 2017, 14: 959-962.
Galletti et al., "Two subsets of stem-like CD8+ memory T cell progenitors with distinct fate commitments in humans," Nature Immunology, 2020, 21: 1552-1562.
Gao et al., "Clades of Adeno-Associated Viruses Are Widely Disseminated in Human Tissues," (2004) J. Virology 78:6381-6388.
GenBank Accession No. AF028704.1, (1998).
GenBank Accession No. AF028705.1, (1998).
GenBank Accession No. AF043303.1, (2010).
GenBank Accession No. AF063497.1, (1999).
GenBank Accession No. AF288061.1, (2001).
GenBank Accession No. AF513851.1, (2002).
GenBank Accession No. AFS13852.1, (2015).
GenBank Accession No. AH009962.2, (2016).
GenBank Accession No. AY028223.1, (2001).
GenBank Accession No. AY028226.1, (2001).
GenBank Accession No. AY530579.1, (2004).
GenBank Accession No. J01901.1, (1993).
GenBank Accession No. J02275.1, (1995).
GenBank Accession No. NC_000883.2, (2018).
GenBank Accession No. NC_001358.1, (2015).
GenBank Accession No. NC_001401, (2018).
GenBank Accession No. NC_001510.1, (2018).
GenBank Accession No. NC_001540.1, (2018).
GenBank Accession No. NC_001701.1, (2018).
GenBank Accession No. NC_001729, (2018).
GenBank Accession No. NC_001829.1, (2018).
GenBank Accession No. NC_001862.1, (2004).
GenBank Accession No. NC_001863.1, (2004).
GenBank Accession No. NC_002077, (2018).
GenBank Accession No. NC_006152.1, (2018).
GenBank Accession No. NC_006261.1, (2018).
GenBank Accession No. U89790.1, (1997).
GenBank Accession No. X01457.1, (2005).
Hao et al., "Integrated analysis of multimodal single-cell data," Cell, 2021, 184: 3573-3587.e29.
Hart et al., "Kruppel-like factors in lymphocyte biology," J Immunol, 2012, 188(2): 521-526.
Joung et al., "Transcription Factor Atlas of Directed Differentiation," Cell, 2023, 186(1): 209-229.e26.
Jung et al. "BLIMP1 and NR4A3 transcription factors reciprocally regulate antitumor CAR T cell stemness and exhaustion," Cancer Immunotherapy, 2022, 14: eabn7336.
Kaminskiy et al., "Neglected, yet significant role of FOXP1 in T-cell quiescence, differentiation and exhaustion," Front. Immunol, 2022, 13: 971045.
Krishna et al., "Stem-like CD8 T cells mediate response of adoptive cell immunotherapy against human cancer," Science, 2020, 370: 1328-1334.
Kuleshov et al., "Enrichr: a comprehensive gene set enrichment analysis web server 2016 update," Nucleic Acids Research, 2016, 44: 90-97.
Liao et al., "featureCounts: an efficient general purpose program for assigning sequence reads to genomic features," Bioinformatics, 2013, 30(7): 923-30.
Martin et al., "CCR7 Deficiency in NOD Mice Leads to Thyroiditis and Primary Hyperthyroidism," The Journal of Immunology, 2009, 183(5): 3073-3080.
Mimitou et al., "Expanding the CITE-seq tool-kit: Detection of proteins, transcriptomes, clonotypes and CRISPR perturbations with multiplexing, in a single assay," Nat. Methods, 2019, 16: 409-412.
Mori et al., "Two novel adeno-associated viruses from cynomolgus monkey: pseudotyping characterization of capsid protein," (2004) Virology 330: 375-383.
Muzyczka, "Use of adeno-associated virus as a general transduction vector for mammalian cells," (1992) Curr. Topics Microbial. Immunol. 158: 97-129.
Philip et al., "Chromatin states define tumour-specific T cell dysfunction and reprogramming," Nature, 2017, 545: 452-456.
Pritykin et al., "A unified atlas of CD8 T cell dysfunctional states in cancer and infection," Mol. Cell 2021, 81: 2477-2493.
Ramirez et al., "deepTools: a flexible platform for exploring deep-sequencing data," Nucleic Acids Research, 2014, 42:W187-91.
Schubert et al., "Autosomal dominant immune dysregulation syndrome in humans with CTLA4 mutations," Nature Medicine, 2014, 20(2): 1410-1416.
Sen et al., "The epigenetic landscape of T cell exhaustion," Science, 2016, 354(6316): 1165-1169.
Wherry et al., "Molecular Signature of CD8+ T Cell Exhaustion during Chronic Viral Infection," Immunity, 2007, 27(4): 670-684.

(56) References Cited

OTHER PUBLICATIONS

Woolf et al., "Runx3 and Runx1 are required for CD8 T cell development during thymopoiesis," PNAS, 2003, 100(13): 7731-7736.
Yang et al., "The transcriptional regulators Id2 and Id3 control the formation of distinct memory CD8+ T cell subsets," Nat Immunol, 2011, 12: 1221-1229.
Yu et al., "ChIPseeker: an R/Bioconductor package for ChIP peak annotation, comparison and visualization," Bioinformatics, 2015, 31(14): 2382-2383.
Yuan et al., "Genetic Modulation of RNA Splicing with a CRISPR-Guided Cytidine Deaminase," Molecular Cell, 2018, 72(2): 380-394.
Zhang et al., "Model-based analysis of ChIP-Seq (MACS)," Genome Biology, 2008, 9(9): R137.
Zheng et al., "Landscape of Infiltrating T Cells in Liver Cancer Revealed by Single-Cell Sequencing," Cell, 2017, 169: 1342-1356.
International Search Report and Written Opinion for Application No. PCT/US2023/078124 dated May 29, 2024 (15 pages).
United States Patent Office Action for U.S. Appl. No. 16/322,234 dated Apr. 22, 2024 (23 pages).
United States Patent Office Action for U.S. Appl. No. 17/471,935 dated Jun. 5, 2024 (7 pages).
Liu et al., "A CRISPR-Cas9 Strategy for Activating the Saccharopolyspora erythraea Erythromycin Biosynthetic Gene Cluster with Knock-in Bidirectional Promoters," ACS Synth. Biol. 2019, 8(5): 1134-1143.
Miyazaki et al., "Characterization of deletion breakpoints in patients with dystrophinopathy carrying a deletion of exons 45-55 of the Duchenne muscular dystrophy (DMD) gene," Journal of Human Genetics, 2009, 54: 127-130.
Razzouk, "CRISPR-Cas9: A cornerstone for the evolution of precision medicine," Annal of Human Genetics, 2018, 82(6): 331-357.
Simeonov et al., "Discovery of stimulation-responsive immune enhancers with CRISPR activation," Nature, 2017, 549(7670): 111-115.
United States Patent Office Action for U.S. Appl. No. 16/322,234 dated Oct. 15, 2024 (23 pages).
Bulcha et al., "Viral vector platforms within the gene therapy landscape," Signal Transduction and Targeted Therapy, 2021, 6: 53.
Duchêne et al., "CRISPR-Induced Deletion with SaCas Restores Dystrophin Expression in Dystrophic Models In Vitro and In Vivo," Molecular Therapy: The Journal of the American Society of Gene Therapy, 2018, 26(11): 2604-2616.
Hideki et al., Geneseq Accession No. BFK30060, 2018. Reference cited in U.S. Appl. No. 16/963,034, U.S. Patent Office Action dated Jun. 27, 2024.
Kotterman et al., "Engineering adeno-associated viruses for clinical gene therapy," Nature Reviews, 2014, 15(7): 445-451.
Lenzi et al., "Oversight and Review of Clinical Gene Transfer Protocols: Assessing the Role of the Recombinant DNA Advisory Committee," NCBI Bookshelf, A Service of the National Library of Medicine, National Institute of Health, Washington, DC, National Academies Press, US, 2014, pp. 1-16.
Liao, "Targeted disruption of DNMT1, DNMT3A and DNMT3B in human embryonic stem cells," Nature Genetics, 2015, 47(5): 469-478.
Long et al., "Correction of Diverse Muscular Dystrohpy Mutations in Human Engineered Heart Muscle by Single-Site Genome Editing," Sci Adv, 2018, 4(1): eaap9004.
Maggio et al., "Adenoviral vectors encoding CRISPR/Cas9 multiplexes rescue dystrophin synthesis in unselected populations of DMD muscle cells," Scientific Reports, 2016, 6: 37051.
Shim et al., "Nonviral Delivery Systems for Cancer Gene Therapy: Strategies and Challenges," Current Gene Therapy, 2017, 17(5): 1-18.
Swiech et al., "In vivo interrogation of gene function in the mammalian brain using CRISPR-Cas9," Nature Biotechnology, 2014, 33(1): 102-106 (Supplementary Information included).
Thule et al., "Engineered Insulin Secretion in Human Primary Thyroid Cells," Molecular Therapy, 2012, 20 (Supplement 1): S164, Article 421.
United States Patent Office Notice of Allowance for U.S. Appl. No. 17/471,935 dated Aug. 19, 2024 (7 pages).
Abdennur et al., "Cooler: scalable storage for Hi-C data and other genomically labeled arrays," Bioinformatics, 2020, 36: 311-316.
Achterberg et al., "The nano-scale mechanical properties of the extracellular matrix regulate dermal fibroblast function," J. Invest. Dermatol, 2014, 134: 1862-1872.
Akter et al., "FAM98A associates with DDX1-C14orf166-FAM98B in a novel complex involved in colorectal cancer progression," Int. J. Biochem. Cell Biol., 2017, 84: 1-13.
Andreu et al.," Mechanical force application to the nucleus regulates nucleocytoplasmic transport," Nat. Cell Biol., 2022, 24: 896-905.
Arda et al., "Quantitative assessment of normal soft-tissue elasticity using shear-wave ultrasound elastography," AJR Am. J. Roentgenol., 2011, 197: 532-536.
Aubel et al., "Mammalian synthetic biology—from tools to therapies," BioEssays, 2010, 32(4): 332-345.
Babic et al., "CYR61, a product of a growth factor-inducible immediate early gene, promotes angiogenesis and tumor growth," Proc. Natl. Acad. Sci. U.S.A., 1998, 95: 6355-6360.
Baek et al., "DNA-free two-gene knockout in Chlamydomonas reinhardtii via CRISPR-Cas9 ribonucleoproteins," Scientific Reports, 2016, 6:30620.
Balko et al., "Activation of MAPK pathways due to DUSP4 loss promotes cancer stem cell-like phenotypes in basal-like breast cancer," Cancer Res, 2013, 73: 6346-6358.
Behan et al., "Prioritization of cancer therapeutic targets using CRISPR-Cas9 screens," Nature, 2019, 568: 511-516.
Benabdallah et al., "Decreased Enhancer-Promoter Proximity Accompanying Enhancer Activation," Mol. Cell, 2019, 76: 473-484.e7.
Beningo et al., "Traction forces of fibroblasts are regulated by the Rho-dependent kinase but not by the myosin light chain kinase," Arch. Biochem. Biophys., 2006, 456: 224-231.
Berginski et al., "The Focal Adhesion Analysis Server: a web tool for analyzing focal adhesion dynamics," F1000Res., 2013, 2: 68.
Bischoff et al., "RanGAP1 induces GTPase activity of nuclear Ras-related Ran," Proc. Natl. Acad. Sci. U.S.A., 1994, 91: 2587-2591.
Bolger et al., "Trimmomatic: a flexible trimmer for Illumina sequence data," Bioinformatics, 2014, 30: 2114-2120.
Braun et al., "Rapid and reversible epigenome editing by endogenous chromatin regulators," Nat Commun, 2017, 8(1): 560.
Canver et al., "BCL11A enhancer dissection by Cas9-mediated in situ saturating mutagenesis," Nature, 2015, 527: 192-197.
Chang et al., "GEF-H1 couples nocodazole-induced microtubule disassembly to cell contractility via RhoA," Mol Biol Cell, 2008, 19: 2147-2153.
Chang et al., "The SWI/SNF complex is a mechanoregulated inhibitor of YAP and TAZ," Nature, 2018, 563: 265-269.
Chen et al., "Connective Tissue Growth Factor: From Molecular Understandings to Drug Discovery," Front Cell Dev Biol, 2020, 8: 593269.
Chen et al., "Geometric control of cell life and death," Science, 1997, 276: 1425-1428.
Chen, "Mechanotransduction—a field pulling together?" J. Cell Sci., 2008, 121: 3285-3292.
Chrzanowska-Wodnicka et al., "Rho-stimulated contractility drives the formation of stress fibers and focal adhesions," J Cell Biol, 1996, 133: 1403-1415.
Clement et al., "CRISPResso2 provides accurate and rapid genome editing sequence analysis," Nat. Biotechnol., 2019, 37: 224-226.
Corces et al., "Omni-ATAC-seq: improved ATAC-seq protocol," Protocol exchange, [Preprint] 2017.
Cosgrove et al., "Mechanosensitive genomic enhancers potentiate the cellular response to matrix stiffnes," Posted Jan. 10, 2024. bioRxiv Jan. 10, 2024:2024.01.10.574997.
Darnell et al. "RNA-seq reveals diverse effects of substrate stiffness on mesenchymal stem cells," Biomaterials, 2018, 181: 182-188.

(56) References Cited

OTHER PUBLICATIONS

Devos et al., "Practical Limits of Fuction Prediction," PROTEINS: Structure, Function, and Genetics, 2000, 41: 98-107.
Ding et al., "Improving CRISPR-Cas9 Genome Editing Efficiency by Fusion with Chromatin-Modulating Peptides," CRISPR J, 2019, 2: 51-63.
Dobin et al., "STAR: ultrafast universal RNA-seq aligner," Bioinformatics, 2013, 29: 15-21.
Dupont et al., "Mechanical regulation of chromatin and transcription," Nat. Rev. Genet., 2022, 23: 624-643.
Dupont et al., "Role of YAP/TAZ in mechanotransduction," Nature, 2011, 474: 179-183.
Durand et al., "Juicer Provides a One-Click System for Analyzing Loop-Resolution Hi-C Experiments," Cell Syst, 2016, 3: 95-98.
Effendi et al., "Connective Tissue Growth Factor in Idiopathic Pulmonary Fibrosis: Breaking the Bridge," Int. J. Mol. Sci., 2022, 23.
Ehrbar et al., "Elucidating the role of matrix stiffness in 3D cell migration and remodeling," Biophys. J., 2011, 100: 284-293.
Elosegui-Artola et al., "Force triggers YAP nuclear entry by regulating transport across nuclear pores," Cell, 2017, 171: 1397-1410. e14.
ENCODE Project Consortium, "An integrated encyclopedia of DNA elements in the human genome," Nature, 2012, 2012, 489: 57-74.
ENCODE Project Consortium, "Expanded encyclopaedias of DNA elements in the human and mouse genomes," Nature, 2020, 583: 699-710.
Engler et al., "Matrix elasticity directs stem cell lineage specification," Cell, 2006, 126: 677-689.
Ernst et al., "ChromHMM: automating chromatin-state discovery and characterization," Nat Methods, 2012, 9: 215-216.
Fan et al., "Hsp90{beta} and p130(cas): novel regulatory factors of MMP-13 expression in human osteoarthritic chondrocytes," Ann. Rheum. Dis., 2009, 68: 976-982.
Finak et al., "MAST: a flexible statistical framework for assessing transcriptional changes and characterizing heterogeneity in single-cell RNA sequencing data," Genome Biol., 2015, 16: 278.
Fiore et al., "Publisher Correction: Mechanics of a multilayer epithelium instruct tumour architecture and function," Nature, 2020, 586: E9.
Freeberg et al., "Mechanical Feed-Forward Loops Contribute to Idiopathic Pulmonary Fibrosis," Am. J. Pathol., 2021, 191: 18-25.
Fulco et al., "Activity-by-contact model of enhancer-promoter regulation from thousands of CRISPR perturbations," Nat. Genet., 2019, 51: 1664-1669.
Galli et al., "YAP Drives Growth by Controlling Transcriptional Pause Release from Dynamic Enhancers," Molecular Cell, 2015, 60(2): p. 328-337.
Gasperini et al., "A Genome-wide Framework for Mapping Gene Regulation via Cellular Genetic Screens," Cell, 2019, 176: 377-390.e19.
GenBank Accession No. U94396.1 "Human dystrophin (DMD) gene, exon 44 and partial cds," 2016.
Gilbert et al., "CRISPR-mediated modular RNA-guided regulation of transcription in eukaryotes," Cell, 2013, 154: 442-451.
Gordon et al., "lentiMPRA and MPRAflow for high-throughput functional characterization of gene regulatory elements," Nat. Protoc., 2020, 15(8): 2387-2412.
Habermann et al., "Single-cell RNA sequencing reveals profibrotic roles of distinct epithelial and mesenchymal lineages in pulmonary fibrosis," Sci Adv, 2020, 6: eaba197.
Hall et al., "Polarity of the CRISPR roadblock to transcription," Nat. Struct. Mol. Biol., 2022, 29: 1217-1227.
Han et al., "CRISPR screens in cancer spheroids identify 3D growth-specific vulnerabilities," Nature, 2020, 580: 136-141.
Hanmandlu et al., "Transcriptomic and Epigenetic Profiling of Fibroblasts in Idiopathic Pulmonary Fibrosis," Am J Respir Cell Mol Biol, 2022, 66(1): 53-63.
Heinz et al., "Simple combinations of lineage-determining transcription factors prime cis-regulatory elements required for macrophage and B cell identities," Mol. Cell, 2010, 38: 576-589.
Heinz et al., "The selection and function of cell type-specific enhancers," Nat. Rev. Mol. Cell Biol., 2015, 16: 144-154.
Heo et al., "Differentiation alters stem cell nuclear architecture, mechanics, and mechano-sensitivity," Elife, 2016, 5.
Herrera et al., "Extracellular matrix as a driver of progressive fibrosis," J. Clin. Invest., 2018, 128: 45-53.
Ho et al., "Lamin A/C and emerin regulate MKL1-SRF activity by modulating actin dynamics," Nature, 2013, 497: 507-511.
Hoffman et al., "Dynamic molecular processes mediate cellular mechanotransduction," Nature, 2011, 475: 316-323.
Horlbeck et al., "Compact and highly active next-generation libraries for CRISPR-mediated gene repression and activation," Elife, 2016, 5: e19760.
Humphrey et al., "Mechanotransduction and extracellular matrix homeostasis," Nat. Rev. Mol. Cell Biol., 2014, 15: 802-812.
Isaac et al., "Nucleosome breathing and remodeling constrain CRISPR-Cas9 function," Elife, 2016, 5: e13450.
Jang et al., "Mechanical cue-induced YAP instructs Skp2-dependent cell cycle exit and oncogenic signaling, " EMBO J., 2017, 36: 2510-2528.
Jeffrey et al., "Targeting dual-specificity phosphatases: manipulating MAP kinase signalling and immune responses," Nat. Rev. Drug Discov., 2007, 6: 391-403.
Jiang et al., "Systematic investigation of cytokine signaling activity at the tissue and single-cell levels," Nat. Methods, 2021, 18: 1181-1191.
Johne et al., "Spred1 and TESK1—two new interaction partners of the kinase MARKK/TAO1 that link the microtubule and actin cytoskeleton," Mol. Biol. Cell, 2008, 19: 1391-1403.
Jones et al., "Mechanoepigenetic regulation of extracellular matrix homeostasis via Yap and Taz," Proc. Natl. Acad. Sci. U.S.A., 2023, 120: e2211947120.
Jones et al., "No place like home: anatomy and function of the stem cell niche," Nat. Rev. Mol. Cell Biol., 2008, 9: 11-21.
Jones et al., "ZNF416 is a pivotal transcriptional regulator of fibroblast mechanoactivation," J. Cell Biol., 2021, 220.
Juric et al., "MAPS: Model-based analysis of long-range chromatin interactions from PLAC-seq and HiChIP experiments," PLoS Comput. Biol., 2019, 15: e1006982.
Katsura et al., "Human Lung Stem Cell-Based Alveolospheres Provide Insights into SARS-CoV-2-Mediated Interferon Responses and Pneumocyte Dysfunction," Cell Stem Cell, 2020, 27(6): 890-904.e8.
Kechin et al., "cutPrimers: A New Tool for Accurate Cutting of Primers from Reads of Targeted Next Generation Sequencing," J. Comput. Biol., 2017, 24: 1138-1143.
Khemlina et al., "The biology of Hepatocellular carcinoma: implications for genomic and immune therapies," Mol. Cancer, 2017, 16: 149.
Kisselev, "Polypeptide Release Factors in Prokaryotes and Eukaryotes: Same Function, Different Structure," Structure, 2002, 10: 8-9.
Klann et al., "CRISPR-Cas9 epigenome editing enables high-throughput screening for functional regulatory elements in the human genome," Nat. Biotechnol., 2017, 35: 561-568.
Korkmaz et al., "Functional genetic screens for enhancer elements in the human genome using CRISPR-Cas9," Nat. Biotechnol., 2016, 34: 192-198.
Krietenstein et al., "Ultrastructural Details of Mammalian Chromosome Architecture," Mol. Cell, 2020, 78(3): 554-565.e7.
Kurppa et al., "Treatment-Induced Tumor Dormancy through YAP-Mediated Transcriptional Reprogramming of the Apoptotic Pathway," Cancer Cell, 2020, 37: 104-122.e12.
Langmead, "Aligning short sequencing reads with Bowtie," Curr. Protoc. Bioinformatics, 2010, Chapter 11, Unit 11.7.
Lau et al., "In vivo epigenome editing and transcriptional modulation using CRISPR technology," Transgenic Res. 2018, 27(6): 489-509.
Le et al., "Mechanical regulation of transcription controls Polycomb-mediated gene silencing during lineage commitment," Nature Cell Biology, 2016, 18(8): 864-875.

(56) References Cited

OTHER PUBLICATIONS

Lee et al., "The novel PIAS-like protein hZimp10 is a transcriptional co-activator of the p53 tumor suppressor," Nucleic Acids Res., 2007, 35: 4523-4534.
Leight et al., "Matrix rigidity regulates a switch between TGF-β1-induced apoptosis and epithelial-mesenchymal transition," Mol. Biol. Cell, 2012, 23: 781-791.
Li et al., "MicroRNA-21 preserves the fibrotic mechanical memory of mesenchymal stem cells," Nat. Mater., 2017, 16: 379-389.
Liao et al., "featureCounts: an efficient general purpose program for assigning sequence reads to genomic features," Bioinformatics, 2014, 30: 923-930.
Liu et al., "Modulating chromatin accessibility by transactivation and targeting proximal dsgRNAs enhances Cas9 editing efficiency in vivo," Genome Biol, 2019, 20(1): 145.
Love et al., "Moderated estimation of fold change and dispersion for RNA-seq data with DESeq2," Genome Biol., 2014, 15: 550.
Ma et al., "Mechanotransduction and anoikis: death and the homeless cell," Cell Cycle, 2008, 7: 2462-2465.
McBeath et al., "Cell shape, cytoskeletal tension, and RhoA regulate stem cell lineage commitment," Dev. Cell, 2004, 6: 483-495.
McDowell et al., "Glucocorticoid receptor recruits to enhancers and drives activation by motif-directed binding," Genome Res., 2018, 28: 1272-1284.
Meng et al., "RAP2 mediates mechanoresponses of the Hippo pathway," Nature, 2018, 560: 655-660.
Meyers et al., "Computational correction of copy number effect improves specificity of CRISPR-Cas9 essentiality screens in cancer cells," Nat. Genet., 2017, 49: 1779-1784.
Miano, "Serum response factor: toggling between disparate programs of gene expression," J. Mol. Cell. Cardiol., 2003, 35: 577-593.
Mifsud et al., "Mapping long-range promoter contacts in human cells with high-resolution capture Hi-C," Nat. Genet., 2015, 47: 598-606.
Miralles et al., "Actin dynamics control SRF activity by regulation of its coactivator MAL," Cell, 2003, 113: 329-342.
Miroshnikova et al., "Emerging roles of mechanical forces in chromatin regulation," J. Cell Sci., 2017, 130: 2243-2250.
Molineros et al., "Mechanistic Characterization of Variants Identifies an hnRNP-K-Regulated Transcriptional Enhancer Contributing to SLE Susceptibility," Front. Immunol., 2019, 10: 1066.
Moore et al., "Regulation and Relevance of Myofibroblast Responses in Idiopathic Pulmonary Fibrosis," Curr. Pathobiol. Rep., 2013, 1: 199-208.
Morrison et al., "Stem cells and niches: mechanisms that promote stem cell maintenance throughout life," Cell, 2008, 132: 598-611.
Muerdter et al., "Resolving systematic errors in widely used enhancer activity assays in human cells," Nat. Methods, 2018, 15: 141-149.
Murthy et al., "Human distal lung maps and lineage hierarchies reveal a bipotent progenitor," Nature, 2022, 604(7904): 111-119.
Namavar et al., "Classification, diagnosis and potential mechanisms in pontocerebellar hypoplasia," Orphanet J. Rare Dis., 2011, 6: 50.
Nava et al., "Heterochromatin-Driven Nuclear Softening Protects the Genome against Mechanical Stress-Induced Damage," Cell, 2020, 181: 800-817.e22.
Noonan et al., "Genomics of long-range regulatory elements," Annu. Rev. Genomics Hum. Genet., 2010, 11: 1-23.
Oliver-De La Cruz et al., "Substrate mechanics controls adipogenesis through YAP phosphorylation by dictating cell spreading," Biomaterials, 2019, 205: 64-80.
Open2C et al., "Pairtools: From sequencing data to chromosome contacts, " PLoS Comput. Biol., 2024, 20: e1012164.
Paoli et al., "Anoikis molecular pathways and its role in cancer progression," Biochim. Biophys. Acta, 2013, 1833: 3481-3498.
Parker et al., "Fibrotic extracellular matrix activates a profibrotic positive feedback loop," J. Clin. Invest., 2014, 124: 1622-1635.
Paszek et al., "Tensional homeostasis and the malignant phenotype," Cancer Cell, 2005, 8: 241-254.
Paulmann et al., "The OTUD6B-LIN28B-MYC axis determines the proliferative state in multiple myeloma," EMBO J., 2022, 41: e110871.
Pelham Jr et al., "Cell locomotion and focal adhesions are regulated by substrate flexibility," Proc. Natl. Acad. Sci. U.S.A., 1997, 94: 13661-13665.
Piccolo et al., "The biology of YAP/TAZ: hippo signaling and beyond, " Physiol. Rev., 2014, 94: 1287-1312.
Plikus et al., "Fibroblasts: Origins, definitions, and functions in health and disease," Cell, 2021, 184: 3852-3872.
Quinlan et al., "BEDTools: a flexible suite of utilities for comparing genomic features," Bioinformatics, 2010, 26: 841-842.
Quinlan, "BEDTools: The Swiss-Army Tool for Genome Feature Analysis," Curr. Protoc. Bioinformatics, 2014, 47: 11.12.1-34.
Ramírez et al., "deepTools: a flexible platform for exploring deep-sequencing data," Nucleic Acids Res., 2014, 42: W187-91.
Ritterhoff et al., "The RanBP2/RanGAP1*SUMO1/Ubc9 SUMO E3 ligase is a disassembly machine for Crm1-dependent nuclear export complexes," Nat. Commun., 2016, 7: 11482.
Robinson et al., "edgeR: a Bioconductor package for differential expression analysis of digital gene expression data," Bioinformatics, 2010, 26: 139-140.
Royer et al., "Mechanobiology in the Comorbidities of Ehlers Danlos Syndrome," Front Cell Dev Biol, 2022, 10: 874840.
Sanson et al., "Optimized libraries for CRISPR-Cas9 genetic screens with multiple modalities," Nat. Commun., 2018, 9: 1-15.
Sanyal et al., "The long-range interaction landscape of gene promoters," Nature, 2012, 489: 109-113.
Schmelzle et al., "Functional role and oncogene-regulated expression of the BH3-only factor Bmf in mammary epithelial anoikis and morphogenesis," Proc. Natl. Acad. Sci. U.S.A., 2007, 104: 3787-3792.
Seo et al., "RNAi-based functional selection identifies novel cell migration determinants dependent on PI3K and AKT pathways," Nat. Commun., 2014, 5: 5217.
Simeonov et al., "Discovery of stimulation-responsive immune enhancers with CRISPR activation," Nature, 2017, 549: 111-115.
Sollis et al., "The NHGRI-EBI GWAS Catalog: knowledgebase and deposition resource," Nucleic Acids Res., 2023, 51: D977-D985.
Song et al., "β-catenin induces A549 alveolar epithelial cell mesenchymal transition during pulmonary fibrosis," Mol. Med. Rep., 2015, 11: 2703-2710.
Stowers et al., "Matrix stiffness induces a tumorigenic phenotype in mammary epithelium through changes in chromatin accessibility," Nat Biomed Eng, 2019, 3: 1009-1019.
Stuart et al., "Comprehensive Integration of Single-Cell Data," Cell, 2019, 177: 1888-1902.e21.
Sun et al., "Effects of Matrix Stiffness on the Morphology, Adhesion, Proliferation and Osteogenic Differentiation of Mesenchymal Stem Cells," Int. J. Med. Sci., 2018, 15: 257-268.
Sun et al., "Force-induced gene up-regulation does not follow the weak power law but depends on H3K9 demethylation," Sci Adv, 2020, 6: eaay9095.
Swift et al., "Nuclear lamin-A scales with tissue stiffness and enhances matrix-directed differentiation," Science, 2013, 341: 1240104.
Tajik et al., "Transcription upregulation via force-induced direct stretching of chromatin," Nat. Mater., 2016, 15: 1287-1296.
Thakore et al., "Highly specific epigenome editing by CRISPR-Cas9 repressors for silencing of distal regulatory elements," Nat. Methods, 2015, 12: 1143-1149.
Torrungruang et al., "DNA binding and gene activation properties of the Nmp4 nuclear matrix transcription factors," J. Biol. Chem., 2002, 277: 16153-16159.
Tycko et al., "Mitigation of off-target toxicity in CRISPR-Cas9 screens for essential non-coding elements," Nat. Commun., 2019, 10: 4063.
Vartiainen et al., "Nuclear actin regulates dynamic subcellular localization and activity of the SRF cofactor MAL," Science, 2007, 316: 1749-1752.
Vicente-Manzanares et al., "Non-muscle myosin II takes centre stage in cell adhesion and migration" Nat. Rev. Mol. Cell Biol., 2009, 10: 778-790.

(56) References Cited

OTHER PUBLICATIONS

Vierbuchen et al., "AP-1 Transcription Factors and the BAF Complex Mediate Signal-Dependent Enhancer Selection," Mol. Cell, 2017, 68: 1067-1082.e12.
Vishwanath et al., "Mechanisms of aortic carboxypeptidase-like protein secretion and identification of an intracellularly retained variant associated with Ehlers-Danlos syndrome," J. Biol. Chem., 2020, 295: 9725-9735.
Wei et al., "HiCAR is a robust and sensitive method to analyze open-chromatin-associated genome organization," Mol. Cell, 2022, 82: 1225-1238.e6.
Wells, "Tissue mechanics and fibrosis," Biochim. Biophys. Acta, 2013, 1832: 884-890.
Witkowski et al., "Conversion of a β-Ketoacyl Synthase to a Malonyl Decarboxylase by Replacement of the Active-Site Cysteine with Glutamine," Biochemistry, 1999, 38: 11643-11650.
Yan et al., "Zinc finger protein 384 enhances colorectal cancer metastasis by upregulating MMP2," Oncol. Rep., 2022, 47.
Yao et al., "The ENCODE4 Consortium, Multi-center integrated analysis of non-coding CRISPR screens," https://doi.org/10.1101/2022.12.21.520137, posted Dec. 22, 2022.
Yu et al., "ChIPseeker: an R/Bioconductor package for ChIP peak annotation, comparison and visualization," Bioinformatics, 2015, 31: 2382-2383.
Zanconato et al., "Genome-wide association between YAP/TAZ/TEAD and AP-1 at enhancers drives oncogenic growth," Nat. Cell Biol., 2015, 17: 1218-1227.
Zhang et al., "BAALC-AS1/G3BP2/c-Myc feedback loop promotes cell proliferation in esophageal squamous cell carcinoma," Cancer Commun., 2021, 41: 240-257.
Zhang et al., "Model-based analysis of ChIP-Seq (MACS)," Genome Biol., 2008, 9: R137.
Zhang et al., "The matricellular protein Cyr61 is a key mediator of platelet-derived growth factor-induced cell migration," J. Biol. Chem., 2015, 290: 8232-8242.
Zhao et al., "Cell detachment activates the Hippo pathway via cytoskeleton reorganization to induce anoikis," Genes Dev., 2012, 26: 54-68.
Zhao et al., "Substrate stiffness regulated migration and angiogenesis potential of A549 cells and HUVECs," J. Cell. Physiol, 2018, 233: 3407-3417.
Zhao et al., "TEAD mediates YAP-dependent gene induction and growth control," Genes Dev., 2008, 22: 1962-1971.
Zhou et al., "Novel identified associations of RGS1 and RASGRP1 variants in IgA Nephropathy," Sci. Rep., 2016, 6: 35781.
United States Patent Office Action for U.S. Appl. No. 17/603,243 dated Jan. 30, 2025 (13 pages).
United States Patent Office Action for U.S. Appl. No. 16/322,234 dated Feb. 24, 2025 (19 pages).
Ahern, "Biochemical, Reagents Kits Offer Scientists Good Return on Investment," The Scientist Magazine, (accessed at https://www.the-scientist.com/technology/biochemical-reagents-kits-offer-scientists-good-return-on-investment-58425 on Dec. 14, 2023) (Year: 1995).
Bennett et al., "Detection of mutations in the dystrophin gene via automated DHPLC screening and direct sequencing," BMC Genet, 2001, 2: 17.
Bikard et al., "Programmable repression and activation of bacterial gene expression using an engineered CRISPR-Cas system," Nucleic Acids Research, 2013, 41(15): 7429-7437.
Echigoya et al., "Multiple Exon Skipping in the Duchenne Muscular Dystrophy Hot Spots: Prospects and Challenges," J Pers Med, 2018, 8(4): 41.
Jangid et al., "Biodirectional promoters exhibit characteristic chromatin modification signature associated with transcription elongation in both sense and antisense directions," BMC Genomics, 2018, 19: 313.
Mitsunobu et al., "Beyond Native Cas9: Manipulating Genomic Information and Function," Trends in Biotechnology, 2017, 35(10): 986-996.
NCBI Reference Sequence: NG_012232.1, "*Homo sapiens* dystrophin (DMD), RefSeqGene (LRG_199) on chromosome X," National Library of Medicine (accessed at: https://www.ncbi.nlm.nih.gov/nuccore/NG_012232.1/) (Year: 1993).
NCBI Reference Sequence: WP_038431314.1 "type II CRISPR RNA-guided endonuclease Cas9 [*Streptococcus pyogenes*]," National Library of Medicine (accessed at: https:// www.ncbi.nlm.nih.gov/protein/WP_038431314.1) (Year: 2005).
Pinder et al., "Nuclear domain 'knock-in' screen for the evaluation and identification of small molecule enhancers of CRISPR-based genome editing," Nucleic Acids Research, 2015,43(19): 9379-9392.
Shimo et al., "A novel human muscle cell model of Duchenne muscular dystrophy created by CRISPR/Cas9 and evaluation of antisense-mediated exon skipping," Journal of Human Genetics, 2018, 63: 365-375.
Tremblay et al., "Gene Editing for Duchenne Muscular Dystrophy Using the CRISPR/Cas9 Technology: The Importance of Fine-tuning the Approach," Molecular Therapy, The Journal of the American Society of Gene Therapy, 2016, 24(11): 1888-1889.
Warnock et al., "Introduction to Viral Vectors," Viral Vectors for Gene Therapy: Methods in Molecular Biology, 2011, vol. 737, Chapter 1, 25 pages.
International Search Report and Written Opinion for Application No. PCT/US2024/025594 dated Nov. 25, 2024 (14 pages).
International Search Report and Written Opinion for Application No. PCT/US2024/027546 dated Nov. 26, 2024 (16 pages).
U.S. Appl. No. 18/957,197, filed Nov. 22, 2024.
U.S. Appl. No. 19/104,624, filed Feb. 18, 2025.
International Search Report and Written Opinion for Application No. PCT/US2024/042821 dated Apr. 2, 2025 (12 pages).
International Search Report and Written Opinion for Application No. PCT/US2024/044668 dated May 7, 2025 (15 pages).
Lee et al., "Synthetically modified guide RNA and donor DNA are a versatile platform for CRISPR-Cas9 engineering," eLife, 2017, 6: e25312.
Kwon et al., "626. Directing Skeletal Myogenic Progenitor Cell Lineage Specification with CRISPR/Cas9 Transcriptional Activators," Molecular Therapy, 2016, 24: S248.
Jiang et al., "CRISPR-Cas9 Structures and Mechanisms," Annu Rev Biophys, 2017, 46: 505-529.
Mathias et al., "Unraveling Immune-Related IncRNAs in Breast Cancer Molecular Subtypes," Front. Oncol., 2021, 11: 692170.
Cui et al., "Long non-coding RNA LINC02613 is a prognostic biomarker for breast cancer and correlates with the cell cycle and immune infiltration based on TCGA data," Translational Cancer Research, 2022, 11(4): 615-628.
Hori et al., "Control of Regulatory T Cell Development by the Transcription Factor Foxp3," Science, 2003, 299: 1057-1061.
Reiner et al., "Epigenetics meets GPCR: inhibition of histone H3 methyltransferase (G9a) and histamine H3 receptor for Prader-Willi Syndrome," Scientific Reports, 2020, 10: 13558.
Burr et al., "Mitochondrial Protein Lipoylation and the 2-Oxoglutarate Dehydrogenase Complex Controls HIF1α Stability in Aerobic Conditions," Cell Metab, 2016, 24(5): 740-752.
Leandro et al., "DHTKD1 and OGDH display in vivo substrate overlap and form a hybrid ketoacid dehydrogenase complex," bioRxiv preprint version posted May 22, 2019.
Bailey et al., "ABHD11 maintains 2-oxoglutarate metabolism by preserving functional lipoylation of the 2-oxoglutarate dehydrogenase complex," Nature Communications, 2020, 11: 4046.
International Search Report and Written Opinion for Application No. PCT/US2024/057925 dated Jun. 25, 2025 (15 pages).
United States Patent Office Action for U.S. Appl. No. 16/322,234 dated Aug. 6, 2025 (20 pages).
United States Patent Office Action for U.S. Appl. No. 17/603,243 dated Aug. 4, 2025 (17 pages).
European Patent Office Action for Application No. 17783164.1 dated Jul. 16, 2025 (6 pages).

* cited by examiner

PCSK9 ELISA

CRISPR/CAS9-BASED REPRESSORS FOR SILENCING GENE TARGETS IN VIVO AND METHODS OF USE

CROSS REFERENCE TO RELATED APPLICATIONS

This application is a continuation of U.S. patent application Ser. No. 16/093,272, filed Oct. 12, 2018, which is the national stage filing under 35 U.S.C. § 371 of International Patent Application No. PCT/US2017/027490, filed Apr. 13, 2017, which claims the benefit of U.S. Provisional Application No. 62/321,947, filed Apr. 13, 2016, and U.S. Provisional Application No. 62/369,248, filed Aug. 1, 2016, the entire contents of each of which are hereby incorporated by reference.

STATEMENT OF GOVERNMENT INTEREST

This invention was made with Government support under Federal Grant Nos. 1 R01 DA036865 and 1 DP2 OD008586 awarded by the NIH. The Government has certain rights to this invention.

SEQUENCE LISTING

The application includes a Sequence Listing which has been submitted electronically in XML format and is hereby incorporated by reference in its entirety. Said XML Sequence Listing, created on Apr. 26, 2024, is named 028193-9264-US05 Sequence Listing.xml, and is 104,406 bytes in size.

BACKGROUND

Engineered DNA-binding proteins that can be customized to target any gene in mammalian cells have enabled rapid advances in biomedical research and are a promising platform for gene therapies. The RNA-guided CRISPR-Cas9 system has emerged as a promising platform for programmable targeted gene regulation. Fusion of catalytically inactive, "dead" Cas9 (dCas9) to the Kruppel-associated box (KRAB) domain generates a synthetic repressor capable of highly specific and potent silencing of target genes in cell culture experiments. However, a technology to deliver CRISPR/Cas9-based gene repressors in vivo has not been developed. Adeno-associated virus (AAV) vectors have been proposed for gene delivery of CRISPR-Cas9 components for in vivo studies and therapeutic applications. AAV vectors provide stable gene expression with low risk of mutagenic integration events. AAV vectors can be engineered to target tissues of interest in vivo, and are already in use in humans in clinical trials. However, gene delivery of *S. pyogenes* dCas9-KRAB in vivo is challenging because the size of the *S. pyogenes* dCas9 and KRAB domain fusion exceeds the packaging limits of standard AAV vectors.

SUMMARY

In an aspect, the disclosure features a method of modulating expression of a gene, in vivo, in a subject comprising administering to, or providing in, the subject:

(a) (i) a fusion molecule comprising a sequence comprising a dCas9 molecule fused to a modulator of gene expression; or (ii) a nucleic acid that encodes a fusion molecule comprising a sequence comprising a dCas9 molecule fused to a modulator of gene expression; and (b) (i) a gRNA which targets the fusion molecule to the gene; or (ii) a nucleic acid that encodes a gRNA which targets the fusion molecule to the gene, in an amount sufficient to modulate expression of the gene.

In an embodiment, the method comprises administering to, or provided in, the subject any of: (a)(ii) and (b)(ii), (a)(i) and (b)(i), (a)(i) and (b)(ii), or (a)(ii) and (b)(i).

In an embodiment, the method comprises administering to, or provided in, the subject:

(a)(ii) a nucleic acid that encodes a fusion molecule comprising a sequence comprising a dCas9 molecule fused to a modulator of gene expression; and (b)(ii) a nucleic acid that encodes a gRNA which targets the fusion molecule to the gene.

In an embodiment, the nucleic acid of (a)(ii) comprises DNA. In an embodiment, the nucleic acid of (b)(ii) comprises DNA. In an embodiment, the nucleic acid of (a)(ii) comprises RNA. In an embodiment, the nucleic acid of (b)(ii) comprises RNA.

In an embodiment, the method comprises one or both of (a) and (b) are packaged in a viral vector. In an embodiment, (a) is packaged in a viral vector. In an embodiment, (b) is packaged in a viral vector. In an embodiment, (a) and (b) are packaged in the same viral vector.

In an embodiment, the viral vector comprises an AAV vector. In an embodiment, the viral vector comprises a lentiviral vector.

In an embodiment, (a) is packaged in a first viral vector and (b) is packaged in a second viral vector. In an embodiment, the first viral vector comprises an AAV vector and the second viral vector comprises an AAV vector.

In an embodiment, the dCas9 molecule comprises a gRNA binding domain of a Cas9 molecule. In an embodiment, the dCas9 molecule comprises one, two or all of: a Rec domain, a bridge helix domain, or a PAM interacting domain, of a Cas9 molecule.

In an embodiment, the dCas9 molecule is a mutant of a wild-type Cas9 molecule, e.g., in which the Cas9 nuclease activity is inactivated. In an embodiment, the dCas9 molecule comprises a mutation that inactivates a Cas9 nuclease activity, e.g., a mutation in a DNA-cleavage domain of a Cas9 molecule. In an embodiment, the dCas9 molecule comprises a mutation that inactivates a Cas9 nuclease activity, e.g., a mutation in a RuvC domain and/or a mutation in a HNH domain.

In an embodiment, the dCas9 molecule comprises a *Staphylococcus aureus* dCas9 molecule, a *Streptococcus pyogenes* dCas9 molecule, a *Campylobacter jejuni* dCas9 molecule, a *Corynebacterium diphtheria* dCas9 molecule, a *Eubacterium ventriosum* dCas9 molecule, a *Streptococcus pasteurianus* dCas9 molecule, a *Lactobacillus farciminis* dCas9 molecule, a *Sphaerochaeta globus* dCas9 molecule, an *Azospirillum* (e.g., strain B510) dCas9 molecule, a *Gluconacetobacter diazotrophicus* dCas9 molecule, a *Neisseria cinerea* dCas9 molecule, a *Roseburia intestinalis* dCas9 molecule, a *Parvibaculum lavamentivorans* dCas9 molecule, a *Nitratifractor salsuginis* (e.g., strain DSM 16511) dCas9 molecule, a *Campylobacter lari* (e.g., strain CF89-12) dCas9 molecule, or a *Streptococcus thermophilus* (e.g., strain LMD-9) dCas9 molecule.

In an embodiment, the dCas9 molecule comprises an *S. aureus* dCas9 molecule, e.g., comprising an *S. aureus* dCas9 sequence described herein.

In an embodiment, the *S. aureus* dCas9 molecule comprises a mutation at an amino acid position, corresponding to position 10, 580, or both (e.g., D10A, N580A, or both), relative to a wild-type *S. aureus* dCas9 molecule, numbered according to SEQ ID NO: 25.

In an embodiment, the *S. aureus* dCas9 molecule comprises the amino acid sequence of SEQ ID NO: 35 or 36, a sequence substantially identical (e.g., at least 80%, 85%, 90%, 92%, 95%, 97%, 98%, 99% or higher identical) to SEQ ID NO: 35 or 36, or a sequence having one, two, three, four, five or more changes, e.g., amino acid substitutions, insertions, or deletions, relative to SEQ ID NO: 35 or 36, or any fragment thereof.

In an embodiment, the dCas9 molecule comprises an *S. pyogenes* dCas9 molecule, e.g., comprising an *S. pyogenes* dCas9 sequence described herein.

In an embodiment, the *S. pyogenes* dCas9 molecule comprises a mutation at an amino acid position, corresponding to position 10, 840, or both (e.g., D10A, H840A, or both), relative to a wild-type *S. pyogenes* dCas9 molecule, numbered according to SEQ ID NO: 24.

In an embodiment, the dCas9 molecule is less than 1400, 1300, 1200, 1100, 1000, 900, 800, 700, 600, or 500 amino acids in length. In an embodiment, the dCas9 molecule is 500-1300, 600-1200, 700-1100, 800-1000, 500-1200, 500-1000, 500-800, 500-600, 1000-1200, 800-1200, or 600-1200 amino acids in length.

In an embodiment, the dCas9 molecule has a size that is less than 90%, 80%, 70%, 60%, 50%, 40%, or 30% of the size of a wild-type Cas9 molecule, e.g., a wild-type *S. pyogenes* Cas9 molecule or a wild-type *S. aureus* dCas9 molecule.

In an embodiment, the modulator of gene expression comprises a modulator of gene expression described herein.

In an embodiment, the modulator of gene expression comprises a repressor of gene expression, e.g., a Kruppel associated box (KRAB) molecule, an mSin3 interaction domain (SID) molecule, four concatenated mSin3 interaction domains (SID4X), MAX-interacting protein 1 (MXI1), or any fragment thereof.

In an embodiment, the modulator of gene expression comprises a Kruppel associated box (KRAB) molecule comprising the sequence of SEQ ID NO: 34, a sequence substantially identical (e.g., at least 80%, 85%, 90%, 92%, 95%, 97%, 98%, 99% or higher identical) to SEQ ID NO: 34, or a sequence having one, two, three, four, five or more changes, e.g., amino acid substitutions, insertions, or deletions, relative to SEQ ID NO: 34, or any fragment thereof.

In an embodiment, the modulator of gene expression comprises an activator of gene expression, e.g., a VP16 transcription activation domain, a VP64 transcriptional activation domain, a p65 activation domain, an Epstein-Barr virus R transactivator Rta molecule, a VP64-p65-Rta fusion (VPR), Ldb1 self-association domain, or any fragment thereof.

In an embodiment, the modulator of gene expression comprises a modulator of epigenetic modification, e.g., a histone acetyltransferase (e.g., p300 catalytic domain), a histone deacetylase, a histone methyltransferase (e.g., SUV39H1 or G9a (EHMT2)), a histone demethylase (e.g., Lys-specific histone demethylase 1 (LSD1)), a DNA methyltransferase (e.g., DNMT3a or DNMT3a-DNMT3L), a DNA demethylase (e.g., TET1 catalytic domain or TDG), or fragment thereof.

In an embodiment, the modulator of gene expression is fused to the C-terminus, N-terminus, or both, of the dCas9 molecule.

In an embodiment, the modulator of gene expression is fused to the dCas9 molecule directly. In an embodiment, the modulator of gene expression is fused to the dCas9 molecule indirectly, e.g., via a non-modulator or a linker, or a second modulator.

In an embodiment, a plurality of modulators of gene expression, e.g., two or more identical, substantially identical, or different modulators, are fused to the dCas9 molecule.

In an embodiment, the fusion molecule further comprises a nuclear localization sequence.

In an embodiment, one or more nuclear localization sequences are fused to the C-terminus, N-terminus, or both, of the dCas9 molecule, e.g., directly or indirectly, e.g., via a linker.

In an embodiment, the one or more nuclear localization sequences comprise the amino acid sequence of SEQ ID NO: 37 or 38, a sequence substantially identical (e.g., at least 80%, 85%, 90%, 92%, 95%, 97%, 98%, 99% or higher identical) to SEQ ID NO: 37 or 38, or a sequence having one, two, three, four, five or more changes, e.g., amino acid substitutions, insertions, or deletions, relative to SEQ ID NO: 37 or 38, or any fragment thereof.

In an embodiment, the fusion molecule comprises the amino acid sequence of SEQ ID NO: 39, 40, or 41, a sequence substantially identical (e.g., at least 80%, 85%, 90%, 92%, 95%, 97%, 98%, 99% or higher identical) to SEQ ID NO: 39, 40, or 41, or a sequence having one, two, three, four, five or more changes, e.g., amino acid substitutions, insertions, or deletions, relative to SEQ ID NO: 39, 40, or 41, or any fragment thereof.

In an embodiment, the nucleic acid that encodes the fusion molecule comprises the sequence of SEQ ID NO: 23, a sequence substantially identical (e.g., at least 80%, 85%, 90%, 92%, 95%, 97%, 98%, 99% or higher identical) to SEQ ID NO: 23, or a sequence having one, two, three, four, five or more changes, e.g., substitutions, insertions, or deletions, relative to SEQ ID NO: 23, or any fragment thereof.

In an embodiment, the gRNA comprises a unimolecular gRNA. In an embodiment, the gRNA comprises a bimolecular gRNA.

In an embodiment, the gRNA comprises a gRNA sequence described herein.

In an embodiment, gene expression is modulated in a cell, tissue, or organ described herein, e.g., Table 2 or 3. In an embodiment, gene expression is modulated in the liver.

In an embodiment, the modulation is sufficient to alter a function of the gene, or a symptom of a disorder associated with the gene, as described herein, e.g., in Table 2 or 3.

In an embodiment, the modulation comprises modulation of transcription. In an embodiment, the modulation comprises down-regulation of transcription. In an embodiment, the modulation comprises up-regulation of transcription.

In an embodiment, the modulation comprises modulating the temporal pattern of expression of the gene. In an embodiment, the modulation comprises modulating the spatial pattern of expression of the gene.

In an embodiment, the modulation comprises modulating a post-transcriptional or co-transcriptional modification, e.g., splicing, 5' capping, 3' cleavage, 3' polyadenylation, or RNA export.

In an embodiment, the modulation comprises modulating the expression of an isoform, e.g., an increase or decrease in the expression of an isoform, the increase or decrease in the expression of a first isoform over a second isoform.

In an embodiment, the modulation comprises modulating chromatin structure, e.g., increasing or decreasing methylation, acetylation, phosphorylation, or ubiquitination, e.g., at a preselected site, or altering the spatial pattern, cell specificity, or temporal occurrence of methylation, acetylation, phosphorylation, or ubiquitination.

In an embodiment, the modulation comprises modulating a post-translational modification (e.g., indirectly), e.g., glycosylation, lipidation, acetylation, phosphorylation, amidation, hydroxylation, methylation, ubiquitination, sulfation, nitrosylation, or proteolysis.

In an embodiment, the modulation does not comprise cleaving the subject's DNA.

In an embodiment, the modulation comprises an inducible modulation.

In an embodiment, the gene is selected from Table 2, optionally wherein the method down-regulates the expression of the gene.

In an embodiment, the gene is selected from Table 3, optionally wherein the method up-regulates the expression of the gene.

In an embodiment, the gene comprises PCSK9.

In an embodiment, the dCas9 molecule does not cleave the genome of the subject.

In another aspect, the disclosure features a method of modulating expression of a gene, in vivo, in a subject comprising administering to, or providing in, the subject:

(a)(ii) a nucleic acid that encodes a fusion molecule comprising a sequence comprising an *S. aureus* dCas9 molecule fused to a KRAB molecule; and (b)(ii) a nucleic acid that encodes a gRNA which targets the fusion molecule to the gene, and wherein one or both of (a)(i) and (b)(ii) are packaged in an AAV vector.

In an embodiment, the fusion molecule comprises a fusion molecule described herein.

In an embodiment, the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

In an embodiment, the gRNA comprises a gRNA sequence described herein.

In an embodiment, the gene is selected from Table 2 or 3. In an embodiment, the gene comprises PCSK9.

In an embodiment, (a)(ii) and (b)(ii) are packaged in different AAV vectors. In an embodiment, (a)(ii) and (b)(ii) are packaged in the same AAV vector.

In another aspect, the disclosure features a pharmaceutical composition, or unit dosage form, comprising, in an amount sufficient for modulating a gene in a human subject, or in an amount sufficient for a therapeutic effect in a human subject, (a)(ii) a nucleic acid that encodes a fusion molecule comprising a sequence comprising a dCas9 molecule, e.g., an *S. aureus* dCas9 molecule, fused to a modulator of gene expression; and/or (b)(ii) a nucleic acid that encodes a gRNA which targets the fusion molecule to the gene, wherein one or both of (a)(ii) and (b)(ii) are packaged in a viral vector.

In an embodiment, the fusion molecule comprises a fusion molecule described herein.

In an embodiment, the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

In an embodiment, the gRNA comprises a gRNA sequence described herein.

In an embodiment, the gene is selected from Table 2 or 3. In an embodiment, the gene comprises PCSK9.

In an embodiment, one or both of (a)(ii) and (b)(ii) are packaged in an AAV vector.

In an embodiment, (a)(ii) and (b)(ii) are packaged in the same viral vector, e.g., an AAV vector. In an embodiment, (a)(ii) and (b)(ii) are packaged in different viral vectors, e.g., AAV vectors.

In an embodiment, the viral vector (e.g., AAV vector) comprising (a)(ii), and the viral vector (e.g., AAV vector) comprising (b)(ii), are provided in separate containers.

In an embodiment, the viral vector (e.g., AAV vector) comprising (a)(ii) and the viral vector (e.g., AAV vector) comprising (b)(ii), are provided in the same container.

In an embodiment, the pharmaceutical composition, or unit dosage form, is formulated for administration, e.g., oral, parenteral, sublingual, transdermal, rectal, transmucosal, topical, intrapleural, intravenous, intraarterial, intraperitoneal, subcutaneous, intramuscular, intranasal intrathecal, or intraarticular administration, or administration via inhalation or via buccal administration, or any combination thereof, to the subject.

In an embodiment, the pharmaceutical composition, or unit dosage form, is formulated for intravenous administration to the subject.

In an embodiment, the pharmaceutical composition, or unit dosage form, is disposed in a device suitable for administration, e.g., oral, parenteral, sublingual, transdermal, rectal, transmucosal, topical, intrapleural, intravenous, intraarterial, intraperitoneal, subcutaneous, intramuscular, intranasal intrathecal, or intraarticular administration, or administration via inhalation or via buccal administration, or any combination thereof, to the subject.

In an embodiment, the pharmaceutical composition, or unit dosage form, is disposed in a device suitable for intravenous administration to the subject.

In an embodiment, the pharmaceutical composition, or unit dosage form, is disposed in a volume of at least 1, 2, 5, 10, 15, 20, 25, 30, 40, 50, 60, 70, 80, 90, 100, 150, 200, 250, 300, 400, or 500 ml.

In an embodiment, the nucleic acid of (a)(ii) comprises DNA. In an embodiment, the nucleic acid of (b)(ii) comprises DNA. In an embodiment, the nucleic acid of (a)(ii) comprises RNA. In an embodiment, the nucleic acid of (b)(ii) comprises RNA.

In an embodiment, the dCas9 molecule comprises a gRNA binding domain of a Cas9 molecule.

In an embodiment, the dCas9 molecule comprises one, two or all of: a Rec domain, a bridge helix domain, or a PAM interacting domain, of a Cas9 molecule. In an embodiment, the dCas9 molecule is a mutant of a wild-type Cas9 molecule, e.g., in which the Cas9 nuclease activity is inactivated. In an embodiment, the dCas9 molecule comprises a mutation that inactivates a Cas9 nuclease activity, e.g., a mutation in a DNA-cleavage domain of a Cas9 molecule. In an embodiment, the dCas9 molecule comprises a mutation that inactivates a Cas9 nuclease activity, e.g., a mutation in a RuvC domain and/or a mutation in a HNH domain.

In an embodiment, the dCas9 molecule comprises a *Staphylococcus aureus* dCas9 molecule, a *Streptococcus pyogenes* dCas9 molecule, a *Campylobacter jejuni* dCas9 molecule, a *Corynebacterium diphtheria* dCas9 molecule, a *Eubacterium ventriosum* dCas9 molecule, a *Streptococcus pasteurianus* dCas9 molecule, a *Lactobacillus farciminis* dCas9 molecule, a *Sphaerochaeta globus* dCas9 molecule, an *Azospirillum* (e.g., strain B510) dCas9 molecule, a *Gluconacetobacter diazotrophicus* dCas9 molecule, a *Neisseria cinerea* dCas9 molecule, a *Roseburia intestinalis* dCas9 molecule, a *Parvibaculum lavamentivorans* dCas9 molecule, a *Nitratifractor salsuginis* (e.g., strain DSM 16511) dCas9 molecule, a *Campylobacter lari* (e.g., strain CF89-12) dCas9 molecule, or a *Streptococcus thermophilus* (e.g., strain LMD-9) dCas9 molecule.

In an embodiment, the dCas9 molecule comprises an *S. aureus* dCas9 molecule, e.g., comprising an *S. aureus* dCas9 sequence described herein. In an embodiment, the *S. aureus* dCas9 molecule comprises a mutation at an amino acid position, corresponding to position 10, 580, or both (e.g., D10A, N580A, or both), relative to a wild-type *S. aureus* dCas9 molecule, numbered according to SEQ ID NO: 25.

In an embodiment, the *S. aureus* dCas9 molecule comprises the amino acid sequence of SEQ ID NO: 35 or 36, a sequence substantially identical (e.g., at least 80%, 85%, 90%, 92%, 95%, 97%, 98%, 99% or higher identical) to SEQ ID NO: 35 or 36, or a sequence having one, two, three, four, five or more changes, e.g., amino acid substitutions, insertions, or deletions, relative to SEQ ID NO: 35 or 36, or any fragment thereof.

In an embodiment, the dCas9 molecule comprises an *S. pyogenes* dCas9 molecule, e.g., comprising an *S. pyogenes* dCas9 sequence described herein. In an embodiment, the *S. pyogenes* dCas9 molecule comprises a mutation at an amino acid position, corresponding to position 10, 840, or both (e.g., D10A, H840A, or both), relative to a wild-type *S. pyogenes* dCas9 molecule, numbered according to SEQ ID NO: 24.

In an embodiment, the dCas9 molecule is less than 1400, 1300, 1200, 1100, 1000, 900, 800, 700, 600, or 500 amino acids in length.

In an embodiment, the dCas9 molecule is 500-1300, 600-1200, 700-1100, 800-1000, 500-1200, 500-1000, 500-800, 500-600, 1000-1200, 800-1200, or 600-1200 amino acids in length.

In an embodiment, the dCas9 molecule has a size that is less than 90%, 80%, 70%, 60%, 50%, 40%, or 30% of the size of a wild-type Cas9 molecule, e.g., a wild-type *S. pyogenes* Cas9 molecule or a wild-type *S. aureus* dCas9 molecule.

In an embodiment, modulator of gene expression comprises a modulator of gene expression described herein.

In an embodiment, modulator of gene expression comprises a KRAB molecule, e.g., comprising the sequence of SEQ ID NO: 34, a sequence substantially identical (e.g., at least 80%, 85%, 90%, 92%, 95%, 97%, 98%, 99% or higher identical) to SEQ ID NO: 34, or a sequence having one, two, three, four, five or more changes, e.g., amino acid substitutions, insertions, or deletions, relative to SEQ ID NO: 34, or any fragment thereof.

In an embodiment, the gRNA comprises a unimolecular gRNA. In an embodiment, the gRNA comprises a bimolecular gRNA. In an embodiment, the gRNA comprises a gRNA sequence described herein.

In an embodiment, gene expression is modulated in a cell, tissue, or organ described herein, e.g., Table 2 or 3. In an embodiment, gene expression is modulated in the liver.

In an embodiment, the modulation is sufficient to alter a function of the gene, or a symptom of a disorder associated with the gene, as described herein, e.g., in Table 2 or 3.

In an embodiment, the modulation comprises modulation of transcription. In an embodiment, the modulation comprises down-regulation of transcription. In an embodiment, the modulation comprises up-regulation of transcription.

In an embodiment, the modulation comprises modulating the temporal pattern of expression of the gene. In an embodiment, the modulation comprises modulating the spatial pattern of expression of the gene.

In an embodiment, the modulation comprises modulating a post-transcriptional or co-transcriptional modification, e.g., splicing, 5' capping, 3' cleavage, 3' polyadenylation, or RNA export.

In an embodiment, the modulation comprises modulating the expression of an isoform, e.g., an increase or decrease in the expression of an isoform, the increase or decrease in the expression of a first isoform over a second isoform.

In an embodiment, the modulation comprises modulating chromatin structure, e.g., increasing or decreasing methylation, acetylation, phosphorylation, or ubiquitination, e.g., at a preselected site, or altering the spatial pattern, cell specificity, or temporal occurrence of methylation, acetylation, phosphorylation, or ubiquitination.

In an embodiment, the modulation comprises modulating a post-translational modification (e.g., indirectly), e.g., glycosylation, lipidation, acetylation, phosphorylation, amidation, hydroxylation, methylation, ubiquitination, sulfation, nitrosylation, or proteolysis.

In an embodiment, the gene is selected from Table 2, optionally wherein the method down-regulates the expression of the gene. In an embodiment, the gene is selected from Table 3, optionally wherein the method up-regulates the expression of the gene. In an embodiment, the gene comprises PCSK9.

In an embodiment, the dCas9 does not cleave the genome of the subject.

In another aspect, the disclosure features a pharmaceutical composition, or unit dosage form, comprising, in an amount sufficient for modulating a gene in a human subject, or in an amount sufficient for a therapeutic effect in a human subject, (a)(ii) a nucleic acid that encodes a fusion molecule comprising a sequence comprising an *S. aureus* dCas9 molecule fused to a KRAB molecule; and/or (b)(ii) a nucleic acid that encodes a gRNA which targets the fusion molecule to the gene, wherein one or both of (a)(ii) and (b)(ii) are packaged in a viral vector.

In an embodiment, the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

In an embodiment, the gRNA comprises a gRNA sequence described herein.

In an embodiment, the gene is selected from Table 2 or 3. In an embodiment, the gene comprises PCSK9.

In an embodiment, one or both of (a)(ii) and (b)(ii) are packaged in an AAV vector.

In an embodiment, (a)(ii) and (b)(ii) are packaged in different AAV vectors. In an embodiment, (a)(ii) and (b)(ii) are packaged in the same AAV vector.

In another aspect, the disclosure features a viral vector comprising:

(a)(ii) a nucleic acid that encodes a fusion molecule comprising a sequence comprising a dCas9 molecule fused to a modulator of gene expression; and/or (b)(ii) a nucleic acid that encodes a gRNA which targets the fusion molecule to a gene.

In an embodiment, the viral vector is an AAV vector.

In an embodiment, the fusion molecule comprises a fusion molecule described herein.

In an embodiment, the dCas9 molecule comprises a dCas9 molecule described herein, e.g., an *S. aureus* dCas9 molecule.

In an embodiment, the modulator of gene expression comprises a modulator described herein.

In an embodiment, the gene is a gene described herein.

In an embodiment, the viral vector comprises:

(a)(ii) a nucleic acid that encodes a fusion molecule comprising a sequence comprising an *S. aureus* dCas9 molecule fused to a KRAB molecule; and (b)(ii) a nucleic acid that encodes a gRNA which targets the fusion molecule to PCSK9, wherein one or both of (a)(ii) and (b)(ii) are packaged in an AAV vector.

In an embodiment, the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

In an embodiment, the gRNA comprises a gRNA sequence described herein.

In an embodiment, the gene is selected from Table 2 or 3. In an embodiment, the gene comprises PCSK9.

In an embodiment, the disclosure features a method of treating a disorder, comprising administering to a subject:

(a)(ii) a nucleic acid that encodes a fusion molecule comprising a sequence comprising a dCas9 molecule fused to a modulator of gene expression; and (b)(ii) a nucleic acid that encodes a gRNA which targets the fusion molecule to a gene associated with the disorder, thereby treating the disorder.

In an embodiment, the disorder is selected from Table 2 or 3. In an embodiment, the gene is selected from Table 2 or 3.

In an embodiment, one or both of (a)(ii) and (b)(ii) are provided in an AAV vector.

In an embodiment, the fusion molecule comprises a fusion molecule described herein.

In an embodiment, the dCas9 molecule comprises a dCas9 molecule described herein.

In an embodiment, the modulator of gene expression comprises a modulator described herein.

In an embodiment, the gRNA comprises a gRNA sequence described herein.

In an embodiment, the disclosure features a method of treating a cardiovascular disease, comprising administering to a subject:

(a)(ii) a nucleic acid that encodes a fusion molecule comprising a sequence comprising a dCas9 molecule fused to a modulator of gene expression; and (b)(ii) a nucleic acid that encodes a gRNA which targets the fusion molecule to a PCSK9 gene, thereby treating the cardiovascular disease.

In an embodiment, the fusion molecule comprises a fusion molecule described herein.

In an embodiment, the dCas9 molecule comprises a dCas9 molecule described herein.

In an embodiment, the modulator of gene expression comprises a modulator described herein.

In an embodiment, the dCas9 molecule is an *S. aureus* dCas9 molecule.

In an embodiment, the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

In an embodiment, the gRNA comprises a gRNA sequence described herein.

In an embodiment, one or both of (a)(ii) and (b)(ii) are provided in an AAV vector.

In another aspect, the disclosure features:

(a) (i) a fusion molecule comprising a sequence comprising a dCas9 molecule fused to a modulator of gene expression; or (ii) a nucleic acid that encodes a fusion molecule comprising a sequence comprising a dCas9 molecule fused to a modulator of gene expression; and (b) (i) a gRNA which targets the fusion molecule to a gene; or (ii) a nucleic acid that encodes a gRNA which targets the fusion molecule to the gene, for use in a method of modulating expression of the gene, in vivo, in a subject.

In an embodiment, the fusion molecule comprises a fusion molecule described herein.

In an embodiment, the dCas9 molecule comprises a dCas9 molecule described herein.

In an embodiment, the modulator of gene expression comprises a modulator described herein.

In an embodiment, the gRNA comprises a gRNA sequence described herein.

In an embodiment, the gene is a gene described herein.

In some embodiments, the method comprises a method described herein.

In another aspect, the disclosure features:

(a) (i) a fusion molecule comprising a sequence comprising a dCas9 molecule fused to a modulator of gene expression; or (ii) a nucleic acid that encodes a fusion molecule comprising a sequence comprising a dCas9 molecule fused to a modulator of gene expression; and (b) (i) a gRNA which targets the fusion molecule to a gene; or (ii) a nucleic acid that encodes a gRNA which targets the fusion molecule to the gene, for use in a method of treating or preventing a disorder associated with the gene, in vivo, in a subject.

In an embodiment, the fusion molecule comprises a fusion molecule described herein.

In an embodiment, the dCas9 molecule comprises a dCas9 molecule described herein.

In an embodiment, the modulator of gene expression comprises a modulator described herein.

In an embodiment, the gRNA comprises a gRNA sequence described herein.

In an embodiment, the gene is a gene described herein.

In some embodiments, the disorder is a disorder described herein.

The present disclosure addresses these shortcomings by creating a modified programmable RNA-guided dCas9-based repressor for efficient packaging in AAV and in vivo gene regulation. This gene delivery system can be customized to target any endogenous gene by designing a new guide RNA molecule, enabling patent and stable gene repression in animal models and therapeutic use.

One aspect of the present disclosure provides a fusion protein comprising, consisting of, or consisting essentially of three heterologous polypeptide domains, wherein the first polypeptide domain comprises, consists of, or consists essentially of a dead Clustered Regularly Interspaced Short Palindromic Repeats associated (dCas) protein, the second polypeptide domain comprises, consists of, or consists essentially of a Kruppel-associated box (KRAB), and the polypeptide domain has an activity selected from the group consisting of transcription activation activity, transcription repression activity, transcription release factor activity, histone modification activity, nuclease activity, nucleic acid association activity, methylase activity, and demethylase activity.

Another aspect of the present disclosure provides a gene therapy construct comprising, consisting of, or consisting essentially of a polynucleotide encoding a fusion protein comprising three heterologous polypeptide domains, wherein the first polypeptide domain comprises, consists of, or consists essentially of a dead Clustered Regularly Interspaced Short Palindromic Repeats associated (dCas) protein, the second polypeptide domain comprises, consists of, or consists essentially of a Kruppel-associated box (KRAB), and the polypeptide domain has an activity selected from the group consisting of transcription activation activity, transcription repression activity, transcription release factor activity, histone modification activity, nuclease activity, nucleic acid association activity, methylase activity, and demethylase activity.

In some embodiments, the gene therapy construct comprises a vector system. In certain embodiments, the vector system comprises an AAV vector system.

In another embodiment, the gene therapy construct further comprises a first and second AAV inverted terminal repeat (ITR) sequence flanking the fusion protein.

Another aspect of the present disclosure provides a pharmaceutical composition comprising the gene therapy construct as described herein in a biocompatible pharmaceutical carrier.

In some embodiments, the Cas protein comprises Cas9.

In some embodiments, the gene therapy construct is designed for the targeted reduction of the PCSK9 gene. In some embodiments, the gene therapy construct is designed for the targeted reduction of the expression of the PCSK9 gene.

Another aspect of the present disclosure provides a method of suppressing the expression of a gene in a cell in vivo comprising, consisting of, or consisting essentially of administering to a cell a therapeutically effective amount of a gene therapy construct as described herein such that the gene expression is suppressed.

Another aspect of the present disclosure provides a method of suppressing a gene in vivo in a subject comprising, consisting of, or consisting essentially of administering to the subject a therapeutically effective amount of a gene therapy construct as described herein such that the gene is suppressed.

In some embodiments, the method is designed for the targeted reduction of the PCSK9 gene. In some embodiments, the method is designed for the targeted reduction of the expression of the PCSK9 gene.

Another aspect of the present disclosure provides a kit for the suppression of a gene in vivo comprising a gene therapy construct or pharmaceutical composition as described herein and instructions for use.

Yet another aspect of the present disclosure provides all that is described and illustrated herein.

BRIEF DESCRIPTION OF THE DRAWINGS

The foregoing aspects and other features of the disclosure are explained in the following description, taken in connection with the accompanying drawings, herein:

FIG. 1A is a schematic graph showing introducing inactivating mutations D10A and N580A into the cleavage domains of SaCas9 to generate a nuclease-null dSaCas9 DNA-binding domain. FIG. 1B is a schematic graph showing a single lentiviral vector with puromycin resistance used to express dSaCas9-KRAB and a U6-gRNA cassette for in vitro testing of dSaCas9 repressors. FIGS. 1C and 1D are bar graphs showing that multiple gRNAs against the synthetic CAG promoter effected potent repression of mRNA by qPCR (FIG. 1C) and protein via luciferase bioluminescence (FIG. 1D) in primary mouse fibroblasts expressing a CAG-luciferase reporter cassette. * indicates $p<0.05$ by Student's t-test compared to non-treated (NT) controls (n=2 independent experiments).

In FIG. 2A, eight gRNAs were designed to target the skeletal muscle DNase-hypersensitivity peak upstream of the transcription start site in the endogenous mouse Acvr2b gene locus. FIG. 2B is a bar graph showing that several single gRNAs effected strong repression of Acvr2b when delivered with dSaCas9-KRAB, compared to no lentivirus (No LV) and dSaCas9-KRAB only (No gRNA) controls. * indicates $p<0.05$ by Student's t-test compared to No LV controls (n=2 independent experiments).

FIG. 3A is a schematic showing a two-vector AAV9 expression system used to deliver dSaCas9-KRAB and Acvr2b gRNA intramuscularly to the right tibialis anterior muscle (TA) of adult wild-type mice. FIGS. 3B and 3D are bar graphs showing that dSaCas9 was efficiently expressed as measured by qPCR in the injected TA at 4 and 8 weeks, respectively, after injection. FIGS. 3C and 3E are bar graphs showing Acvr2b expression in the injected TA as assayed by qPCR at 4 and 8 weeks, respectively, post-AAV treatment. (n=3 mice, * indicates $p<0.05$ compared to PBS sham controls)

FIGS. 5A and 5C are bar graphs showing that intramuscular delivery of AAV9 expressing dSaCas9-KRAB results in efficient transgene expression in the liver and heart, respectively, 8 weeks after transduction in adult wild-type mice. FIGS. 5B and 5D are bar graphs showing that delivery of dSaCas9-KRAB with Acvr2b gRNA reduces target gene expression in the liver and heart, respectively, at 8 weeks after treatment. (n=3 mice, * indicates $p<0.05$ by Student's t-test compared to PBS sham controls)

In FIG. 10A, a nuclease-null *S. aureus* dCas9 DNA-binding domain was generated by introducing two catalytically inactivating mutations to the nuclease domains of Cas9. dCas9 derived from *S. aureus* was fused to a KRAB synthetic repressor to create a synthetic repressor for in vivo gene delivery. Dual vector (FIG. 10B) and single AAV vector (FIG. 10C) platforms were designed to efficiently express dCas9-KRAB and a custom guide RNA target molecule in vivo.

FIG. 11A is a schematic showing vectors used for targeted reduction of PCSK9 expression. *S. aureus* dCas9-KRAB (dCas9-KRAB) was targeted to the mouse PCSK9 gene and delivered in a dual-vector AAV system intravenously in C57Bl/6 wild-type 7-week old mice. At 2 weeks post-systemic treatment, circulating PCSK9 (FIG. 11B) and total cholesterol levels (FIG. 11C) are significantly repressed in the serum compared to sham PBS-injected controls and dCas9-KRAB-treated controls without a guide RNA (* indicates $p<0.05$ by Student's t-test compared to PBS sham controls, n=4 mice per condition).

FIG. 12A is a graph showing serum PCSK9 levels for the three treatment groups as measured by ELISA. FIG. 12B is a bar graph showing relative PCSK9 mRNA levels in the liver, as normalized to GAPDH mRNA levels, for the three treatment groups. FIG. 12C is a graph showing data from an RNA-Seq study comparing the RNA levels in the liver in the dSaCas9-KRAB and gRNA treatment group with those in the dSaCas9-KRAB alone treatment group. The dot representing PCSK9 RNA levels is labeled in the figure. FIGS. 12D and 12E are graphs showing the serum levels of total and LDL cholesterol for the three treatment groups as measured in a colorimetric assay.

FIGS. 13A and 13B are graphs showing serum PCSK9 levels for the three treatment groups as measured by ELISA. In FIG. 13B, the serum PCSK9 levels are normalized to the levels at Day 0. FIGS. 13C and 13D are graphs showing total cholesterol levels in the serum for the three treatment groups as measured in a colorimetric assay. In FIG. 13D, the serum total cholesterol levels are normalized to the levels at Day 0. FIGS. 13E and 13F are graphs showing LDL cholesterol levels in the serum for the three treatment groups as measured in a colorimetric assay. In FIG. 13F, the serum LDL cholesterol levels are normalized to the levels at Day 0.

FIG. 14A is a graph showing serum PCSK9 levels for the three treatment groups as measured by ELISA. FIGS. 14B and 14C are graphs showing total cholesterol levels in the serum.

DETAILED DESCRIPTION

Figures 1A, 1B, 1C, 1D:
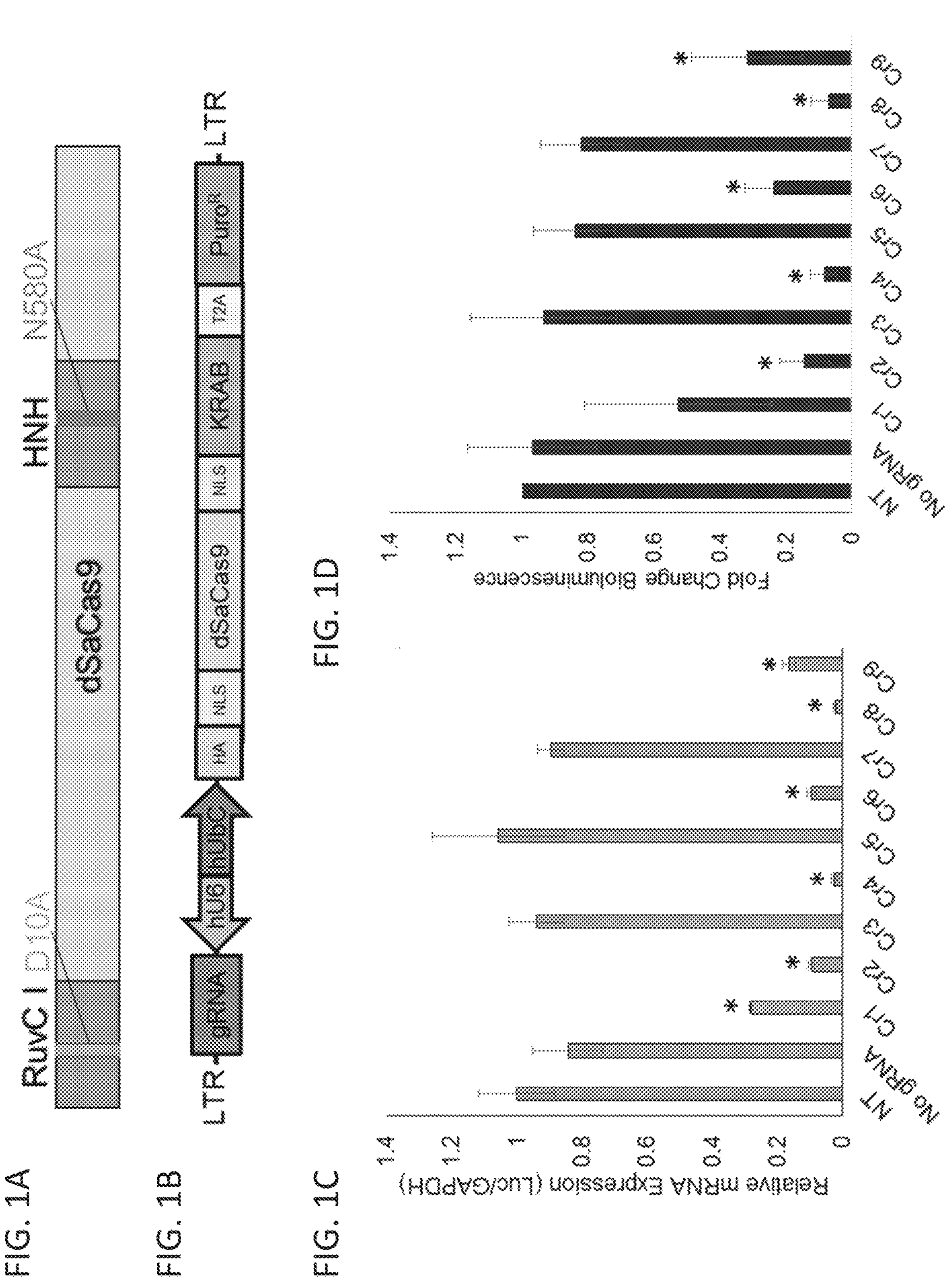
FIGS. 1A-1D are graphs showing the adaptation of SaCas9 for transcriptional repression.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

A. Definitions

As used herein, the term "coding sequence" or "encoding nucleic acid" means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

The term "complement" or "complementary" as used herein with reference to a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

The term "correcting", "genome editing" and "restoring" refers to changing a mutant gene that encodes a mutant protein, a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

As used herein, the term "donor DNA", "donor template" and "repair template" refers to a double-stranded DNA fragment or molecule that includes at least a portion of the gene of interest. The donor DNA may encode a full-functional protein or a partially-functional protein.

As used herein, the terms "frameshift" or "frameshift mutation" are used interchangeably and refer to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

As used herein, the term "functional" and "full-functional" describes a protein that has biological activity. A "functional gene" refers to a gene transcribed to mRNA, which is translated to a functional protein.

As used herein, the term "fusion protein" refers to a chimeric protein created through the covalent or non-covalent joining of two or more genes, directly or indirectly, that originally coded for separate proteins. In some embodiments, the translation of the fusion gene results in a single polypeptide with functional properties derived from each of the original proteins.

As used herein, the term "genetic construct" refers to the DNA or RNA molecules that comprise a nucleotide sequence that encodes a protein. The coding sequence includes initiation and termination signals operably linked to regulatory elements including a promoter and polyadenylation signal capable of directing expression in cells.

The term "Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the site specific nuclease, such as with a CRISPR/Cas9-based systems, then the cellular machinery will repair the break by homologous recombination, which is enhanced several orders of magnitude in the presence of DNA cleavage. When the homologous DNA piece is absent, nonhomologous end joining may take place instead.

The term "genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

The term "identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0. Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al, SIAM J. Applied Math. 48, 1073 (1988), herein incorporated by reference in their entirety.

As used herein, the terms "mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

The term "non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

The term "normal gene" as used herein refers to a gene that has not undergone a change, such as a loss, gain, or exchange of genetic material. The normal gene undergoes normal gene transmission and gene expression.

The term "nuclease mediated NHEJ" as used herein refers to NHEJ that is initiated after a nuclease, such as a cas9, cuts double stranded DNA.

As used herein, the term "nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

As used herein, the term "operably linked" means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

The term "partially-functional" as used herein describes a protein that is encoded by a mutant gene and has less biological activity than a functional protein but more than a non-functional protein. In one embodiment, a partially-functional protein shows a biological activity that is less than 95%, 90%, 85%, 80%, 75%, 70%, 65%, 60%, 55%, 50%, 45%, 40%, 35%, or 30% of that of a corresponding functional protein.

The term "premature stop codon" or "out-of-frame stop codon" as used interchangeably herein refers to nonsense mutation in a sequence of DNA, which results in a stop codon at a location not normally found in the wild-type gene. A premature stop codon may cause a protein to be truncated or shorter compared to the full-length version of the protein.

The term "promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of a nucleic acid. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, and CMV IE promoter.

The term "target gene" as used herein refers to any nucleotide sequence encoding a known or putative gene product. The target gene may be a mutated gene involved in a genetic disease or disorder.

The term "target region" as used herein refers to the region of the target gene to which the site-specific nuclease is designed to bind.

As used herein, the term "transgene" refers to a gene or genetic material containing a gene sequence that has been isolated from one organism and is introduced into a different organism. Alternatively, the term "transgene" also refers to a gene or genetic material that is chemically synthesized and introduced into an organism. This non-native segment of DNA may retain the ability to produce RNA or protein in the transgenic organism, or it may alter the normal function of the transgenic organism's genetic code. The introduction of a transgene has the potential to change the phenotype of an organism.

As used herein, the term "variant" when used with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto. "Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., J. Mol. Biol. 157: 105-132 (1982), incorporated herein by reference in its entirety. The hydropathic index of an amino acid is based on a consideration of its hydrophobicity and charge. It is known in the art that amino acids of similar hydropathic indexes may be substituted and still retain protein function. In one aspect, amino acids having hydropathic indexes of 2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, the term "vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, such as a DNA plasmid.

As used herein, the terms "gene transfer," "gene delivery," and "gene transduction" refer to methods or systems for reliably inserting a particular nucleotide sequence (e.g., DNA or RNA), fusion protein, polypeptide and the like into targeted cells. The vector may also comprise an adenovirus (AAV) vector. As used herein, the terms "adenoviral associated virus (AAV) vector," "AAV gene therapy vector," and "gene therapy vector" refer to a vector having functional or partly functional ITR sequences and transgenes. As used herein, the term "ITR" refers to inverted terminal repeats (ITR). The ITR sequences may be derived from an adeno-associated virus serotype, including without limitation, AAV-1, AAV-2, AAV-3, AAV-4, AAV-5, and AAV-6. The ITRs, however, need not be the wild-type nucleotide sequences, and may be altered (e.g., by the insertion, deletion or substitution of nucleotides), so long as the sequences retain function to provide for functional rescue, replication and packaging. AAV vectors may have one or more of the AAV wild-type genes deleted in whole or part, preferably the rep and/or cap genes but retain functional flanking ITR sequences. Functional ITR sequences function to, for example, rescue, replicate and package the AAV virion or particle. Thus, an "AAV vector" is defined herein to include at least those sequences required for insertion of the transgene into a subject's cells. Optionally included are those sequences necessary in cis for replication and packaging (e.g., functional ITRs) of the virus.

As used herein, the term "gene therapy" refers to a method of treating a patient wherein polypeptides or nucleic acid sequences are transferred into cells of a patient such that activity and/or the expression of a particular gene is modulated. In certain embodiments, the expression of the gene is suppressed. In certain embodiments, the expression of the gene is enhanced. In certain embodiments, the temporal or spatial pattern of the expression of the gene is modulated.

The terms "adeno-associated virus inverted terminal repeats" or "AAV ITRs" refer to the palindromic regions found at each end of the AAV genome which function together in cis as origins of DNA replication and as packaging signals for the virus. For use in some embodiments of the present invention, flanking AAV ITRs are positioned 5' and 3' of one or more selected heterologous nucleotide sequences. Optionally, the ITRs together with the rep coding region or the Rep expression products provide for the integration of the selected sequences into the genome of a target cell.

As used herein, the term "AAV rep coding region" refers to the region of the AAV genome that encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Muzyczka (Muzyczka, Curr. Top. Microbiol. Immunol., 158:97-129 (1992)) and Kotin (Kotin, Hum. Gene Ther., 5:793-801 (1994)), incorporated herein by reference in their entirety, provide additional descriptions of the AAV rep coding region, as well as the cap coding region described below. Suitable homologues of the AAV rep coding region include the human herpesvirus 6 (HHV-6) rep gene which is also known to mediate AAV-2 DNA replication (Thomson et al., Virol., 204:304-311 (1994), incorporated herein by reference in its entirety).

As used herein, the term "AAV cap coding region" refers to the region of the AAV genome that encodes the capsid proteins VP1, VP2, and VP3, or functional homologues thereof. These cap expression products supply the packaging functions, which are collectively required for packaging the viral genome. In some embodiments, AAV2 Cap proteins may be used.

As used herein, the term "AAV helper function" refers to AAV coding regions capable of being expressed in a host cell to complement AAV viral functions missing from the AAV vector. Typically, the AAV helper functions include the AAV rep coding region and the AAV cap coding region. The helper functions may be contained in a "helper plasmid" or "helper construct." An AAV helper construct as used herein, refers to a molecule that provides all or part of the elements necessary for AAV replication and packaging. Such AAV helper constructs may be a plasmid, virus or genes integrated into cell lines or into the cells of a subject. It may be provided as DNA, RNA, or protein. The elements do not have to be arranged co-linearly (i.e., in the same molecule). For example, rep78 and rep68 may be on different molecules. An "AAV helper construct" may be, for example, a vector containing AAV coding regions required to complement AAV viral functions missing from the AAV vector (e.g., the AAV rep coding region and the AAV cap coding region).

As used herein, the terms "accessory functions" and "accessory factors" refer to functions and factors that are required by AAV for replication, but are not provided by the AAV vector or AAV helper construct. Thus, these accessory functions and factors must be provided by the host cell, a virus (e.g., adenovirus or herpes simplex virus), or another expression vector that is co-expressed in the same cell. Generally, the E1, E2A, E4 and VA coding regions of adenovirus are used to supply the necessary accessory function required for AAV replication and packaging (Matsushita et al., Gene Therapy 5:938 (1998), incorporated herein by reference in its entirety).

Portions of the AAV genome have the capability of integrating into the DNA of cells to which it is introduced. As used herein, "integrate," refers to portions of the genetic construct that become covalently bound to the genome of the cell to which it is administered, for example through the mechanism of action mediated by the AAV Rep protein and the AAV ITRs. For example, the AAV virus has been shown to integrate at 19q13.3-qter in the human genome. The minimal elements for AAV integration are the inverted terminal repeat (ITR) sequences and a functional Rep 78/68 protein. In some embodiments, the present invention incorporates the ITR sequences into a vector for integration to facilitate the integration of the transgene into the host cell genome for sustained transgene expression. The genetic transcript may also integrate into other chromosomes if the chromosomes contain the AAV integration site.

The predictability of insertion site reduces the danger of random insertional events into the cellular genome that may activate or inactivate host genes or interrupt coding sequences, consequences that limit the use of vectors whose integration is random, e.g., retroviruses. The Rep protein mediates the integration of the genetic construct containing the AAV ITRs and the transgene. The use of AAV is advantageous for its predictable integration site and because it has not been associated with human or non-human primate diseases, thus obviating many of the concerns that have been raised with virus-derived gene therapy vectors.

"Portion of the genetic construct integrates into a chromosome" refers to the portion of the genetic construct that will become covalently bound to the genome of the cell upon introduction of the genetic construct into the cell via administration of the gene therapy particle. The integration is mediated by the AAV ITRs flanking the transgene and the AAV Rep protein. Portions of the genetic construct that may be integrated into the genome include the transgene and the AAV ITRs.

The "transgene" may contain a transgenic sequence or a native or wild-type DNA sequence. The transgene may become part of the genome of the primate subject. A transgenic sequence can be partly or entirely species-heterologous, i.e., the transgenic sequence, or a portion thereof, can be from a species which is different from the cell into which it is introduced.

As used herein, the term "stably maintained" refers to characteristics of transgenic subject (e.g., a human or non-human primate) that maintain at least one of their transgenic elements (i.e., the element that is desired) through multiple generations of cells. For example, it is intended that the term encompass many cell division cycles of the originally transfected cell. The term "stable transfection" or "stably transfected" refers to the introduction and integration of foreign DNA into the genome of the cell. The term "stable transfectant" refers to a cell that has stably integrated foreign DNA into the genomic DNA.

As used herein, the terms "transgene encoding," "nucleic acid molecule encoding," "DNA sequence encoding," and "DNA encoding" refer to the order or sequence of deoxyribonucleotides along a strand of deoxyribonucleic acid. The order of these deoxyribonucleotides may, for example, determine the order of amino acids along the polypeptide (protein) chain. The DNA sequence thus may code for the amino acid sequence.

As used herein, the term "wild type" (wt) refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants may be isolated, which are identified by the acquisition of altered characteristics when compared to the wild-type gene or gene product.

As used herein, the term "AAV virion," "AAV particle," or "AAV gene therapy particle," "AAV gene therapy vector," or "rAAV gene therapy vector" refers to a complete virus unit, such as a wt AAV virus particle (comprising a linear, single-stranded AAV nucleic acid genome associated with at least one AAV capsid protein coat). In this regard, single-stranded AAV nucleic acid molecules of either complementary sense (e.g., "sense" or "antisense" strands) can be packaged into any one AAV virion and both strands are equally infectious. Also included are infectious viral particles containing a heterologous DNA molecule of interest (e.g., CFTR or a biologically active portion thereof), which is flanked on both sides by AAV ITRs.

As used herein, the term "transfection" refers to the uptake of a foreign nucleic acid (e.g., DNA or RNA) by a cell. A cell has been "transfected" when an exogenous nucleic acid (DNA or RNA) has been introduced inside the cell membrane. A number of transfection techniques are generally known in the art (See, e.g., Graham et al., Virol., 52:456 (1973); Sambrook et al., Molecular Cloning, a Laboratory Manual, Cold Spring Harbor Laboratories, New York (1989); Davis et al., Basic Methods in Molecular Biology, Elsevier, (1986); and Chu et al., Gene 13:197 (1981), incorporated herein by reference in their entirety). Such techniques may be used to introduce one or more exogenous DNA moieties, such as a gene transfer vector and other nucleic acid molecules, into suitable recipient cells.

As used herein, the terms "stable transfection" and "stably transfected" refers to the introduction and integration of foreign DNA into the genome of the transfected cell. The term "stable transfectant" refers to a cell, which has stably integrated foreign DNA into the genomic DNA.

As used herein, the term "transient transfection" or "transiently transfected" refers to the introduction of foreign DNA into a cell wherein the foreign DNA fails to integrate into the genome of the transfected cell and is maintained as an episome. During this time the foreign DNA is subject to the regulatory controls that govern the expression of endogenous genes in the chromosomes. The term "transient transfectant" refers to cells which have taken up foreign DNA but have failed to integrate this DNA. As used herein, the term "transduction" denotes the delivery of a DNA molecule to a recipient cell either in vivo or in vitro, via a replication-defective viral vector, such as via a recombinant AAV virion.

As used herein, the term "recipient cell" refers to a cell which has been transfected or transduced, or is capable of being transfected or transduced, by a nucleic acid construct or vector bearing a selected nucleotide sequence of interest. The term includes the progeny of the parent cell, whether or not the progeny are identical in morphology or in genetic make-up to the original parent, so long as the selected nucleotide sequence is present. The recipient cell may be the cells of a subject to which the gene therapy particles and/or gene therapy vector has been administered.

As used herein, the term "recombinant DNA molecule" refers to a DNA molecule which is comprised of segments of DNA joined together by means of molecular biological techniques.

As used herein, the term "regulatory element" refers to a genetic element which can control the expression of nucleic acid sequences. For example, a promoter is a regulatory element that facilitates the initiation of transcription of an operably linked coding region. Other regulatory elements are splicing signals, polyadenylation signals, termination signals, etc.

The term DNA "control sequences" refers collectively to regulatory elements such as promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need be present.

Transcriptional control signals in eukaryotes generally comprise "promoter" and "enhancer" elements. Promoters and enhancers consist of short arrays of DNA sequences that interact specifically with cellular proteins involved in transcription (Maniatis et al., Science 236:1237 (1987), incorporated herein by reference in its entirety). Promoter and enhancer elements have been isolated from a variety of eukaryotic sources including genes in yeast, insect and mammalian cells and viruses (analogous control sequences, i.e., promoters, are also found in prokaryotes). The selection of a particular promoter and enhancer depends on the recipient cell type. Some eukaryotic promoters and enhancers have a broad host range while others are functional in a limited subset of cell types (See e.g., Voss et al., Trends Biochem. Sci., 11:287 (1986); and Maniatis et al., supra, for reviews, incorporated herein by reference in their entirety). For example, the SV40 early gene enhancer is very active in a variety of cell types from many mammalian species and has been used to express proteins in a broad range of mammalian cells (Dijkema et al, EMBO J. 4:761 (1985), incorporated herein by reference in its entirety). Promoter and enhancer elements derived from the human elongation factor 1-alpha gene (Uetsuki et al., J. Biol. Chem., 264:5791 (1989); Kim et al., Gene 91:217 (1990); and Mizushima and Nagata, Nucl. Acids. Res., 18:5322 (1990)), the long terminal repeats of the Rous sarcoma virus (Gorman et al., Proc. Natl. Acad. Sci. U.S.A. 79:6777 (1982)), and the human cytomegalovirus (Boshart et al., Cell 41:521 (1985)) are also of utility for expression of proteins in diverse mammalian cell types, incorporated herein by reference in their entirety. Promoters and enhancers can be found naturally, alone or together. For example, retroviral long terminal repeats comprise both promoter and enhancer elements. Generally promoters and enhancers act independently of the gene being transcribed or translated. Thus, the enhancer and promoter used can be "endogenous," "exogenous," or "heterologous" with respect to the gene to which they are operably linked. An "endogenous" enhancer/promoter is one which is naturally linked with a given gene in the genome. An "exogenous" or "heterologous" enhancer or promoter is one which is placed in juxtaposition to a gene by means of genetic manipulation (i.e., molecular biological techniques) such that transcription of that gene is directed by the linked enhancer/promoter.

As used herein, the term "CBA" promoter refers to a fusion of the chicken 3-actin promoter and CMV immediate-early enhancer.

As used herein, the term "tissue specific" refers to regulatory elements or control sequences, such as a promoter, an enhancer, etc., wherein the expression of the nucleic acid sequence is substantially greater in a specific cell type(s) or tissue(s). In particularly preferred embodiments, the CB promoter (CB is the same as CBA defined above) displays good expression of human CFTR, rAAV5-CB-.DELTA.264CFTR, rAAV5-CB-.DELTA.27-264CFTR, or another biologically active portion of CFTR. It is not intended, however, that the present invention be limited to the CB promoter or to lung specific expression, as other tissue specific regulatory elements, or regulatory elements that display altered gene expression patterns, are encompassed within the invention.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York (1989), pp. 16.7-16.8, incorporated herein by reference in its entirety). A commonly used splice donor and acceptor site is the splice junction from the 16S RNA of SV40.

Transcription termination signals are generally found downstream of a polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which has been isolated from one gene and operably linked to the 3' end of another gene. A commonly used heterologous poly A signal is the SV40 poly A signal. The SV40 poly A signal is contained on a 237 bp BamHI/BclI restriction fragment and directs both termination and polyadenylation (Sambrook et al., supra, at 16.6-16.7, incorporated herein by reference in its entirety).

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

As defined herein, a "therapeutically effective amount" or "therapeutic effective dose" is an amount or dose of a fusion protein, polypeptide, nucleic acid, AAV particle(s), or virion(s) capable of producing sufficient amounts of a desired protein to modulate the activity of the protein in a desired manner, thus providing a palliative tool for clinical intervention. In some embodiments, a therapeutically effective amount or dose of a transfected fusion protein, polypeptide, nucleic acid, AAV particle(s), or virion(s) as described herein is enough to confer suppression of a gene targeted by the fusion protein/gene therapy construct.

As used herein, the term "treat", e.g., a disorder, means that a subject (e.g., a human) who has a disorder, is at risk of having a disorder, and/or experiences a symptom of a disorder, will, in an embodiment, suffer a less severe symptom and/or will recover faster, when a fusion molecule or a nucleic acid that encodes the fusion molecule, and/or a gRNA or a nucleic acid that encodes the gRNA, e.g., as described herein, is administered than if the fusion molecule or a nucleic acid that encodes the fusion molecule, and/or the gRNA or a nucleic acid that encodes the gRNA, were never administered.

B. CRISPR System

"Clustered Regularly Interspaced Short Palindromic Repeats" and "CRISPRs", as used interchangeably herein, refer to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the single guide RNA (sgRNA), and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the CRISPR RNA (crRNA), i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a trans-encoded small RNA (tracrRNA), which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-expressing a single Cas9 protein with two or more sgRNAs. For example, the *Streptococcus pyogenes* (*S. pyogenes*) Type II system naturally prefers to use an "NGG" sequence, where "N" can be any nucleotide, but also accepts other PAM sequences, such as "NAG" in engineered systems (Hsu et al, Nature Biotechnology (2013) doi: 10.1038/nbt.2647, incorporated herein by reference in its entirety). Similarly, the Cas9 derived from *Neisseria meningitidis* (NmCas9) normally has a native PAM of NNNNGATT, but has activity across a variety of PAMs, including a highly degenerate NNNNGNNN PAM (Esvelt et al. Nature Methods (2013) doi: 10.1038/nmeth.2681, incorporated herein by reference in its entirety).

C. CRISPR/Cas9-Based System

An engineered form of the Type II effector system of *S. pyogenes* was shown to function in human cells for genome engineering. In this system, the Cas9 protein was directed to genomic target sites by a synthetically reconstituted "guide RNA" ("gRNA", also used interchangeably herein as a chimeric single guide RNA ("sgRNA")), which is a crRNA-tracrRNA fusion that obviates the need for RNase III and crRNA processing in general. Provided herein are CRISPR/Cas9-based engineered systems for use in genome editing and treating genetic diseases. The CRISPR/Cas9-based engineered systems may be designed to target any gene, including genes involved in a genetic disease, aging, tissue regeneration, or wound healing. The CRISPR/Cas9-based systems may include a Cas9 protein or Cas9 fusion protein and at least one gRNA. The Cas9 fusion protein may, for example, include a domain that has a different activity from what is endogenous to Cas9, such as a transactivation domain.

The target gene may be involved in differentiation of a cell or any other process in which activation of a gene may be desired, or may have a mutation such as a frameshift mutation or a nonsense mutation. If the target gene has a mutation that causes a premature stop codon, an aberrant splice acceptor site or an aberrant splice donor site, the CRISPR/Cas9-based system may be designed to recognize and bind a nucleotide sequence upstream or downstream from the premature stop codon, the aberrant splice acceptor site or the aberrant splice donor site. The CRISPR-Cas9-based system may also be used to disrupt normal gene splicing by targeting splice acceptors and donors to induce skipping of premature stop codons or restore a disrupted reading frame. The CRISPR/Cas9-based system may or may not mediate off-target changes to protein-coding regions of the genome. In some embodiments, the expression of the target gene is to be suppressed.

D. Cas9

The CRISPR/Cas9-based system may include a Cas9 protein or a fragment thereof, a Cas9 fusion protein, a nucleic acid encoding a Cas9 protein or a fragment thereof, or a nucleic acid encoding a Cas9 fusion protein. As used herein, a "Cas9 molecule" may refer to a Cas9 protein, or a fragment thereof. Cas9 protein is an endonuclease that cleaves nucleic acid and is encoded by the CRISPR loci and is involved in the Type II CRISPR system. The Cas9 protein may be from any bacterial or archaea species, such as *Streptococcus pyogenes*. Cas9 sequences and structures from different species are known in the art, see, e.g., Ferretti et al., Proc Natl Acad Sci USA. (2001); 98(8): 4658-63; Deltcheva et al., Nature. 2011 Mar. 31; 471(7340):602-7; and Jinek et al., Science. (2012); 337(6096):816-21, incorporated herein by reference in their entirety. Exemplary *S. pyogenes* Cas9 sequence is available at the Uniprot database under accession number Q99ZW2. Exemplary *Staphylococcus aureus* (*S. aureus*) Cas9 sequence is available at the Uniprot database under accession number J7RUA5. Exemplary Cas9 sequences are also shown in Table 1.

*S. pyogenes* Cas9 is the most commonly studied Cas9 molecule. Notably, *S. pyogenes* Cas9 is quite large (the gene itself is over 4.1 Kb), making it challenging to be packed into certain delivery vectors. For example, Adeno-associated virus (AAV) vector has a packaging limit of 4.5 or 4.75 Kb. This means that Cas9 as well as regulatory elements such as a promoter and a transcription terminator all have to fit into the same viral vector. Constructs larger than 4.5 or 4.75 Kb will lead to significantly reduced virus production. One possibility is to use a functional fragment of *S. pyogenes* Cas9. Another possibility is to split Cas9 into its sub-portions (e.g., the N-terminal lobe and the C-terminal lobe of Cas9). Each sub-portion is expressed by a separate vector, and these sub-portions associate to form a functional Cas9. See, e.g., Chew et al., Nat Methods. 2016; 13:868-74; Truong et al., Nucleic Acids Res. 2015; 43: 6450-6458; and Fine et al., Sci Rep. 2015; 5: 10777, incorporated by reference herein in their entirety.

Alternatively, shorter Cas9 molecules from other species can be used in the compositions and methods disclosed herein, e.g., Cas9 molecules from *Staphylococcus aureus, Campylobacter jejuni, Corynebacterium diphtheria, Eubacterium ventriosum, Streptococcus pasteurianus, Lactobacillus farciminis, Sphaerochaeta globus, Azospirillum* (strain B510), *Gluconacetobacter diazotrophicus, Neisseria cinerea, Roseburia intestinalis, Parvibaculum lavamentivorans, Nitratifractor salsuginis* (strain DSM 16511), *Campylobacter lari* (strain CF89-12), or *Streptococcus thermophilus* (strain LMD-9). Exemplary Cas9 sequences from these species are also shown in Table 1. In certain embodiments, the present disclosure provides an AAV vector comprising a nucleotide encoding a Cas9 molecule from *Streptococcus pyogenes, Staphylococcus aureus, Campylobacter jejuni, Corynebacterium diphtheria, Eubacterium ventriosum, Streptococcus pasteurianus, Lactobacillus farciminis, Sphaerochaeta globus, Azospirillum* (strain B510), *Gluconacetobacter diazotrophicus, Neisseria cinerea, Roseburia intestinalis, Parvibaculum lavamentivorans, Nitratifractor salsuginis* (strain DSM 16511), *Campylobacter lari* (strain CF89-12), or *Streptococcus thermophilus* (strain LMD-9), or fragment thereof.

TABLE 1

| Exemplary Cas9 amino acid sequences | | |
|---|---|---|
| SEQ ID NO: | Description | Sequence |
| 24 | *S. pyogenes* serotype M1 Cas9 (Q99ZW2) | MDKKYSIGLDIGTNSVGWAVITDEYKVPSKKFKVLGNTDRH<br>SIKKNLIGALLFDSGETAEATRLKRTARRRYTRRKNRICYLQ<br>EIFSNEMAKVDDSFFHRLEESFLVEEDKKHERHPIFGNIVDE<br>VAYHEKYPTIYHLRKKLVDSTDKADLRLIYLALAHMIKFRG<br>HFLIEGDLNPDNSDVDKLFIQLVQTYNQLFEENPINASGVDA<br>KAILSARLSKSRRLENLIAQLPGEKKNGLFGNLIALSLGLTPN<br>FKSNFDLAEDAKLQLSKDTYDDDLDNLLAQIGDQYADLFLA<br>AKNLSDAILLSDILRVNTEITKAPLSASMIKRYDEHHQDLTLL<br>KALVRQQLPEKYKEIFFDQSKNGYAGYIDGGASQEEFYKFIK<br>PILEKMDGTEELLVKLNREDLLRKQRTFDNGSIPHQIHLGEL<br>HAILRRQEDFYPFLKDNREKIEKILTFRIPYYVGPLARGNSRF<br>AWMTRKSEETITPWNFEEVVDKGASAQSFIERMTNFDKNLP<br>NEKVLPKHSLLYEYFTVYNELTKVKYVTEGMRKPAFLSGEQ<br>KKAIVDLLFKTNRKVTVKQLKEDYFKKIECFDSVEISGVEDR<br>FNASLGTYHDLLKIIKDKDFLDNEENEDILEDIVLTLTLFEDR<br>EMIEERLKTYAHLFDDKVMKQLKRRRYTGWGRLSRKLINGI<br>RDKQSGKTILDFLKSDGFANRNFMQLIHDDSLTFKEDIQKAQ<br>VSGQGDSLHEHIANLAGSPAIKKGILQTVKVVDELVKVMGR<br>HKPENIVIEMARENQTTQKGQKNSRERMKRIEEGIKELGSQI<br>LKEHPVENTQLQNEKLYLYYLQNGRDMYVDQELDINRLSD<br>YDVDHIVPQSFLKDDSIDNKVLTRSDKNRGKSDNVPSEEVV<br>KKMKNYWRQLLNAKLITQRKFDNLTKAERGGLSELDKAGF<br>IKRQLVETRQITKHVAQILDSRMNTKYDENDKLIREVKVITL<br>KSKLVSDFRKDFQFYKVREINNYHHAHDAYLNAVVGTALI<br>KKYPKLESEFVYGDYKVYDVRKMIAKSEQEIGKATAKYFFY<br>SNIMNFFKTEITLANGEIRKRPLIETNGETGEIVWDKGRDFAT<br>VRKVLSMPQVNIVKKTEVQTGGFSKESILPKRNSDKLIARKK<br>DWDPKKYGGFDSPTVAYSVLVVAKVEKGKSKKLKSVKELL<br>GITIMERSSFEKNPIDFLEAKGYKEVKKDLIIKLPKYSLFELEN<br>GRKRMLASAGELQKGNELALPSKYVNFLYLASHYEKLKGS<br>PEDNEQKQLFVEQHKHYLDEIIEQISEFSKRVILADANLDKV<br>LSAYNKHRDKPIREQAENIIHLFTLTNLGAPAAFKYFDTTIDR<br>KRYTSTKEVLDATLIHQSITGLYETRIDLSQLGGD |
| 25 | *S. aureus* Cas9 (J7RUA5) | MKRNYILGLDIGITSVGYGIIDYETRDVIDAGVRLFKEANVE<br>NNEGRRSKRGARRLKRRRRHRIQRVKKLLFDYNLLTDHSEL<br>SGINPYEARVKGLSQKLSEEEFSAALLHLAKRRGVHNVNEV<br>EEDTGNELSTKEQISRNSKALEEKYVAELQLERLKKDGEVR<br>GSINRFKTSDYVKEAKQLLKVQKAYHQLDQSFIDTYIDLLET<br>RRTYYEGPGEGSPFGWKDIKEWYEMLMGHCTYFPEELRSV<br>KYAYNADLYNALNDLNNLVITRDENEKLEYYEKFQIIENVF<br>KQKKKPTLKQIAKEILVNEEDIKGYRVTSTGKPEFTNLKVYH<br>DIKDITARKEIIENAELLDQIAKILTIYQSSEDIQEELTNLNSEL<br>TQEEIEQISNLKGYTGTHNLSLKAINLILDELWHTNDNQIAIF<br>NRLKLVPKKVDLSQQKEIPTTLVDDFILSPVVKRSFIQSIKVI<br>NAIIKKYGLPNDIIIELAREKNSKDAQKMINEMQKRNRQTNE<br>RIEEIIRTTGKENAKYLIEKIKLHDMQEGKCLYSLEAIPLEDL<br>LNNPFNYEVDHIIPRSVSFDNSFNNKVLVKQEENSKKGNRTP<br>FQYLSSSDSKISYETFKKHILNLAKGKGRISKTKKEYLLEERD<br>INRFSVQKDFINRNLVDTRYATRGLMNLLRSYFRVNNLDVK<br>VKSINGGFTSFLRRKWKFKKERNKGYKHHAEDALIIANADFI<br>FKEWKKLDKAKKVMENQMFEEKQAESMPEIETEQEYKEIFI<br>TPHQIKHIKDFKDYKYSHRVDKKPNRELINDTLYSTRKDDK<br>GNTLIVNNLNGLYDKDNDKLKKLINKSPEKLLMYHHDPQT<br>YQKLKLIMEQYGDEKNPLYKYYEETGNYLTKYSKKDNGPV<br>IKKIKYYGNKLNAHLDITDDYPNSRNKVVKLSLKPYRFDVY<br>LDNGVYKFVTVKNLDVIKKENYYEVNSKCYEEAKKLKKIS<br>NQAEFIASFYNNDLIKINGELYRVIGVNNDLLNRIEVNMIDIT<br>YREYLENMNDKRPPRIIKTIASKTQSIKKYSTDILGNLYEVKS<br>KKHPQIIKKG |
| 26 | *Eubacterium ventriosum* Cas9 (A5Z395) | MGYTVGLDIGVASVGVAVLDENDNIVEAVSNIFDEADTSNN<br>KVRRTLREGRRTKRRQKTRIEDFKQLWETSGYIIPHKLHLNII<br>ELRNKGLTELLSLDELYCVLLSMLKHRGISYLEDADDGEKG<br>NAYKKGLAFNEKQLKEKMPCEIQLERMKKYGKYHGEFIIEI<br>NDEKEYQSNVFTTKAYKKELEKIFETQRCNGNKINTKFIKKY<br>MEIYERKREYYIGPGNEKSRTDYGIYTTRTDEEGNFIDEKNIF<br>GKLIGKCSVYPEEYRASSASYTAQEFNLLNDLNNLKINNEKL<br>TEFQKKEIVEIIKDASSVNMRKIIKKVIDEDIEQYSGARIDKK<br>GKEIYHTFEIYRKLKKELKTINVDIDSFTREELDKTMDILTLN<br>TERESIVKAFDEQKFVYEENLIKKLIEFRKNNQRLFSGWHSF<br>SYKAMLQLIPVMYKEPKEQMQLLTEMNVFKSKKEKYVNY<br>KYIPENEVVKEIYNPVVVKSIRTTVKILNALIKKYGYPESVVI<br>EMPRDKNSDDEKEKIDMNQKKNQEEYEKILNKIYDEKGIEIT<br>NKDYKKQKKLVLKLKLWNEQEGLCLYSGKKIAIEDLLNHP |

TABLE 1-continued

Exemplary Cas9 amino acid sequences

| SEQ ID NO: | Description | Sequence |
|---|---|---|
| | | EFFEIDHIIPKSISLDDSRSNKVLVYKTENSIKENDTPYHYLTR<br>INGKWGFDEYKANVLELRRRGKIDDKKVNNLLCMEDITKID<br>VVKGFINRNLNDTRYASRVVLNEMQSFFESRKYCNTKVKVI<br>RGSLTYQMRQDLHLKKNREESYSHHAVDAMLIAFSQKGYE<br>AYRKIQKDCYDFETGEILDKEKWNKYIDDDEFDDILYKERM<br>NEIRKKIIEAEEKVKYNYKIDKKCNRGLCNQTIYGTREKDGK<br>IHKISSYNIYDDKECNSLKKMINSGKGSDLLMYNNDPKTYR<br>DMLKILETYSSEKNPFVAYNKETGDYFRKYSKNHNGPKVEK<br>VKYYSGQINSCIDISHKYGHAKNSKKVVLVSLNPYRTDVYY<br>DNDTGKYYLVGVKYNHIKCVGNKYVIDSETYNELLRKEGV<br>LNSDENLEDLNSKNITYKFSLYKNDIIQYEKGGEYYTERFLS<br>RIKEQKNLIETKPINKPNFQRKNKKGEWENTRNQIALAKTK<br>YVGKLVTDVLGNCYIVNMEKFSLVVDK |
| 27 | *Azospirillum* (strain B510) Cas9 (D3NT09) | MARPAFRAPRREHVNGWTPDPHRISKPFFILVSWHLLSRVVI<br>DSSSGCFPGTSRDHTDKFAEWECAVQPYRLSFDLGTNSIGW<br>GLLNLDRQGKPREIRALGSRIFSDGRDPQDKASLAVARRLA<br>RQMRRRRDRYLTRRTRLMGALVRFGLMPADPAARKRLEV<br>AVDPYLARERATRERLEPFEIGRALFHLNQRRGYKPVRTAT<br>KPDEEAGKVKEAVERLEAAIAAAGAPTLGAWFAWRKTRGE<br>TLRARLAGKGKEAAYPFYPARRMLEAEFDTLWAEQARHHP<br>DLLTAEAREILRHRIFHQRPLKPPPVGRCTLYPDDGRAPRAL<br>PSAQRLRLFQELASLRVIHLDLSERPLTPAERDRIVAFVQGRP<br>PKAGRKPGKVQKSVPFEKLRGLLELPPGTGFSLESDKRPELL<br>GDETGARIAPAFGPGWTALPLEEQDALVELLLTEAEPERAIA<br>ALTARWALDEATAAKLAGATLPDFHGRYGRRAVAELLPVL<br>ERETRGDPDGRVRPIRLDEAVKLLRGGKDHSDFSREGALLD<br>ALPYYGAVLERHVAFGTGNPADPEEKRVGRVANPTVHIAL<br>NQLRHLVNAILARHGRPEEIVIELARDLKRSAEDRRREDKRQ<br>ADNQKRNEERKRLILSLGERPTPRNLLKLRLWEEQGPVENR<br>RCPYSGETISMRMLLSEQVDIDHILPFSVSLDDSAANKVVCL<br>REANRIKRNRSPWEAFGHDSERWAGILARAEALPKNKRWR<br>FAPDALEKLEGEGGLRARHLNDTRHLSRLAVEYLRCVCPKV<br>RVSPGRLTALLRRRWGIDAILAEADGPPPEVPAETLDPSPAE<br>KNRADHRHHALDAVVIGCIDRSMVQRVQLAAASAEREAAA<br>REDNIRRVLEGFKEEPWDGFRAELERRARTIVVSHRPEHGIG<br>GALHKETAYGPVDPPEEGFNLVVRKPIDGLSKDEINSVRDPR<br>LRRALIDRLAIRRRDANDPATALAKAAEDLAAQPASRGIRR<br>VRVLKKESNPIRVEHGGNPSGPRSGGPFHKLLLAGEVHHVD<br>VALRADGRRWVGHWVTLFEAHGGRGADGAAAPPRLGDGE<br>RFLMRLHKGDCLKLEHKGRVRVMQVVKLEPSSNSVVVVEP<br>HQVKTDRSKHVKISCDQLRARGARRVTVDPLGRVRVHAPG<br>ARVGIGGDAGRTAMEPAEDIS |
| 28 | *Gluconacetobacter diazotrophicus* (strain ATCC 49037) Cas9 (A9HKP2) | MGENMIDESLTFGIDLGIGSCGWAVLRRPSAFGRKGVIEGM<br>GSWCFDVPETSKERTPTNQIRRSNRLLRRVIRRRRNRMAAIR<br>RLLHAAGLLPSTDSDALKRPGHDPWELRARGLDKPLKPVEF<br>AVVLGHIAKRRGFKSAAKRKATNISSDDKKMLTALEATRER<br>LGRYRTVGEMFARDPDFASRRRNREGKYDRTTARDDLEHE<br>VHALFAAQRRLGQGFASPELEEAFTASAFHQRPMQDSERLV<br>GFCPFERTEKRAAKLTPSFERFRLLARLLNLRITTPDGERPLT<br>VDEIALVTRDLGKTAKLSIKRVRTLIGLEDNQRFTTIRPEDED<br>RDIVARTGGAMTGTATLRKALGEALWTDMQERPEQLDAIV<br>QVLSFFEANETITEKLREIGLTLAVLDVLLTALDAGVFAKFK<br>GAAHISTKAARNLLPHLEQGRRYDEACTMAGYDHAASRLS<br>HHGQIVAKTQFNALVTEIGESIANPIARKALIEGLKQIWAMR<br>NHWGLPGSIHVELARDVGNSIEKRREIEKHIEKNTALRARER<br>REVHDLLDLEDVNGDTLLRYRLWKEQGGKCLYTGKAIHIR<br>QIAATDNSVQVDHILPWSRFGDDSFNNKTLCLASANQQKKR<br>STPYEWLSGQTGDAWNAFVQRIETNKELRGFKKRNYLLKN<br>AKEAEEKFRSRNLNDTRYAARLFAEAVKLLYAFGERQEKG<br>GNRRVFTRPGALTAALRQAWGVESLKKQDGKRINDDRHHA<br>LDALTVAAVDEAEIQRLTKSFHEWEQQGLGRPLRRVEPPWE<br>SFRADVEATYPEVFVARPERRRARGEGHAATIRQVKERECT<br>PIVFERKAVSSLKEADLERIKDGERNEAIVEAIRSWIATGRPA<br>DAPPRSPRGDIITKIRLATTIKAAVPVRGGTAGRGEMVRADV<br>FSKPNRRGKDEWYLVPVYPHQIMNRKAWPKPPMRSIVANK<br>DEDEWTEVGPEHQFRFSLYPRSNIEIIRPSGEVIEGYFVGLHR<br>NTGALTISAHNDPKSIHSGIGTKTLLAISKYQVDRFGRKSPVR<br>KEVRTWHGEACISPTPPG |
| 29 | *Neisseria cinerea* Cas9 (D0W2Z9) | MAAFKPNPMNYILGLDIGIASVGWAIVEIDEEENPIRLIDLGV<br>RVFERAEVPKTGDSLAAARRLARSVRRLTRRRAHRLLRARR<br>LLKREGVLQAADFDENGLIKSLPNTPWQLRAAALDRKLTPL<br>EWSAVLLHLIKHRGYLSQRKNEGETADKELGALLKGVADN |

TABLE 1-continued

Exemplary Cas9 amino acid sequences

| SEQ ID NO: | Description | Sequence |
|---|---|---|
| | | THALQTGDFRTPAELALNKFEKESGHIRNQRGDYSHTFNRK DLQAELNLLFEKQKEFGNPHVSDGLKEGIETLLMTQRPALS GDAVQKMLGHCTFEPTEPKAAKNTYTAERFVWLTKLNNLR ILEQGSERPLTDTERATLMDEPYRKSKLTYAQARKLLDLDD TAFFKGLRYGKDNAEASTLMEMKAYHAISRALEKEGLKDK KSPLNLSPELQDEIGTAFSLFKTDEDITGRLKDRVQPEILEAL LKHISFDKFVQISLKALRRIVPLMEQGNRYDEACTEIYGDHY GKKNTEEKIYLPPIPADEIRNPVVLRALSQARKVINGVVRRY GSPARIHIETAREVGKSFKDRKEIEKRQEENRKDREKSAAKF REYFPNFVGEPKSKDILKLRLYEQQHGKCLYSGKEINLGRLN EKGYVEIDHALPFSRTWDDSFNNKVLALGSENQNKGNQTP YEYFNGKDNSREWQEFKARVETSRFPRSKKQRILLQKFDED GFKERNLNDTRYINRFLCQFVADHMLLTGKGKRRVFASNG QITNLLRGFWGLRKVRAENDRHHALDAVVVACSTIAMQQK ITRFVRYKEMNAFDGKTIDKETGEVLHQKAHFPQPWEFFAQ EVMIRVFGKPDGKPEFEEADTPEKLRTLLAEKLSSRPEAVHK YVTPLFISRAPNRKMSGQGHMETVKSAKRLDEGISVLRVPL TQLKLKDLEKMVNREREPKLYEALKARLEAHKDDPAKAFA EPFYKYDKAGNRTQQVKAVRVEQVQKTGVWVHNHNGIAD NATIVRVDVFEKGGKYYLVPIYSWQVAKGILPDRAVVQGK DEEDWTVMDDSFEFKFVLYANDLIKLTAKKNEFLGYFVSLN RATGAIDIRTHDTDSTKGKNGIFQSVGVKTALSFQKYQIDEL GKEIRPCRLKKRPPVR |
| 30 | *Roseburia intestinalis* Cas9 (C7G697) | MRENGSDERRRNMDEKMDYRIGLDIGIASVGWAVLQNNSD DEPVRIVDLGVRIFDTAEIPKTGESLAGPRRAARTTRRRLRR RKHRLDRIKWLFENQGLINIDDFLKRYNMAGLPDVYQLRYE ALDRKLTDEELAQVLLHIAKHRGFRSTRKAETAAKENGAVL KATDENQKRMQEKGYRTVGEMIYLDEAFRTGCSWSEKGYI LTPRNKAENYQHTMLRAMLVEEVKEIFSSQRRLGNEKATEE LEEKYLEIMTSQRSFDLGPGMQPDGKPSPYAMEGFSDRVGK CTFLGDQGELRGAKGTYTAEYFVALQKINHTKLVNQDGET RNFTEEERRALTLLLFTQKEVKYAAVRKKLGLPEDILFYNLN YKKAATKEEQQKENQNTEKAKFIGMPYYHDYKKCLEERVK YLTENEVRDLFDEIGMILTCYKNDDSRTERLAKLGLVPIEME GLLAYTPTKFQHLSMKAMRNIIPFLEKGMTYDKACEEAGYD FKADSKGTKQKLLTGENVNQTINEITNPVVKRSVSQTVKVIN AIIRTYGSPQAINIELAREMSKTFEERRKIKGDMEKRQKNNE DVKKQIQELGKLSPTGQDILKYRLWQEQQGICMYSGKTIPLE ELFKPGYDIDHILPYSITFDDSFRNKVLVTSQENRQKGNRTP YEYMGNDEQRWNEFETRVKTTIRDYKKQQKLLKKHFSEEE RSEFKERNLTDTKYITTVIYNMIRQNLEMAPLNRPEKKKQV RAVNGAITAYLRKRWGLPQKNRETDTHHAMDAVVIACCTD GMIQKISRYTKVRERCYSKGTEFVDAETGEIFRPEDYSRAEW DEIFGVHIPKPWETFRAELDVRMGDDPKGFLDTHSDVALEL DYPEYIYENLRPIFVSRMPNHKVTGAAHADTIRSPRHFKDEG IVLTKTALTDLKLDKDGEIDGYYNPQSDLLLYEALKKQLLL YGNDAKKAFAQDFHKPKADGTEGPVVRKVKIQKKQTMGV FVDSGNGIAENGGMVRIDVFRVNGKYYFVPVYTADVVKKV LPNRASTAHKPYGEWKVMEDKDFLFSLYSRDLIHIKSKKDIP IKMVNGGMEGIKETYAYYIGADISAANIQGIAHDSRYKFRGL GIQSLDVLEKCQIDVLGHVSVVRSEKRMGFS |
| 31 | *Parvibaculum lavamentivorans* (strain DS-1) Cas9 (A7HP89) | MERIFGFDIGTTSIGFSVIDYSSTQSAGNIQRLGVRIFPEARDP DGTPLNQQRRQKRMMRRQLRRRRIRRKALNETLHEAGFLP AYGSADWPVVMADEPYELRRRGLEEGLSAYEFGRAIYHLA QHRHFKGRELEESDTPDPDVDDEKEAANERAATLKALKNE QTTLGAWLARRPPSDRKRGIHAHRNVVAEEFERLWEVQSK FHPALKSEEMRARISDTIFAQRPVFWRKNTLGECRFMPGEPL CPKGSWLSQQRRMLEKLNNLAIAGGNARPLDAEERDAILSK LQQQASMSWPGVRSALKALYKQRGEPGAEKSLKFNLELGG ESKLLGNALEAKLADMFGPDWPAHPRKQEIRHAVHERLWA ADYGETPDKKRVIILSEKDRKAHREAAANSFVADFGITGEQ AAQLQALKLPTGWEPYSIPALNLFLAELEKGERFGALVNGP DWEGWRRTNFPHRNQPTGEILDKLPSPASKEERERISQLRNP TVVRTQNELRKVVNNLIGLYGKPDRIRIEVGRDVGKSKRER EEIQSGIRRNEKQRKKATEDLIKNGIANPSRDDVEKWILWKE GQERCPYTGDQIGFNALFREGRYEVEHIWPRSRSFDNSPRNK TLCRKDVNIEKGNRMPFEAFGHDEDRWSAIQIRLQGMVSAK GGTGMSPGKVKRFLAKTMPEDFAARQLNDTRYAAKQILAQ LKRLWPDMGPEAPVKVEAVTGQVTAQLRKLWTLNNILADD GEKTRADHRHHAIDALTVACTHPGMTNKLSRYWQLRDDPR AEKPALTPPWDTIRADAEKAVSEIVVSHRVRKKVSGPLHKE TTYGDTGTDIKTKSGTYRQFVTRKKIESLSKGELDEIRDPRIK EIVAAHVAGRGGDPKKAFPPYPCVSPGGPEIRKVRLTSKQQL |

TABLE 1-continued

Exemplary Cas9 amino acid sequences

| SEQ ID NO: | Description | Sequence |
|---|---|---|
| | | NLMAQTGNGYADLGSNHHIAIYRLPDGKADFEIVSLFDASR<br>RLAQRNPIVQRTRADGASFVMSLAAGEAIMIPEGSKKGIWIV<br>QGVWASGQVVLERDTDADHSTTTRPMPNPILKDDAKKVSI<br>DPIGRVRPSND |
| 32 | *Nitratifractor salsuginis* (strain DSM 16511) Cas9 (E6WZS9) | MKKILGVDLGITSFGYAILQETGKDLYRCLDNSVVMRNNPY<br>DEKSGESSQSIRSTQKSMRRLIEKRKKRIRCVAQTMERYGIL<br>DYSETMKINDPKNNPIKNRWQLRAVDAWKRPLSPQELFAIF<br>AHMAKHRGYKSIATEDLIYELELELGLNDPEKESEKKADER<br>RQVYNALRHLEELRKKYGGETIAQTIHRAVEAGDLRSYRNH<br>DDYEKMIRREDIEEEIEKVLLRQAELGALGLPEEQVSELIDEL<br>KACITDQEMPTIDESLFGKCTFYKDELAAPAYSYLYDLYRL<br>YKKLADLNIDGYEVTQEDREKVIEWVEKKIAQGKNLKKITH<br>KDLRKILGLAPEQKIFGVEDERIVKGKKEPRTFVPFFFLADIA<br>KFKELFASIQKHPDALQIFRELAEILQRSKTPQEALDRLRAL<br>MAGKGIDTDDRELLELFKNKRSGTRELSHRYILEALPLFLEG<br>YDEKEVQRILGFDDREDYSRYPKSLRHLHLREGNLFEKEEN<br>PINNHAVKSLASWALGLIADLSWRYGPFDEIILETTRDALPE<br>KIRKEIDKAMREREKALDKIIGKYKKEFPSIDKRLARKIQLW<br>ERQKGLDLYSGKVINLSQLLDGSADIEHIVPQSLGGLSTDYN<br>TIVTLKSVNAAKGNRLPGDWLAGNPDYRERIGMLSEKGLID<br>WKKRKNLLAQSLDEIYTENTHSKGIRATSYLEALVAQVLKR<br>YYPFPDPELRKNGIGVRMIPGKVTSKTRSLLGIKSKSRETNFH<br>HAEDALILSTLTRGWQNRLHRMLRDNYGKSEAELKELWKK<br>YMPHIEGLTLADYIDEAFRRFMSKGEESLFYRDMFDTIRSISY<br>WVDKKPLSASSHKETVYSSRHEVPTLRKNILEAFDSLNVIKD<br>RHKLTTEEFMKRYDKEIRQKLWLHRIGNTNDESYRAVEERA<br>TQIAQILTRYQLMDAQNDKEIDEKFQQALKELITSPIEVTGKL<br>LRKMRFVYDKLNAMQIDRGLVETDKNMLGIHISKGPNEKLI<br>FRRMDVNNAHELQKERSGILCYLNEMLFIFNKKGLIHYGCL<br>RSYLEKGQGSKYIALFNPRFPANPKAQPSKFTSDSKIKQVGI<br>GSATGIIKAHLDLDGHVRSYEVFGTLPEGSIEWFKEESGYGR<br>VEDDPHH |
| 33 | *Campylobacter lari* Cas9 (G1UFN3) | MRILGFDIGINSIGWAFVENDELKDCGVRIFTKAENPKNKES<br>LALPRRNARSSRRRLKRRKARLIAIKRILAKELKLNYKDYVA<br>ADGELPKAYEGSLASVYELRYKALTQNLETKDLARVILHIA<br>KHRGYMNKNEKKSNDAKKGKILSALKNNALKLENYQSVG<br>EYFYKEFFQKYKKNTKNFIKIRNTKDNYNNCVLSSDLEKEL<br>KLILEKQKEFGYNYSEDFINEILKVAFFQRPLKDFSHLVGAC<br>TFFEEEKRACKNSYSAWEFVALTKIINEIKSLEKISGEIVPTQT<br>INEVLNLILDKGSITYKKFRSCINLHESISFKSLKYDKENAEN<br>AKLIDFRKLVEFKKALGVHSLSRQELDQISTHITLIKDNVKL<br>KTVLEKYNLSNEQINNLLEIEFNDYINLSFKALGMILPLMRE<br>GKRYDEACEIANLKPKTVDEKKDFLPAFCDSIFAHELSNPVV<br>NRAISEYRKVLNALLKKYGKVHKIHLELARDVGLSKKAREK<br>IEKEQKENQAVNAWALKECENIGLKASAKNILKLKLWKEQ<br>KEICIYSGNKISIEHLKDEKALEVDHIYPYSRSFDDSFINKVLV<br>FTKENQEKLNKTPFEAFGKNIEKWSKIQTLAQNLPYKKKNKI<br>LDENFKDKQQEDFISRNLNDTRYIATLIAKYTKEYLNFLLLS<br>ENENANLKSGEKGSKIHVQTISGMLTSVLRHTWGFDKKDRN<br>NHLHHALDAIIVAYSTNSIIKAFSDFRKNQELLKARFYAKEL<br>TSDNYKHQVKFFEPFKSFREKILSKIDEIFVSKPPRKRARRAL<br>HKDTFHSENKIIDKCSYNSKEGLQIALSCGRVRKIGTKYVEN<br>DTIVRVDIFKKQNKFYAIPIYAMDFALGILPNKIVITGKDKNN<br>NPKQWQTIDESYEFCFSLYKNDLILLQKKNMQEPEFAYYND<br>FSISTSSICVEKHDNKFENLTSNQKLLFSNAKEGSVKVESLGI<br>QNLKVFEKYIITPLGDKIKADFQPRENISLKTSKKYGLR |

In one embodiment, Cas9 comprises one or more of the following domains: a Rec1 domain, a Rec2 domain, a bridge helix domain, a PAM interacting domain, an HNH nuclease domain, and a RuvC nuclease domain. Without wishing to be bound by theory, the Rec domain is responsible for binding guide RNA. The arginine-rich bridge helix domain plays an important role in initiating cleavage activity upon binding of target DNA. The PAM-Interacting domain confers PAM specificity and is therefore responsible for initiating binding to target DNA. The HNH and RuvC domains are nuclease domains that cut single-stranded DNA complementary and noncomplementary to the guide RNA, respectively. See, e.g., Nishimasu et al., Cell (2014) 156:935-49; Anders et al., Nature (2014) 513: 569-73; Jinek et al., Science (2014) 343: 1247997; Sternberg et al., Nature (2014) 507: 62-7, incorporated by reference herein in their entirety.

E. dCas9

The Cas9 protein may be mutated so that the nuclease activity is inactivated. An inactivated Cas9 protein from *S. pyogenes* (iCas9, also referred to as "dCas9") with no endonuclease activity has been recently targeted to genes in bacteria, yeast, and human cells by gRNA to silence gene expression through steric hindrance. As used herein, a "dCas molecule" may refer to a dCas protein, or a fragment thereof. As used herein, a "dCas9 molecule" may refer to a dCas9 protein, or a fragment thereof. As used herein, the terms "iCas" and "dCas" are used interchangeably and refer to a catalytically inactive CRISPR associated protein. In one embodiment, the dCas molecule comprises one or more mutations in a DNA-cleavage domain. In one embodiment, the dCas molecule comprises one or more mutations in the RuvC or HNH domain. In one embodiment, the dCas molecule comprises one or more mutations in both the RuvC and HNH domain. In one embodiment, the dCas molecule is a fragment of a wild-type Cas molecule. In one embodiment, the dCas molecule comprises a functional domain from a wild-type Cas molecule, wherein the functional domain is chosen from a Rec domain, a bridge helix domain, or a PAM interacting domain. In one embodiment, the nuclease activity of the dCas molecule is reduced by at least 40%, 45%, 50%, 55%, 60%, 65%, 70%, 75%, 80%, 85%, 90%, 95%, 99% compared to that of a corresponding wild type Cas molecule.

Suitable dCas molecule can be derived from a wild type Cas molecule. The Cas molecule can be from a type I, type II, or type III CRISPR-Cas systems. In one embodiment, suitable dCas molecules can be derived from a Cas1, Cas2, Cas3, Cas4, Cas5, Cas6, Cas7, Cas8, Cas9, or Cas10 molecule. In one embodiment, the dCas molecule is derived from a Cas9 molecule. The dCas9 molecule can be obtained, for example, by introducing point mutations (e.g., substitutions, deletions, or additions) in the Cas9 molecule at the DNA-cleavage domain, e.g., the nuclease domain, e.g., the RuvC and/or HNH domain. See, e.g., Jinek et al., Science (2012) 337:816-21, incorporated by reference herein in its entirety. For example, introducing two point mutations in the RuvC and HNH domains reduces the Cas9 nuclease activity while retaining the Cas9 sgRNA and DNA binding activity. In one embodiment, the two point mutations within the RuvC and HNH active sites are D10A and H840A mutations of the *S. pyogenes* Cas9 molecule. Alternatively, D10 and H840 of the *S. pyogenes* Cas9 molecule can be deleted to abolish the Cas9 nuclease activity while retaining its sgRNA and DNA binding activity. In one embodiment, the two point mutations within the RuvC and HNH active sites are D10A and N580A mutations of the *S. aureus* Cas9 molecule. In one embodiment, the dCas molecule is an *S. aureus* dCas9 molecule comprising a mutation at D10 and/or N580, numbered according to SEQ ID NO: 25. In one embodiment, the dCas molecule is an *S. aureus* dCas9 molecule comprising D10A and/or N580A mutations, numbered according to SEQ ID NO: 25. In one embodiment, the dCas molecule is an *S. aureus* dCas9 molecule comprising the amino acid sequence of SEQ ID NO: 35 or 36, a sequence substantially identical (e.g., at least 80%, 85%, 90%, 92%, 95%, 97%, 98%, 99% or higher identical) to SEQ ID NO: 35 or 36, or a sequence having one, two, three, four, five or more changes, e.g., amino acid substitutions, insertions, or deletions, relative to SEQ ID NO: 35 or 36, or any fragment thereof.

SEQ ID NO: 35

(exemplary *S. aureus* dCas9)

KRNYILGLAIGITSVGYGIIDYETRDVIDAGVRLFKEANVENNEGRRSKR

GARRLKRRRRHRIQRVKKLLFDYNLLTDHSELSGINPYEARVKGLSQKLS

-continued

EEEFSAALLHLAKRRGVHNVNEVEEDTGNELSTKEQISRNSKALEEKYVA

ELQLERLKKDGEVRGSINRFKTSDYVKEAKQLLKVQKAYHQLDQSFIDTY

IDLLETRRTYYEGPGEGSPFGWKDIKEWYEMLMGHCTYFPEELRSVKYAY

NADLYNALNDLNNLVITRDENEKLEYYEKFQIIENVFKQKKKPTLKQIAK

EILVNEEDIKGYRVTSTGKPEFTNLKVYHDIKDITARKEIIENAELLDQI

AKILTIYQSSEDIQEELTNLNSELTQEEIEQISNLKGYTGTHNLSLKAIN

LILDELWHTNDNQIAIFNRLKLVPKKVDLSQQKEIPTTLVDDFILSPVVK

RSFIQSIKVINAIIKKYGLPNDIIIELAREKNSKDAQKMINEMQKRNRQT

NERIEEIIRTTGKENAKYLIEKIKLHDMQEGKCLYSLEAIPLEDLLNNPF

NYEVDHIIPRSVSFDNSFNNKVLVKQEEASKKGNRTPFQYLSSSDSKISY

ETFKKHILNLAKGKGRISKTKKEYLLEERDINRFSVQKDFINRNLVDTRY

ATRGLMNLLRSYFRVNNLDVKVKSINGGFTSFLRRKWKFKKERNKGYKHH

AEDALIIANADFIFKEWKKLDKAKKVMENQMFEEKQAESMPEIETEQEYK

EIFITPHQIKHIKDFKDYKYSHRVDKKPNRELINDTLYSTRKDDKGNTLI

VNNLNGLYDKDNDKLKKLINKSPEKLLMYHHDPQTYQKLKLIMEQYGDEK

NPLYKYYEETGNYLTKYSKKDNGPVIKKIKYYGNKLNAHLDITDDYPNSR

NKVVKLSLKPYRFDVYLDNGVYKFVTVKNLDVIKKENYYEVNSKCYEEAK

KLKKISNQAEFIASFYNNDLIKINGELYRVIGVNNDLLNRIEVNMIDITY

REYLENMNDKRPPRIIKTIASKTQSIKKYSTDILGNLYEVKSKKHPQIIK

KG

SEQ ID NO: 36

(exemplary *S. aureus* dCas9)

MKRNYILGLAIGITSVGYGIIDYETRDVIDAGVRLFKEANVENNEGRRSK

RGARRLKRRRRHRIQRVKKLLFDYNLLTDHSELSGINPYEARVKGLSQKL

SEEEFSAALLHLAKRRGVHNVNEVEEDTGNELSTKEQISRNSKALEEKYV

AELQLERLKKDGEVRGSINRFKTSDYVKEAKQLLKVQKAYHQLDQSFIDT

YIDLLETRRTYYEGPGEGSPFGWKDIKEWYEMLMGHCTYFPEELRSVKYA

YNADLYNALNDLNNLVITRDENEKLEYYEKFQIIENVFKQKKKPTLKQIA

KEILVNEEDIKGYRVTSTGKPEFTNLKVYHDIKDITARKEIIENAELLDQ

IAKILTIYQSSEDIQEELTNLNSELTQEEIEQISNLKGYTGTHNLSLKAI

NLILDELWHTNDNQIAIFNRLKLVPKKVDLSQQKEIPTTLVDDFILSPVV

KRSFIQSIKVINAIIKKYGLPNDIIIELAREKNSKDAQKMINEMQKRNRQ

TNERIEEIIRTTGKENAKYLIEKIKLHDMQEGKCLYSLEAIPLEDLLNNP

FNYEVDHIIPRSVSFDNSFNNKVLVKQEEASKKGNRTPFQYLSSSDSKIS

YETFKKHILNLAKGKGRISKTKKEYLLEERDINRFSVQKDFINRNLVDTR

YATRGLMNLLRSYFRVNNLDVKVKSINGGFTSFLRRKWKFKKERNKGYKH

HAEDALIIANADFIFKEWKKLDKAKKVMENQMFEEKQAESMPEIETEQEY

KEIFITPHQIKHIKDFKDYKYSHRVDKKPNRELINDTLYSTRKDDKGNTL

IVNNLNGLYDKDNDKLKKLINKSPEKLLMYHHDPQTYQKLKLIMEQYGDE

KNPLYKYYEETGNYLTKYSKKDNGPVIKKIKYYGNKLNAHLDITDDYPNS

RNKVVKLSLKPYRFDVYLDNGVYKFVTVKNLDVIKKENYYEVNSKCYEEA

-continued

KKLKKISNQAEFIASFYNNDLIKINGELYRVIGVNNDLLNRIEVNMIDIT

YREYLENMNDKRPPRIIKTIASKTQSIKKYSTDILGNLYEVKSKKHPQII

KKG

Similar mutations can also apply to any other naturally-occurring Cas9 (e.g., Cas9 from other species) or engineered Cas9 molecules. In certain embodiments, the dCas9 molecule comprises a *Streptococcus pyogenes* dCas9 molecule, a *Staphylococcus aureus* dCas9 molecule, a *Campylobacter jejuni* dCas9 molecule, a *Corynebacterium diphtheria* dCas9 molecule, a *Eubacterium ventriosum* dCas9 molecule, a *Streptococcus* pasteurianus dCas9 molecule, a *Lactobacillus farciminis* dCas9 molecule, a *Sphaerochaeta globus* dCas9 molecule, an *Azospirillum* (strain B510) dCas9 molecule, a *Gluconacetobacter diazotrophicus* dCas9 molecule, a *Neisseria cinerea* dCas9 molecule, a *Roseburia intestinalis* dCas9 molecule, a *Parvibaculum lavamentivorans* dCas9 molecule, a *Nitratifractor salsuginis* (strain DSM 16511) dCas9 molecule, a *Campylobacter lari* (strain CF89-12) dCas9 molecule, a *Streptococcus thermophilus* (strain LMD-9) dCas9 molecule, or fragment thereof. In certain embodiments, the present disclosure provides an AAV vector comprising a nucleotide encoding a *Streptococcus pyogenes* dCas9 molecule, a *Staphylococcus aureus* dCas9 molecule, a *Campylobacter jejuni* dCas9 molecule, a *Corynebacterium diphtheria* dCas9 molecule, a *Eubacterium ventriosum* dCas9 molecule, a *Streptococcus* pasteurianus dCas9 molecule, a *Lactobacillus farciminis* dCas9 molecule, a *Sphaerochaeta globus* dCas9 molecule, an *Azospirillum* (strain B510) dCas9 molecule, a *Gluconacetobacter diazotrophicus* dCas9 molecule, a *Neisseria cinerea* dCas9 molecule, a *Roseburia intestinalis* dCas9 molecule, a *Parvibaculum lavamentivorans* dCas9 molecule, a *Nitratifractor salsuginis* (strain DSM 16511) dCas9 molecule, a *Campylobacter lari* (strain CF89-12) dCas9 molecule, a *Streptococcus thermophilus* (strain LMD-9) dCas9 molecule, or fragment thereof.

In one embodiment, as used herein, "iCas9" and "dCas9" both refer to a Cas9 protein that has the amino acid substitutions D10A and H840A and has its nuclease activity inactivated. In certain embodiments, the Cas9 protein comprises dCas9.

F. Cas9 Fusion Protein

The CRISPR/Cas9-based system may include a fusion protein. The fusion protein may comprise three heterologous polypeptide domains, wherein the first polypeptide domain comprises, consists of, or consists essentially of a dead Clustered Regularly Interspaced Short Palindromic Repeats associated (dCas) protein, the second polypeptide domain comprises, consists of, or consists essentially of a Kruppel-associated box (KRAB), and the polypeptide domain has an activity selected from the group consisting of transcription activation activity, transcription repression activity, transcription release factor activity, histone modification activity, nuclease activity, nucleic acid association activity, methylase activity, and demethylase activity.

(1) Transcription Activation Activity

The third polypeptide domain may have transcription activation activity, i.e., a transactivation domain. For example, gene expression of endogenous mammalian genes, such as human genes, may be achieved by targeting a fusion protein of iCas9 and a transactivation domain to mammalian promoters via combinations of gRNAs. The transactivation domain may include a VP 16 protein, multiple VP 16 proteins, such as a VP48 domain or VP64 domain, or p65 domain of NF kappa B transcription activator activity. For example, the fusion protein may be iCas9-VP64.

(2) Transcription Repression Activity

The third polypeptide domain may have transcription repression activity. The second polypeptide domain may have a Kruppel associated box activity, such as a KRAB domain, ERF repressor domain activity, Mxi1 repressor domain activity, SID4X repressor domain activity, Mad-SID repressor domain activity or TATA box binding protein activity. For example, the fusion protein may be dCas9-KRAB.

(3) Transcription Release Factor Activity

The third polypeptide domain may have transcription release factor activity. The second polypeptide domain may have eukaryotic release factor 1 (ERF1) activity or eukaryotic release factor 3 (ERF3) activity.

(4) Histone Modification Activity

The third polypeptide domain may have histone modification activity. The second polypeptide domain may have histone deacetylase, histone acetyltransferase, histone demethylase, or histone methyltransferase activity. The histone acetyltransferase may be p300 or CREB-binding protein (CBP) protein, or fragments thereof. For example, the fusion protein may be dCas9-p300.

(5) Nuclease Activity

The third polypeptide domain may have nuclease activity that is different from the nuclease activity of the Cas9 protein. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

(6) Nucleic Acid Association Activity

The third polypeptide domain may have nucleic acid association activity or nucleic acid binding protein-DNA-binding domain (DBD) is an independently folded protein domain that contains at least one motif that recognizes double- or single-stranded DNA. A DBD can recognize a specific DNA sequence (a recognition sequence) or have a general affinity to DNA. nucleic acid association region selected from the group consisting of helix-turn-helix region, leucine zipper region, winged helix region, winged helix-turn-helix region, helix-loop-helix region, immunoglobulin fold, B3 domain, Zinc finger, HMG-box, Wor3 domain, TAL effector DNA-binding domain.

(7) Methylase Activity

The third polypeptide domain may have methylase activity, which involves transferring a methyl group to DNA, RNA, protein, small molecule, cytosine or adenine. The second polypeptide domain may include a DNA methyltransferase.

(8) Demethylase Activity

The third polypeptide domain may have demethylase activity. The second polypeptide domain may include an enzyme that remove methyl (CH3-) groups from nucleic acids, proteins (in particular histones), and other molecules. Alternatively, the second polypeptide may covert the methyl group to hydroxymethylcytosine in a mechanism for demethylating DNA. The second polypeptide may catalyze this reaction. For example, the second polypeptide that catalyzes this reaction may be Tetl.

In one aspect, the CRISPR/Cas9-based system may include a dCas molecule and a modulator of gene expression, or a nucleic acid encoding a dCas molecule and a modulator of gene expression. In one embodiment, the dCas molecule and the modulator of gene expression are linked covalently. In one embodiment, the modulator of gene expression is covalently fused to the dCas molecule directly. In one embodiment, the modulator of gene expression is covalently fused to the dCas molecule indirectly, e.g., via a non-modulator or linker, or via a second modulator. In one embodiment, the modulator of gene expression is at the N-terminus and/or C-terminus of the dCas molecule. In one embodiment, the dCas molecule and the modulator of gene expression are linked non-covalently. In one embodiment, the dCas molecule is fused to a first tag, e.g., a first peptide tag. In one embodiment, the modulator of gene expression is fused to a second tag, e.g., a second peptide tag. In one embodiment, the first and second tag, e.g., the first peptide tag and the second peptide tag, non-covalently interact with each other, thereby brining the dCas molecule and the modulator of gene expression into close proximity.

In one embodiment, the CRISPR/Cas9-based system includes a fusion molecule or a nucleic acid encoding a fusion molecule. In one embodiment, the fusion molecule comprises a sequence comprising a dCas molecule fused to a modulator of gene expression. In one embodiment, the dCas molecule comprises a *Streptococcus pyogenes* dCas9 molecule, a *Staphylococcus aureus* dCas9 molecule, a *Campylobacter jejuni* dCas9 molecule, a *Corynebacterium diphtheria* dCas9 molecule, a *Eubacterium ventriosum* dCas9 molecule, a *Streptococcus pasteurianus* dCas9 molecule, a *Lactobacillus farciminis* dCas9 molecule, a *Sphaerochaeta globus* dCas9 molecule, an *Azospirillum* (strain B510) dCas9 molecule, a *Gluconacetobacter diazotrophicus* dCas9 molecule, a *Neisseria cinerea* dCas9 molecule, a *Roseburia intestinalis* dCas9 molecule, a *Parvibaculum lavamentivorans* dCas9 molecule, a *Nitratifractor salsuginis* (strain DSM 16511) dCas9 molecule, a *Campylobacter lari* (strain CF89-12) dCas9 molecule, a *Streptococcus thermophilus* (strain LMD-9) dCas9 molecule, or fragment thereof. In one embodiment, the modulator of gene expression is chosen from a repressor of gene expression, an activator of gene expression, or a modulator of epigenetic modification.

Different modulators of gene expression are known in the art, see, e.g., Thakore et al., Nat Methods. 2016; 13:127-37, incorporated by reference herein in its entirety.

(1) Repressor of Gene Expression

The repressor may be any known repressor of gene expression, for example, a repressor chosen from Krüppel associated box (KRAB) domain, mSin3 interaction domain (SID), MAX-interacting protein 1 (MXI1), a chromo shadow domain, an EAR-repression domain (SRDX), eukaryotic release factor 1 (ERF1), eukaryotic release factor 3 (ERF3), tetracycline repressor, the lad repressor, *Catharanthus roseus* G-box binding factors 1 and 2, *Drosophila* Groucho, Tripartite motif-containing 28 (TRIM28), Nuclear receptor co-repressor 1, Nuclear receptor co-repressor 2, or fragment or fusion thereof.

Krüppel Associated Box (KRAB)

The KRAB domain is a type of transcriptional repression domains present in the N-terminal part of many zinc finger protein-based transcription factors. The KRAB domain functions as a transcriptional repressor when tethered to a target DNA by a DNA-binding domain. The KRAB domain is enriched in charged amino acids and can be divided into sub-domains A and B. The KRAB A and B sub-domains can be separated by variable spacer segments and many KRAB proteins contain only the A sub-domain. A sequence of 45 amino acids in the KRAB A sub-domain has been shown to be important for transcriptional repression. The B sub-domain does not repress transcription by itself but does potentiate the repression exerted by the KRAB A sub-domain. The KRAB domain recruits corepressors KAP1 (KRAB-associated protein-1, also known as transcription intermediary factor 1 beta, KRAB-A interacting protein and tripartite motif protein 28) and heterochromatin protein 1 (HPI), as well as other chromatin modulating proteins, leading to transcriptional repression through heterochromatin formation. In one embodiment, the methods and compositions disclosed herein include a fusion molecule comprising a dCas9 molecule fused to a KRAB domain or fragment thereof. In one embodiment, the KRAB domain or fragment thereof is fused to the N-terminus of the dCas9 molecule. In one embodiment, the KRAB domain or fragment thereof is fused to the C-terminus of the dCas9 molecule. In one embodiment, the KRAB domain or fragment thereof is fused to both the N-terminus and the C-terminus of the dCas9 molecule. In one embodiment, the fusion molecule comprises a KRAB domain comprising the sequence of SEQ ID NO: 34, a sequence substantially identical (e.g., at least 80%, 85%, 90%, 92%, 95%, 97%, 98%, 99% or higher identical) to SEQ ID NO: 34, or a sequence having one, two, three, four, five or more changes, e.g., amino acid substitutions, insertions, or deletions, relative to SEQ ID NO: 34, or any fragment thereof.

```
                                         SEQ ID NO: 34
(exemplary KRAB)
DAKSLTAWSRTLVTFKDVFVDFTREEWKLLDTAQQILYRNVMLENYKNLV

SLGYQLTKPDVILRLEKGEEPWLVEREIHQETHPDSETAFEIKSSVPKKK

RKV
```

mSin3 Interaction Domain (SID)

The mSin3 interaction domain (SID) is an interaction domain that is present on several transcription repressor proteins. It interacts with the paired amphipathic alpha-helix 2 (PAH2) domain of mSin3, a transcriptional repressor domain that is attached to transcription repressor proteins such as the mSin3A corepressor. In one embodiment, the methods and compositions disclosed herein include a fusion molecule comprising a dCas9 molecule fused to an mSin3 interaction domain or fragment thereof. In one embodiment, the methods and compositions disclosed herein include a fusion molecule comprising a dCas9 molecule fused to four concatenated mSin3 interaction domains (SID4X). In one embodiment, the four concatenated mSin3 interaction domains (SID4X) are fused to the C-terminus of the dCas9 molecule.

MAX-Interacting Protein 1 (MXI1)

Mxi1 is a repressor of MYC. Mxi1 antagonizes MYC transcriptional activity possibly by competing for binding to MYC-associated factor X (MAX), which binds to MYC and is required for MYC to function. In one embodiment, the methods and compositions disclosed herein include a fusion molecule comprising a dCas9 molecule fused to Mxi1 or fragment thereof. In one embodiment, Mxi1 is fused to the C-terminus of the dCas9 molecule.

(2) Activator of Gene Expression

The activator may be any known activator of gene expression, for example, a VP16 activation domain, a VP64 activation domain, a p65 activation domain, an Epstein-Barr virus R transactivator Rta molecule, or fragment thereof.

Activations that can be used with a dCas9 molecule are known in the art. See, e.g., Chavez et al., Nat Methods. (2016) 13: 563-67, incorporated by reference herein in its entirety.

VP16, VP64, VP160

VP16 is a viral protein sequence of 16 amino acids that recruits transcriptional activators to promoters and enhancers. VP64 is a transcription activator comprising four copies of VP16, e.g., a molecule comprising four tandem copies of VP16 connected by Gly-Ser linkers. VP160 is a transcription activator comprising 10 copies of VP16. In one embodiment, the methods and compositions disclosed herein include a fusion molecule comprising a dCas9 molecule fused to 1, 2, 3, 4, 5, 6, 7, 8, 9, 10, or more copies of VP16.

In one embodiment, the methods and compositions disclosed herein include a fusion molecule comprising a dCas9 molecule fused to VP64. In one embodiment, the methods and compositions disclosed herein include a fusion molecule comprising a dCas9 molecule fused to VP160. In one embodiment, VP64 is fused to the C-terminus, the N-terminus, or both the N-terminus and the C-terminus of the dCas9 molecule.

p65 Activation Domain (p65AD)

p65AD is the principal transactivation domain of the 65 kDa polypeptide of the nuclear form of the NF-κB transcription factor. An exemplary sequence of human transcription factor p65 is available at the Uniprot database under accession number Q04206. In one embodiment, the methods and compositions disclosed herein include a fusion molecule comprising a dCas9 molecule fused to p65 or fragment thereof, e.g., p65AD.

Epstein-Barr Virus (EBV) R Transactivator (Rta)

Rta, an immediate-early protein of EBV, is a transcriptional activator that induces lytic gene expression and triggers virus reactivation. In one embodiment, the methods and compositions disclosed herein include a fusion molecule comprising a dCas9 molecule fused to Rta or fragment thereof.

VP64, p65, Rta Fusions

In one embodiment, the methods and compositions disclosed herein include a fusion molecule comprising a dCas9 molecule fused to VP64, p65, Rta, or any combination thereof. The tripartite activator VP64-p65-Rta (also known as VPR), in which the three transcription activation domains are fused using short amino acid linkers, can effectively up-regulate target gene expression when fused to a dCas9 molecule. In one embodiment, the methods and compositions disclosed herein include a fusion molecule comprising a dCas9 molecule fused to VPR.

Synergistic Activation Mediators (SAM)

In one embodiment, the methods and compositions disclosed herein include a CRISPR-Cas system that comprises three components: (1) a dCas9-VP64 fusion, (2) a gRNA incorporating two MS2 RNA aptamers at the tetraloop and stem-loop, and (3) the MS2-P65-HSF1 activation helper protein. This system, named Synergistic Activation Mediators (SAM), brings together three activation domains—VP64, P65 and HSF1 and has been described in Konermann et al., Nature. 2015; 517:583-8, incorporated by reference herein in its entirety.

Ldb1 Self-Association Domain

In one embodiment, the methods and compositions disclosed herein include a fusion molecule comprising a dCas9 molecule fused to Ldb1 self-association domain. Ldb1 self-association domain recruits enhancer-associated endogenous Ldb1.

(3) Modulator of Epigenetic Modification

In one embodiment, the methods and compositions disclosed herein include a fusion molecule comprising a dCas9 molecule fused to a modular of epigenetic modification. In one embodiment, the fusion molecule modulates target gene expression via epigenetic modification, e.g., via histone acetylation or methylation, or DNA methylation, at a regulatory element of target gene, e.g., a promoter or enhancer. The modulator may be any known modulator of epigenetic modification, e.g., a histone acetyltransferase (e.g., p300 catalytic domain), a histone deacetylase, a histone methyltransferase (e.g., SUV39H1 or G9a (EHMT2)), a histone demethylase (e.g., LSD1), a DNA methyltransferase (e.g., DNMT3a or DNMT3a-DNMT3L), a DNA demethylase (e.g., TET1 catalytic domain or TDG), or fragment thereof.

In one embodiment, the methods and compositions disclosed herein include a fusion molecule comprising a dCas9 molecule fused to Lys-specific histone demethylase 1 (LSD1) or fragment thereof. In one embodiment, the methods and compositions disclosed herein include a fusion molecule comprising a dCas9 molecule fused to acetyltransferase p300 or fragment thereof, e.g., the catalytic core of p300. In one embodiment, the methods and compositions disclosed herein include a fusion molecule comprising a dCas9 molecule fused to CREB-binding protein (CBP) protein or fragment thereof. In one embodiment, the methods and compositions disclosed herein include a fusion molecule comprising a dCas9 molecule fused to Ten-eleven translocation methylcytosine dioxygenase 1 (TET1) or fragment thereof. In one embodiment, the methods and compositions disclosed herein include a fusion molecule comprising a dCas9 molecule fused to thymine DNA glycosylase (TDG) or fragment thereof. In one embodiment, the methods and compositions disclosed herein include a fusion molecule comprising a dCas9 molecule fused to SUV39H1 or fragment thereof. In one embodiment, the methods and compositions disclosed herein include a fusion molecule comprising a dCas9 molecule fused to G9a (EHMT2) or fragment thereof. In one embodiment, the methods and compositions disclosed herein include a fusion molecule comprising a dCas9 molecule fused to DNMT3a or fragment thereof. In one embodiment, the methods and compositions disclosed herein include a fusion molecule comprising a dCas9 molecule fused to DNMT3a-DNMT3L or fragment thereof.

In one embodiment, the Cas9 fusion protein also comprises a nuclear localization sequence (NLS), e.g., a NLS fused to the N-terminus and/or C-terminus of Cas9. Nuclear localization sequences are known in the art. In one embodiment, the NLS comprises the amino acid sequence of SEQ ID NO: 37 or 38, a sequence substantially identical (e.g., at least 80%, 85%, 90%, 92%, 95%, 97%, 98%, 99% or higher identical) to SEQ ID NO: 37 or 38, or a sequence having one, two, three, four, five or more changes, e.g., amino acid substitutions, insertions, or deletions, relative to SEQ ID NO: 37 or 38, or any fragment thereof.

```
                                          SEQ ID NO: 37
(exemplary nuclear localization sequence)
APKKKRKVGIHGVPAA

                                          SEQ ID NO: 38
(exemplary nuclear localization sequence)
KRPAATKKAGQAKKKK
```

In one embodiment, the fusion molecule is a NLS-dSaCas9-NLS-KRAB fusion molecule comprising from the N-terminus to the C-terminus: a first NLS, an *S. aureus* dCas9 molecule, a second NLS, and a KRAB, fused directly or indirectly (e.g., via a linker). In one embodiment, the fusion molecule is a HA-NLS-dSaCas9-NLS-KRAB fusion molecule comprising from the N-terminus to the C-terminus: a HA tag, a first NLS, an *S. aureus* dCas9 molecule, a second NLS, and a KRAB, fused directly or indirectly (e.g., via a linker). In one embodiment, the fusion molecule is encoded by a nucleic acid comprising the sequence of SEQ ID NO: 23, a sequence substantially identical (e.g., at least 80%, 85%, 90%, 92%, 95%, 97%, 98%, 99% or higher identical) to SEQ ID NO: 23, or a sequence having one, two, three, four, five or more changes, e.g., substitutions, insertions, or deletions, relative to SEQ ID NO: 23, or any fragment thereof. In one embodiment, the fusion molecule comprises the fusion molecule comprises the amino acid sequence of SEQ ID NO: 39, 40, or 41, a sequence substantially identical (e.g., at least 80%, 85%, 90%, 92%, 95%, 97%, 98%, 99% or higher identical) to SEQ ID NO: 39, 40, or 41, or a sequence having one, two, three, four, five or more changes, e.g., amino acid substitutions, insertions, or deletions, relative to SEQ ID NO: 39, 40, or 41, or any fragment thereof.

SEQ ID NO: 39
(exemplary HA-NLS-dSaCas9-NLS-KRAB sequence)

MYPYDVPDYAAPKKKRKVGIHGVPAAKRNYILGLAIGITSVGYGIIDYET
RDVIDAGVRLFKEANVENNEGRRSKRGARRLKRRRRHRIQRVKKLLFDYN
LLTDHSELSGINPYEARVKGLSQKLSEEEFSAALLHLAKRRGVHNVNEVE
EDTGNELSTKEQISRNSKALEEKYVAELQLERLKKDGEVRGSINRFKTSD
YVKEAKQLLKVQKAYHQLDQSFIDTYIDLLETRRTYYEGPGEGSPFGWKD
IKEWYEMLMGHCTYFPEELRSVKYAYNADLYNALNDLNNLVITRDENEKL
EYYEKFQIIENVFKQKKKPTLKQIAKEILVNEEDIKGYRVTSTGKPEFTN
LKVYHDIKDITARKEIIENAELLDQIAKILTIYQSSEDIQEELTNLNSEL
TQEEIEQISNLKGYTGTHNLSLKAINLILDELWHTNDNQIAIFNRLKLVP
KKVDLSQQKEIPTTLVDDFILSPVVKRSFIQSIKVINAIIKKYGLPNDII
IELAREKNSKDAQKMINEMQKRNRQTNERIEEIIRTTGKENAKYLIEKIK
LHDMQEGKCLYSLEAIPLEDLLNNPFNYEVDHIIPRSVSFDNSFNNKVLV
KQEEASKKGNRTPFQYLSSSDSKISYETFKKHILNLAKGKGRISKTKKEY
LLEERDINRFSVQKDFINRNLVDTRYATRGLMNLLRSYFRVNNLDVKVKS
INGGFTSFLRRKWKFKKERNKGYKHHAEDALIIANADFIFKEWKKLDKAK
KVMENQMFEEKQAESMPEIETEQEYKEIFITPHQIKHIKDFKDYKYSHRV
DKKPNRELINDTLYSTRKDDKGNTLIVNNLNGLYDKDNDKLKKLINKSPE
KLLMYHHDPQTYQKLKLIMEQYGDEKNPLYKYYEETGNYLTKYSKKDNGP
VIKKIKYYGNKLNAHLDITDDYPNSRNKVVKLSLKPYRFDVYLDNGVYKF
VTVKNLDVIKKENYYEVNSKCYEEAKKLKKISNQAEFIASFYNNDLIKIN
GELYRVIGVNNDLLNRIEVNMIDITYREYLENMNDKRPPRIIKTIASKTQ
SIKKYSTDILGNLYEVKSKKHPQIIKKGKRPAATKKAGQAKKKKGSDAKS
LTAWSRTLVTFKDVFVDFTREEWKLLDTAQQILYRNVMLENYKNLVSLGY
QLTKPDVILRLEKGEEPWLVEREIHQETHPDSETAFEIKSSVPKKKRKV

-continued

SEQ ID NO: 40
(exemplary HA-NLS-dSaCas9-NLS-KRAB sequence)
YPYDVPDYAAPKKKRKVGIHGVPAAKRNYILGLAIGITSVGYGIIDYETR
DVIDAGVRLFKEANVENNEGRRSKRGARRLKRRRRHRIQRVKKLLFDYNL
LTDHSELSGINPYEARVKGLSQKLSEEEFSAALLHLAKRRGVHNVNEVEE
DTGNELSTKEQISRNSKALEEKYVAELQLERLKKDGEVRGSINRFKTSDY
VKEAKQLLKVQKAYHQLDQSFIDTYIDLLETRRTYYEGPGEGSPFGWKDI
KEWYEMLMGHCTYFPEELRSVKYAYNADLYNALNDLNNLVITRDENEKLE
YYEKFQIIENVFKQKKKPTLKQIAKEILVNEEDIKGYRVTSTGKPEFTNL
KVYHDIKDITARKEIIENAELLDQIAKILTIYQSSEDIQEELTNLNSELT
QEEIEQISNLKGYTGTHNLSLKAINLILDELWHTNDNQIAIFNRLKLVPK
KVDLSQQKEIPTTLVDDFILSPVVKRSFIQSIKVINAIIKKYGLPNDIII
ELAREKNSKDAQKMINEMQKRNRQTNERIEEIIRTTGKENAKYLIEKIKL
HDMQEGKCLYSLEAIPLEDLLNNPFNYEVDHIIPRSVSFDNSFNNKVLVK
QEEASKKGNRTPFQYLSSSDSKISYETFKKHILNLAKGKGRISKTKKEYL
LEERDINRFSVQKDFINRNLVDTRYATRGLMNLLRSYFRVNNLDVKVKSI
NGGFTSFLRRKWKFKKERNKGYKHHAEDALIIANADFIFKEWKKLDKAKK
VMENQMFEEKQAESMPEIETEQEYKEIFITPHQIKHIKDFKDYKYSHRVD
KKPNRELINDTLYSTRKDDKGNTLIVNNLNGLYDKDNDKLKKLINKSPEK
LLMYHHDPQTYQKLKLIMEQYGDEKNPLYKYYEETGNYLTKYSKKDNGPV
IKKIKYYGNKLNAHLDITDDYPNSRNKVVKLSLKPYRFDVYLDNGVYKFV
TVKNLDVIKKENYYEVNSKCYEEAKKLKKISNQAEFIASFYNNDLIKING
ELYRVIGVNNDLLNRIEVNMIDITYREYLENMNDKRPPRIIKTIASKTQS
IKKYSTDILGNLYEVKSKKHPQIIKKGKRPAATKKAGQAKKKKGSDAKSL
TAWSRTLVTFKDVFVDFTREEWKLLDTAQQILYRNVMLENYKNLVSLGYQ
LTKPDVILRLEKGEEPWLVEREIHQETHPDSETAFEIKSSVPKKKRKV SEQ ID NO: 41
(exemplary NLS-dSaCas9-NLS-KRAB)

APKKKRKVGIHGVPAAKRNYILGLAIGITSVGYGIIDYETRDVIDAGVRL
FKEANVENNEGRRSKRGARRLKRRRRHRIQRVKKLLFDYNLLTDHSELSG
INPYEARVKGLSQKLSEEEFSAALLHLAKRRGVHNVNEVEEDTGNELSTK
EQISRNSKALEEKYVAELQLERLKKDGEVRGSINRFKTSDYVKEAKQLLK
VQKAYHQLDQSFIDTYIDLLETRRTYYEGPGEGSPFGWKDIKEWYEMLMG
HCTYFPEELRSVKYAYNADLYNALNDLNNLVITRDENEKLEYYEKFQIIE
NVFKQKKKPTLKQIAKEILVNEEDIKGYRVTSTGKPEFTNLKVYHDIKDI
TARKEIIENAELLDQIAKILTIYQSSEDIQEELTNLNSELTQEEIEQISN
LKGYTGTHNLSLKAINLILDELWHTNDNQIAIFNRLKLVPKKVDLSQQKE
IPTTLVDDFILSPVVKRSFIQSIKVINAIIKKYGLPNDIIIELAREKNSK
DAQKMINEMQKRNRQTNERIEEIIRTTGKENAKYLIEKIKLHDMQEGKCL
YSLEAIPLEDLLNNPFNYEVDHIIPRSVSFDNSFNNKVLVKQEEASKKGN
RTPFQYLSSSDSKISYETFKKHILNLAKGKGRISKTKKEYLLEERDINRF
SVQKDFINRNLVDTRYATRGLMNLLRSYFRVNNLDVKVKSINGGFTSFLR

-continued

```
RKWKFKKERNKGYKHHAEDALIIANADFIFKEWKKLDKAKKVMENQMFEE

KQAESMPEIETEQEYKEIFITPHQIKHIKDFKDYKYSHRVDKKPNRELIN

DTLYSTRKDDKGNTLIVNNLNGLYDKDNDKLKKLINKSPEKLLMYHHDPQ

TYQKLKLIMEQYGDEKNPLYKYYEETGNYLTKYSKKDNGPVIKKIKYYGN

KLNAHLDITDDYPNSRNKVVKLSLKPYRFDVYLDNGVYKFVTVKNLDVIK

KENYYEVNSKCYEEAKKLKKISNQAEFIASFYNNDLIKINGELYRVIGVN

NDLLNRIEVNMIDITYREYLENMNDKRPPRIIKTIASKTQSIKKYSTDIL

GNLYEVKSKKHPQIIKKGKRPAATKKAGQAKKKKGSDAKSLTAWSRTLVT

FKDVFVDFTREEWKLLDTAQQILYRNVMLENYKNLVSLGYQLTKPDVILR

LEKGEEPWLVEREIHQETHPDSETAFEIKSSVPKKKRKV
```

G. gRNA

As described above, the CRISPR/Cas9 system utilizes gRNA that provides the targeting of the CRISPR/Cas9-based system. The gRNA is a fusion of two noncoding RNAs: a crRNA and a tracrRNA. The sgRNA may target any desired DNA sequence by exchanging the sequence encoding a 20 bp protospacer which confers targeting specificity through complementary base pairing with the desired DNA target. gRNA mimics the naturally occurring crRNA: tracrRNA duplex involved in the Type II Effector system. This duplex, which may include, for example, a 42-nucleotide crRNA and a 75-nucleotide tracrRNA, acts as a guide for the Cas9 to cleave the target nucleic acid. The term "target region", "target sequence" or "protospacer" as used interchangeably herein refers to the region of the target gene to which the CRISPR/Cas9-based system targets. The CRISPR/Cas9-based system may include at least one gRNA, wherein the gRNAs target different DNA sequences. The target DNA sequences may be overlapping. The target sequence or protospacer is followed by a PAM sequence at the 3' end of the protospacer. Different Type II systems have differing PAM requirements. For example, the *S. pyogenes* Type II system uses an "NGG" sequence, where "N" can be any nucleotide.

The number of gRNA administered to the cell may be at least 1 gRNA, at least 2 different gRNAs, at least 3 different gRNAs, at least 4 different gRNAs, at least 5 different gRNAs, at least 6 different gRNAs, at least 7 different gRNAs, at least 8 different gRNAs, at least 9 different gRNAs, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 19 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA administered to the cell may be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, or 8 different gRNAs to at least 12 different gRNAs.

In one embodiment, the gRNA is selected to increase or decrease transcription of a target gene. In one embodiment, the gRNA targets a region upstream of the transcription start site of a target gene, e.g., between 0-1000 bp upstream of the transcription start site of a target gene. In one embodiment, the gRNA targets a region downstream of the transcription start site of a target gene, e.g., between 0-1000 bp downstream of the transcription start site of a target gene. In one embodiment, the gRNA targets a promoter region of a target gene. In one embodiment, the gRNA targets an enhancer region of a target gene.

gRNA can be divided into a target binding region, a Cas9 binding region, and a transcription termination region. The target binding region hybridizes with a target region in a target gene. Methods for designing such target binding regions are known in the art, see, e.g., Doench et al., Nat Biotechnol. (2014) 32:1262-7; and Doench et al., Nat Biotechnol. (2016) 34:184-91, incorporated by reference herein in their entirety. Design tools are available at, e.g., Feng Zhang lab's target Finder, Michael Boutros lab's Target Finder (E-CRISP), RGEN Tools (Cas-OF Finder), CasFinder, and CRISPR Optimal Target Finder. In certain embodiments, the target binding region can be between about 15 and about 50 nucleotides in length (about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides in length). In certain embodiments, the target binding region can be between about 19 and about 21 nucleotides in length. In one embodiment, the target binding region is 15, 16, 17, 18, 19, 20, 21, 22, 23, 24, or 25 nucleotides in length.

In one embodiment, the target binding region is complementary, e.g., completely complementary, to the target region in the target gene. In one embodiment, the target binding region is substantially complementary to the target region in the target gene. In one embodiment, the target binding region comprises no more than 1, 2, 3, 4, 5, 6, 7, 8, 9, or 10 nucleotides that are not complementary to the target region in the target gene.

In one embodiment, the target binding region is engineered to improve stability or extend half-life, e.g., by incorporating a non-natural nucleotide or a modified nucleotide in the target binding region, by removing or modifying an RNA destabilizing sequence element, by adding an RNA stabilizing sequence element, or by increasing the stability of the Cas9/gRNA complex. In one embodiment, the target binding region is engineered to enhance its transcription. In one embodiment, the target binding region is engineered to reduce secondary structure formation.

In one embodiment, the Cas9 binding region of gRNA is modified to enhance the transcription of the gRNA. In one embodiment, the Cas9 binding region of gRNA is modified to improve stability or assembly of the Cas9/gRNA complex.

H. Gene Therapy Construct

Another aspect of the present disclosure provides a gene therapy construct comprising, consisting of, or consisting essentially of a fusion protein comprising three heterologous polypeptide domains, wherein the first polypeptide domain comprises, consists of, or consists essentially of a dead Clustered Regularly Interspaced Short Palindromic Repeats associated (dCas) protein, the second polypeptide domain comprises, consists of, or consists essentially of a Kruppel-associated box (KRAB), and the polypeptide domain has an activity selected from the group consisting of transcription activation activity, transcription repression activity, transcription release factor activity, histone modification activity, nuclease activity, nucleic acid association activity, methylase activity, and demethylase activity.

In one aspect, the present disclosure provides a nucleic acid encoding a fusion protein comprising a dCas9 molecule fused to a modulator of gene expression. In one embodiment, the nucleic acid contains a promoter operably linked to a polynucleotide encoding the fusion protein. In one embodiment, the promoter is constitutive. In one embodiment, the promoter is inducible. In one embodiment, the promoter is tissue specific. In one embodiment, the promoter is specific for liver expression. In one embodiment, the promoter for the polynucleotide encoding the fusion protein is selected to express an amount of the fusion protein that is proportional to the amount of gRNA, or amount of gRNA expression.

In another aspect, the present disclosure provides a nucleic acid encoding gRNA. In one embodiment, the nucleic acid contains a promoter operably linked to a polynucleotide encoding the gRNA. In one embodiment, the promoter is constitutive. In one embodiment, the promoter is inducible. In one embodiment, the promoter is tissue specific. In one embodiment, the promoter is specific for liver expression. In one embodiment, the promoter for the polynucleotide encoding the gRNA is selected to express an amount of the gRNA that is proportional to the amount of the fusion protein, or amount of fusion protein expression.

In some embodiments, the gene therapy construct comprises a vector system. In certain embodiments, the vector system comprises an AAV vector system.

In another embodiment, the gene therapy construct further comprises a first and second AAV inverted terminal repeat (ITR) sequence flanking the fusion protein.

In one embodiment, the vector system is a single viral vector system comprising a viral vector. In one embodiment, the vector is an adeno-associated virus (AAV) vector. In one embodiment, the adeno-associated virus is selected from the serotype 2, the serotype 5, the serotype 7, the serotype 8, and the serotype 9. In one embodiment, the vector comprises a first nucleic acid molecule that encodes a fusion molecule comprising a dCas9 molecule fused to a modulator that regulates the expression of a gene, and a second nucleic acid molecule that encodes a gRNA that targets the fusion molecule to the gene.

In one embodiment, the vector system comprises two or more viral vectors. In one embodiment, the vector system is a dual viral vector system comprising a first viral vector and a second viral vector. In one embodiment, the first and second vectors are adeno-associated virus (AAV) vectors. In one embodiment, the adeno-associated virus (AAV) vectors are the same or different AAV serotypes. In one embodiment, the adeno-associated virus is selected from the serotype 2, the serotype 5, the serotype 7, the serotype 8, and the serotype 9. In one embodiment, the first vector comprises a first nucleic acid molecule that encodes a fusion molecule comprising a dCas9 molecule fused to a modulator that regulates the expression of a gene; and the second vector comprises a second nucleic acid molecule that encodes a gRNA that targets the fusion molecule to the gene.

Different AAV capsids may be used in the compositions and methods described herein. For example, suitable AAV includes, but is not limited to, AAV8 (see, e.g., U.S. Pat. Nos. 7,790,449 and 7,282,199, incorporated by reference herein in their entirety), AAV9 (see, e.g., U.S. Pat. No. 7,906,111 and US 2011/0236353, incorporated by reference herein in their entirety), hu.37 (see, e.g., U.S. Pat. No. 7,906,111 and US 2011/0236353, incorporated by reference herein in their entirety), AAV1, AAV2, AAV3, AAV4, AAV5, AAV6, AAV6.2, AAV7, and AAV8 (see, e.g., U.S. Pat. Nos. 7,790,449 and 7,282,199, incorporated by reference herein in their entirety). The sequences of additional suitable AAV vectors and methods for generating them are disclosed in WO 2003/042397, WO 2005/033321, WO 2006/110689, U.S. Pat. Nos. 7,790,449, 7,282,199, and 7,588,772, incorporated by reference herein in their entirety. Still other AAV may be selected, optionally taking into consideration tissue preferences of the selected AAV capsid. A recombinant AAV vector (AAV viral particle) may comprise, packaged within an AAV capsid, a nucleic acid molecule containing a 5' AAV ITR, the expression cassettes described herein and a 3' AAV ITR. As described herein, an expression cassette may contain regulatory elements for an open reading frame(s) within each expression cassette and the nucleic acid molecule may optionally contain additional regulatory elements.

The AAV vector may contain a full-length AAV 5' inverted terminal repeat (ITR) and a full-length 3' ITR. A shortened version of the 5' ITR, termed AITR, has been described in which the D-sequence and terminal resolution site (trs) are deleted. The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., McCarty et al, Gene Ther. 2001, 8:1248-54, incorporated by reference herein in its entirety. Self-complementary AAVs are described in, e.g., U.S. Pat. Nos. 6,596,535; 7,125,717, and 7,456,683, incorporated by reference herein in their entirety.

A single-stranded AAV viral vector may be used. Methods for generating and isolating AAV viral vectors suitable for delivery to a subject are known in the art. See, e.g., U.S. Pat. Nos. 7,790,449; 7,282,199; WO 2003/042397; WO 2005/033321; WO 2006/110689; and U.S. Pat. No. 7,588,772. In one system, a producer cell line is transiently transfected with a construct that encodes the transgene flanked by ITRs and a construct(s) that encodes rep and cap. In a second system, a packaging cell line that stably supplies rep and cap is transfected (transiently or stably) with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., Hum Gene Ther. 2009; 20:922-9, incorporated by reference herein in its entirety. Methods of making and using these and other AAV production systems are also described in the following U.S. patents, incorporated by reference herein in their entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

In another embodiment, other viral vectors may be used, including integrating viruses, e.g., herpesvirus or lentivirus vectors. Suitably, where one of these other vectors is generated, it is produced as a replication-defective viral vector. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production.

In another embodiment, a non-viral delivery system may be used. For example, a composition disclosed herein comprising a nucleic acid may be formulated with nanoparticles, micelles, liposomes, cationic lipids, poly-glycans, polymers, lipids and/or cholesterols. See, e.g., Su et al., Mol. Pharmaceutics, 2011, 8, 774-787; WO 2013/182683, WO 2010/053572, and WO 2012/170930, incorporated by reference herein in their entirety.

Another aspect of the present disclosure provides a pharmaceutical composition comprising the gene therapy construct as described herein in a biocompatible pharmaceutical carrier.

In another aspect, the present disclosure provides a modified programmable RNA-guided dCas9-based repressor for efficient packaging in AAV and in vivo gene regulation. This gene delivery system can be customized to target any endogenous gene by designing a new guide RNA molecule, enabling patent and stable gene repression in animal models and therapeutic use.

In some embodiments, the Cas protein comprises Cas9.

In some embodiments, the gene therapy construct is designed for the targeted reduction of the PCSK9 gene.

I. Gene Therapy Target

The invention disclosed herein can be used to modulate the expression of a gene of interest. In one embodiment, the expression of the gene is down-regulated. In one embodiment, the expression of the gene is up-regulated. In one embodiment, the temporal pattern of the expression of the gene is modulated. In one embodiment, the spatial pattern of the expression of the gene is modulated. Exemplary genes, tissues expressing these genes, and relevant disease indications are disclosed in Tables 2 and 3. Table 2 provides genes, the expression of which can be down-regulated to treat diseases shown alongside the genes. Table 3 provides genes, the expression of which can be up-regulated to treat diseases shown alongside the genes.

TABLE 2

Exemplary genes for expression modulation (e.g., repression) and Exemplary Diseases and Tissues

| Gene | Disease | Tissue |
|---|---|---|
| proprotein convertase subtilisin/kexin type 9 (PCSK9) | Hypercholesteremia | Liver |
| activin receptor type-2B (ACVR2B) | muscle weakness | Muscle |
| huntingtin gene (HTT) | Huntington's disease | Brain |
| superoxide dismutase 1 (SOD1) | Amyotrophic lateral sclerosis | Brain |
| transthyretin (TTR) | Hereditary ATTR amyloidosis | Liver |
| antithrombin | Hemophilia | Liver |
| complement component C5 | Complement-mediated disease | Liver |
| aminolevulinic acid synthase 1 | Hepatic porphyria | Liver |
| glycolate oxidase | Primary hyperoxaluria type 1 | Liver |
| transmembrane protease, serine 6 (Tmprss6) | Beta thalassemia | Liver |
| alpha-antitrypsin (AAT) | Alpha-1 antitrypsin (AAT) deficiency | Liver |
| vascular endothelial growth factor (VEGF) | Age-related macular degeneration | Retina |
| C9orf72 | Familial frontotemporal dementia (FTD) and amyotrophic lateral sclerosis (ALS) | Brain |
| KRAS | Cancer | tumor |
| human epidermal growth factor receptor 2 (HER2) | Cancer | tumor |
| Beta catenin | Cancer | tumor |
| angiopoietin-like 3 (ANGPTL3) | Hyperlipidemia | Liver |
| apolipoprotein C-III (apoCIII) | Hyperlipidemia | Liver |
| PD-L1 | Chronic liver infection | Liver |
| HBV, HCV, HDV viral genomes | Hepatitis | Liver |
| vascular endothelial growth factor receptor 1 (VEGFR1) | Age-related macular degeneration | Retina |
| RTP801 | Age-related macular degeneration | Retina |
| beta-2 adrenergic receptor (ADRB2) | Glaucoma, Ocular hypertension | Retina |
| Caspase 2 | Glaucoma, Ocular hypertension | Retina |
| IKKbeta | Glaucoma | Retina |
| apolipoprotein A | Cardiovascular disease | Liver |
| factor 12 | Hereditary angioedema | Liver |
| prekallikrein | Hereditary angioedema | Liver |
| apolipoprotein B-100 | Hypercholesteremia | Liver |
| glucagon receptor | Diabetes | Liver |
| microRNA-103/107 | Nonalcoholic steatohepatitis (NASH) in patients with type 2 diabetes | Liver |
| Diacylglycerol O-Acyltransferase 2 (DGAT2) | Nonalcoholic steatohepatitis (NASH) in patients with type 2 diabetes | Liver |
| Ube3a-ATS | Angelman Syndrome | Brain |
| TNFR | Autoimmmune disease | Various-cartilage |
| FRG1 | Facioscapulohumeral muscular dystrophy | Muscle |
| BCR-ABL | Chronic myelogenous leukemia | Blood tumor |
| TEL-AML1 | Acute lymphoblastic leukemia | Blood tumor |

TABLE 2-continued

Exemplary genes for expression modulation (e.g., repression) and Exemplary Diseases and Tissues

| Gene | Disease | Tissue |
|---|---|---|
| PTEN | Cancer | Tumor |
| Other tumor suppressors | Cancer | Tumor |
| Mendelian disorders | Various | Various |
| Triggering receptor expressed on myeloid cells 2 (TREM-2) | Neurodegenerative disease, e.g., Alzheimer's disease, amyotrophic lateral sclerosis, and Parkinson's disease | CNS |
| APOE4 | Alzheimer's disease | CNS |
| CD33 | Alzheimer's disease | CNS |
| Other disease risk genes | Various | Various |

TABLE 3

Exemplary genes for expression modulation (e.g., activation) and Exemplary Diseases and Tissues

| Gene | Disease | Tissue |
|---|---|---|
| aromatic L-amino acid decarboxylase (AADC) | Parkinson's disease | Brain |
| triggering receptor expressed on myeloid cells 2 (TREM2) | Alzheimer's Disease | Brain |
| vascular endothelial growth factor (VEGF) | Tissue regeneration | Various - muscle |
| brain-derived neurotrophic factor (BDNF) | Neurological conditions | Brain |
| platelet-derived growth factor (PDGF) | Tissue regeneration | Various - muscle |
| utrophin | Muscular dystrophy | Skeletal and cardiac muscle |
| frataxin | Friedreich's ataxia | Brain |
| sodium voltage-gated channel alpha subunit 1 (SCN1A) | Dravet Syndrome | Brain |
| pigment epithelium-derived factor (PEDF) | Wet AMD, cancer | Eye, tumor |
| BCL2 Associated X (BAX) | Cancer | Tumor |
| mammary serine protease inhibitor (maspin) | Cancer | Tumor |
| p53 | Cancer | Tumor |
| cystic fibrosis transmembrane conductance regulator (CFTR) | Cystic fibrosis | Lung |
| fragile X mental retardation 1 (FMR1) | Fragile X | Brain |
| methyl-CpG-binding protein 2 (MECP2) | Rhett syndrome | Brain |
| ubiquitin-protein ligase E3A (Ube3a) | Angelman syndrome | Brain |
| ubiquitin-protein ligase E3A (Ube3a) | Prader-Willi syndrome | Brain |
| IL1RA | rheumatoid arthritis | Cartilage |
| HBG1/HBG2 | sickle cell anemia | Blood |
| IL-10 | Collitis, inflammatory bowel disease | Gut - T cells |
| IL-2 | Various- graft versus host disease, rheumatoid arthritis, lupus, type 1 diabetes | Various |
| Growth factors (e.g., having a protective or regenerative function) | Various | Various |

J. Methods

A variety of different diseases and conditions (e.g., one or more diseases described herein), e.g., diseases and conditions associated with one or more genes described herein, including, e.g., genetic deletions, insertions or mutations, can be treated using the method described herein. The compositions described herein can be delivered to any of the cells, tissues, or organs described herein to treat a disorder or condition associated with a gene described herein. Exemplary genes for expression modulation (e.g., repression or activation), and exemplary diseases and tissues, are described in Tables 2 and 3.

In one aspect, the present disclosure provides a method of suppressing the expression of a gene in a cell in vivo comprising, consisting of, or consisting essentially of administering to a cell a therapeutically effective amount of a gene therapy construct as described herein such that the gene expression is suppressed.

In one aspect, the present disclosure provides a method of suppressing the expression of a gene in vivo in a subject comprising, consisting of, or consisting essentially of administering to the subject a therapeutically effective amount of a gene therapy construct as described herein such that the gene expression is suppressed.

In some embodiments, the method is designed for the targeted reduction of the PCSK9 gene. In some embodiments, the method is designed for the targeted reduction of the expression of the PCSK9 gene.

In one aspect, the present disclosure provides a method of increasing the expression of a gene in a cell in vivo comprising, consisting of, or consisting essentially of administering to a cell a therapeutically effective amount of a gene therapy construct as described herein such that the gene expression is increased.

In one aspect, the present disclosure provides a method of increasing the expression of a gene in vivo in a subject comprising, consisting of, or consisting essentially of administering to the subject a therapeutically effective amount of a gene therapy construct as described herein such that the gene expression is increased.

In one embodiment, the aforementioned methods comprise administering to the cell or subject: a first nucleic acid that encodes a fusion molecule comprising a sequence comprising a dCas9 molecule fused to a modulator of gene expression, and a second nucleic acid that encodes a gRNA which targets the fusion molecule to the gene, in an amount sufficient to modulate expression of the gene. In one embodiment, the first and second nucleic acids are packaged in a same vector or different vectors. In one embodiment the first and second nucleic acids are packaged in a same AAV vector or different AAV vectors. In one embodiment, the first nucleic acid is a DNA. In one embodiment, the first nucleic acid is an mRNA.

In one embodiment, the aforementioned methods comprise administering to the cell or subject: a fusion molecule comprising a sequence comprising a dCas9 molecule fused to a modulator of gene expression, and a nucleic acid that encodes a gRNA which targets the fusion molecule to the gene, in an amount sufficient to modulate expression of the gene. In one embodiment, the nucleic acid is packaged in a viral vector, e.g., an AAV vector.

In one embodiment, the aforementioned methods comprise administering to the cell or subject: a fusion molecule comprising a sequence comprising a dCas9 molecule fused to a modulator of gene expression, and a gRNA which targets the fusion molecule to the gene, in an amount sufficient to modulate expression of the gene.

In one embodiment, the aforementioned methods comprise administering to the cell or subject: a nucleic acid that encodes a fusion molecule comprising a sequence comprising a dCas9 molecule fused to a modulator of gene expression, and a gRNA which targets the fusion molecule to the gene, in an amount sufficient to modulate expression of the gene. In one embodiment, the nucleic acid is packaged in a viral vector, e.g., an AAV vector. In one embodiment, the nucleic acid is a DNA. In one embodiment, the nucleic acid is an mRNA.

Different administration routes may be used for the methods disclosed herein. The compositions disclosed herein can be administered systemically or locally. In some embodiments, the compositions disclosed herein are administered intravenously, subcutaneously, orally, via inhalation, intranasally, intratracheally, intraarterially, intraocularly, or intramuscularly. In some embodiments, the compositions may be delivered in a single administration or multiple administrations. In one embodiment, two or more AAV vectors may be delivered, see, e.g., WO 2011/126808 and WO 2013/049493, incorporated by reference herein in their entirety.

In the case of AAV viral vectors, quantification of the genome copies ("GC") may be used as the measure of the dose contained in the formulation. Any method known in the art can be used to determine the genome copy (GC) number of the replication-defective virus compositions of the invention.

Production of lentivirus is measured as IU per volume (e.g., mL). IU is infectious unit, or alternatively transduction units (TU); IU and TU can be used interchangeably as a quantitative measure of the titer of a viral vector particle preparation.

Any known RNA delivery method can be used in the methods disclosed herein, including but not limited to, delivering RNA using block copolymers (see, e.g., US 2011/0286957, EP2620161, and WO 2015/017519, incorporated by reference herein in their entirety), and delivering RNA using cationic complexes or liposomal formulations (see, e.g., Landen et al., Cancer Biol. Ther. (2006) 5(12); Khoury et al., Arthritis Rheumatol. (2006) 54: 1867-77, incorporated by reference herein in their entirety). Local administration to the liver has also been demonstrated by injecting double stranded RNA directly into the circulatory system surrounding the liver using renal vein catheterization, see, e.g., Hamar et al., PNAS (2004) 101: 14883-8, incorporated by reference herein in its entirety.

Other methods are disclosed in WO 2013/143555; US 2013/0323001; US 2012/0195917; Soutschek et al., Nature (2004) 432: 173-8; Morrissey et al., Hepatol. (2005) 41: 1349-56; Uchida et al, (2013) PLoS ONE 8: e56220, incorporated by reference herein in their entirety.

K. Kits

Another aspect of the present disclosure provides a kit for the suppression of a gene in vivo comprising a gene therapy construct or pharmaceutical composition as described herein and instructions for use.

Yet another aspect of the present disclosure provides all that is described and illustrated herein.

The present invention may be defined in any of the following numbered paragraphs:

1. A method of modulating expression of a gene, in vivo, in a subject comprising administering to, or providing in, the subject:
   (a) (i) a fusion molecule comprising a sequence comprising a dCas9 molecule fused to a modulator of gene expression; or (ii) a nucleic acid that encodes a fusion molecule comprising a sequence comprising a dCas9 molecule fused to a modulator of gene expression; and
   (b) (i) a gRNA which targets the fusion molecule to the gene; or (ii) a nucleic acid that encodes a gRNA which targets the fusion molecule to the gene, in an amount sufficient to modulate expression of the gene.
2. The method of paragraph 1, comprising administering to, or provided in, the subject any of: (a)(ii) and (b)(ii), (a)(i) and (b)(i), (a)(i) and (b)(ii), or (a)(ii) and (b)(i).
3. The method of paragraph 1 or 2, comprising administering to, or provided in, the subject:
   (a)(ii) a nucleic acid that encodes a fusion molecule comprising a sequence comprising a dCas9 molecule fused to a modulator of gene expression; and
   (b)(ii) a nucleic acid that encodes a gRNA which targets the fusion molecule to the gene.
4. The method of any of the preceding paragraphs, wherein the nucleic acid of (a)(ii) comprises DNA.
5. The method of any of the preceding paragraphs, wherein the nucleic acid of (b)(ii) comprises DNA.
6. The method of any of the preceding paragraphs, wherein the nucleic acid of (a)(ii) comprises RNA.
7. The method of any of the preceding paragraphs, wherein the nucleic acid of (b)(ii) comprises RNA.
8. The method of any of the preceding paragraphs, wherein one or both of (a) and (b) are packaged in a viral vector.
9. The method of any of the preceding paragraphs, wherein (a) is packaged in a viral vector.
10. The method of any of the preceding paragraphs, wherein (b) is packaged in a viral vector.
11. The method of any of the preceding paragraphs, wherein (a) and (b) are packaged in the same viral vector.
12. The method of any of paragraphs 8-11, wherein the viral vector comprises an AAV vector.
13. The method of any of paragraphs 8-11, wherein the viral vector comprises a lentiviral vector.
14. The method of any of paragraphs 1-10, wherein (a) is packaged in a first viral vector and (b) is packaged in a second viral vector.
15. The method of paragraph 14, wherein the first viral vector comprises an AAV vector and the second viral vector comprises an AAV vector.
16. The method of any of the preceding paragraphs, wherein the dCas9 molecule comprises a gRNA binding domain of a Cas9 molecule.
17. The method of any of the preceding paragraphs, wherein the dCas9 molecule comprises one, two or all of: a Rec domain, a bridge helix domain, or a PAM interacting domain, of a Cas9 molecule.
18. The method of any of the preceding paragraphs, wherein the dCas9 molecule is a mutant of a wild-type Cas9 molecule, e.g., in which the Cas9 nuclease activity is inactivated.
19. The method of any of the preceding paragraphs, wherein the dCas9 molecule comprises a mutation that inactivates a Cas9 nuclease activity, e.g., a mutation in a DNA-cleavage domain of a Cas9 molecule.
20. The method of any of the preceding paragraphs, wherein the dCas9 molecule comprises a mutation that inactivates a Cas9 nuclease activity, e.g., a mutation in a RuvC domain and/or a mutation in a HNH domain.
21. The method of any of the preceding paragraphs, wherein the dCas9 molecule comprises a *Staphylococcus aureus* dCas9 molecule, a *Streptococcus pyogenes* dCas9 molecule, a *Campylobacter jejuni* dCas9 molecule, a *Corynebacterium diphtheria* dCas9 molecule, a *Eubacterium ventriosum* dCas9 molecule, a *Streptococcus* pasteurianus dCas9 molecule, a *Lactobacillus farciminis* dCas9 molecule, a *Sphaerochaeta globus* dCas9 molecule, an *Azospirillum* (e.g., strain B510) dCas9 molecule, a *Gluconacetobacter diazotrophicus* dCas9 molecule, a *Neisseria cinerea* dCas9 molecule, a *Roseburia intestinalis* dCas9 molecule, a *Parvibaculum lavamentivorans* dCas9 molecule, a *Nitratifractor salsuginis* (e.g., strain DSM 16511) dCas9 molecule, a *Campylobacter lari* (e.g., strain CF89-12) dCas9 molecule, or a *Streptococcus thermophilus* (e.g., strain LMD-9) dCas9 molecule.

22. The method of any of the preceding paragraphs, wherein the dCas9 molecule comprises an *S. aureus* dCas9 molecule, e.g., comprising an *S. aureus* dCas9 sequence described herein.

23. The method of any of the preceding paragraphs, wherein the *S. aureus* dCas9 molecule comprises a mutation at an amino acid position, corresponding to position 10, 580, or both (e.g., D10A, N580A, or both), relative to a wild-type *S. aureus* dCas9 molecule, numbered according to SEQ ID NO: 25.

24. The method of any of the preceding paragraphs, wherein the *S. aureus* dCas9 molecule comprises the amino acid sequence of SEQ ID NO: 35 or 36, a sequence substantially identical (e.g., at least 80%, 85%, 90%, 92%, 95%, 97%, 98%, 99% or higher identical) to SEQ ID NO: 35 or 36, or a sequence having one, two, three, four, five or more changes, e.g., amino acid substitutions, insertions, or deletions, relative to SEQ ID NO: 35 or 36, or any fragment thereof.

25. The method of any of paragraphs 1-20, wherein the dCas9 molecule comprises an *S. pyogenes* dCas9 molecule, e.g., comprising an *S. pyogenes* dCas9 sequence described herein.

26. The method of any of paragraphs 1-20, the *S. pyogenes* dCas9 molecule comprises a mutation at an amino acid position, corresponding to position 10, 840, or both (e.g., D10A, H840A, or both), relative to a wild-type *S. pyogenes* dCas9 molecule, numbered according to SEQ ID NO: 24.

27. The method of any of the preceding paragraphs, wherein the dCas9 molecule is less than 1400, 1300, 1200, 1100, 1000, 900, 800, 700, 600, or 500 amino acids in length.

28. The method of any of the preceding paragraphs, wherein the dCas9 molecule is 500-1300, 600-1200, 700-1100, 800-1000, 500-1200, 500-1000, 500-800, 500-600, 1000-1200, 800-1200, or 600-1200 amino acids in length.

29. The method of any of the preceding paragraphs, wherein the dCas9 molecule has a size that is less than 90%, 80%, 70%, 60%, 50%, 40%, or 30% of the size of a wild-type Cas9 molecule, e.g., a wild-type *S. pyogenes* Cas9 molecule or a wild-type *S. aureus* dCas9 molecule.

30. The method of any of the preceding paragraphs, wherein the modulator of gene expression comprises a modulator of gene expression described herein.

31. The method of any of the preceding paragraphs, wherein the modulator of gene expression comprises a repressor of gene expression, e.g., a Kruppel associated box (KRAB) molecule, an mSin3 interaction domain (SID) molecule, four concatenated mSin3 interaction domains (SID4X), MAX-interacting protein 1 (MXI1), or any fragment thereof.

32. The method of any of the preceding paragraphs, wherein the modulator of gene expression comprises a Kruppel associated box (KRAB) molecule comprising the sequence of SEQ ID NO: 34, a sequence substantially identical (e.g., at least 80%, 85%, 90%, 92%, 95%, 97%, 98%, 99% or higher identical) to SEQ ID NO: 34, or a sequence having one, two, three, four, five or more changes, e.g., amino acid substitutions, insertions, or deletions, relative to SEQ ID NO: 34, or any fragment thereof.

33. The method of any of the preceding paragraphs, wherein the modulator of gene expression comprises an activator of gene expression, e.g., a VP16 transcription activation domain, a VP64 transcriptional activation domain, a p65 activation domain, an Epstein-Barr virus R transactivator Rta molecule, a VP64-p65-Rta fusion (VPR), Ldb1 self-association domain, or any fragment thereof.

34. The method of any of the preceding paragraphs, wherein the modulator of gene expression comprises a modulator of epigenetic modification, e.g., a histone acetyltransferase (e.g., p300 catalytic domain), a histone deacetylase, a histone methyltransferase (e.g., SUV39H1 or G9a (EHMT2)), a histone demethylase (e.g., Lys-specific histone demethylase 1 (LSD1)), a DNA methyltransferase (e.g., DNMT3a or DNMT3a-DNMT3L), a DNA demethylase (e.g., TET1 catalytic domain or TDG), or fragment thereof.

35. The method of any of the preceding paragraphs, wherein the modulator of gene expression is fused to the C-terminus, N-terminus, or both, of the dCas9 molecule.

36. The method of any of the preceding paragraphs, wherein the modulator of gene expression is fused to the dCas9 molecule directly.

37. The method of any of paragraphs 1-34, wherein the modulator of gene expression is fused to the dCas9 molecule indirectly, e.g., via a non-modulator or a linker, or a second modulator.

38. The method of any of the preceding paragraphs, wherein a plurality of modulators of gene expression, e.g., two or more identical, substantially identical, or different modulators, are fused to the dCas9 molecule.

39. The method of any of the preceding paragraphs, wherein the fusion molecule further comprises a nuclear localization sequence.

40. The method of paragraph 39, wherein one or more nuclear localization sequences are fused to the C-terminus, N-terminus, or both, of the dCas9 molecule, e.g., directly or indirectly, e.g., via a linker.

41. The method of paragraph 40, wherein the one or more nuclear localization sequences comprise the amino acid sequence of SEQ ID NO: 37 or 38, a sequence substantially identical (e.g., at least 80%, 85%, 90%, 92%, 95%, 97%, 98%, 99% or higher identical) to SEQ ID NO: 37 or 38, or a sequence having one, two, three, four, five or more changes, e.g., amino acid substitutions, insertions, or deletions, relative to SEQ ID NO: 37 or 38, or any fragment thereof.

42. The method of any of the preceding paragraphs, wherein the fusion molecule comprises the amino acid sequence of SEQ ID NO: 39, 40, or 41, a sequence substantially identical (e.g., at least 80%, 85%, 90%, 92%, 95%, 97%, 98%, 99% or higher identical) to SEQ ID NO: 39, 40, or 41, or a sequence having one, two, three, four, five or more changes, e.g., amino acid substitutions, insertions, or deletions, relative to SEQ ID NO: 39, 40, or 41, or any fragment thereof.

43. The method of any of the preceding paragraphs, wherein the nucleic acid that encodes the fusion molecule comprises the sequence of SEQ ID NO: 23, a sequence substantially identical (e.g., at least 80%, 85%, 90%, 92%, 95%, 97%, 98%, 99% or higher identical) to SEQ ID NO: 23, or a sequence having one, two, three, four, five or more changes, e.g., substitutions, insertions, or deletions, relative to SEQ ID NO: 23, or any fragment thereof.

44. The method of any of the preceding paragraphs, wherein the gRNA comprises a unimolecular gRNA.

45. The method of any of paragraphs 1-43, wherein the gRNA comprises a bimolecular gRNA.

46. The method of any of the preceding paragraphs, wherein the gRNA comprises a gRNA sequence described herein.

47. The method of any of the preceding paragraphs, wherein gene expression is modulated in a cell, tissue, or organ described herein, e.g., Table 2 or 3.

48. The method of any of the preceding paragraphs, wherein gene expression is modulated in the liver.

49. The method of any of the preceding paragraphs, wherein the modulation is sufficient to alter a function of the gene, or a symptom of a disorder associated with the gene, as described herein, e.g., in Table 2 or 3.

50. The method of any of the preceding paragraphs, wherein the modulation comprises modulation of transcription.

51. The method of any of the preceding paragraphs, wherein the modulation comprises down-regulation of transcription.

52. The method of any of the preceding paragraphs, wherein the modulation comprises up-regulation of transcription.

53. The method of any of the preceding paragraphs, wherein the modulation comprises modulating the temporal pattern of expression of the gene.

54. The method of any of the preceding paragraphs, wherein the modulation comprises modulating the spatial pattern of expression of the gene.

55. The method of any of the preceding paragraphs, wherein the modulation comprises modulating a post-transcriptional or co-transcriptional modification, e.g., splicing, 5' capping, 3' cleavage, 3' polyadenylation, or RNA export.

56. The method of any of the preceding paragraphs, wherein the modulation comprises modulating the expression of an isoform, e.g., an increase or decrease in the expression of an isoform, the increase or decrease in the expression of a first isoform over a second isoform.

57. The method of any of the preceding paragraphs, wherein the modulation comprises modulating chromatin structure, e.g., increasing or decreasing methylation, acetylation, phosphorylation, or ubiquitination, e.g., at a preselected site, or altering the spatial pattern, cell specificity, or temporal occurrence of methylation, acetylation, phosphorylation, or ubiquitination.

58. The method of any of the preceding paragraphs, wherein the modulation comprises modulating a post-translational modification (e.g., indirectly), e.g., glycosylation, lipidation, acetylation, phosphorylation, amidation, hydroxylation, methylation, ubiquitination, sulfation, nitrosylation, or proteolysis.

59. The method of any of the preceding paragraphs, wherein the modulation does not comprise cleaving the subject's DNA.

60. The method of any of the preceding paragraphs, wherein the modulation comprises an inducible modulation.

61. The method of any of the preceding paragraphs, wherein the gene is selected from Table 2, optionally wherein the method down-regulates the expression of the gene.

62. The method of any of paragraphs 1-60, wherein the gene is selected from Table 3, optionally wherein the method up-regulates the expression of the gene.

63. The method of any of the preceding paragraphs, wherein the gene comprises PCSK9.

64. The method of any of the preceding paragraphs, wherein the dCas9 molecule does not cleave the genome of the subject.

65. A method of modulating expression of a gene, in vivo, in a subject comprising administering to, or providing in, the subject:

(a)(ii) a nucleic acid that encodes a fusion molecule (e.g., a fusion molecule described herein) comprising a sequence comprising an *S. aureus* dCas9 molecule fused to a KRAB molecule; and (b)(ii) a nucleic acid that encodes a gRNA (e.g., a gRNA described herein) which targets the fusion molecule to the gene, and wherein one or both of (a)(i) and (b)(ii) are packaged in an AAV vector.

66. The method of paragraph 65, wherein the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

67. The method of paragraph 65 or 66, wherein the gRNA comprises a gRNA sequence described herein.

68. The method of any of paragraphs 65-67, wherein the gene is selected from Table 2 or 3.

69. The method of any of paragraphs 65-68, wherein the gene comprises PCSK9.

70. The method of any of paragraphs 65-69, wherein (a)(ii) and (b)(ii) are packaged in different AAV vectors.

71. The method of any of paragraphs 65-70, wherein (a)(ii) and (b)(ii) are packaged in the same AAV vector.

72. A pharmaceutical composition, or unit dosage form, comprising, in an amount sufficient for modulating a gene in a human subject, or in an amount sufficient for a therapeutic effect in a human subject, (a)(ii) a nucleic acid that encodes a fusion molecule (e.g., a fusion molecule described herein) comprising a sequence comprising a dCas9 molecule, e.g., an *S. aureus* dCas9 molecule, fused to a modulator of gene expression (e.g., a modulator described herein); and/or (b)(ii) a nucleic acid that encodes a gRNA which targets the fusion molecule to the gene, wherein one or both of (a)(ii) and (b)(ii) are packaged in a viral vector, e.g., an AAV vector.

73. The pharmaceutical composition, or unit dosage form, of paragraph 72, wherein the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

74. The pharmaceutical composition, or unit dosage form, of paragraph 72 or 73, wherein the gRNA comprises a gRNA sequence described herein.
75. The pharmaceutical composition, or unit dosage form, of any of paragraphs 72-74, wherein the gene is selected from Table 2 or 3.
76. The method of any of paragraphs 72-75, wherein the gene comprises PCSK9.
77. The pharmaceutical composition, or unit dosage form, of any of paragraphs 72-76, wherein (a)(ii) and (b)(ii) are packaged in the same viral vector, e.g., an AAV vector.
78. The pharmaceutical composition, or unit dosage form, of any of paragraphs 72-77, wherein (a)(ii) and (b)(ii) are packaged in different viral vectors, e.g., AAV vectors.
79. The pharmaceutical composition, or unit dosage form, of any of paragraphs 72-78, wherein the viral vector (e.g., AAV vector) comprising (a)(ii), and the viral vector (e.g., AAV vector) comprising (b)(ii), are provided in separate containers.
80. The pharmaceutical composition, or unit dosage form, of any of paragraphs 72-79, wherein the viral vector (e.g., AAV vector) comprising (a)(ii) and the viral vector (e.g., AAV vector) comprising (b)(ii), are provided in the same container.
81. The pharmaceutical composition, or unit dosage form, of any of paragraphs 72-80, which is formulated for administration, e.g., oral, parenteral, sublingual, transdermal, rectal, transmucosal, topical, intrapleural, intravenous, intraarterial, intraperitoneal, subcutaneous, intramuscular, intranasal intrathecal, or intraarticular administration, or administration via inhalation or via buccal administration, or any combination thereof, to the subject.
82. The pharmaceutical composition, or unit dosage form, of any of paragraphs 72-81, which is formulated for intravenous administration to the subject.
83. The pharmaceutical composition, or unit dosage form, of any of paragraphs 72-82, which is disposed in a device suitable for administration, e.g., oral, parenteral, sublingual, transdermal, rectal, transmucosal, topical, intrapleural, intravenous, intraarterial, intraperitoneal, subcutaneous, intramuscular, intranasal intrathecal, or intraarticular administration, or administration via inhalation or via buccal administration, or any combination thereof, to the subject.
84. The pharmaceutical composition, or unit dosage form, of any of paragraphs 72-83, which is disposed in a device suitable for intravenous administration to the subject.
85. The pharmaceutical composition, or unit dosage form, of any of paragraphs 72-84, which is disposed in a volume of at least 1, 2, 5, 10, 15, 20, 25, 30, 40, 50, 60, 70, 80, 90, 100, 150, 200, 250, 300, 400, or 500 ml.
86. The pharmaceutical composition, or unit dosage form, of any of paragraphs 72-85, wherein the nucleic acid of (a)(ii) comprises DNA.
87. The pharmaceutical composition, or unit dosage form, of any of paragraphs 72-86, wherein the nucleic acid of (b)(ii) comprises DNA.
88. The pharmaceutical composition, or unit dosage form, of paragraphs 72-85 or
87, wherein the nucleic acid of (a)(ii) comprises RNA.
89. The pharmaceutical composition, or unit dosage form, of paragraphs 72-86 or
88, wherein the nucleic acid of (b)(ii) comprises RNA.
90. The pharmaceutical composition, or unit dosage form, of paragraphs 72-89, wherein the dCas9 molecule comprises a gRNA binding domain of a Cas9 molecule.
91. The pharmaceutical composition, or unit dosage form, of paragraphs 72-90, wherein the dCas9 molecule comprises one, two or all of: a Rec domain, a bridge helix domain, or a PAM interacting domain, of a Cas9 molecule.
92. The pharmaceutical composition, or unit dosage form, of paragraphs 72-91, wherein the dCas9 molecule is a mutant of a wild-type Cas9 molecule, e.g., in which the Cas9 nuclease activity is inactivated.
93. The pharmaceutical composition, or unit dosage form, of paragraphs 72-90, wherein the dCas9 molecule comprises a mutation that inactivates a Cas9 nuclease activity, e.g., a mutation in a DNA-cleavage domain of a Cas9 molecule.
94. The pharmaceutical composition, or unit dosage form, of paragraphs 72-93, wherein the dCas9 molecule comprises a mutation that inactivates a Cas9 nuclease activity, e.g., a mutation in a RuvC domain and/or a mutation in a HNH domain.
95. The pharmaceutical composition, or unit dosage form, of paragraphs 72-94, wherein the dCas9 molecule comprises a *Staphylococcus aureus* dCas9 molecule, a *Streptococcus pyogenes* dCas9 molecule, a *Campylobacter jejuni* dCas9 molecule, a *Corynebacterium diphtheria* dCas9 molecule, a *Eubacterium ventriosum* dCas9 molecule, a *Streptococcus* pasteurianus dCas9 molecule, a *Lactobacillus farciminis* dCas9 molecule, a *Sphaerochaeta globus* dCas9 molecule, an *Azospirillum* (e.g., strain B510) dCas9 molecule, a *Gluconacetobacter diazotrophicus* dCas9 molecule, a *Neisseria cinerea* dCas9 molecule, a *Roseburia intestinalis* dCas9 molecule, a *Parvibaculum lavamentivorans* dCas9 molecule, a *Nitratifractor salsuginis* (e.g., strain DSM 16511) dCas9 molecule, a *Campylobacter lari* (e.g., strain CF89-12) dCas9 molecule, or a *Streptococcus thermophilus* (e.g., strain LMD-9) dCas9 molecule.
96. The pharmaceutical composition, or unit dosage form, of paragraphs 72-95, wherein the dCas9 molecule comprises an *S. aureus* dCas9 molecule, e.g., comprising an *S. aureus* dCas9 sequence described herein.
97. The pharmaceutical composition, or unit dosage form, of paragraph 96, wherein the *S. aureus* dCas9 molecule comprises a mutation at an amino acid position, corresponding to position 10, 580, or both (e.g., D10A, N580A, or both), relative to a wild-type *S. aureus* dCas9 molecule, numbered according to SEQ ID NO: 25.
98. The pharmaceutical composition, or unit dosage form, of paragraph 96, wherein the *S. aureus* dCas9 molecule comprises the amino acid sequence of SEQ ID NO: 35 or 36, a sequence substantially identical (e.g., at least 80%, 85%, 90%, 92%, 95%, 97%, 98%, 99% or higher identical) to SEQ ID NO: 35 or 36, or a sequence having one, two, three, four, five or more changes, e.g., amino acid substitutions, insertions, or deletions, relative to SEQ ID NO: 35 or 36, or any fragment thereof.

99. The pharmaceutical composition, or unit dosage form, of any of paragraphs 72-95, wherein the dCas9 molecule comprises an *S. pyogenes* dCas9 molecule, e.g., comprising an *S. pyogenes* dCas9 sequence described herein.

100. The pharmaceutical composition, or unit dosage form, of paragraph 99, wherein the *S. pyogenes* dCas9 molecule comprises a mutation at an amino acid position, corresponding to position 10, 840, or both (e.g., D10A, H840A, or both), relative to a wild-type *S. pyogenes* dCas9 molecule, numbered according to SEQ ID NO: 24.

101. The pharmaceutical composition, or unit dosage form, of paragraphs 72-100, wherein the dCas9 molecule is less than 1400, 1300, 1200, 1100, 1000, 900, 800, 700, 600, or 500 amino acids in length.

102. The pharmaceutical composition, or unit dosage form, of paragraphs 72-101, wherein the dCas9 molecule is 500-1300, 600-1200, 700-1100, 800-1000, 500-1200, 500-1000, 500-800, 500-600, 1000-1200, 800-1200, or 600-1200 amino acids in length.

103. The pharmaceutical composition, or unit dosage form, of paragraphs 72-102, wherein the dCas9 molecule has a size that is less than 90%, 80%, 70%, 60%, 50%, 40%, or 30% of the size of a wild-type Cas9 molecule, e.g., a wild-type *S. pyogenes* Cas9 molecule or a wild-type *S. aureus* dCas9 molecule.

104. The pharmaceutical composition, or unit dosage form, of any of paragraphs 72-103, wherein modulator of gene expression comprises a modulator of gene expression described herein.

105. The pharmaceutical composition, or unit dosage form, of any of paragraphs 72-104, wherein modulator of gene expression comprises a KRAB molecule, e.g., comprising the sequence of SEQ ID NO: 34, a sequence substantially identical (e.g., at least 80%, 85%, 90%, 92%, 95%, 97%, 98%, 99% or higher identical) to SEQ ID NO: 34, or a sequence having one, two, three, four, five or more changes, e.g., amino acid substitutions, insertions, or deletions, relative to SEQ ID NO: 34, or any fragment thereof.

106. The pharmaceutical composition, or unit dosage form, of any of paragraphs 72-105, wherein the gRNA comprises a unimolecular gRNA.

107. The pharmaceutical composition, or unit dosage form, of any of paragraphs 72-105, wherein the gRNA comprises a bimolecular gRNA.

108. The pharmaceutical composition, or unit dosage form, of any of paragraphs 72-107, wherein the gRNA comprises a gRNA sequence described herein.

109. The pharmaceutical composition, or unit dosage form, of any of paragraphs 72-108, wherein gene expression is modulated in a cell, tissue, or organ described herein, e.g., Table 2 or 3.

110. The pharmaceutical composition, or unit dosage form, of any of paragraphs 72-109, wherein gene expression is modulated in the liver.

111. The pharmaceutical composition, or unit dosage form, of any of paragraphs 72-110, wherein the modulation is sufficient to alter a function of the gene, or a symptom of a disorder associated with the gene, as described herein, e.g., in Table 2 or 3.

112. The pharmaceutical composition, or unit dosage form, of any of paragraphs 72-111, wherein the modulation comprises modulation of transcription.

113. The pharmaceutical composition, or unit dosage form, of any of paragraphs 72-112, wherein the modulation comprises down-regulation of transcription.

114. The pharmaceutical composition, or unit dosage form, of any of paragraphs 72-113, wherein the modulation comprises up-regulation of transcription.

115. The pharmaceutical composition, or unit dosage form, of any of paragraphs 72-114, wherein the modulation comprises modulating the temporal pattern of expression of the gene.

116. The pharmaceutical composition, or unit dosage form, of any of paragraphs 72-115, wherein the modulation comprises modulating the spatial pattern of expression of the gene.

117. The pharmaceutical composition, or unit dosage form, of any of paragraphs 72-116, wherein the modulation comprises modulating a post-transcriptional or co-transcriptional modification, e.g., splicing, 5' capping, 3' cleavage, 3' polyadenylation, or RNA export.

118. The pharmaceutical composition, or unit dosage form, of any of paragraphs 72-117, wherein the modulation comprises modulating the expression of an isoform, e.g., an increase or decrease in the expression of an isoform, the increase or decrease in the expression of a first isoform over a second isoform.

119. The pharmaceutical composition, or unit dosage form, of any of paragraphs 72-118, wherein the modulation comprises modulating chromatin structure, e.g., increasing or decreasing methylation, acetylation, phosphorylation, or ubiquitination, e.g., at a preselected site, or altering the spatial pattern, cell specificity, or temporal occurrence of methylation, acetylation, phosphorylation, or ubiquitination.

120. The pharmaceutical composition, or unit dosage form, of any of paragraphs 72-119, wherein the modulation comprises modulating a post-translational modification (e.g., indirectly), e.g., glycosylation, lipidation, acetylation, phosphorylation, amidation, hydroxylation, methylation, ubiquitination, sulfation, nitrosylation, or proteolysis.

121. The pharmaceutical composition, or unit dosage form, of any of paragraphs 72-120, wherein the gene is selected from Table 2, optionally wherein the method down-regulates the expression of the gene.

122. The pharmaceutical composition, or unit dosage form, of any of paragraphs 72-120, wherein the gene is selected from Table 3, optionally wherein the method up-regulates the expression of the gene.

123. The pharmaceutical composition, or unit dosage form, of any of paragraphs 72-122, wherein the gene comprises PCSK9.

124. The pharmaceutical composition, or unit dosage form, of any of paragraphs 72-123, wherein the dCas9 does not cleave the genome of the subject.

125. A pharmaceutical composition, or unit dosage form, comprising, in an amount sufficient for modulating a gene in a human subject, or in an amount sufficient for a therapeutic effect in a human subject, (a)(ii) a nucleic acid that encodes a fusion molecule comprising a sequence comprising an *S. aureus* dCas9 molecule fused to a KRAB molecule; and/or (b)(ii) a nucleic acid that encodes a gRNA which targets the fusion molecule to the gene, wherein one or both of (a)(ii) and (b)(ii) are packaged in a viral vector, e.g., an AAV vector.

126. The pharmaceutical composition, or unit dosage form, of paragraph 125, wherein the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

127. The pharmaceutical composition, or unit dosage form, of paragraph 125 or 126, wherein the gRNA comprises a gRNA sequence described herein.

128. The pharmaceutical composition, or unit dosage form, of any of paragraphs 125-127, wherein the gene is selected from Table 2 or 3.

129. The pharmaceutical composition, or unit dosage form, of any of paragraphs 125-128, wherein the gene comprises PCSK9.

130. The pharmaceutical composition, or unit dosage form, of any of paragraphs 125-129, wherein (a)(ii) and (b)(ii) are packaged in different AAV vectors.

131. The pharmaceutical composition, or unit dosage form, of any of paragraphs 125-130, wherein (a)(ii) and (b)(ii) are packaged in the same AAV vector.

132. A viral vector comprising:

(a)(ii) a nucleic acid that encodes a fusion molecule (e.g., a fusion molecule described herein) comprising a sequence comprising a dCas9 molecule (e.g., a dCas9 molecule described herein), e.g., an *S. aureus* dCas9 molecule, fused to a modulator of gene expression (e.g., a modulator described herein); and/or (b)(ii) a nucleic acid that encodes a gRNA (e.g., a gRNA described herein) which targets the fusion molecule to a gene (e.g., a gene described herein).

133. The viral vector of paragraph 132, which is an AAV vector.

134. The viral vector of paragraph 132 and 133, comprising:

(a)(ii) a nucleic acid that encodes a fusion molecule comprising a sequence comprising an *S. aureus* dCas9 molecule fused to a KRAB molecule; and (b)(ii) a nucleic acid that encodes a gRNA which targets the fusion molecule to PCSK9, wherein one or both of (a)(ii) and (b)(ii) are packaged in an AAV vector.

135. The viral vector of any of paragraphs 132-134, wherein the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

136. The viral vector of any of paragraphs 132-135, wherein the gRNA comprises a gRNA sequence described herein.

137. The viral vector of any of paragraphs 132-136, wherein the gene is selected from Table 2 or 3.

138. The viral vector of any of paragraphs 132-137, wherein the gene comprises PCSK9.

139. A method of treating a disorder, comprising administering to a subject:

(a)(ii) a nucleic acid that encodes a fusion molecule (e.g., a fusion molecule described herein) comprising a sequence comprising a dCas9 molecule (e.g., a dCas9 molecule) fused to a modulator of gene expression (e.g., a modulator describe herein); and (b)(ii) a nucleic acid that encodes a gRNA (e.g., a gRNA described herein) which targets the fusion molecule to a gene associated with the disorder, thereby treating the disorder.

140. The method of paragraph 139, wherein the disorder is selected from Table 2 or 3.

141. The method of paragraph 139 or 140, wherein the gene is selected from Table 2 or 3.

142. The method of any of paragraphs 139-140, wherein one or both of (a)(ii) and (b)(ii) are provided in an AAV vector.

143. A method of treating a cardiovascular disease, comprising administering to a subject:

(a)(ii) a nucleic acid that encodes a fusion molecule (e.g., a fusion molecule described herein) comprising a sequence comprising a dCas9 molecule (e.g., a dCas9 molecule described herein) fused to a modulator of gene expression (e.g., a modulator describe herein); and (b)(ii) a nucleic acid that encodes a gRNA (e.g., a gRNA described herein) which targets the fusion molecule to a PCSK9 gene, thereby treating the cardiovascular disease.

144. The method of paragraph 143, wherein the dCas9 molecule is an *S. aureus* dCas9 molecule.

145. The method of paragraph 143 or 144, wherein the fusion molecule comprises a sequence described herein, e.g., the amino acid sequence of SEQ ID NO: 34, 35, 36, 37, 38, 39, 40, or 41, a sequence substantially identical (e.g., at least 80%, 85%, 90%, 92%, 95%, 97%, 98%, 99% or higher identical) to SEQ ID NO: 34, 35, 36, 37, 38, 39, 40, or 41, or a sequence having one, two, three, four, five or more changes, e.g., amino acid substitutions, insertions, or deletions, relative to SEQ ID NO: 34, 35, 36, 37, 38, 39, 40, or 41, or any fragment thereof.

146. The method of any of paragraphs 143-145, wherein the gRNA comprises a gRNA sequence described herein.

147. The method of any of paragraphs 143-146, wherein one or both of (a)(ii) and (b)(ii) are provided in an AAV vector.

The following examples are provided by way of illustration and not by way of limitation.

EXAMPLES

1. In Vivo Transcriptional Repression of Endogenous Genes Using *S. aureus* Cas9-Based Repressors

1.1 Synopsis

RNA-guided dCas9-KRAB repressors have demonstrated promise in cell culture models for silencing target gene expression efficiently and specifically. An exciting application of this technology would be to study gene regulation in development and disease in animal models and to design novel gene therapies. However, a technology to deliver CRISPR/Cas9-based gene repressors in vivo has not been developed. AAV vectors have been used as a delivery platform for CRISPR/Cas9 nuclease components for in vivo studies and therapeutic applications (Ran, F. A. et al. Nature 520, 186-91 (2015), incorporated by reference herein in its entirety). Recently, a smaller Cas9 nuclease protein derived from *S. aureus* was described for AAV delivery and in vivo gene editing (Ran, F. A. et al. Nature 520, 186-91 (2015)).

In this example, a KRAB repressor motif was fused to *S. aureus* nuclease-null dCas9 (dSaCas9), thereby generating a programmable RNA-guided repressor for in vivo gene regulation. dSaCas9-KRAB repressors efficiently silenced a reporter luciferase gene in primary fibroblasts and the myostatin receptor Acvr2b in a mouse myoblast cell line. When delivered intramuscularly via an AAV9 dual-vector expression system, dSaCas9-KRAB and Acvr2b gRNA were efficiently expressed in the injected tibialis anterior, heart, and liver tissues of adult wild-type mice. No appreciable silencing of Acvr2b was achieved in skeletal muscle, but dSaCas9-KRAB was biologically active and significantly silenced Acvr2b expression in heart and liver when delivered with a target guide RNA molecule. This gene delivery system can be customized to target any endogenous gene, enabling potent and stable gene repression in animal models and for therapeutic applications.

1.2 Introduction

RNA-guided gene regulation with the CRISPR/Cas9 system has enabled functional genomics studies in cell culture systems (Kearns, N. A. et al. Nat Methods (2015); Gilbert, L. A. et al. Cell 159, 647-61 (2014); Thakore, P. I. et al. Nat Methods 12, 1143-9 (2015); Konermann, S. et al. Nature 517, 583-8 (2015), incorporated by reference herein in their entirety). The potency and specificity of dCas9-KRAB epigenetic repressors, in particular, are promising for loss-of-function studies and guiding cell phenotype in vitro (Thakore, P. I., et al. Nat Methods 13, 127-37 (2016); Gilbert, L. A. et al. Cell 159, 647-61 (2014); Thakore, P. I. et al. Nat Methods 12, 1143-9 (2015), incorporated by reference herein in their entirety). Adapting programmable transcriptional modulators for use in vivo would allow for the study of gene regulation in complex organisms and enable the development of therapies to address aberrant gene regulation in disease.

The large packaging capacity of lentiviral vectors, a commonly used method to stably deliver CRISPR/Cas9 components in vitro, can accommodate the 4.2 kb *S. pyogenes* Cas9, epigenetic modulator fusions, a single gRNA, and associated regulatory elements required for expression. While efficacious for in vitro delivery, under certain circumstances, lentiviral delivery is typically not suitable for in vivo gene regulation due to concerns for insertional mutagenesis. Adeno-associated viral (AAV) vectors are a promising gene delivery vehicle as they provide stable episomal gene expression with minimal integration and have been extensively engineered to target a variety of tissue types (Asokan, A., et al. Mol Ther 20, 699-708 (2012), incorporated by reference herein in its entirety). However, the packaging capacity of AAV is limited to 4.5 kb, precluding delivery of the 4.2 kb *S. pyogenes* dCas9 DNA-binding domain, KRAB repressor motif, and associated regulatory elements. A smaller 3.2 kb Cas9 nuclease derived from *S. aureus* (SaCas9) has recently been identified and adapted for genome editing in vivo in the liver and skeletal muscle (Ran, F. A. et al. Nature 520, 186-91 (2015); Nelson, C. E. et al. Science 351, 403-7 (2016); Tabebordbar, M. et al. Science 351, 407-11 (2016), incorporated by reference herein in their entirety). A SaCas9-based transcriptional repressor was generated for AAV-based delivery and silencing of endogenous genes in vivo.

The SaCas9-based transcriptional repressor was tested in vitro for silencing a luciferase reporter gene in primary fibroblasts. For in vivo gene regulation, the myostatin receptor, Acvr2b, was targeted. Inhibiting the myostatin signaling pathway is a potential method for treating skeletal muscle degeneration. Myostatin is a secreted protein that acts as a negative regulator of skeletal muscle growth by binding the activin type II receptor (Acvr2b) and activating TGF-β signaling pathways (Lee, S. J. Annu Rev Cell Dev Biol 20, 61-86 (2004), incorporated by reference herein in its entirety). Knockout animal models of myostatin and Acvr2b demonstrate a double muscling phenotype (Lee, S. J. Annu Rev Cell Dev Biol 20, 61-86 (2004); Lee, S. J. et al. Proc Natl Acad Sci USA 109, E2353-60 (2012), incorporated by reference herein in its entirety). Blocking myostatin signaling through systemic administration of blocking antibodies or soluble Acvr2b receptors has been tested in clinical trials for the treatment of muscular dystrophy, but has thus far showed limited efficacy and safety concerns over adverse side effects (Wagner, K. R. et al. Ann Neurol 63, 561-71 (2008); Smith, R. C. & Lin, B. K. Curr Opin Support Palliat Care 7, 352-60 (2013), incorporated by reference herein in their entirety). A more targeted strategy to localize myostatin inhibition to skeletal muscle may increase the efficacy and safety of this strategy for treating muscle disorders.

An AAV9 two-vector system was designed for expressing SaCas9 repressors and targeting guide RNA (gRNA) molecule. AAV9 can provide stable and high transgene expression in skeletal and cardiac muscle (Asokan, A., et al. Mol Ther 20, 699-708 (2012); Zincarelli, C., et al. Mol Ther 16, 1073-80 (2008), incorporated by reference herein in their entirety) and is currently being evaluated in clinical trials for spinal muscular atrophy. When delivered intramuscularly in adult wild-type mice, SaCas9 repressors effected significant silencing of the endogenous Acvr2b gene in the heart and liver. These studies demonstrate that SaCas9-based repressors can regulate genes in animal models and will facilitate the development of gene-regulation based therapies.

1.3 Materials and Methods 1.3.1 Plasmid Constructs and AAV Design

An inactive version of SaCas9 (dSaCas9) was created by introducing D10A and N580A mutations (Ran, F. A. et al. Nature 520, 186-91 (2015), incorporated by reference herein in its entirety). dSaCas9 was cloned into a lentiviral vector driven by the human Ubiquitin C (hUbC) promoter, fused to a KRAB repressor motif, and linked to a puromycin resistance cassette via T2A ribosome skipping peptide. For sgRNA screening, the oligonucleotides containing protospacer sequences were synthesized (IDT-DNA), hybridized, phosphorylated, and inserted into a phU6-SaCas9 gRNA plasmid using BbsI sites. U6-gRNA cassettes were then cloned in reverse orientation upstream of the hUbC promoter in dSaCas9-KRAB lentiviral vectors for stable expression.

A *Staphylococcus aureus* Cas9 (SaCas9) AAV expression plasmid (Addgene #61592) was received as a gift from the Zhang lab (Ran, F. A. et al. Nature 520, 186-U98 (2015), incorporated by reference herein in its entirety). We replaced the nuclease-active SaCas9 with dSaCas9-KRAB. We also removed the C' terminal 3× HA epitope tag and incorporated a single N' terminal HA tag for tracking protein expression. For the AAV-U6 gRNA plasmid, a U6-Acvr2b gRNA cassette was cloned into a pTR-eGFP backbone replacing the CMV with the gRNA.

1.3.2 Cell Culture

C2C12s cells and HEK293T cells were obtained from the American Tissue Collection Center (ATCC) through the Duke University Cancer Center Facilities. Primary fibroblasts were harvested from the tail and ear of adult mice expressing a CAG-Luciferase-P2A-GFP cassette (Jackson Laboratories). C2C12 cells were maintained in DMEM supplemented with 20% FBS and 1% penicillin-streptomycin. HEK293T cells were cultured in DMEM supplemented with 10% FBS and 1% penicillin-streptomycin. Mouse fibroblasts were cultured in DMEM supplemented with 10% FBS and 1% penicillin-streptomycin. All cell lines were cultured at 37 C with 5% $CO_2$.

1.3.3 Lentiviral Production

C2C12s and primary fibroblasts were transduced with lentivirus to stably express dSaCas9-KRAB and target gRNA molecules. To produce VSV-G pseudotyped lentivirus, HEK293T cells were plated at a density of 5.1e3 cells/$cm^2$ in high glucose DMEM supplemented with 10% FBS and 1% penicillin-streptomycin. The next day after seeding, cells in 10-cm plates were co-transfected with the appropriate dSaCas9-KRAB lentiviral expression plasmid (20 μg), the second-generation packaging plasmid psPAX2 (Addgene #12260, 15 μg), and the envelope plasmid pMD2.G (Addgene #12259, 6 μg) by calcium phosphate precipitation (Salmon, P. & Trono, D. Curr Protoc Neurosci Chapter 4, Unit 4 21 (2006), incorporated by reference herein in its entirety). After 14-20 hours, transfection medium was exchanged for 10 mL of fresh 293T medium. Conditioned medium containing lentivirus was collected 24 and 48 hours after the first media exchange. Residual producer cells were cleared from the lentiviral supernatant by filtration through 0.45 μm cellulose acetate filters and incubated overnight by incubation with Lenti-X. Concentrated virus was pelleted by centrifugation according to the manufacturer's protocol and resuspended at 20-fold concentration in PBS. Concentrated viral supernatant was snap-frozen in liquid nitrogen and stored at −80° C. for future use. For transduction, concentrated viral supernatant was diluted 1:20 with media. To facilitate transduction, the cationic polymer polybrene was added at a concentration of 4 μg/mL to the viral media. Non-transduced (NT) cells did not receive virus but were treated with polybrene as a control. The day after transduction, the medium was exchanged to remove the virus. Puromycin at 2 ug/mL (C2C12s) or 4 ug/mL (fibroblasts) was used to initiate selection for transduced cells approximately 48 hours after transduction.

1.3.4 AAV Production

ITRs were verified by SmaI digest before production. AAV-dSaCas9-KRAB and AAV-U6 Acvr2b gRNA were used to generate AAV9 in two separate batches by the Gene Transfer Vector Core at Schepens Eye Research Institute, Massachusetts Eye and Ear. Titers were provided at $5.3\times10^{13}$ vp/mL (AAV-dSaCas9-KRAB) and $1.6\times10^{13}$ vp/mL (AAV-U6 Acvr2b gRNA).

1.3.5 Animal Studies

Animal studies were conducted with adherence to the guidelines for the care and use of laboratory animals of the National Institutes of Health (NIH). All the experiments with animals were approved by the Institutional Animal Care and Use Committee (IACUC) at Duke University. 6-8 week old C57Bl/6 mice (Jackson Labs) were anesthetized and maintained at 37° C. The right tibialis anterior muscle was prepared and injected with 30-40 μL of AAV solution ($5.6\times10^{11}$-$7.46\times10^{11}$ vp) or sterile PBS using a 30 G needle. Mice were injected with a saline control, a 5e11 vp dose AAV-dSaCas9-KRAB alone, or a 1:1 mixture of 1e12 total dose of AAV-dSaCas9-KRAB and AAV-U6 Acvr2b gRNA. At 4 and 8 weeks post-injection, mice were euthanized by $CO_2$ inhalation and tissue was collected into RNALater® (Life Technologies) for DNA and RNA or snap-frozen for protein analysis.

1.3.6 qRT-PCR

Cells were harvested for total RNA isolation using the RNeasy Plus RNA isolation kit (Qiagen). Tissue samples were stored in RNALater (Ambion) and total RNA was isolated using the RNA Universal Plus Kit (Qiagen). cDNA synthesis was performed using the SuperScript VILO cDNA Synthesis Kit (Invitrogen). For genomic qPCR experiments, genomic DNA from tissue samples was isolated using a Blood and Tissue Kit (Qiagen). Quantitative real-time PCR (qRT-PCR) using QuantIT Perfecta Supermix was performed with the CFX96 Real-Time PCR Detection System (Bio-Rad) with the oligonucleotide primers optimized for 90-110% amplification efficiency. The results are expressed as fold-increase mRNA expression of the gene of interest normalized to Gapdh expression by the $\Delta\Delta C_t$ method.

1.3.7 Western Blot

Cells or minced tissue were lysed in RIPA buffer (Sigma), and the BCA assay (Pierce) was performed to quantify total protein. Lysates were mixed with LDS sample buffer (Invitrogen) and boiled for 5 min; equal amounts of total protein were run in NuPAGE Novex 4-12% Bis-Tris polyacrylamide gels (Life Technologies) and transferred to nitrocellulose membranes. Nonspecific antibody binding was blocked with 5% nonfat milk in TBS-T (50 mM Tris, 150 mM NaCl and 0.1% Tween-20) for 30 min. The membranes were then incubated with primary antibody in 5% milk in TBS-T: rabbit anti-ACTRIIB diluted 1:1000 overnight at 4° C., anti-HA diluted 1:1000 for 60 min at room temperature, or rabbit anti-GAPDH diluted 1:5000 for 60 min at room temperature. Membranes labeled with primary antibodies were incubated with anti-mouse (Santa Cruz, SC-2005) or anti-rabbit HRP-conjugated antibody (Sigma-Aldrich, A6154) diluted 1:5000 for 60 min and washed with TBS-T for 60 min. Membranes were visualized using the Immun-Star WesternC Chemiluminescence Kit (Bio-Rad) and images were captured using a ChemiDoc XRS+ system and processed using ImageLab software (Bio-Rad).

1.4 Results 1.4.1 Generation of a transcriptional repressor from *S. aureus* Cas9

D10A and N580A mutations were introduced into the SaCas9 nuclease in order to abrogate catalytic activity and create a nuclease-null programmable DNA-binding domain (Ran, F. A. et al. Nature 520, 186-91 (2015), incorporated by reference herein in its entirety) (FIG. 1A). Fusion of a synthetic KRAB motif generated a dSaCas9 repressor. An N-terminal HA-tag was included to facilitate protein analysis and an N- and C-terminal nuclear localization sequence was included to enable trafficking of dSaCas9-KRAB into the cell nucleus.

For initial testing in vitro, dSaCas9-KRAB and single gRNAs were stably expressed using a lentiviral delivery system with puromycin selection (FIG. 1). dSaCas9-KRAB was first tested in primary mouse fibroblasts expressing a luciferase reporter knocked in at chromosome 7 of the genome. Nine gRNAs to the synthetic CAG promoter driving transgene expression were designed, searching for base pair target sequences followed by the SaCas9 PAM, 5' NNGRRT 3' (SEQ ID NO: 1, wherein N is any nucleotide, and R is G or A). Multiple gRNAs exhibited robust repression of luciferase expression via qPCR and Western 7 days after transduction of fibroblasts (FIGS. 1C and 1D). These results confirmed that dSaCas9-KRAB repressors were effective at silencing a reporter gene in vitro.

1.4.2 Silencing Endogenous Acvr2b in Myoblasts

SaCas9-based repressors were targeted to the myostatin receptor Acvr2b in C2C12 mouse myoblasts. gRNAs were targeted to the DNase I hypersensitivity site (DHS) containing the transcription start site (TSS) of Acvr2b according to DNase-seq data on mouse skeletal muscle from the ENCODE project (Consortium, E. P. et al. Nature 489, 57-74

Figures 2A, 2B:
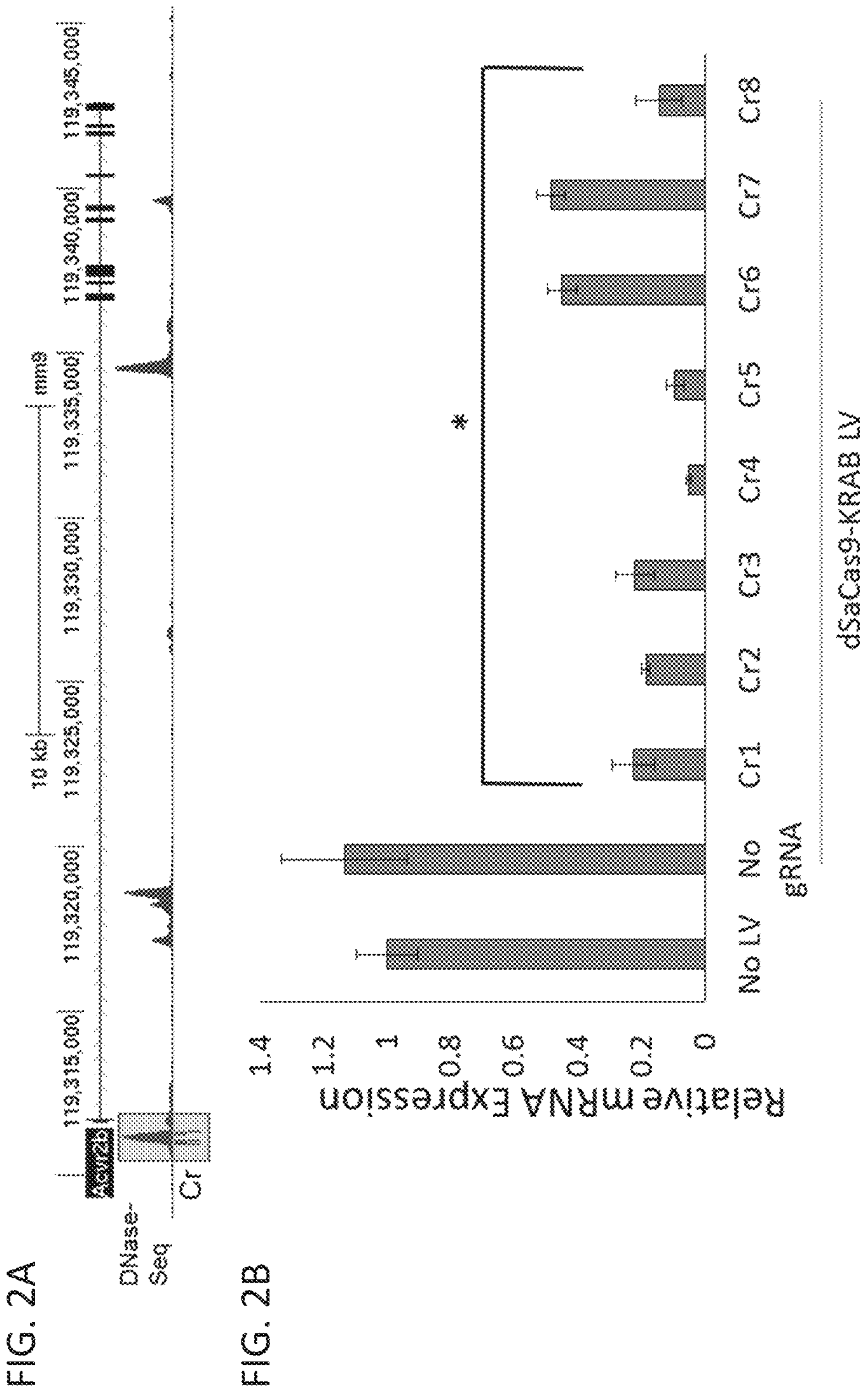
FIGS. 2A and 2B are graphs showing the silencing of endogenous genes with the dSaCas9-KRAB repressor.

(2012), incorporated by reference herein in its entirety) (FIG. 2A). dSaCas9-KRAB and a single gRNA were stably expressed using a lentiviral delivery system, and multiple gRNAs effected potent repression of endogenous Acvr2b by qPCR 7 days after transduction and selection in C2C12s (FIG. 2B).

Figures 3A, 3B, 3C, 3D, 3E:
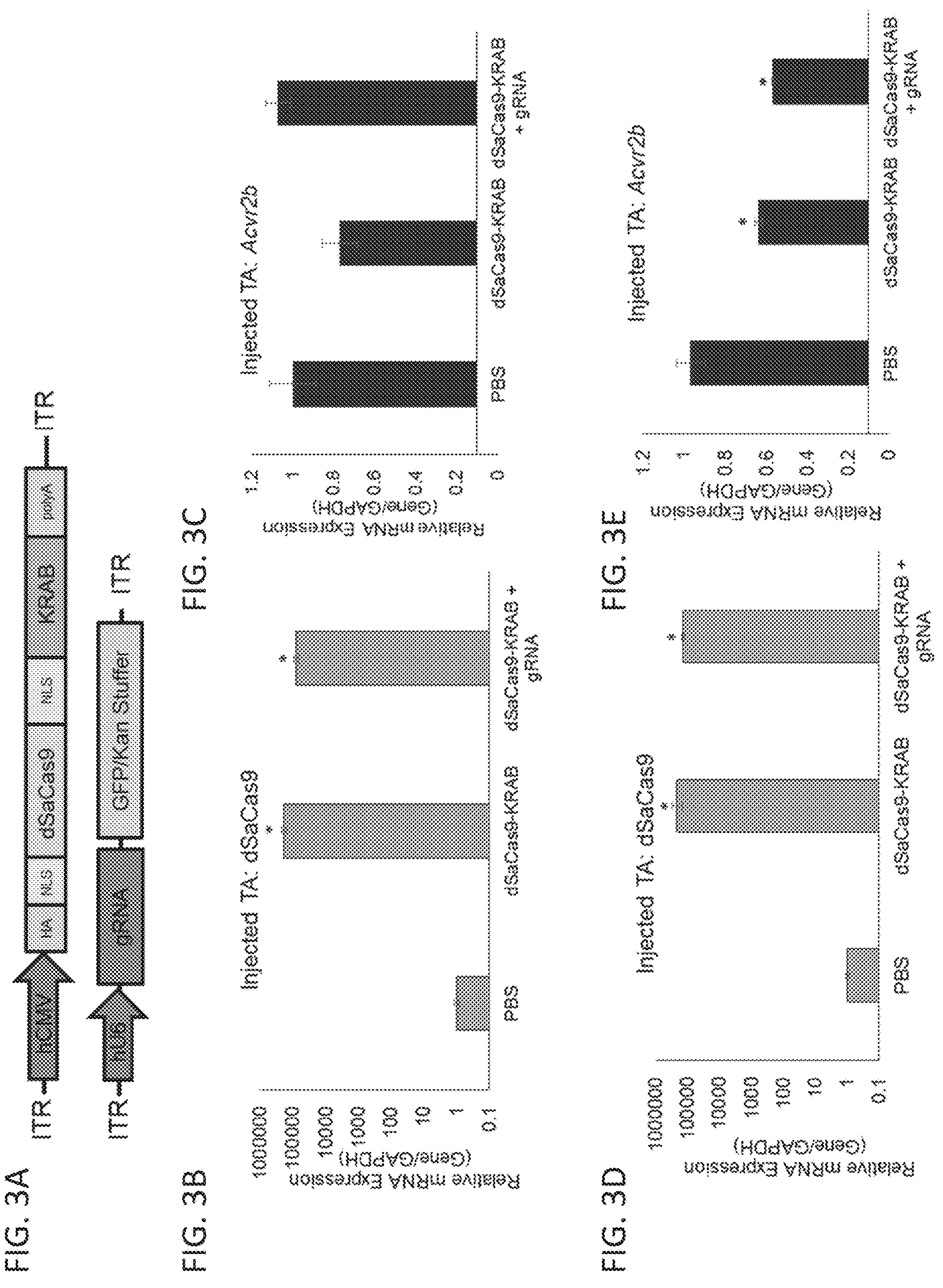
FIGS. 3A-3E are graphs showing the targeting of Acvr2b with AAV-dSaCas9-KRAB in vivo.

1.4.3 Transcriptional Repression of the Acvr2b Gene In Vivo with AAV Delivery of *S. aureus* Cas9 Repressors To accommodate the limited packaging capacity of AAV, a two-vector system was designed to deliver dSaCas9-KRAB and a single gRNA for targeted gene repression (FIG. 3A). AAV9 vectors expressing dSaCas9-KRAB and an Acvr2b gRNA were generated and purified by the Massachusetts General Hospital Ear and Eye Vector Core. The Cr4 Acvr2b gRNA was chosen for AAV in vivo studies. AAV9 is a muscle-tropic serotype capable of producing high levels of transgene expression (Zincarelli, C., et al. Mol Ther 16, 1073-80 (2008), incorporated by reference herein in its entirety).

Adult C57Bl/6 wild-type mice were injected in the tibialis anterior of the right limb with a mixture of AAV-dSaCas9-KRAB and AAV-Acvr2b-gRNA, at 5e11 vector genome copies delivered per AAV per limb. Age-matched controls received a PBS sham injection or AAV-dSaCas9-KRAB injection without gRNA. At 4 and 8 weeks post-transduction, dSaCas9-KRAB was steadily expressed via qPCR in the injected TA muscle (FIGS. 3B and 3D). Acvr2b expression was not significantly affected by delivery of dSaCas9-KRAB alone or dSaCas9-KRAB with Acvr2b gRNA at 4 weeks post-treatment (FIG. 3C). At 8 weeks post-AAV delivery, Acvr2b mRNA expression was significantly reduced compared to sham-injected muscles in both AAV treatment groups (FIG. 3E). However, targeting dSaCas9-KRAB with Acvr2b gRNA result in stronger repression than delivery of dSaCas9-KRAB alone.

Figure 4:
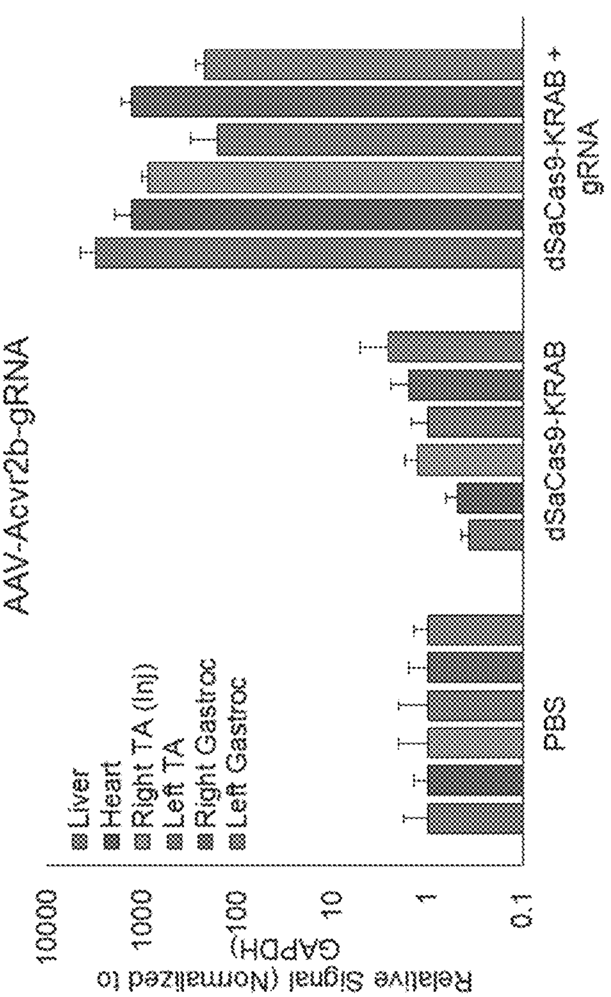
FIG. 4 is a bar graph showing the analysis of AAV-gRNA vector genome signal in intramuscularly injected mice. For PBS sham, AAV-dSaCas9-KRAB only, and AAV-dSaCas9-KRAB and AAV-Acvr2b-gRNA treated mice, the bars from left to right show the presence of the AAV-U6-gRNA vector, as measured by qPCR, in the liver, heart, right tibialis anterior (TA), left TA, right gastrocnemius (gastroc), and left gastroc, respectively.

To determine if delivered AAV escaped the injected muscle and distributed systemically, vector genome signal was quantified in the liver, heart, and tibialis anterior muscles of treated mice at 8 weeks post-transduction. For AAV-Acvr2b-gRNA, the highest vector genome signals were found in the liver, heart, the right gastrocnemius muscle, and the injected tibialis anterior muscle (FIG. 4). Various AAV serotypes demonstrate tropism for the liver, and AAV9 can efficiently transduce cardiac muscle (Asokan, A., et al. Mol Ther 20, 699-708 (2012); Zincarelli, C., et al. Mol Ther 16, 1073-80 (2008), incorporated by reference herein in their entirety). dSaCas9-KRAB was expressed in the liver and heart at 4 and 8 weeks post-transduction via qPCR (FIG. 5). At 8 weeks post-transduction, Acvr2b expression in the heart was reduced by ~50% with delivery of dSaCas9-KRAB with gRNA. dSaCas9-KRAB alone did not have a significant effect on Acvr2b expression. Changes in Acvr2b expression in the liver were not statistically significant at 8 weeks post-transduction. These results indicate that dSaCas9-KRAB is biologically active in vivo and AAV delivery is a promising method for achieving targeted repression in animal models.

1.5 Discussion

The efficiency and specificity of CRISPR/Cas9 gene silencing has shown great preclinical promise. In this example, a platform was presented to translate RNA-guided gene repression in vivo in a wild-type mouse model. dSaCas9-KRAB potently silenced reporter and endogenous genes in vitro, and AAV9 delivery of CRISPR/Cas9 components in an adult wild-type mouse model resulted in efficient silencing of the Acvr2b gene in the heart.

Muscle tissue contains large and multinucleated fibers and a progenitor population capable of proliferation and regeneration. These are all factors that may have contributed to the lack of repression observed in skeletal muscle. dSaCas9-KRAB repression in muscle may have limited by replication-mediated AAV dilution, diffusion of the repressor protein and delivered gRNA molecule along the myofiber, or inability of dSaCas9-KRAB to silence the majority of nuclei within a fiber. In contrast, cardiomyocytes of the heart are binucleated and post-mitotic, factors that may have contributed to the more efficient silencing observed in this tissue.

Interestingly, in some cases, it was observed that delivering dSaCas9-KRAB alone significantly downregulated Acvr2b expression. This unexpected biological effect may be related to potential host immune responses of high doses of AAV or expressing foreign SaCas9-based proteins in mouse tissue. An influx of immune cells or inflammatory responses could lead to gene expression changes in AAV-treated tissues and apparent silencing of the target gene.

The CRISPR/Cas9 platform is highly flexible, and the AAV delivery system developed in this example can easily be adapted to target other gene products. The extent of immune response to foreign Cas9 proteins and synthetic gRNA molecules, as well as the specificity of SaCas9-based gene regulation, can also be evaluated. A major determinant of off-site target binding is the presence of a PAM sequence, and thus the more stringent PAM requirement of SaCas9 compared to SpCas9 may be indicative of at least comparable levels of specificity for gene regulation. Lastly, minimal and tissue-specific promoters may enable implementation of a single AAV vector system for future in vivo gene regulation applications.

1.6. Appendix 1.6.1 Lentiviral *S. aureus* Cas9 KRAB-Based Repressor

Figure 6:
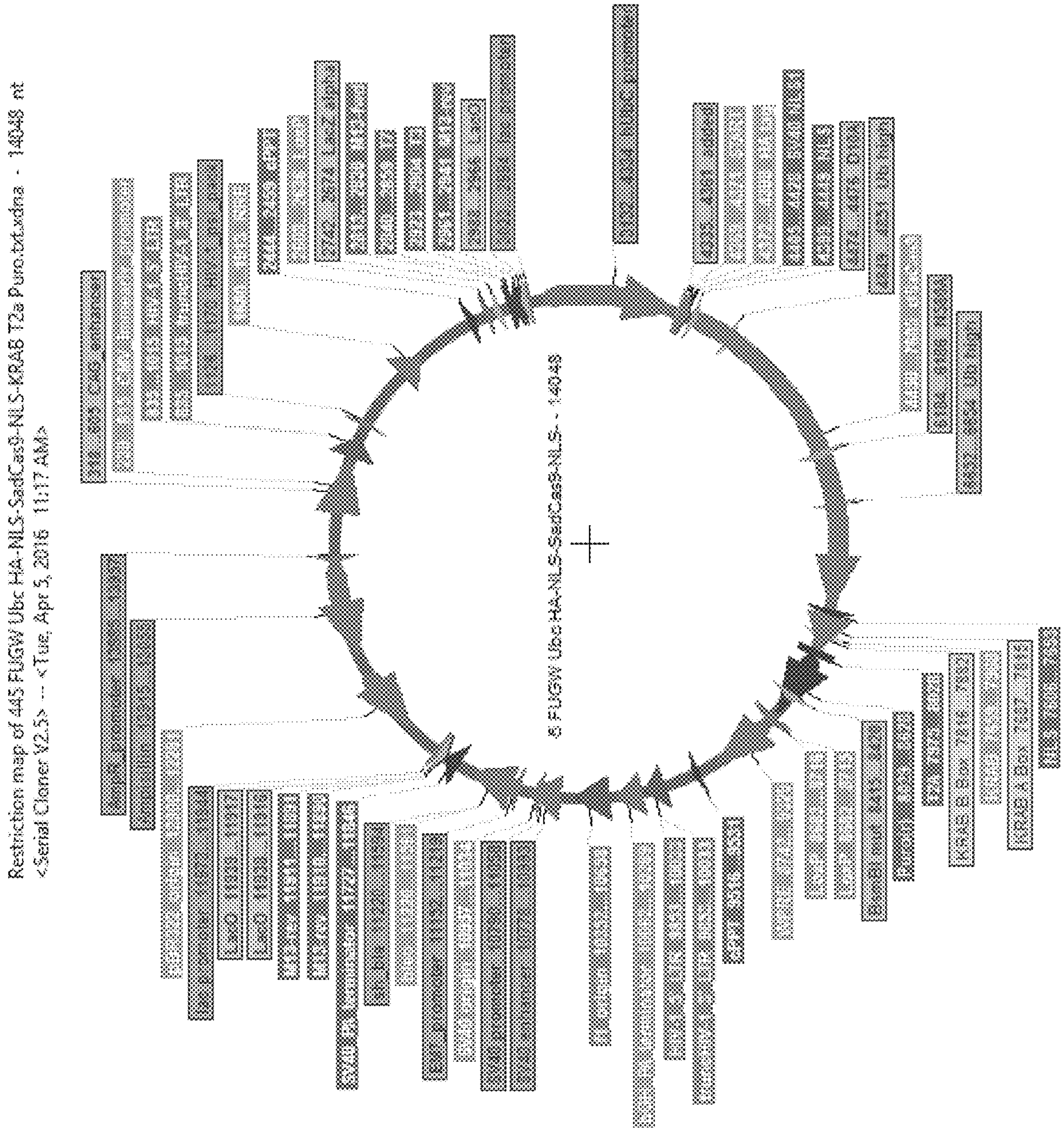
FIG. 6 is a graph showing a restriction map of a lentiviral vector encoding *S. aureus* Cas9 KRAB-based repressor.

A restriction map of a lentiviral vector encoding *S. aureus* Cas9 KRAB-based repressor is shown in FIG. 6. SEQ ID NO: 2 provides the nucleic acid sequence of the lentivial vector encoding *S. aureus* Cas9 KRAB-based repressor.

SEQ ID NO: 2

```
GTCGACGGATCGGGAGATCTCCCGATCCCCTATGGTGCACTCTCAGTACA

ATCTGCTCTGATGCCGCATAGTTAAGCCAGTATCTGCTCCCTGCTTGTGT

GTTGGAGGTCGCTGAGTAGTGCGCGAGCAAAATTTAAGCTACAACAAGGC

AAGGCTTGACCGACAATTGCATGAAGAATCTGCTTAGGGTTAGGCGTTTT

GCGCTGCTTCGCGATGTACGGGCCAGATATACGCGTTGACATTGATTATT

GACTAGTTATTAATAGTAATCAATTACGGGGTCATTAGTTCATAGCCCAT

ATATGGAGTTCCGCGTTACATAACTTACGGTAAATGGCCCGCCTGGCTGA

CCGCCCAACGACCCCCGCCCATTGACGTCAATAATGACGTATGTTCCCAT

AGTAACGCCAATAGGGACTTTCCATTGACGTCAATGGGTGGAGTATTTAC

GGTAAACTGCCCACTTGGCAGTACATCAAGTGTATCATATGCCAAGTACG

CCCCCTATTGACGTCAATGACGGTAAATGGCCCGCCTGGCATTATGCCCA

GTACATGACCTTATGGGACTTTCCTACTTGGCAGTACATCTACGTATTAG

TCATCGCTATTACCATGGTGATGCGGTTTTGGCAGTACATCAATGGGCGT

GGATAGCGGTTTGACTCACGGGGATTTCCAAGTCTCCACCCCATTGACGT

CAATGGGAGTTTGTTTTGGCACCAAAATCAACGGGACTTTCCAAAATGTC

GTAACAACTCCGCCCCATTGACGCAAATGGGCGGTAGGCGTGTACGGTGG
```

GAGGTCTATATAAGCAGCGCGTTTTGCCTGTACTGGGTCTCTCTGGTTAG
ACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCT
GTTGTGTGACTCTGGTAACTAGAGATCCCTCAGACCCTTTTAGTCAGTGT
GGAAAATCTCTAGCAGTGGCGCCCGAACAGGGACTTGAAAGCGAAAGGGA
AACCAGAGGAGCTCTCTCGACGCAGGACTCGGCTTGCTGAAGCGCGCACG
GCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGG
GGAGAATTAGATCGCGATGGGAAAAAATTCGGTTAAGGCCAGGGGGAAAG
AAAAAATATAAATTAAAACATATAGTATGGGCAAGCAGGGAGCTAGAACG
ATTCGCAGTTAATCCTGGCCTGTTAGAAACATCAGAAGGCTGTAGACAAA
TACTGGGACAGCTACAACCATCCCTTCAGACAGGATCAGAAGAACTTAGA
TCATTATATAATACAGTAGCAACCCTCTATTGTGTGCATCAAAGGATAGA
GATAAAAGACACCAAGGAAGCTTTAGACAAGATAGAGGAAGAGCAAAACA
AAAGTAAGACCACCGCACAGCAAGCGGCCGCTGATCTTCAGACCTGGAGG
AGGAGATATGAGGGACAATTGGAGAAGTGAATTATATAAATATAAAGTAG
TAAAAATTGAACCATTAGGAGTAGCACCCACCAAGGCAAAGAGAAGAGTG
GTGCAGAGAGAAAAAAGAGCAGTGGGAATAGGAGCTTTGTTCCTTGGGTT
CTTGGGAGCAGCAGGAAGCACTATGGGCGCAGCGTCAATGACGCTGACGG
TACAGGCCAGACAATTATTGTCTGGTATAGTGCAGCAGCAGAACAATTTG
CTGAGGGCTATTGAGGCGCAACAGCATCTGTTGCAACTCACAGTCTGGGG
CATCAAGCAGCTCCAGGCAAGAATCCTGGCTGTGGAAAGATACCTAAAGG
ATCAACAGCTCCTGGGGATTTGGGGTTGCTCTGGAAAACTCATTTGCACC
ACTGCTGTGCCTTGGAATGCTAGTTGGAGTAATAAATCTCTGGAACAGAT
TTGGAATCACACGACCTGGATGGAGTGGGACAGAGAAATTAACAATTACA
CAAGCTTAATACACTCCTTAATTGAAGAATCGCAAAACCAGCAAGAAAAG
AATGAACAAGAATTATTGGAATTAGATAAATGGGCAAGTTTGTGGAATTG
GTTTAACATAACAAATTGGCTGTGGTATATAAAATTATTCATAATGATAG
TAGGAGGCTTGGTAGGTTTAAGAATAGTTTTTGCTGTACTTTCTATAGTG
AATAGAGTTAGGCAGGGATATTCACCATTATCGTTTCAGACCCACCTCCC
AACCCCGAGGGGACCCGACAGGCCCGAAGGAATAGAAGAAGAAGGTGGAG
AGAGAGACAGAGACAGATCCATTCGATTAGTGAACGGATCGGCACTGCGT
GCGCCAATTCTGCAGACAAATGGCAGTATTCATCCACAATTTTAAAAGAA
AAGGGGGGATTGGGGGGTACAGTGCAGGGGAAAGAATAGTAGACATAATA
GCAACAGACATACAAACTAAAGAATTACAAAAACAAATTACAAAAATTCA
AAATTTTCGGGTTTATTACAGGGACAGCAGAGATCCAGTTTGGTTAAtTA
AATAACTTCGTATAGCATACATTATACGAAGTTATGATAAGAGACGGTGG
TGgcgccgctacagggcgcgtcccattcgccattcaggctgcgcaactgt
tgggaagggcgatcggtgcgggcctcttcgctattacgccagctggcgaa
agggggatgtgctgcaaggcgattaagttgggtaacgccagggttttccc agtcacgacgttgtaaaacgacggccagtgagcgcgcgtaatacgactca
ctatagggcgaattgggtaccgggccccccctcgaggtcctccagctttt
gttccctttagtgagggttaattgcgcgcttggcgtaatcatggtcatag
ctgtttcctgtgtgaaattgttatccgctcacaattccacacaacatacg
agccggaagcataaagtgtaaagcctggggtgcctaatgagtgagctaac
tcacattaattgcgttgcgctcactgcccgctttccaCTGCATGACGTCT
CCACAATTAAtTAAgggtgcagcggcctccgcgcccgggttttggcgcctc
ccgcgggcgcccccctcctcacggcgagcgctgccacgtcagacgaaggg
cgcaggagcgttcctgatccttccgcccggacgctcaggacagcggcccg
ctgctcataagactcggccttagaaccccagtatcagcagaaggacattt
taggacgggacttgggtgactctagggcactggttttctttccagagagc
ggaacaggcgaggaaaagtagtcccttctcggcgattctgcggagggatc
tccgtggggcggtgaacgccgatgattatataaggacgcgccgggtgtgg
cacagctagttccgtcgcagccgggatttgggtcgcggttcttgtttgtg
gatcgctgtgatcgtcacttggtgagttgcgggctgctgggctggccggg
gctttcgtggccgccgggccgctcggtgggacggaagcgtgtggagagac
cgccaagggctgtagtctgggtccgcgagcaaggttgccctgaactgggg
gttggggggagcgcacaaaatggcggctgttcccgagtcttgaatggaag
acgcttgtaaggcgggctgtgaggtcgttgaaacaaggtgggggggcatgg
tgggcggcaagaacccaaggtcttgaggccttcgctaatgcgggaaagct
cttattcgggtgagatgggctggggcaccatctggggaccctgacgtgaa
gtttgtcactgactggagaactcgggtttgtcgtctggttgcgggggcgg
cagttatgcggtgccgttgggcagtgcacccgtacctttgggagcgcgcg
cctcgtcgtgtcgtgacgtcacccgttctgttggcttataatgcagggtg
gggccacctgccggtaggtgtgcggtaggcttttctccgtcgcaggacgc
agggttcgggcctagggtaggctctcctgaatcgacaggcgccggacctc
tggtgaggggagggataagtgaggcgtcagtttctttggtcggttttatg
tacctatcttcttaagtagctgaagctccggttttgaactatgcgctcgg
ggttggcgagtgtgttttgtgaagttttttaggcaccttttgaaatgtaa
tcatttgggtcaatatgtaattttcagtgttagactagTaaattgtccgc
taaattctggccgtttttggcttttttgttagacGAAGCTTGGGCTGCAG
GTCGACTctagagccaccatgtacccatacgatgttccagattacgctAT
GGCCCCAAAGAAGAAGCGGAAGGTCGGTATCCACGGAGTCCCAGCAGCCA
AGCGGAACTACATCCTGGGCCTGGCCATCGGCATCACCAGCGTGGGCTAC
GGCATCATCGACTACGAGACACGGGACGTGATCGATGCCGGCGTGCGGCT
GTTCAAAGAGGCCAACGTGGAAAACAACGAGGGCAGGCGGAGCAAGAGAG
GCGCCAGAAGGCTGAAGCGGCGGAGGCGGCATAGAATCCAGAGAGTGAAG
AAGCTGCTGTTCGACTACAACCTGCTGACCGACCACAGCGAGCTGAGCGG
CATCAACCCCTACGAGGCCAGAGTGAAGGGCCTGAGCCAGAAGCTGAGCG
AGGAAGAGTTCTCTGCCGCCCTGCTGCACCTGGCCAAGAGAAGAGGCGTG
CACAACGTGAACGAGGTGGAAGAGGACACCGGCAACGAGCTGTCCACCAA -continued AGAGCAGATCAGCCGGAACAGCAAGGCCCTGGAAGAGAAATACGTGGCCG
AACTGCAGCTGGAACGGCTGAAGAAAGACGGCGAAGTGCGGGGCAGCATC
AACAGATTCAAGACCAGCGACTACGTGAAAGAAGCCAAACAGCTGCTGAA
GGTGCAGAAGGCCTACCACCAGCTGGACCAGAGCTTCATCGACACCTACA
TCGACCTGCTGGAAACCCGGCGGACCTACTATGAGGGACCTGGCGAGGGC
AGCCCCTTCGGCTGGAAGGACATCAAAGAATGGTACGAGATGCTGATGGG
CCACTGCACCTACTTCCCCGAGGAACTGCGGAGCGTGAAGTACGCCTACA
ACGCCGACCTGTACAACGCCCTGAACGACCTGAACAATCTCGTGATCACC
AGGGACGAGAACGAGAAGCTGGAATATTACGAGAAGTTCCAGATCATCGA
GAACGTGTTCAAGCAGAAGAAGAAGCCCACCCTGAAGCAGATCGCCAAAG
AAATCCTCGTGAACGAAGAGGATATTAAGGGCTACAGAGTGACCAGCACC
GGCAAGCCCGAGTTCACCAACCTGAAGGTGTACCACGACATCAAGGACAT
TACCGCCCGGAAAGAGATTATTGAGAACGCCGAGCTGCTGGATCAGATTG
CCAAGATCCTGACCATCTACCAGAGCAGCGAGGACATCCAGGAAGAACTG
ACCAATCTGAACTCCGAGCTGACCCAGGAAGAGATCGAGCAGATCTCTAA
TCTGAAGGGCTATACCGGCACCCACAACCTGAGCCTGAAGGCCATCAACC
TGATCCTGGACGAGCTGTGGCACACCAACGACAACCAGATCGCTATCTTC
AACCGGCTGAAGCTGGTGCCCAAGAAGGTGGACCTGTCCCAGCAGAAAGA
GATCCCCACCACCCTGGTGGACGACTTCATCCTGAGCCCCGTCGTGAAGA
GAAGCTTCATCCAGAGCATCAAAGTGATCAACGCCATCATCAAGAAGTAC
GGCCTGCCCAACGACATCATTATCGAGCTGGCCCGCGAGAAGAACTCCAA
GGACGCCCAGAAAATGATCAACGAGATGCAGAAGCGGAACCGGCAGACCA
ACGAGCGGATCGAGGAAATCATCCGGACCACCGGCAAAGAGAACGCCAAG
TACCTGATCGAGAAGATCAAGCTGCACGACATGCAGGAAGGCAAGTGCCT
GTACAGCCTGGAAGCCATCCCTCTGGAAGATCTGCTGAACAACCCCTTCA
ACTATGAGGTGGACCACATCATCCCCAGAAGCGTGTCCTTCGACAACAGC
TTCAACAACAAGGTGCTCGTGAAGCAGGAAGAAgcCAGCAAGAAGGGCAA
CCGGACCCCATTCCAGTACCTGAGCAGCAGCGACAGCAAGATCAGCTACG
AAACCTTCAAGAAGCACATCCTGAATCTGGCCAAGGGCAAGGGCAGAATC
AGCAAGACCAAGAAAGAGTATCTGCTGGAAGAACGGGACATCAACAGGTT
CTCCGTGCAGAAAGACTTCATCAACCGGAACCTGGTGGATACCAGATACG
CCACCAGAGGCCTGATGAACCTGCTGCGGAGCTACTTCAGAGTGAACAAC
CTGGACGTGAAAGTGAAGTCCATCAATGGCGGCTTCACCAGCTTTCTGCG
GCGGAAGTGGAAGTTTAAGAAAGAGCGGAACAAGGGGTACAAGCACCACG
CCGAGGACGCCCTGATCATTGCCAACGCCGATTTCATCTTCAAAGAGTGG
AAGAAACTGGACAAGGCCAAAAAAGTGATGGAAAACCAGATGTTCGAGGA
AAAGCAGGCCGAGAGCATGCCCGAGATCGAAACCGAGCAGGAGTACAAAG
AGATCTTCATCACCCCCCACCAGATCAAGCACATTAAGGACTTCAAGGAC
TACAAGTACAGCCACCGGGTGGACAAGAAGCCTAATAGAGAGCTGATTAA
CGACACCCTGTACTCCACCCGGAAGGACGACAAGGGCAACACCCTGATCG -continued TGAACAATCTGAACGGCCTGTACGACAAGGACAATGACAAGCTGAAAAAG
CTGATCAACAAGAGCCCCGAAAAGCTGCTGATGTACCACCACGACCCCCA
GACCTACCAGAAACTGAAGCTGATTATGGAACAGTACGGCGACGAGAAGA
ATCCCCTGTACAAGTACTACGAGGAAACCGGGAACTACCTGACCAAGTAC
TCCAAAAAGGACAACGGCCCCGTGATCAAGAAGATTAAGTATTACGGCAA
CAAACTGAACGCCCATCTGGACATCACCGACGACTACCCCAACAGCAGAA
ACAAGGTCGTGAAGCTGTCCCTGAAGCCCTACAGATTCGACGTGTACCTG
GACAATGGCGTGTACAAGTTCGTGACCGTGAAGAATCTGGATGTGATCAA
AAAAGAAAACTACTACGAAGTGAATAGCAAGTGCTATGAGGAAGCTAAGA
AGCTGAAGAAGATCAGCAACCAGGCCGAGTTTATCGCCTCCTTCTACAAC
AACGATCTGATCAAGATCAACGGCGAGCTGTATAGAGTGATCGGCGTGAA
CAACGACCTGCTGAACCGGATCGAAGTGAACATGATCGACATCACCTACC
GCGAGTACCTGGAAAACATGAACGACAAGAGGCCCCCCAGGATCATTAAG
ACAATCGCCTCCAAGACCCAGAGCATTAAGAAGTACAGCACAGACATTCT
GGGCAACCTGTATGAAGTGAAATCTAAGAAGCACCCTCAGATCATCAAAA
AGGGCAAAAGGCCGGCGGCCACGAAAAAGGCCGGCCAGGCAAAAAAGAAA
AAGggatcCGATGCTAAGTCACTGACTGCCTGGTCCCGGACACTGGTGAC
CTTCAAGGATGTGTTTGTGGACTTCACCAGGGAGGAGTGGAAGCTGCTGG
ACACTGCTCAGCAGATCCTGTACAGAAATGTGATGCTGGAGAACTATAAG
AACCTGGTTTCCTTGGGTTATCAGCTTACTAAGCCAGATGTGATCCTCCG
GTTGGAGAAGGGAGAAGAGCCCTGGCTGGTGGAGAGAGAAATTCACCAAG
AGACCCATCCTGATTCAGAGACTGCATTTGAAATCAAATCATCAGTTCCG
AAAAAGAAACGCAAAGTTgctagCGAGGGCAGAGGAAGTCTTCTAACATG
CGGTGACGTGGAGGAGAATCCCGGCCCTATGACCGAGTACAAGCCCACGG
TGCGCCTCGCCACCCGCGACGACGTCCCCaGGGCCGTACGCACCCTCGCC
GCCGCGTTCGCCGACTACCCCGCCACGCGCCACACCGTCGATCCGGACCG
CCACATCGAGCGGGTCACCGAGCTGCAAGAACTCTTCCTCACGCGCGTCG
GGCTCGACATCGGCAAGGTGTGGGTCGCGGACGACGGCGCCGCGGTGGCG
GTCTGGACCACGCCGGAGAGCGTCGAAGCGGGGGCGGTGTTCGCCGAGAT
CGGCCCGCGCATGGCCGAGTTGAGCGGTTCCCGGCTGGCCGCGCAGCAAC
AGATGGAAGGCCTCCTGGCGCCGCACCGGCCCAAGGAGCCCGCGTGGTTC
CTGGCCACCGTCGGCGTGTCGCCCGACCACCAGGGCAAGGGTCTGGGCAG
CGCCGTCGTGCTCCCCGGAGTGGAGGCGGCCGAGCGCGCCGGGGTGCCCG
CCTTCCTGGAGACCTCCGCGCCCCGCAACCTCCCCTTCTACGAGCGGCTC
GGCTTCACCGTCACCGCCGACGTCGAGGTGCCCGAAGGACCGCGCACCTG
GTGCATGACCCGCAAGCCCGGTGCCTGACCAGcacactggcggcCGTTAC
TAGCTTCTGCAGCACGACcggTTGATAATAGATAACTTCGTATAGCATAC
ATTATACGAAGTTATGaattCGATATCAAGCTTATCGATAATCAACCTCT
GGATTACAAAATTTGTGAAAGATTGACTGGTATTCTTAACTATGTTGCTC
CTTTTACGCTATGTGGATACGCTGCTTTAATGCCTTTGTATCATGCTATT
GCTTCCCGTATGGCTTTCATTTTCTCCTCCTTGTATAAATCCTGGTTGCT -continued

GTCTCTTTATGAGGAGTTGTGGCCCGTTGTCAGGCAACGTGGCGTGGTGT

GCACTGTGTTTGCTGACGCAACCCCCACTGGTTGGGGCATTGCCACCACC

TGTCAGCTCCTTTCCGGGACTTTCGCTTTCCCCCTCCCTATTGCCACGGC

GGAACTCATCGCCGCCTGCCTTGCCCGCTGCTGGACAGGGGCTCGGCTGT

TGGGCACTGACAATTCCGTGGTGTTGTCGGGGAAATCATCGTCCTTTCCT

TGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGC

TGCCGGCTCTGCGGCCTCTTCCGCGTCTTCGCCTTCGCCCTCAGACGAGT

CGGATCTCCCTTTGGGCCGCCTCCCCGCATCGATACCGTCGACCTCGAGA

CCTAGAAAAACATGGAGCAATCACAAGTAGCAATACAGCAGCTACCAATG

CTGATTGTGCCTGGCTAGAAGCACAAGAGGAGGAGGAGGTGGGTTTTCCA

GTCACACCTCAGGTACCTTTAAGACCAATGACTTACAAGGCAGCTGTAGA

TCTTAGCCACTTTTTAAAAGAAAAGGGGGGACTGGAAGGGCTAATTCACT

CCCAACGAAGACAAGATATCCTTGATCTGTGGATCTACCACACACAAGGC

TACTTCCCTGATTGGCAGAACTACACACCAGGGCCAGGGATCAGATATCC

ACTGACCTTTGGATGGTGCTACAAGCTAGTACCAGTTGAGCAAGAGAAGG

TAGAAGAAGCCAATGAAGGAGAGAACACCCGCTTGTTACACCCTGTGAGC

CTGCATGGGATGGATGACCCGGAGAGAGAAGTATTAGAGTGGAGGTTTGA

CAGCCGCCTAGCATTTCATCACATGGCCCGAGAGCTGCATCCGGACTGTA

CTGGGTCTCTCTGGTTAGACCAGATCTGAGCCTGGGAGCTCTCTGGCTAA

CTAGGGAACCCACTGCTTAAGCCTCAATAAAGCTTGCCTTGAGTGCTTCA

AGTAGTGTGTGCCCGTCTGTTGTGTGACTCTGGTAACTAGAGATCCCTCA

GACCCTTTTAGTCAGTGTGGAAAATCTCTAGCAGGGCCCGTTTAAACCCG

CTGATCAGCCTCGACTGTGCCTTCTAGTTGCCAGCCATCTGTTGTTTGCC

CCTCCCCCGTGCCTTCCTTGACCCTGGAAGGTGCCACTCCCACTGTCCTT

TCCTAATAAAATGAGGAAATTGCATCGCATTGTCTGAGTAGGTGTCATTC

TATTCTGGGGGGTGGGGTGGGGCAGGACAGCAAGGGGGAGGATTGGGAAG

ACAATAGCAGGCATGCTGGGGATGCGGTGGGCTCTATGGCTTCTGAGGCG

GAAAGAACCAGCTGGGGCTCTAGGGGGTATCCCCACGCGCCCTGTAGCGG

CGCATTAAGCGCGGCGGGTGTGGTGGTTACGCGCAGCGTGACCGCTACAC

TTGCCAGCGCCCTAGCGCCCGCTCCTTTCGCTTTCTTCCCTTCCTTTCTC

GCCACGTTCGCCGGCTTTCCCCGTCAAGCTCTAAATCGGGGGCTCCCTTT

AGGGTTCCGATTTAGTGCTTTACGGCACCTCGACCCCAAAAAACTTGATT

AGGGTGATGGTTCACGTAGTGGGCCATCGCCCTGATAGACGGTTTTTCGC

CCTTTGACGTTGGAGTCCACGTTCTTTAATAGTGGACTCTTGTTCCAAAC

TGGAACAACACTCAACCCTATCTCGGTCTATTCTTTTGATTTATAAGGGA

TTTTGCCGATTTCGGCCTATTGGTTAAAAAATGAGCTGATTTAACAAAAA

TTTAACGCGAATTAATTCTGTGGAATGTGTGTCAGTTAGGGTGTGGAAAG

TCCCCAGGCTCCCCAGCAGGCAGAAGTATGCAAAGCATGCATCTCAATTA

GTCAGCAACCAGGTGTGGAAAGTCCCCAGGCTCCCCAGCAGGCAGAAGTA

-continued

TGCAAAGCATGCATCTCAATTAGTCAGCAACCATAGTCCCGCCCCTAACT

CCGCCCATCCCGCCCCTAACTCCGCCCAGTTCCGCCCATTCTCCGCCCCA

TGGCTGACTAATTTTTTTTATTTATGCAGAGGCCGAGGCCGCCTCTGCCT

CTGAGCTATTCCAGAAGTAGTGAGGAGGCTTTTTTGGAGGCCTAGGCTTT

TGCAAAAAGCTCCCGGGAGCTTGTATATCCATTTTCGGATCTGATCAGCA

CGTGTTGACAATTAATCATCGGCATAGTATATCGGCATAGTATAATACGA

CAAGGTGAGGAACTAAACCATGGCCAAGTTGACCAGTGCCGTTCCGGTGC

TCACCGCGCGCGACGTCGCCGGAGCGGTCGAGTTCTGGACCGACCGGCTC

GGGTTCTCCCGGGACTTCGTGGAGGACGACTTCGCCGGTGTGGTCCGGGA

CGACGTGACCCTGTTCATCAGCGCGGTCCAGGACCAGGTGGTGCCGGACA

ACACCCTGGCCTGGGTGTGGGTGCGCGGCCTGGACGAGCTGTACGCCGAG

TGGTCGGAGGTCGTGTCCACGAACTTCCGGGACGCCTCCGGGCCGGCCAT

GACCGAGATCGGCGAGCAGCCGTGGGGGCGGGAGTTCGCCCTGCGCGACC

CGGCCGGCAACTGCGTGCACTTCGTGGCCGAGGAGCAGGACTGACACGTG

CTACGAGATTTCGATTCCACCGCCGCCTTCTATGAAAGGTTGGGCTTCGG

AATCGTTTTCCGGGACGCCGGCTGGATGATCCTCCAGCGCGGGGATCTCA

TGCTGGAGTTCTTCGCCCACCCCAACTTGTTTATTGCAGCTTATAATGGT

TACAAATAAAGCAATAGCATCACAAATTTCACAAATAAAGCATTTTTTTC

ACTGCATTCTAGTTGTGGTTTGTCCAAACTCATCAATGTATCTTATCATG

TCTGTATACCGTCGACCTCTAGCTAGAGCTTGGCGTAATCATGGTCATAG

CTGTTTCCTGTGTGAAATTGTTATCCGCTCACAATTCCACACAACATACG

AGCCGGAAGCATAAAGTGTAAAGCCTGGGGTGCCTAATGAGTGAGCTAAC

TCACATTAATTGCGTTGCGCTCACTGCCCGCTTTCCAGTCGGGAAACCTG

TCGTGCCAGCTGCATTAATGAATCGGCCAACGCGCGGGGAGAGGCGGTTT

GCGTATTGGGCGCTCTTCCGCTTCCTCGCTCACTGACTCGCTGCGCTCGG

TCGTTCGGCTGCGGCGAGCGGTATCAGCTCACTCAAAGGCGGTAATACGG

TTATCCACAGAATCAGGGGATAACGCAGGAAAGAACATGTGAGCAAAAGG

CCAGCAAAAGGCCAGGAACCGTAAAAAGGCCGCGTTGCTGGCGTTTTTCC

ATAGGCTCCGCCCCCCTGACGAGCATCACAAAAATCGACGCTCAAGTCAG

AGGTGGCGAAACCCGACAGGACTATAAAGATACCAGGCGTTTCCCCCTGG

AAGCTCCCTCGTGCGCTCTCCTGTTCCGACCCTGCCGCTTACCGGATACC

TGTCCGCCTTTCTCCCTTCGGGAAGCGTGGCGCTTTCTCATAGCTCACGC

TGTAGGTATCTCAGTTCGGTGTAGGTCGTTCGCTCCAAGCTGGGCTGTGT

GCACGAACCCCCCGTTCAGCCCGACCGCTGCGCCTTATCCGGTAACTATC

GTCTTGAGTCCAACCCGGTAAGACACGACTTATCGCCACTGGCAGCAGCC

ACTGGTAACAGGATTAGCAGAGCGAGGTATGTAGGCGGTGCTACAGAGTT

CTTGAAGTGGTGGCCTAACTACGGCTACACTAGAAGAACAGTATTTGGTA

TCTGCGCTCTGCTGAAGCCAGTTACCTTCGGAAAAAGAGTTGGTAGCTCT

TGATCCGGCAAACAAACCACCGCTGGTAGCGGTGGTTTTTTTGTTTGCAA

GCAGCAGATTACGCGCAGAAAAAAAGGATCTCAAGAAGATCCTTTGATCT

TTTCTACGGGGTCTGACGCTCAGTGGAACGAAAACTCACGTTAAGGGATT

-continued

TTGGTCATGAGATTATCAAAAAGGATCTTCACCTAGATCCTTTTAAATTA

AAAATGAAGTTTTAAATCAATCTAAAGTATATATGAGTAAACTTGGTCTG

ACAGTTACCAATGCTTAATCAGTGAGGCACCTATCTCAGCGATCTGTCTA

TTTCGTTCATCCATAGTTGCCTGACTCCCCGTCGTGTAGATAACTACGAT

ACGGGAGGGCTTACCATCTGGCCCCAGTGCTGCAATGATACCGCGAGACC

CACGCTCACCGGCTCCAGATTTATCAGCAATAAACCAGCCAGCCGGAAGG

GCCGAGCGCAGAAGTGGTCCTGCAACTTTATCCGCCTCCATCCAGTCTAT

TAATTGTTGCCGGGAAGCTAGAGTAAGTAGTTCGCCAGTTAATAGTTTGC

GCAACGTTGTTGCCATTGCTACAGGCATCGTGGTGTCACGCTCGTCGTTT

GGTATGGCTTCATTCAGCTCCGGTTCCCAACGATCAAGGCGAGTTACATG

ATCCCCCATGTTGTGCAAAAAAGCGGTTAGCTCCTTCGGTCCTCCGATCG

TTGTCAGAAGTAAGTTGGCCGCAGTGTTATCACTCATGGTTATGGCAGCA

CTGCATAATTCTCTTACTGTCATGCCATCCGTAAGATGCTTTTCTGTGAC

TGGTGAGTACTCAACCAAGTCATTCTGAGAATAGTGTATGCGGCGACCGA

GTTGCTCTTGCCCGGCGTCAATACGGGATAATACCGCGCCACATAGCAGA

ACTTTAAAAGTGCTCATCATTGGAAAACGTTCTTCGGGGCGAAAACTCTC

AAGGATCTTACCGCTGTTGAGATCCAGTTCGATGTAACCCACTCGTGCAC

CCAACTGATCTTCAGCATCTTTTACTTTCACCAGCGTTTCTGGGTGAGCA

AAAACAGGAAGGCAAAATGCCGCAAAAAAGGGAATAAGGGCGACACGGAA

ATGTTGAATACTCATACTCTTCCTTTTTCAATATTATTGAAGCATTTATC

AGGGTTATTGTCTCATGAGCGGATACATATTTGAATGTATTTAGAAAAAT

Figure 7:
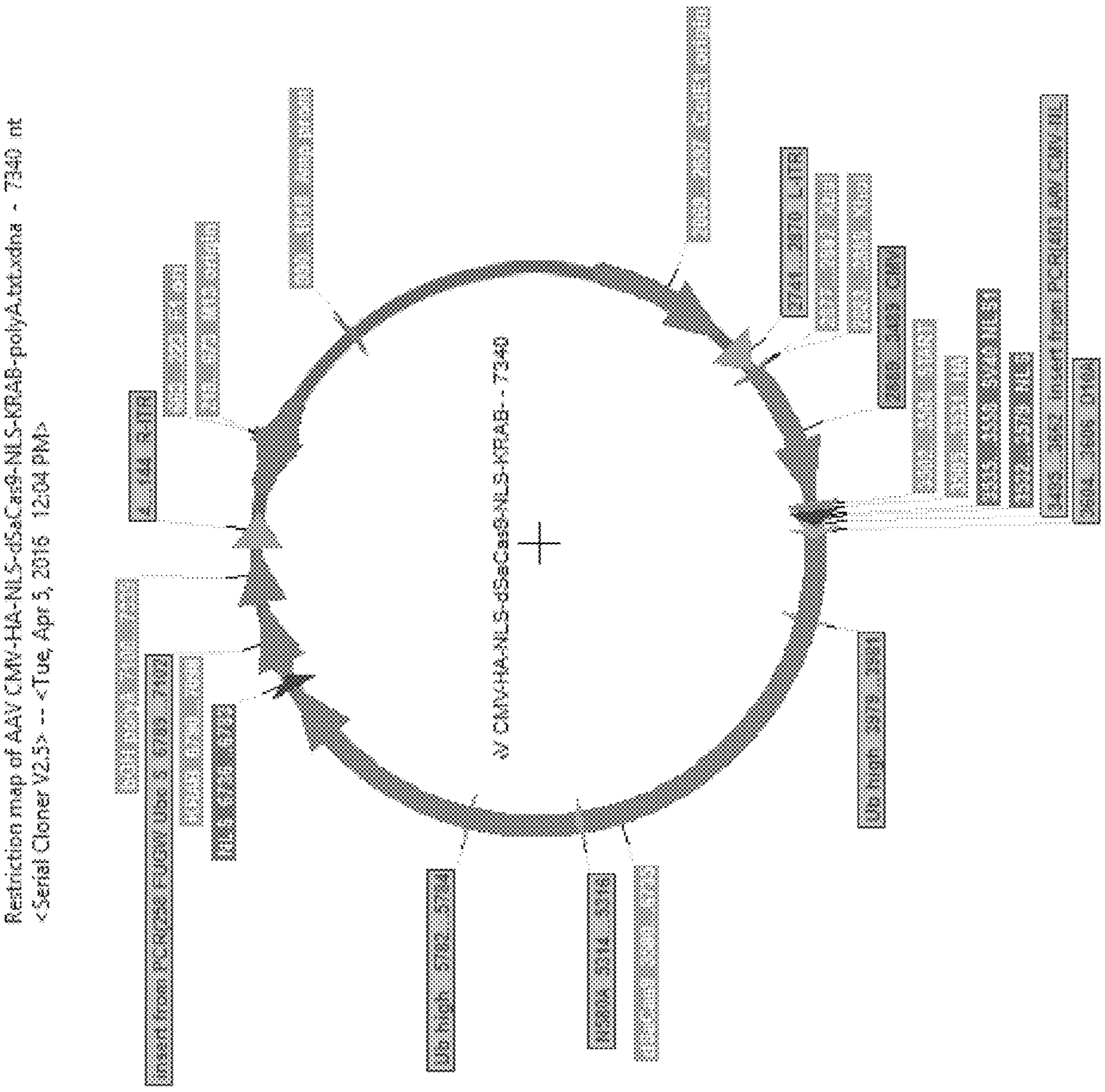
FIG. 7 is a graph showing a restriction map of an AAV vector encoding *S. aureus* Cas9 KRAB-based repressor.

AAACAAATAGGGGTTCCGCGCACATTTCCCCGAAAAGTGCCACCTGAC 1.6.2 AAV *S. aureus* Cas9 KRAB-Based Repressor A restriction map of an AAV vector encoding *S. aureus* Cas9 KRAB-based repressor is shown in FIG. 7. SEQ ID NO: 3 provides the nucleic acid sequence of the AAV vector encoding *S. aureus* Cas9 KRAB-based repressor.

SEQ ID NO: 3 gcaggaacccctagtgatggagttggccactccctctctgcgcgctcgct cgctcactgaggccgggcgaccaaaggtcgcccgacgcccgggctttgcc cgggcggcctcagtgagcgagcgagcgcgcagctgcctgcaggggcgcct gatgcggtattttctccttacgcatctgtgcggtatttcacaccgcatac gtcaaagcaaccatagtacgcgccctgtagcggcgcattaagcgcggcgg gtgtggtggttacgcgcagcgtgaccgctacacttgccagcgccctagcg cccgctcctttcgctttcttcccttcctttctcgccacgttcgccggctt tccccgtcaagctctaaatcgggggctccctttagggttccgatttagtg ctttacggcacctcgaccccaaaaaacttgatttgggtgatggttcacgt agtgggccatcgccctgatagacggtttttcgccctttgacgttggagtc cacgttctttaatagtggactcttgttccaaactggaacaacactcaacc ctatctcgggctattcttttgatttataagggattttgccgatttcggcc tattggttaaaaaatgagctgatttaacaaaaatttaacgcgaattttaa -continued caaaatattaacgtttacaattttatggtgcactctcagtacaatctgct ctgatgccgcatagttaagccagccccgacacccgccaacacccgctgac gcgccctgacgggcttgtctgctcccggcatccgcttacagacaagctgt gaccgtctccgggagctgcatgtgtcagaggttttcaccgtcatcaccga aacgcgcgagacgaaagggcctcgtgatacgcctatttttataggttaat gtcatgataataatggtttcttagacgtcaggtggcacttttcggggaaa tgtgcgcggaacccctatttgtttatttttctaaatacattcaaatatgt atccgctcatgagacaataaccctgataaatgcttcaataatattgaaaa aggaagagtatgagtattcaacatttccgtgtcgcccttattcccttttt tgcggcattttgccttcctgtttttgctcacccagaaacgctggtgaaag taaaagatgctgaagatcagttgggtgcacgagtgggttacatcgaactg gatctcaacagcggtaagatccttgagagttttcgccccgaagaacgttt tccaatgatgagcacttttaaagttctgctatgtggcgcggtattatccc gtattgacgccgggcaagagcaactcggtcgccgcatacactattctcag aatgacttggttgagtactcaccagtcacagaaaagcatcttacggatgg catgacagtaagagaattatgcagtgctgccataaccatgagtgataaca ctgcggccaacttacttctgacaacgatcggaggaccgaaggagctaacc gcttttttgcacaacatgggggatcatgtaactcgccttgatcgttggga accggagctgaatgaagccataccaaacgacgagcgtgacaccacgatgc ctgtagcaatggcaacaacgttgcgcaaactattaactggcgaactactt actctagcttcccggcaacaattaatagactggatggaggcggataaagt tgcaggaccacttctgcgctcggcccttccggctggctggtttattgctg ataaatctggagccggtgagcgtggaagccgcggtatcattgcagcactg gggccagatggtaagccctcccgtatcgtagttatctacacgacggggag tcaggcaactatggatgaacgaaatagacagatcgctgagataggtgcct cactgattaagcattggtaactgtcagaccaagtttactcatatatactt tagattgatttaaaacttcatttttaatttaaaaggatctaggtgaagat cctttttgataatctcatgaccaaaatcccttaacgtgagttttcgttcc actgagcgtcagaccccgtagaaaagatcaaaggatcttcttgagatcct ttttttctgcgcgtaatctgctgcttgcaaacaaaaaaaccaccgctacc agcggtggtttgtttgccggatcaagagctaccaactctttttccgaagg taactggcttcagcagagcgcagataccaaatactgtccttctagtgtag ccgtagttaggccaccacttcaagaactctgtagcaccgcctacatacct cgctctgctaatcctgttaccagtggctgctgccagtggcgataagtcgt gtcttaccgggttggactcaagacgatagttaccggataaggcgcagcgg tcgggctgaacggggggttcgtgcacacagcccagcttggagcgaacgac ctacaccgaactgagatacctacagcgtgagctatgagaaagcgccacgc ttcccgaagggagaaaggcggacaggtatccggtaagcggcagggtcgga acaggagagcgcacgagggagcttccagggggaaacgcctggtatcttta tagtcctgtcgggtttcgccacctctgacttgagcgtcgatttttgtgat gctcgtcaggggggcggagcctatggaaaaacgccagcaacgcggccttt -continued

```
ttacggttcctggccttttgctggccttttgctcacatgtcctgcaggca
gctgcgcgctcgctcgctcactgaggccgcccgggcgtcgggcgaccttt
ggtcgcccggcctcagtgagcgagcgagcgcgcagagagggagtggccaa
ctccatcactaggggttcctgcggcctctagactcgaggcgttgacattg
attattgactagttattaatagtaatcaattacggggtcattagttcata
gcccatatatggagttccgcgttacataacttacggtaaatggcccgcct
ggctgaccgcccaacgacccccgcccattgacgtcaataatgacgtatgt
tcccatagtaacgccaatagggactttccattgacgtcaatgggtggagt
atttacggtaaactgcccacttggcagtacatcaagtgtatcatatgcca
agtacgccccctattgacgtcaatgacggtaaatggcccgcctggcatta
tgcccagtacatgaccttatgggactttcctacttggcagtacatctacg
tattagtcatcgctattaccatggtgatgcggttttggcagtacatcaat
gggcgtggatagcggtttgactcacggggatttccaagtctccaccccat
tgacgtcaatgggagtttgttttggcaccaaaatcaacgggactttccaa
aatgtcgtaacaactccgccccattgacgcaaatgggcggtaggcgtgta
cggtgggaggtctatataagcagagctctctggctaactaccggtgccac
catgtacccatacgatgttccagattacgctGCCCCAAAGAAGAAGCGGA
AGGTCGGTATCCACGGAGTCCCAGCAGCCAAGCGGAACTACATCCTGGGC
CTGGCCATCGGCATCACCAGCGTGGGCTACGGCATCATCGACTACGAGAC
ACGGGACGTGatcgATGCCGGCGTGCGGCTGTTCAAAGAGGCCAACGTGG
AAAACAACGAGGGCAGGCGGAGCAAGAGAGGCGCCAGAAGGCTGAAGCGG
CGGAGGCGGCATAGAATCCAGAGAGTGAAGAAGCTGCTGTTCGACTACAA
CCTGCTGACCGACCACAGCGAGCTGAGCGGCATCAACCCCTACGAGGCCA
GAGTGAAGGGCCTGAGCCAGAAGCTGAGCGAGGAAGAGTTCTCTGCCGCC
CTGCTGCACCTGGCCAAGAGAAGAGGCGTGCACAACGTGAACGAGGTGGA
AGAGGACACCGGCAACGAGCTGTCCACCAAAGAGCAGATCAGCCGGAACA
GCAAGGCCCTGGAAGAGAAATACGTGGCCGAACTGCAGCTGGAACGGCTG
AAGAAAGACGGCGAAGTGCGGGGCAGCATCAACAGATTCAAGACCAGCGA
CTACGTGAAAGAAGCCAAACAGCTGCTGAAGGTGCAGAAGGCCTACCACC
AGCTGGACCAGAGCTTCATCGACACCTACATCGACCTGCTGGAAACCCGG
CGGACCTACTATGAGGGACCTGGCGAGGGCAGCCCCTTCGGCTGGAAGGA
CATCAAAGAATGGTACGAGATGCTGATGGGCCACTGCACCTACTTCCCCG
AGGAACTGCGGAGCGTGAAGTACGCCTACAACGCCGACCTGTACAACGCC
CTGAACGACCTGAACAATCTCGTGATCACCAGGGACGAGAACGAGAAGCT
GGAATATTACGAGAAGTTCCAGATCATCGAGAACGTGTTCAAGCAGAAGA
AGAAGCCCACCCTGAAGCAGATCGCCAAAGAAATCCTCGTGAACGAAGAG
GATATTAAGGGCTACAGAGTGACCAGCACCGGCAAGCCCGAGTTCACCAA
CCTGAAGGTGTACCACGACATCAAGGACATTACCGCCCGGAAAGAGATTA
TTGAGAACGCCGAGCTGCTGGATCAGATTGCCAAGATCCTGACCATCTAC
CAGAGCAGCGAGGACATCCAGGAAGAACTGACCAATCTGAACTCCGAGCT
```

-continued

```
GACCCAGGAAGAGATCGAGCAGATCTCTAATCTGAAGGGCTATACCGGCA
CCCACAACCTGAGCCTGAAGGCCATCAACCTGATCCTGGACGAGCTGTGG
CACACCAACGACAACCAGATCGCTATCTTCAACCGGCTGAAGCTGGTGCC
CAAGAAGGTGGACCTGTCCCAGCAGAAAGAGATCCCCACCACCCTGGTGG
ACGACTTCATCCTGAGCCCCGTCGTGAAGAGAAGCTTCATCCAGAGCATC
AAAGTGATCAACGCCATCATCAAGAAGTACGGCCTGCCCAACGACATCAT
TATCGAGCTGGCCCGCGAGAAGAACTCCAAGGACGCCCAGAAAATGATCA
ACGAGATGCAGAAGCGGAACCGGCAGACCAACGAGCGGATCGAGGAAATC
ATCCGGACCACCGGCAAAGAGAACGCCAAGTACCTGATCGAGAAGATCAA
GCTGCACGACATGCAGGAAGGCAAGTGCCTGTACAGCCTGGAAGCCATCC
CTCTGGAAGATCTGCTGAACAACCCCTTCAACTATGAGGTGGACCACATC
ATCCCCAGAAGCGTGTCCTTCGACAACAGCTTCAACAACAAGGTGCTCGT
GAAGCAGGAAGAAgcCAGCAAGAAGGGCAACCGGACCCCATTCCAGTACC
TGAGCAGCAGCGACAGCAAGATCAGCTACGAAACCTTCAAGAAGCACATC
CTGAATCTGGCCAAGGGCAAGGGCAGAATCAGCAAGACCAAGAAAGAGTA
TCTGCTGGAAGAACGGGACATCAACAGGTTCTCCGTGCAGAAAGACTTCA
TCAACCGGAACCTGGTGGATACCAGATACGCCACCAGAGGCCTGATGAAC
CTGCTGCGGAGCTACTTCAGAGTGAACAACCTGGACGTGAAAGTGAAGTC
CATCAATGGCGGCTTCACCAGCTTTCTGCGGCGGAAGTGGAAGTTTAAGA
AAGAGCGGAACAAGGGGTACAAGCACCACGCCGAGGACGCCCTGATCATT
GCCAACGCCGATTTCATCTTCAAAGAGTGGAAGAAACTGGACAAGGCCAA
AAAAGTGATGGAAAACCAGATGTTCGAGGAAAAGCAGGCCGAGAGCATGC
CCGAGATCGAAACCGAGCAGGAGTACAAAGAGATCTTCATCACCCCCCAC
CAGATCAAGCACATTAAGGACTTCAAGGACTACAAGTACAGCCACCGGGT
GGACAAGAAGCCTAATAGAGAGCTGATTAACGACACCCTGTACTCCACCC
GGAAGGACGACAAGGGCAACACCCTGATCGTGAACAATCTGAACGGCCTG
TACGACAAGGACAATGACAAGCTGAAAAAGCTGATCAACAAGAGCCCCGA
AAAGCTGCTGATGTACCACCACGACCCCCAGACCTACCAGAAACTGAAGC
TGATTATGGAACAGTACGGCGACGAGAAGAATCCCCTGTACAAGTACTAC
GAGGAAACCGGGAACTACCTGACCAAGTACTCCAAAAAGGACAACGGCCC
CGTGATCAAGAAGATTAAGTATTACGGCAACAAACTGAACGCCCATCTGG
ACATCACCGACGACTACCCCAACAGCAGAAACAAGGTCGTGAAGCTGTCC
CTGAAGCCCTACAGATTCGACGTGTACCTGGACAATGGCGTGTACAAGTT
CGTGACCGTGAAGAATCTGGATGTGATCAAAAAAGAAAACTACTACGAAG
TGAATAGCAAGTGCTATGAGGAAGCTAAGAAGCTGAAGAAGATCAGCAAC
CAGGCCGAGTTTATCGCCTCCTTCTACAACAACGATCTGATCAAGATCAA
CGGCGAGCTGTATAGAGTGATCGGCGTGAACAACGACCTGCTGAACCGGA
TCGAAGTGAACATGATCGACATCACCTACCGCGAGTACCTGGAAAACATG
AACGACAAGAGGCCCCCCAGGATCATTAAGACAATCGCCTCCAAGACCCA
GAGCATTAAGAAGTACAGCACAGACATTCTGGGCAACCTGTATGAAGTGA
AATCTAAGAAGCACCCTCAGATCATCAAAAAGGGCAAAAGGCCGGCGGCC
```

-continued

```
ACGAAAAAGGCCGGCCAGGCAAAAAAGAAAAAGggatcCGATGCTAAGTC
ACTGACTGCCTGGTCCCGGACACTGGTGACCTTCAAGGATGTGTTTGTGG
ACTTCACCAGGGAGGAGTGGAAGCTGCTGGACACTGCTCAGCAGATCCTG
TACAGAAATGTGATGCTGGAGAACTATAAGAACCTGGTTTCCTTGGGTTA
TCAGCTTACTAAGCCAGATGTGATCCTCCGGTTGGAGAAGGGAGAAGAGC
CCTGGCTGGTGGAGAGAGAAATTCACCAAGAGACCCATCCTGATTCAGAG
ACTGCATTTGAAATCAAATCATCAGTTCCGAAAAAGAAACGCAAAGttta
aGaattcctagagctcgctgatcagcctcgactgtgccttctagttgcca
gccatctgttgtttgcccctcccccgtgccttccttgaccctggaaggtg
ccactcccactgtcctttcctaataaaatgaggaaattgcatcgcattgt
ctgagtaggtgtcattctattctggggggtggggtggggcaggacagcaa
gggggaggattgggaagagaatagcaggcatgctggggag
```

1.6.3 AAV *S. aureus* Cas9 U6-gRNA Vector with GFP-Kan Stuffer

Figure 8:
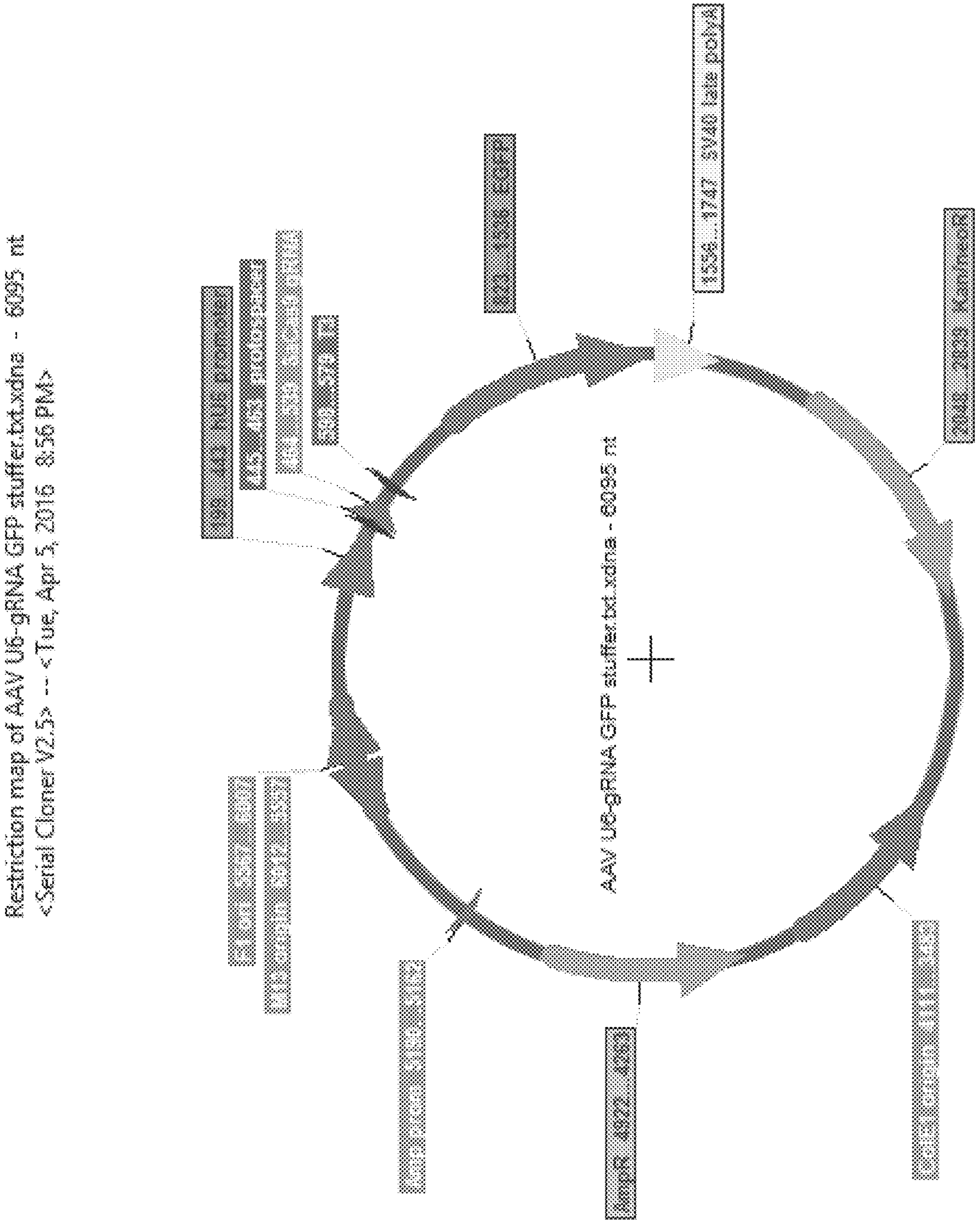
FIG. 8 is a graph showing a restriction map of an AAV vector encoding *S. aureus* Cas9 U6-gRNA.

A restriction map of an AAV vector encoding *S. aureus* Cas9 U6-gRNA is shown in FIG. 8. SEQ ID NO: 4 provides the nucleic acid sequence of the AAV vector encoding *S. aureus* Cas9 U6-gRNA (with sample protospacer gRNA sequence).

```
                                           SEQ ID NO: 4
gggggggggggggggggttggccactccctctctgcgcgctcgctcgct
cactgaggccgggcgaccaaaggtcgcccgacgcccgggctttgcccggg
cggcctcagtgagcgagcgagcgcgcagagagggagtggccaactccatc
actaggggttcctagatctgaattcggtacCagatctaggaaCCTAGGgc
ctatttcccatgattccttcatatttgcatatacgatacaaggctgttag
agagataattggaattaatttgactgtaaacacaaagatattagtacaaa
atacgtgacgtagaaagtaataatttcttgggtagtttgcagttttaaaa
ttatgttttaaaatggactatcatatgcttaccgtaacttgaaagtattt
cgatttcttggctttatatatcttgTGGAAAGGACGAAACACCgagcgcg
ccccgcctagcccgttttagtactctggaaacagaatctactaaaacaag
gcaaaatgccgtgtttatctcgtcaacttgttggcgagatttttttGCGG
CCGCCCgcggtggagctccagcttttgttccctttagtgagggttaatTc
tagaggatccggtactcgaggaactgaaaaaccagaaagttaactggtaa
gtttagtctttttgtcttttatttcaggtcccggatccggtggtggtgca
aatcaaagaactgctcctcagtggatgttgcctttacttctaggcctgta
cggaagtgttacttctgctctaaaagctgcggaattgtacccgcggcccg
ggatccaccggtcgccaccatggtgagcaagggcgaggagctgttcaccg
gggtggtgcccatcctggtcgagctggacggcgacgtaaacggccacaag
ttcagcgtgtccggcgagggcgagggcgatgccacctacggcaagctgac
cctgaagttcatctgcaccaccggcaagctgcccgtgccctggcccaccc
tcgtgaccaccctgacctacggcgtgcagtgcttcagccgctaccccgac
cacatgaagcagcacgacttcttcaagtccgccatgcccgaaggctacgt
```

-continued

```
ccaggagcgcaccatcttcttcaaggacgacggcaactacaagacccgcg
ccgaggtgaagttcgagggcgacaccctggtgaaccgcatcgagctgaag
ggcatcgacttcaaggaggacggcaacatcctggggcacaagctggagta
caactacaacagccacaacgtctatatcatggccgacaagcagaagaacg
gcatcaaggtgaacttcaagatccgccacaacatcgaggacggcagcgtg
cagctcgccgaccactaccagcagaacacccccatcggcgacggccccgt
gctgctgcccgacaaccactacctgagcacccagtccgccctgagcaaag
accccaacgagaagcgcgatcacatggtcctgctggagttcgtgaccgcc
gccgggatcactctcggcatggacgagctgtacaagtaaagcggccgcgg
ggatccagacatgataagatacattgatgagtttggacaaaccacaacta
gaatgcagtgaaaaaaatgctttatttgtgaaatttgtgatgctattgct
ttatttgtaaccattataagctgcaataaacaagttaacaacaacaattg
cattcattttatgtttcaggttcagggggaggtgtgggaggttttttagt
cgacctcgagcagtgtggttttgcaagaggaagcaaaaagcctctccacc
caggcctggaatgtttccacccaagtcgaaggcagtgtggttttgcaaga
ggaagcaaaaagcctctccacccaggcctggaatgtttccacccaatgtc
gagcaaccccgcccagcgtcttgtcattggcgaattcgaacacgcagatg
cagtcggggcggcgcggtcccaggtccacttcgcatattaaggtgacgcg
tgtggcctcgaacaccgagcgaccctgcagccaatatgggatcggccatt
gaacaagatggattgcacgcaggttctccggccgcttgggtggagaggct
attcggctatgactgggcacaacagacaatcggctgctctgatgccgccg
tgttccggctgtcagcgcaggggcgcccggttctttttgtcaagaccgac
ctgtccggtgccctgaatgaactgcaggacgaggcagcgcggctatcgtg
gctggccacgacgggcgttccttgcgcagctgtgctcgacgttgtcactg
aagcgggaagggactggctgctattgggcgaagtgccggggcaggatctc
ctgtcatctcaccttgctcctgccgagaaagtatccatcatggctgatgc
aatgcggcggctgcatacgcttgatccggctacctgcccattcgaccacc
aagcgaaacatcgcatcgagcgagcacgtactcggatggaagccggtctt
gtcgatcaggatgatctggacgaagagcatcaggggctcgcgccagccga
actgttcgccaggctcaaggcgcgcatgcccgacggcgaggatctcgtcg
tgacccatggcgatgcctgcttgccgaatatcatggtggaaaatggccgc
ttttctggattcatcgactgtggccggctgggtgtggcggaccgctatca
ggacatagcgttggctacccgtgatattgctgaagagcttggcggcgaat
gggctgaccgcttcctcgtgctttacggtatcgccgctcccgattcgcag
cgcatcgccttctatcgccttcttgacgagttcttctgaggggatccgtc
gactagagctcgctgatcagcctcgactgtgccttctagttgccagccat
ctgttgtttgcccctcccccgtgccttccttgaccctggaaggtgccact
cccactgtcctttcctaataaaatgaggaaattgcatcgcattgtctgag
taggtgtcattctattctggggggtggggtggggcaggacagcaaggggg
aggattgggaagacaatagcaggcatgctggggagagatctaggaacccc
tagtgatggagttggccactccctctctgcgcgctcgctcgctcactgag
```

-continued

```
gccgcccgggcaaagcccgggcgtcgggcgacctttggtcgcccggcctc
agtgagcgagcgagcgcgcagagagggagtggccaacccccccccccccc
cccctgcagcccagctgcattaatgaatcggccaacgcgcggggagaggc
ggtttgcgtattgggcgctcttccgcttcctcgctcactgactcgctgcg
ctcggtcgttcggctgcggcgagcggtatcagctcactcaaaggcggtaa
tacggttatccacagaatcaggggataacgcaggaaagaacatgtgagca
aaaggccagcaaaaggccaggaaccgtaaaaaggccgcgttgctggcgtt
tttccataggctccgcccccctgacgagcatcacaaaaatcgacgctcaa
gtcagaggtggcgaaacccgacaggactataaagataccaggcgtttccc
cctggaagctccctcgtgcgctctcctgttccgaccctgccgcttaccgg
atacctgtccgcctttctcccttcgggaagcgtggcgctttctcaatgct
cacgctgtaggtatctcagttcggtgtaggtcgttcgctccaagctgggc
tgtgtgcacgaaccccccgttcagcccgaccgctgcgccttatccggtaa
ctatcgtcttgagtccaacccggtaagacacgacttatcgccactggcag
cagccactggtaacaggattagcagagcgaggtatgtaggcggtgctaca
gagttcttgaagtggtggcctaactacggctacactagaaggacagtatt
tggtatctgcgctctgctgaagccagttaccttcggaaaaagagttggta
gctcttgatccggcaaacaaaccaccgctggtagcggtggtttttttgtt
tgcaagcagcagattacgcgcagaaaaaaaggatctcaagaagatccttt
gatcttttctacggggtctgacgctcagtggaacgaaaactcacgttaag
ggattttggtcatgagattatcaaaaaggatcttcacctagatcctttta
aattaaaaatgaagttttaaatcaatctaaagtatatatgagtaaacttg
gtctgacagttaccaatgcttaatcagtgaggcacctatctcagcgatct
gtctatttcgttcatccatagttgcctgactccccgtcgtgtagataact
acgatacgggagggcttaccatctggccccagtgctgcaatgataccgcg
agacccacgctcaccggctccagatttatcagcaataaaccagccagccg
gaagggccgagcgcagaagtggtcctgcaactttatccgcctccatccag
tctattaattgttgccgggaagctagagtaagtagttcgccagttaatag
tttgcgcaacgttgttgccattgctacaggcatcgtggtgtcacgctcgt
cgtttggtatggcttcattcagctccggttcccaacgatcaaggcgagtt
acatgatcccccatgttgtgcaaaaaagcggttagctccttcggtcctcc
gatcgttgtcagaagtaagttggccgcagtgttatcactcatggttatgg
cagcactgcataattctcttactgtcatgccatccgtaagatgcttttct
gtgactggtgagtactcaaccaagtcattctgagaatagtgtatgcggcg
accgagttgctcttgcccggcgtcaatacgggataataccgcgccacata
gcagaactttaaaagtgctcatcattggaaaacgttcttcggggcgaaaa
ctctcaaggatcttaccgctgttgagatccagttcgatgtaacccactcg
tgcacccaactgatcttcagcatcttttactttcaccagcgtttctgggt
gagcaaaaacaggaaggcaaaatgccgcaaaaaagggaataagggcgaca
cggaaatgttgaatactcatactcttcctttttcaatattattgaagcat
ttatcagggttattgtctcatgagcggatacatatttgaatgtatttaga
aaaataaacaaataggggttccgcgcacatttccccgaaaagtgccacct
gacgtctaagaaaccattattatcatgacattaacctataaaaataggcg
tatcacgaggccctttcgtctcgcgcgtttcggtgatgacggtgaaaacc
tctgacacatgcagctcccggagacggtcacagcttgtctgtaagcggat
gccgggagcagacaagcccgtcagggcgcgtcagcgggtgttggcgggtg
tcggggctggcttaactatgcggcatcagagcagattgtactgagagtgc
accatatgcggtgtgaaataccgcacagatgcgtaaggagaaaataccgc
atcaggaaattgtaaacgttaatattttgttaaaattcgcgttaaatttt
tgttaaatcagctcattttttaaccaataggccgaaatcggcaaaatccc
ttataaatcaaaagaatagaccgagatagggttgagtgttgttccagttt
ggaacaagagtccactattaaagaacgtggactccaacgtcaaagggcga
aaaaccgtctatcagggcgatggcccactacgtgaaccatcaccctaatc
aagttttttggggtcgaggtgccgtaaagcactaaatcggaaccctaaag
ggagcccccgatttagagcttgacggggaaagccggcgaacgtggcgaga
aaggaagggaagaaagcgaaaggagcgggcgctagggcgctggcaagtgt
agcggtcacgctgcgcgtaaccaccacacccgccgcgcttaatgcgccgc
tacagggcgcgtcgcgccattcgccattcaggctacgcaactgttgggaa
gggcgatcggtgcgggcctcttcgctattacgccagctggctgca
```

1.6.5 AAV *S. aureus* Cas9 U6-gRNA Vector with GFP-Kan Stuffer

Figure 9:
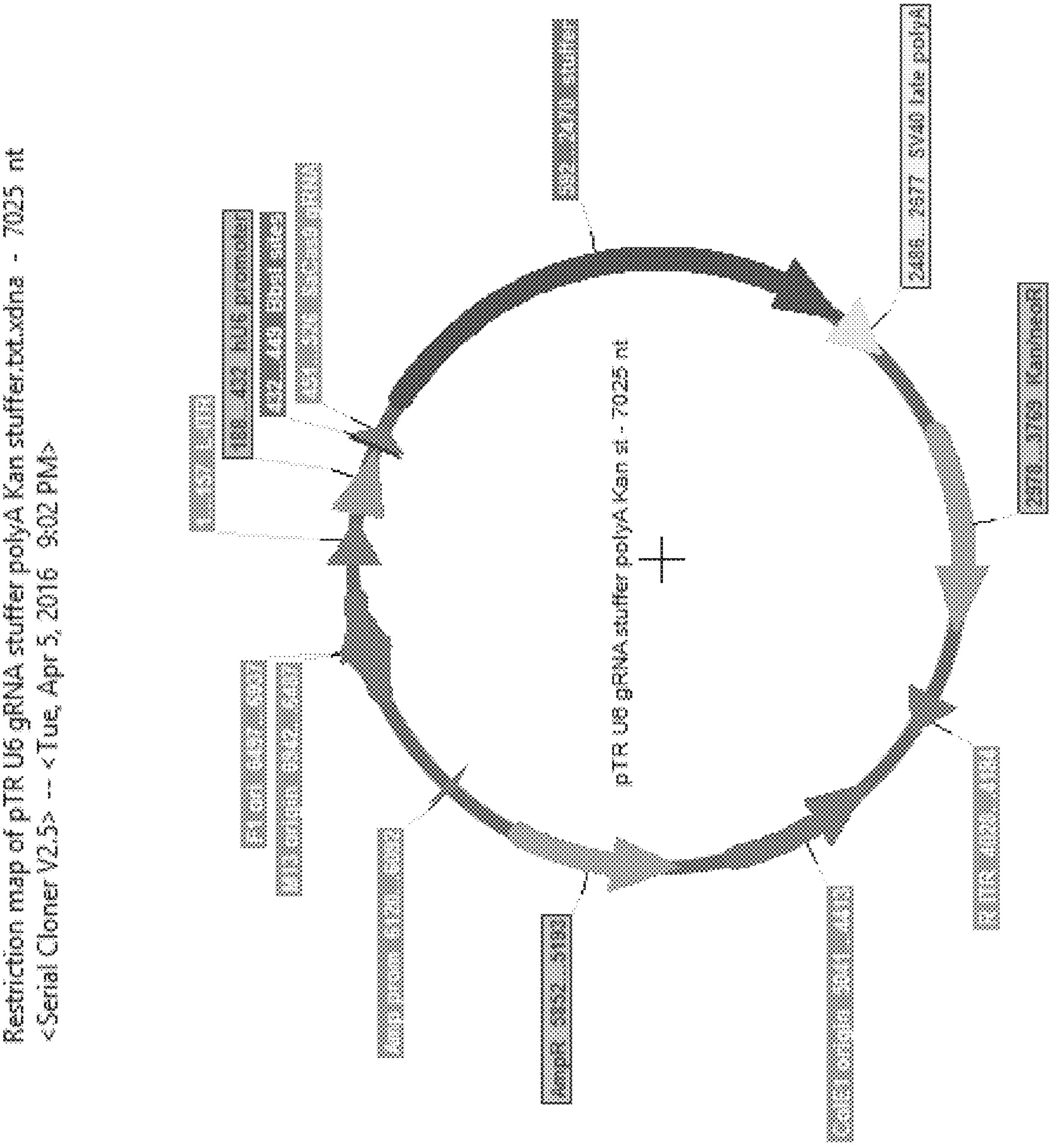
FIG. 9 is a graph showing a restriction map of an AAV vector encoding *S. aureus* Cas9 U6-gRNA.

A restriction map of an AAV vector encoding *S. aureus* Cas9 U6-gRNA is shown in FIG. 9. SEQ ID NO: 5 provides the nucleic acid sequence of the AAV vector encoding *S. aureus* Cas9 U6-gRNA (Protospacer is cloned into the BbsI sites).

SEQ ID NO: 5

```
ggggggggggggggggggttggccactccctctctgcgcgctcgctcgct
cactgaggccgggcgaccaaaggtcgcccgacgcccgggctttgcccggg
cggcctcagtgagcgagcgagcgcgcagagagggagtggccaactccatc
actaggggttcctagatctgaattcggtaccaagctTgcctatttcccat
gattccttcatatttgcatatacgatacaaggctgttagagagataattg
gaattaatttgactgtaaacacaaagatattagtacaaaatacgtgacgt
agaaagtaataatttcttgggtagtttgcagttttaaaattatgttttaa
aatggactatcatatgcttaccgtaacttgaaagtatttcgatttcttgg
ctttatatatcttgTGGAAAGGACGAAACACCgggtcttcgagaagacct
gttttagtactctggaaacagaatctactaaaacaaggcaaaatgccgtg
tttatctcgtcaacttgttggcgagatttttttGCGGCCGCCCgcggtgg
agctccagcttttgttccctttagtgagggttaatTctagAgagacgtac
aaaaaagagcaagaagctaaaaaagatttaaaaattatttttagcgcagt
taatggaacaggaactaaatttaccccaaaaatattacgtgaatcaggat
ataacgttattgaggttgaagagcatgcatttgaagatgaaacatttaaa
aatgttgtaaatccaaatccagaatttgatcctgcatgaaaaataccgct
```

-continued tgaatatggtattaaacatgatgcagatattattattatgaatgacccag
atgctgacagatttggaatggcaataaaacatgatggtcattttgtaaga
ttagatggaaatcaaacaggaccaattttaattgattgaaaattatcaaa
tctaaaacgcttaaatagcattccaaaaaatccggctctatattcaagtt
ttgtaacaagtgatttgggtgatagaatcgctcatgaaaaatatggagtt
aatattgtaaaaactttaactggatttaaatgaatgggtagagaaattgc
taaagaagaagataacggattaaattttgtttttgcttatgaagaaagtt
atggatatgtaattgatgactcagctagagataaagatggaatacaagct
tctatattaatagcagaggctgcttgattttataaaaaacaaaataaaac
attagtagactatttagaagatttatttaaagaaatgggtgcatattaca
ctttcactttaaacttgaattttaaaccagaagaaaagaaattaaaaatt
gaaccattaatgaaatcattgagagcaacacccttaactcaaattgctgg
acttaaagttgttaatgttgaagactacatcgatggaatgtataatatgc
caggacaagacttactaaaattttatttagaagataagtcatgatttgct
gttcgcccaagtggaactgaacctaaactaaaaatttattttataggtgt
tggtgaatctgttcaaaacgctaaagttaaagtagacgaaattattaaag
aattaaaattaaaaatgaatatataggagaaaaaatgaaactaaacaaat
atatagatcacacattattaaaacaagatgctacgaaagctgaaattaaa
caattatgtgatgaagcaattgaatttgattttgcaacagtttgtgttaa
ttcatattgaacaagctattgtaaagaattattaaaaggcacaaatgtag
gaataacaaatgttgtaggttttcctctaggtgcatgcacaacagctaca
aaagcattcgaagtttctgaagcaattaaagatggtgcaacagaaattga
tatggtattaaatattggtgcattaaaagacaaaaattatgaattagttt
tagaagacatgaaagctgtaaaaaaagcagctggatcacatgttgttaaa
tgtattatggaaaattgtttattaacaaaagaagaaatcatgaaagcttg
tgaaatagctgttgaagctggattagaatttgttaaaacatcaacaggat
tttcaaaatcaggtgcaacatttgaagatgttaaactaatgaagtcagtt
gttaaagacaatgctttagttaaagcagctggtggagttagaacatttga
agatgctcaaaaaatgattgaagcaggagctgaccgcttaggaacaagtg
gtggagtagctattattaaaggtgaagaaaacaacgcgagttactaaaac
tagcgtttttttatttgctcatttttattaaaagtttgcaaaaaggaac
ataaaaattctaattattgatactaaagttattaaaaagaagattttggt
tgattttataaaggtcatagaatataatattttagcatgtgtattttgtg
tgctcatttacaaccgtctcGCggccgcggggatccagacatgataagat
acattgatgagtttggacaaaccacaactagaatgcagtgaaaaaaatgc
tttatttgtgaaatttgtgatgctattgctttatttgtaaccattataag
ctgcaataaacaagttaacaacaacaattgcattcattttatgtttcagg
ttcagggggaggtgtgggaggttttttagtcgacctcgagcagtgtggtt
ttgcaagaggaagcaaaaagcctctccacccaggcctggaatgtttccac
ccaagtcgaaggcagtgtggttttgcaagaggaagcaaaaagcctctcca -continued cccaggcctggaatgtttccacccaatgtcgagcaaccccgcccagcgtc
ttgtcattggcgaattcgaacacgcagatgcagtcggggcggcgcggtcc
caggtccacttcgcatattaaggtgacgcgtgtggcctcgaacaccgagc
gaccctgcagccaatatgggatcggccattgaacaagatggattgcacgc
aggttctccggccgcttgggtggagaggctattcggctatgactgggcac
aacagacaatcggctgctctgatgccgccgtgttccggctgtcagcgcag
gggcgcccggttctttttgtcaagaccgacctgtccggtgccctgaatga
actgcaggacgaggcagcgcggctatcgtggctggccacgacgggcgttc
cttgcgcagctgtgctcgacgttgtcactgaagcgggaagggactggctg
ctattgggcgaagtgccggggcaggatctcctgtcatctcaccttgctcc
tgccgagaaagtatccatcatggctgatgcaatgcggcggctgcatacgc
ttgatccggctacctgcccattcgaccaccaagcgaaacatcgcatcgag
cgagcacgtactcggatggaagccggtcttgtcgatcaggatgatctgga
cgaagagcatcaggggctcgcgccagccgaactgttcgccaggctcaagg
cgcgcatgcccgacggcgaggatctcgtcgtgacccatggcgatgcctgc
ttgccgaatatcatggtggaaaatggccgcttttctggattcatcgactg
tggccggctgggtgtggcggaccgctatcaggacatagcgttggctaccc
gtgatattgctgaagagcttggcggcgaatgggctgaccgcttcctcgtg
ctttacggtatcgccgctcccgattcgcagcgcatcgccttctatcgcct
tcttgacgagttcttctgaggggatccgtcgactagagctcgctgatcag
cctcgactgtgccttctagttgccagccatctgttgtttgcccctccccc
gtgccttccttgaccctggaaggtgccactcccactgtcctttcctaata
aaatgaggaaattgcatcgcattgtctgagtaggtgtcattctattctgg
ggggtggggtggggcaggacagcaagggggaggattgggaagacaatagc
aggcatgctggggagagatctaggaacccctagtgatggagttggccact
ccctctctgcgcgctcgctcgctcactgaggccgcccgggcaaagcccgg
gcgtcgggcgacctttggtcgcccggcctcagtgagcgagcgagcgcgca
gagagggagtggccaacccccccccccccccccctgcagcccagctgcat
taatgaatcggccaacgcgcggggagaggcggtttgcgtattgggcgctc
ttccgcttcctcgctcactgactcgctgcgctcggtcgttcggctgcggc
gagcggtatcagctcactcaaaggcggtaatacggttatccacagaatca
ggggataacgcaggaaagaacatgtgagcaaaaggccagcaaaaggccag
gaaccgtaaaaaggccgcgttgctggcgtttttccataggctccgccccc
ctgacgagcatcacaaaaatcgacgctcaagtcagaggtggcgaaacccg
acaggactataaagataccaggcgtttccccctggaagctccctcgtgcg
ctctcctgttccgaccctgccgcttaccggatacctgtccgcctttctcc
cttcgggaagcgtggcgctttctcaatgctcacgctgtaggtatctcagt
tcggtgtaggtcgttcgctccaagctgggctgtgtgcacgaacccccgt
tcagcccgaccgctgcgccttatccggtaactatcgtcttgagtccaacc
cggtaagacacgacttatcgccactggcagcagccactggtaacaggatt
agcagagcgaggtatgtaggcggtgctacagagttcttgaagtggtggcc -continued taactacggctacactagaaggacagtatttggtatctgcgctctgctga
agccagttaccttcggaaaaagagttggtagctcttgatccggcaaacaa
accaccgctggtagcggtggtttttttgtttgcaagcagcagattacgcg
cagaaaaaaaggatctcaagaagatcctttgatcttttctacggggtctg
acgctcagtggaacgaaaactcacgttaagggattttggtcatgagatta
tcaaaaaggatcttcacctagatccttttaaattaaaaatgaagttttaa
atcaatctaaagtatatatgagtaaacttggtctgacagttaccaatgct
taatcagtgaggcacctatctcagcgatctgtctatttcgttcatccata
gttgcctgactccccgtcgtgtagataactacgatacgggagggcttacc
atctggccccagtgctgcaatgataccgcgagacccacgctcaccggctc
cagatttatcagcaataaaccagccagccggaagggccgagcgcagaagt
ggtcctgcaactttatccgcctccatccagtctattaattgttgccggga
agctagagtaagtagttcgccagttaatagtttgcgcaacgttgttgcca
ttgctacaggcatcgtggtgtcacgctcgtcgtttggtatggcttcattc
agctccggttcccaacgatcaaggcgagttacatgatcccccatgttgtg
caaaaaagcggttagctccttcggtcctccgatcgttgtcagaagtaagt
tggccgcagtgttatcactcatggttatggcagcactgcataattctctt
actgtcatgccatccgtaagatgcttttctgtgactggtgagtactcaac
caagtcattctgagaatagtgtatgcggcgaccgagttgctcttgcccgg
cgtcaatacgggataataccgcgccacatagcagaactttaaaagtgctc
atcattggaaaacgttcttcggggcgaaaactctcaaggatcttaccgct
gttgagatccagttcgatgtaacccactcgtgcacccaactgatcttcag
catcttttactttcaccagcgtttctgggtgagcaaaaacaggaaggcaa
aatgccgcaaaaaagggaataagggcgacacggaaatgttgaatactcat
actcttcctttttcaatattattgaagcatttatcagggttattgtctca
tgagcggatacatatttgaatgtatttagaaaaataaacaaataggggtt
ccgcgcacatttccccgaaaagtgccacctgacgtctaagaaaccattat
tatcatgacattaacctataaaaataggcgtatcacgaggccctttcgtc
tcgcgcgtttcggtgatgacggtgaaaacctctgacacatgcagctcccg
gagacggtcacagcttgtctgtaagcggatgccgggagcagacaagcccg
tcagggcgcgtcagcgggtgttggcgggtgtcggggctggcttaactatg
cggcatcagagcagattgtactgagagtgcaccatatgcggtgtgaaata
ccgcacagatgcgtaaggagaaaataccgcatcaggaaattgtaaacgtt
aatattttgttaaaattcgcgttaaatttttgttaaatcagctcattttt
taaccaataggccgaaatcggcaaaatcccttataaatcaaaagaataga
ccgagatagggttgagtgttgttccagtttggaacaagagtccactatta
aagaacgtggactccaacgtcaaagggcgaaaaaccgtctatcagggcga
tggcccactacgtgaaccatcaccctaatcaagttttttggggtcgaggt
gccgtaaagcactaaatcggaaccctaaagggagcccccgatttagagct
tgacggggaaagccggcgaacgtggcgagaaaggaagggaagaaagcgaa -continued aggagcgggcgctagggcgctggcaagtgtagcggtcacgctgcgcgtaa
ccaccacacccgccgcgcttaatgcgccgctacagggcgcgtcgcgccat
tcgccattcaggctacgcaactgttgggaagggcgatcggtgcgggcctc
ttcgctattacgccagctggctgca 1.6.6 Protospacer Sequences for gRNAs

TABLE 4

| CAG Luciferase gRNAs | | |
|---|---|---|
| SEQ ID NO | Description | Sequence |
| 6 | SaCr1 | GTCATTATTGACGTCAATGGGC |
| 7 | SaCr2 | gtgctcagcaactcggggag |
| 8 | SaCr3 | ctcggggagggggtgcagg |
| 9 | SaCr4 | ACTTTCCATTGACGTCAATGGG |
| 10 | SaCr5 | CTTCGGGGGGGACGGGGCAGGG |
| 11 | SaCr6 | cttcgccccgcgcccgctaga |
| 12 | SaCr7 | tcggggagggggtgcagg |
| 13 | SaCr8 | tgctcagcaactcggggag |
| 14 | SaCr9 | gcggggggtggcggcaggt |

TABLE 5

| Mouse Acvr2b gRNAs | | |
|---|---|---|
| SEQ ID NO | Description | Sequence |
| 15 | SaCr1 | gctcctctgggacccctga |
| 16 | SaCr2 | tgctatggagcccacgcta |
| 17 | SaCr3 | ggcgcgctctccgagctgg |
| 18 | SaCr4 | agcgcgccccgcctagccc |
| 19 | SaCr5 | gcctctttgtatccaacat |
| 20 | SaCr6 | gcacgctcctctgggacccctga |
| 21 | SaCr7 | gtgggggaggggacctgaa |
| 22 | SaCr8 | gaggggccatgaacggggg |

1.6.7 *S. aureus* Cas9-based repressor gene sequence SEQ ID NO: 23 provides a nucleic acid sequence encoding HA-NLS-dSaCas9-NLS-KRAB. Residues 1-3 are a start codon. Residues 4-30 encode a HA tag. Residues 31-78 encode a first nuclear localization sequence (NLS). Residues 79-3234 encode *S. aureus* "dead" Cas9. Residues 103-105 encode the first inactivating mutation. Residues 1813-1815 encode the second inactivating mutation. Residues 3235-3282 encode a second NLS. Residues 3289-3597 encode KRAB. Residues 3598-3600 are a stop codon. All the residues are numbered based on SEQ ID NO: 23.

SEQ ID NO: 23 atgtacccatacgatgttccagattacgctGCCCCAAAGAAGAAGCGGAA
GGTCGGTATCCACGGAGTCCCAGCAGCCAAGCGGAACTACATCCTGGGCC -continued

TGGCCATCGGCATCACCAGCGTGGGCTACGGCATCATCGACTACGAGACA

CGGGACGTGatcgATGCCGGCGTGCGGCTGTTCAAAGAGGCCAACGTGGA

AAACAACGAGGGCAGGCGGAGCAAGAGAGGCGCCAGAAGGCTGAAGCGGC

GGAGGCGGCATAGAATCCAGAGAGTGAAGAAGCTGCTGTTCGACTACAAC

CTGCTGACCGACCACAGCGAGCTGAGCGGCATCAACCCCTACGAGGCCAG

AGTGAAGGGCCTGAGCCAGAAGCTGAGCGAGGAAGAGTTCTCTGCCGCCC

TGCTGCACCTGGCCAAGAGAAGAGGCGTGCACAACGTGAACGAGGTGGAA

GAGGACACCGGCAACGAGCTGTCCACCAAAGAGCAGATCAGCCGGAACAG

CAAGGCCCTGGAAGAGAAATACGTGGCCGAACTGCAGCTGGAACGGCTGA

AGAAAGACGGCGAAGTGCGGGGCAGCATCAACAGATTCAAGACCAGCGAC

TACGTGAAAGAAGCCAAACAGCTGCTGAAGGTGCAGAAGGCCTACCACCA

GCTGGACCAGAGCTTCATCGACACCTACATCGACCTGCTGGAAACCCGGC

GGACCTACTATGAGGGACCTGGCGAGGGCAGCCCCTTCGGCTGGAAGGAC

ATCAAAGAATGGTACGAGATGCTGATGGGCCACTGCACCTACTTCCCCGA

GGAACTGCGGAGCGTGAAGTACGCCTACAACGCCGACCTGTACAACGCCC

TGAACGACCTGAACAATCTCGTGATCACCAGGGACGAGAACGAGAAGCTG

GAATATTACGAGAAGTTCCAGATCATCGAGAACGTGTTCAAGCAGAAGAA

GAAGCCCACCCTGAAGCAGATCGCCAAAGAAATCCTCGTGAACGAAGAGG

ATATTAAGGGCTACAGAGTGACCAGCACCGGCAAGCCCGAGTTCACCAAC

CTGAAGGTGTACCACGACATCAAGGACATTACCGCCCGGAAAGAGATTAT

TGAGAACGCCGAGCTGCTGGATCAGATTGCCAAGATCCTGACCATCTACC

AGAGCAGCGAGGACATCCAGGAAGAACTGACCAATCTGAACTCCGAGCTG

ACCCAGGAAGAGATCGAGCAGATCTCTAATCTGAAGGGCTATACCGGCAC

CCACAACCTGAGCCTGAAGGCCATCAACCTGATCCTGGACGAGCTGTGGC

ACACCAACGACAACCAGATCGCTATCTTCAACCGGCTGAAGCTGGTGCCC

AAGAAGGTGGACCTGTCCCAGCAGAAAGAGATCCCCACCACCCTGGTGGA

CGACTTCATCCTGAGCCCCGTCGTGAAGAGAAGCTTCATCCAGAGCATCA

AAGTGATCAACGCCATCATCAAGAAGTACGGCCTGCCCAACGACATCATT

ATCGAGCTGGCCCGCGAGAAGAACTCCAAGGACGCCCAGAAAATGATCAA

CGAGATGCAGAAGCGGAACCGGCAGACCAACGAGCGGATCGAGGAAATCA

TCCGGACCACCGGCAAAGAGAACGCCAAGTACCTGATCGAGAAGATCAAG

CTGCACGACATGCAGGAAGGCAAGTGCCTGTACAGCCTGGAAGCCATCCC

TCTGGAAGATCTGCTGAACAACCCCTTCAACTATGAGGTGGACCACATCA

TCCCCAGAAGCGTGTCCTTCGACAACAGCTTCAACAACAAGGTGCTCGTG

AAGCAGGAAGAAgcCAGCAAGAAGGGCAACCGGACCCCATTCCAGTACCT

GAGCAGCAGCGACAGCAAGATCAGCTACGAAACCTTCAAGAAGCACATCC

TGAATCTGGCCAAGGGCAAGGGCAGAATCAGCAAGACCAAGAAAGAGTAT

CTGCTGGAAGAACGGGACATCAACAGGTTCTCCGTGCAGAAAGACTTCAT

CAACCGGAACCTGGTGGATACCAGATACGCCACCAGAGGCCTGATGAACC

TGCTGCGGAGCTACTTCAGAGTGAACAACCTGGACGTGAAAGTGAAGTCC

ATCAATGGCGGCTTCACCAGCTTTCTGCGGCGGAAGTGGAAGTTTAAGAA

-continued

AGAGCGGAACAAGGGGTACAAGCACCAGCGCCAGGACGCCCTGATCATTG

CCAACGCCGATTTCATCTTCAAAGAGTGGAAGAAACTGGACAAGGCCAAA

AAAGTGATGGAAAACCAGATGTTCGAGGAAAAGCAGGCCGAGAGCATGCC

CGAGATCGAAACCGAGCAGGAGTACAAAGAGATCTTCATCACCCCCCACC

AGATCAAGCACATTAAGGACTTCAAGGACTACAAGTACAGCCACCGGGTG

GACAAGAAGCCTAATAGAGAGCTGATTAACGACACCCTGTACTCCACCCG

GAAGGACGACAAGGGCAACACCCTGATCGTGAACAATCTGAACGGCCTGT

ACGACAAGGACAATGACAAGCTGAAAAAGCTGATCAACAAGAGCCCCGAA

AAGCTGCTGATGTACCACCACGACCCCCAGACCTACCAGAAACTGAAGCT

GATTATGGAACAGTACGGCGACGAGAAGAATCCCCTGTACAAGTACTACG

AGGAAACCGGGAACTACCTGACCAAGTACTCCAAAAAGGACAACGGCCCC

GTGATCAAGAAGATTAAGTATTACGGCAACAAACTGAACGCCCATCTGGA

CATCACCGACGACTACCCCAACAGCAGAAACAAGGTCGTGAAGCTGTCCC

TGAAGCCCTACAGATTCGACGTGTACCTGGACAATGGCGTGTACAAGTTC

GTGACCGTGAAGAATCTGGATGTGATCAAAAAAGAAAACTACTACGAAGT

GAATAGCAAGTGCTATGAGGAAGCTAAGAAGCTGAAGAAGATCAGCAACC

AGGCCGAGTTTATCGCCTCCTTCTACAACAACGATCTGATCAAGATCAAC

GGCGAGCTGTATAGAGTGATCGGCGTGAACAACGACCTGCTGAACCGGAT

CGAAGTGAACATGATCGACATCACCTACCGCGAGTACCTGGAAAACATGA

ACGACAAGAGGCCCCCCAGGATCATTAAGACAATCGCCTCCAAGACCCAG

AGCATTAAGAAGTACAGCACAGACATTCTGGGCAACCTGTATGAAGTGAA

ATCTAAGAAGCACCCTCAGATCATCAAAAAGGGCAAAAGGCCGGCGGCCA

CGAAAAAGGCCGGCCAGGCAAAAAAGAAAAAGggatcCGATGCTAAGTCA

CTGACTGCCTGGTCCCGGACACTGGTGACCTTCAAGGATGTGTTTGTGGA

CTTCACCAGGGAGGAGTGGAAGCTGCTGGACACTGCTCAGCAGATCCTGT

ACAGAAATGTGATGCTGGAGAACTATAAGAACCTGGTTTCCTTGGGTTAT

CAGCTTACTAAGCCAGATGTGATCCTCCGGTTGGAGAAGGGAGAAGAGCC

CTGGCTGGTGGAGAGAGAAATTCACCAAGAGACCCATCCTGATTCAGAGA

CTGCATTTGAAATCAAATCATCAGTTCCGAAAAAGAAACGCAAAGtttaa

2. Additional Information

Figure 5A:
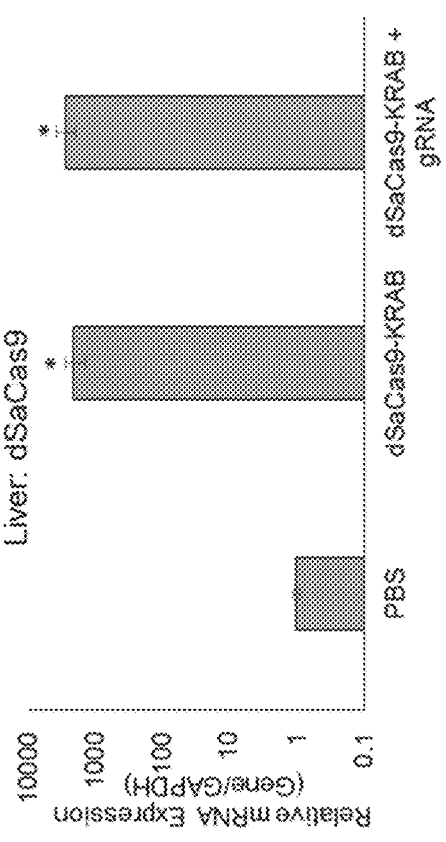
FIGS. 5A-5D are graphs showing the silencing of endogenous genes in vivo with AAV-dSaCas9-KRAB.
Figure 5B:
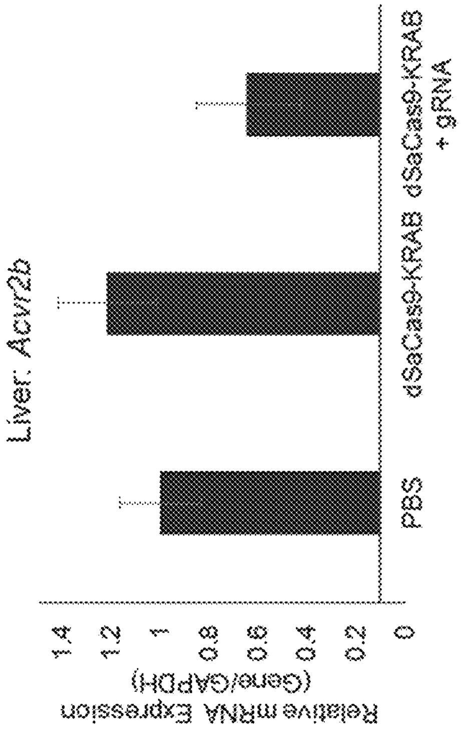
Figure 5C:
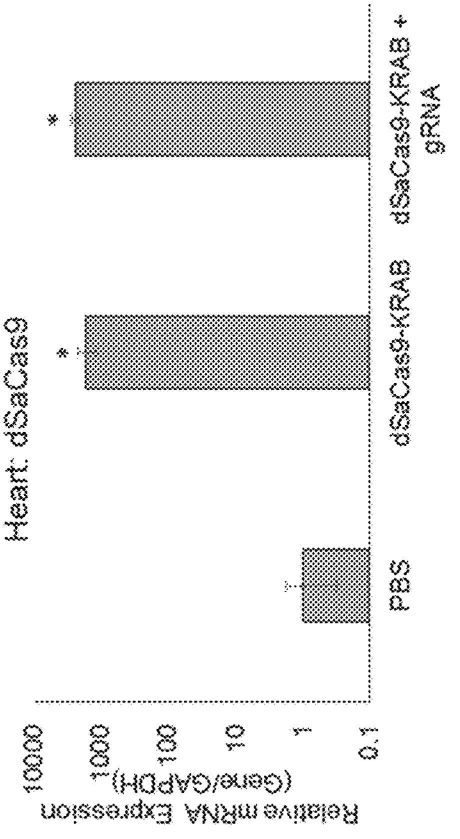
Figure 5D:
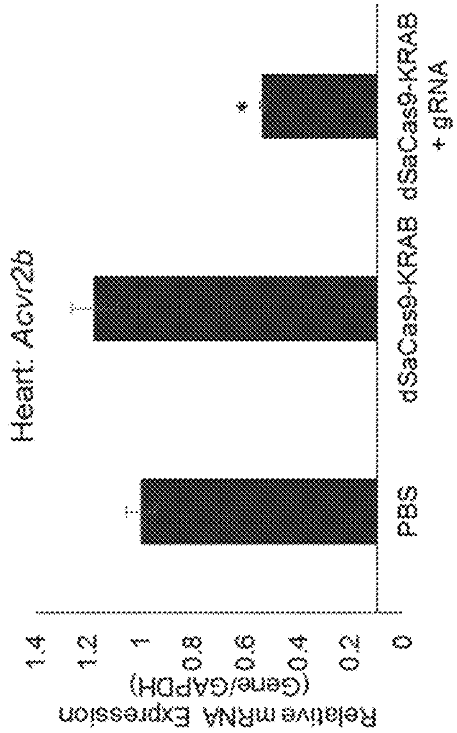
Figures 10A, 10B, 10C:
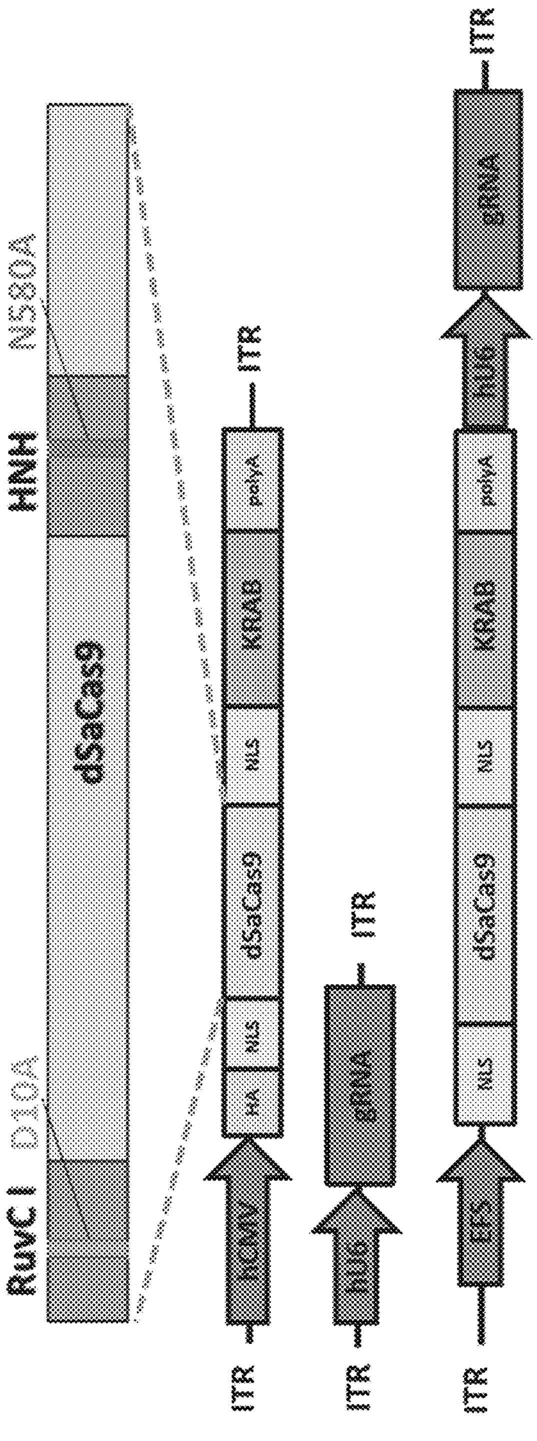
FIGS. 10A-10C are schematics showing an AAV-based gene delivery system for CRISPR/Cas9-based synthetic repressors.

Engineered DNA-binding proteins that can be customized to target any gene in mammalian cells have enabled rapid advances in biomedical research and are a promising platform for gene therapies. The RNA-guided CRISPR/Cas9 system has emerged as a promising platform for programmable targeted gene regulation. Current Cas9 transcriptional repressors are based on Cas9 derived from the *S. pyogenes* bacterial strain. Fusion of catalytically inactive, "dead" Cas9 (dCas9) to the Kruppel-associated box (KRAB) domain generates a synthetic repressor capable of highly specific and potent silencing of target genes in cell culture experiments. However, a technology to deliver CRISPR/Cas9-based gene repressors in vivo has not been developed. Adeno-associated virus (AAV) vectors have been proposed for gene delivery of CRISPR/Cas9 components for in vivo studies and therapeutic applications. AAV vectors provide stable gene expression with low risk of mutagenic integration events, can be engineered to target tissues of interest in vivo, and are already in use in humans in clinical trials. However, gene delivery of *S. pyogenes* dCas9-KRAB in vivo is challenging because the size of the *S. pyogenes* dCas9 and KRAB domain fusion exceeds the packaging limit of standard AAV vectors. Recently, a smaller Cas9 nuclease protein derived from *S. aureus* was described for AAV delivery and in vivo gene editing. An *S. aureus* nuclease-null dCas9 was generated and fused to a synthetic KRAB repressor to create a programmable RNA-guided repressor for in vivo gene regulation (FIG. 10A). An AAV-based expression system was designed to deliver dCas9-KRAB fusion proteins and CRISPR gRNA targeting molecules in vivo (FIGS. 10B and 10C). When delivered intramuscularly using an AAV9 serotype vector, *S. aureus* dCas9-KRAB protein was expressed efficiently in skeletal muscle up to 8 weeks after delivery in a wild-type mouse model (FIG. 3D). Furthermore, it was demonstrated that *S. aureus* dCas9-KRAB is biologically active and can effectively silence an endogenous gene, acvr2b, in the injected muscle, heart and liver when delivered with a target guide RNA molecule (FIGS. 3E, 5B and 5D). This gene delivery system can be customized to target any endogenous gene by designing a new guide RNA molecule, enabling potent and stable gene repression in animal models and for human use.

3. Hypercholesterolemia

Figure 11A:
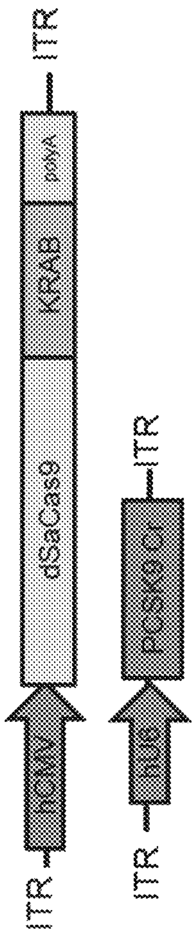
FIGS. 11A-11C are graphs showing targeted reduction of the PCSK9 gene in vivo with engineered synthetic repressors.
Figure 11B:
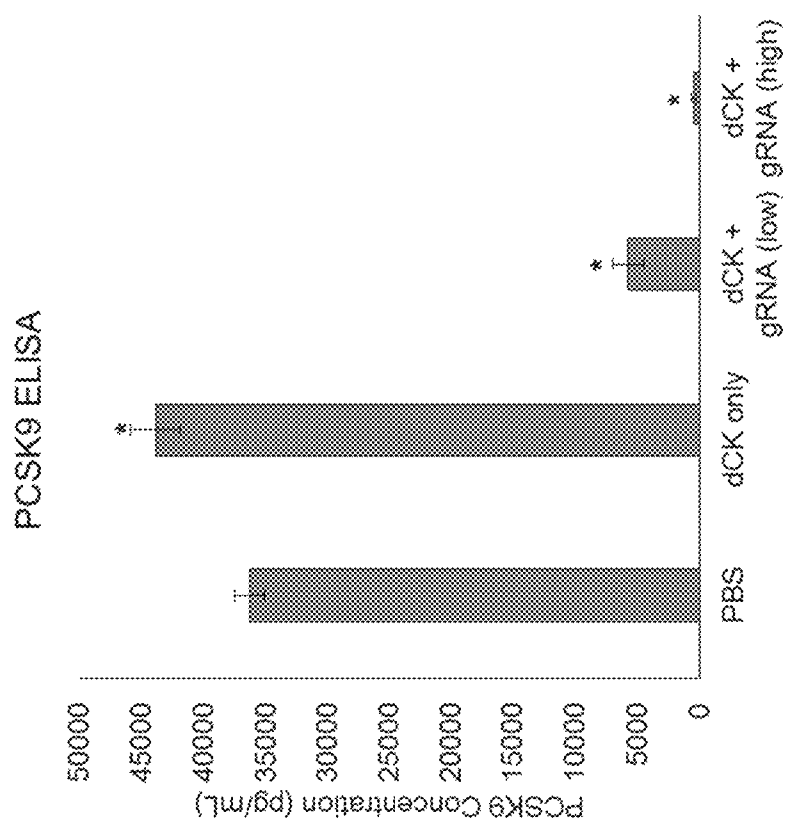
Figure 11C:
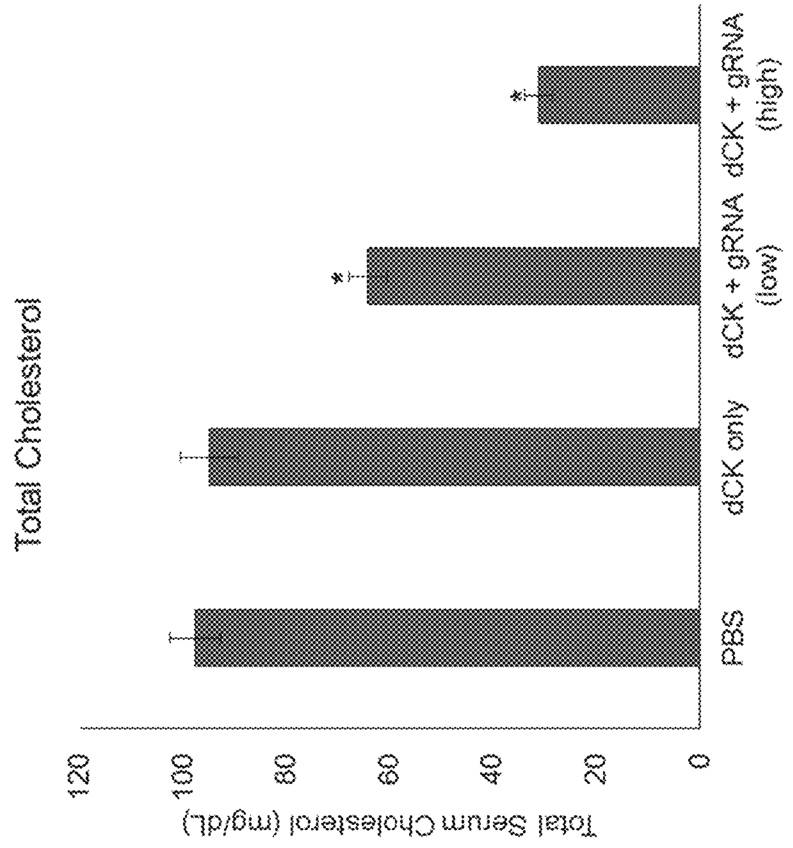

Hypercholesterolemia is a risk factor for cardiovascular disease, a leading cause of mortality in the United States. PCSK9 is a circulating protease that binds and facilitates degradation of low density lipoprotein (LDL) receptors. Individuals with naturally reduced PCSK9 demonstrate hypocholesterolemia, and silencing PCSK9 expression has been proposed as a mechanism to lower levels of harmful LDL cholesterol in the serum. RNA-guided CRISPR/Cas9-based transcriptional modulators can enable efficient and specific gene repression. An adeno-associated virus (AAV)-based gene modulation platform was developed using CRISPR/Cas9 repressors to enable targeted silencing of PCSK9 gene expression in vivo. To generate RNA-guided repressors, nuclease-inactive *S. aureus* Cas9 was fused to the KRAB domain, a motif found in mammalian transcription factors. CRISPR guide RNAs were targeted to the transcriptional start site region of the mouse PCSK9 gene. The dCas9-KRAB repressor and PCSK9 guide RNA (protospacer sequence: gagggaagggatacaggctgga (SEQ ID NO: 42); mm10 coordinates: chr4 106464536-106464557) were expressed on separate adeno-associated viral vectors and delivered intravenously to wild-type mice (FIG. 11A). Two weeks after treatment, mice expressing dCas9-KRAB and PCSK9 guide RNA had significantly reduced circulating PCSK9 and total cholesterol levels in serum, compared to sham-treated and dCas9-KRAB only-treated controls (FIGS. 11B and 11C). The magnitude of PCSK9 repression and cholesterol reduction depended on the dose of AAV administered. Overall these results demonstrate that RNA-guided CRISPR/dCas9-KRAB repressors can effectively silence target liver gene expression in mouse models and show the potential of this technology for basic research and clinical applications.

4. Regulation of PCSK9 Expression In Vivo 4.1 Materials and Methods

Plasmid Constructs and AAV Design

An inactive version of *S. aureus* Cas9 (dSaCas9) was created by introducing D10A and N580A mutations (Ran et al., Nature. 2015; 520:186-91, incorporated by reference herein in its entirety). A SaCas9 AAV expression plasmid (Addgene #61592) was received as a gift from the Zhang lab (Ran et al. Nature. 2005; 520:186-U98, incorporated by reference herein in its entirety). The nuclease-active SaCas9 was replaced with dSaCas9-KRAB. The C' terminal 3× HA epitope tag was also removed and a single N' terminal HA tag was incorporated for tracking protein expression. For the AAV-U6 gRNA plasmid, a U6-PCSK9 gRNA cassette was cloned into a pTR-eGFP backbone replacing the CMV with the gRNA.

AAV Production

ITRs were verified by SmaI digest before production. AAV-dSaCas9-KRAB and AAV-U6 PCSK9 gRNA were used to generate AAV9 in two separate batches by the Gene Transfer Vector Core at Schepens Eye Research Institute, Massachusetts Eye and Ear.

Animal Studies

Animal studies were conducted with adherence to the guidelines for the care and use of laboratory animals of the National Institutes of Health (NIH). All the experiments with animals were approved by the Institutional Animal Care and Use Committee (IACUC) at Duke University. 6-8 week old C57Bl/6 mice (Jackson Labs) were anesthetized and maintained at 37° C. The tail vein was prepared and injected with 200 μL of AAV solution ($2\times10^{11}$-$4\times10^{12}$ viral genomes/total dose) or sterile PBS using a 31 G needle. Low dose treatment was defined as $2\times10^{11}$ viral genomes per vector per mouse (vg/v/m), and moderate dose was defined as $4\times10^{11}$ vg/v/m. Mice were injected with a saline control, AAV-dSaCas9-KRAB alone, AAV-U6 PCSK9 gRNA alone, or a 1:1 mixture of AAV-dSaCas9-KRAB and AAV-U6 PCSK9 gRNA. Mice were fasted for 12-14 hours and submandibular vein blood collections were performed every two weeks, starting on day 0 four to six hours prior to tail vein injection. At 6 and 14 weeks post-injection, mice were euthanized by $CO_2$ inhalation, perfused with PBS, and tissue was collected into RNALater® (Life Technologies) for DNA and RNA, snap-frozen for protein analysis, or fixed in 4% PFA and embedded in OCT for histology.

qRT-PCR

Tissue samples were stored in RNALater (Ambion) and total RNA was isolated using the RNA Universal Plus Kit (Qiagen). cDNA synthesis was performed using the SuperScript VILO cDNA Synthesis Kit (Invitrogen). For genomic qPCR experiments, genomic DNA from tissue samples was isolated using a Blood and Tissue Kit (Qiagen). Quantitative real-time PCR (qRT-PCR) using QuantIT Perfecta Supermix was performed with the CFX96 Real-Time PCR Detection System (Bio-Rad) with the oligonucleotide primers optimized for 90-110% amplification efficiency. The results are expressed as fold-increase mRNA expression of the gene of interest normalized to Gapdh expression by the $\Delta\Delta C_t$ method.

RNA-Sequencing mRNA was purified from total RNA using oligo(dT) Dynabeads (Invitrogen). First-strand cDNA was synthesized using the SuperScript VILO cDNA Synthesis Kit (Invitrogen) and second-strand cDNA was synthesized using DNA polymerase I (New England Biolabs). cDNA was purified using Agencourt AMPure XP beads (Beckman Coulter). Purified cDNA was treated with Nextera transposase (Illumina) for 5 min at 55° C. to simultaneously fragment and insert sequencing primers into the double-stranded cDNA. Transposase activity was halted using QG buffer (Qiagen) and fragmented cDNA was purified on AMPure XP beads. Indexed sequencing libraries were PCR-amplified and sequenced for 50-bp paired-end reads on an Illumina HiSeq 2000 instrument at the Duke Genome Sequencing Shared Resource. Reads aligned to the delivered AAV vector were removed from analysis. Filtered reads were then aligned to mouse RefSeq transcripts using Bowtie 2 (Langmead and Salzberg, Nat Methods. 2012; 9:357-9, incorporated by reference herein in its entirety). Statistical analysis, including multiple hypothesis testing, on three independent biological replicates was performed using DESeq (Anders and Huber, Genome Biol. 2010; 11:R106, incorporated by reference herein in its entirety).

Western Blot

Minced tissue was lysed in RIPA buffer (Sigma), and the BCA assay (Pierce) was performed to quantify total protein. Lysates were mixed with LDS sample buffer (Invitrogen) and boiled for 5 min; equal amounts of total protein were run in NuPAGE Novex 4-12% Bis-Tris polyacrylamide gels (Life Technologies) and transferred to nitrocellulose membranes. Nonspecific antibody binding was blocked with 5% nonfat milk in TBS-T (50 mM Tris, 150 mM NaCl and 0.1% Tween-20) for 30 min. The membranes were then incubated with primary antibody in 5% milk in TBS-T: rabbit anti-LDLR diluted 1:1000 overnight at 4° C. or rabbit anti-GAPDH diluted 1:5000 for 60 min at room temperature. Membranes labeled with primary antibodies were incubated with anti-rabbit HRP-conjugated antibody (Sigma-Aldrich, A6154) diluted 1:5000 for 60 min and washed with TBS-T for 60 min. Membranes were visualized using the Immun-Star WesternC Chemiluminescence Kit (Bio-Rad) and images were captured using a ChemiDoc XRS+ system and processed using ImageLab software (Bio-Rad).

Histology

A cross section of the median liver lobe was fixed overnight in 4% PFA and embedded in OCT using liquid nitrogen-cooled isopentane. 10 μm sections were cut onto pre-treated histological slides. Hematoxylin and eosin was used to reveal general liver histopathology.

Serum Analysis

After harvest, serum was stored in one-time use aliquots at −80 C. Total cholesterol and LDL cholesterol levels were measured from serum via a colorimetric assay according to manufacturer's instructions (ThermoScientific Total Cholesterol Reagents #TR13421 and WakoChemical LDL Cholesterol #993-00404). PCSK9 serum protein levels were quantified by ELISA with a standard curve according to the manufacturer's instructions (R&D Systems #MPC900).

4.2 Results

Three independent studies were conducted, in which dSaCas9-KRAB repressor and PCSK9 guide RNA were delivered by AAV vectors to mice.

Figure 12A:
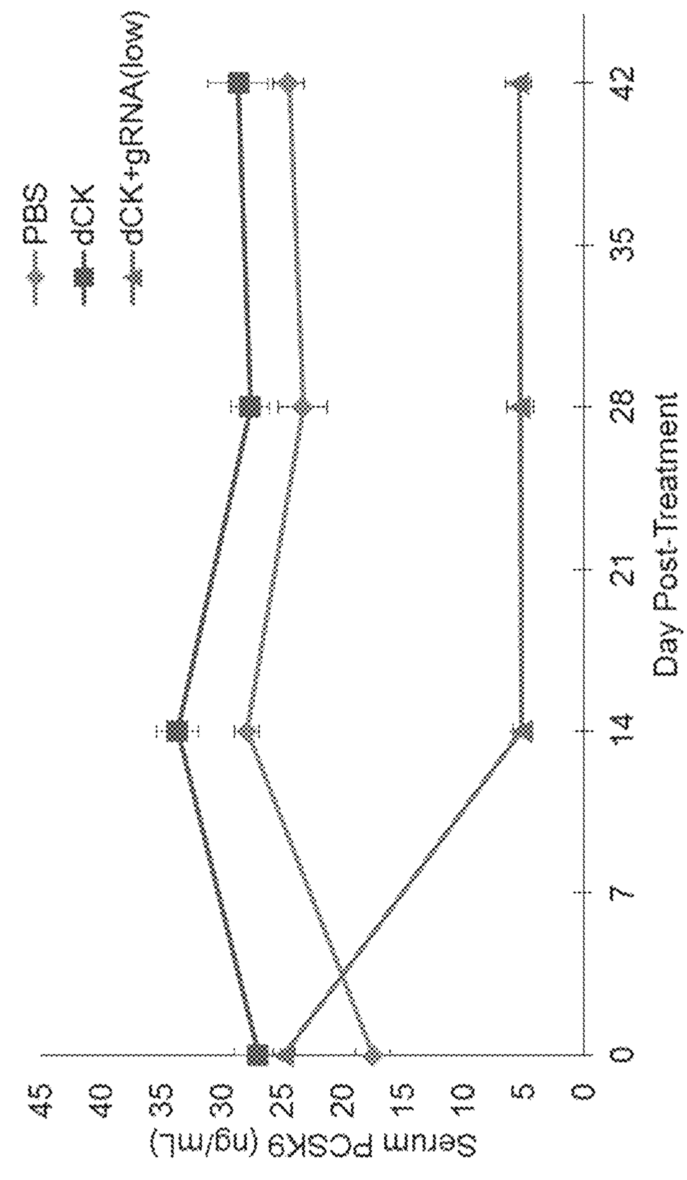
FIGS. 12A-12E are graphs showing results from a study in which mice were intravenously administered with PBS, or AAV vectors encoding dSaCas9-KRAB (dCK) alone, or low-dose dSaCas9-KRAB (dCK) and PCSK9 guide RNA (gRNA).
Figure 12B:
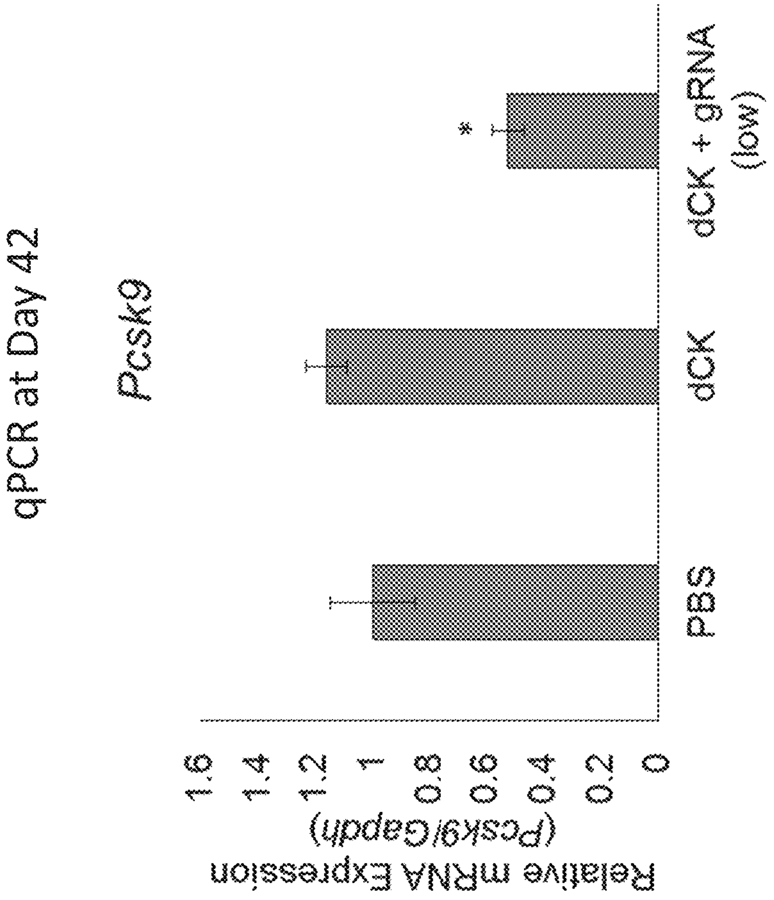
Figure 12C:
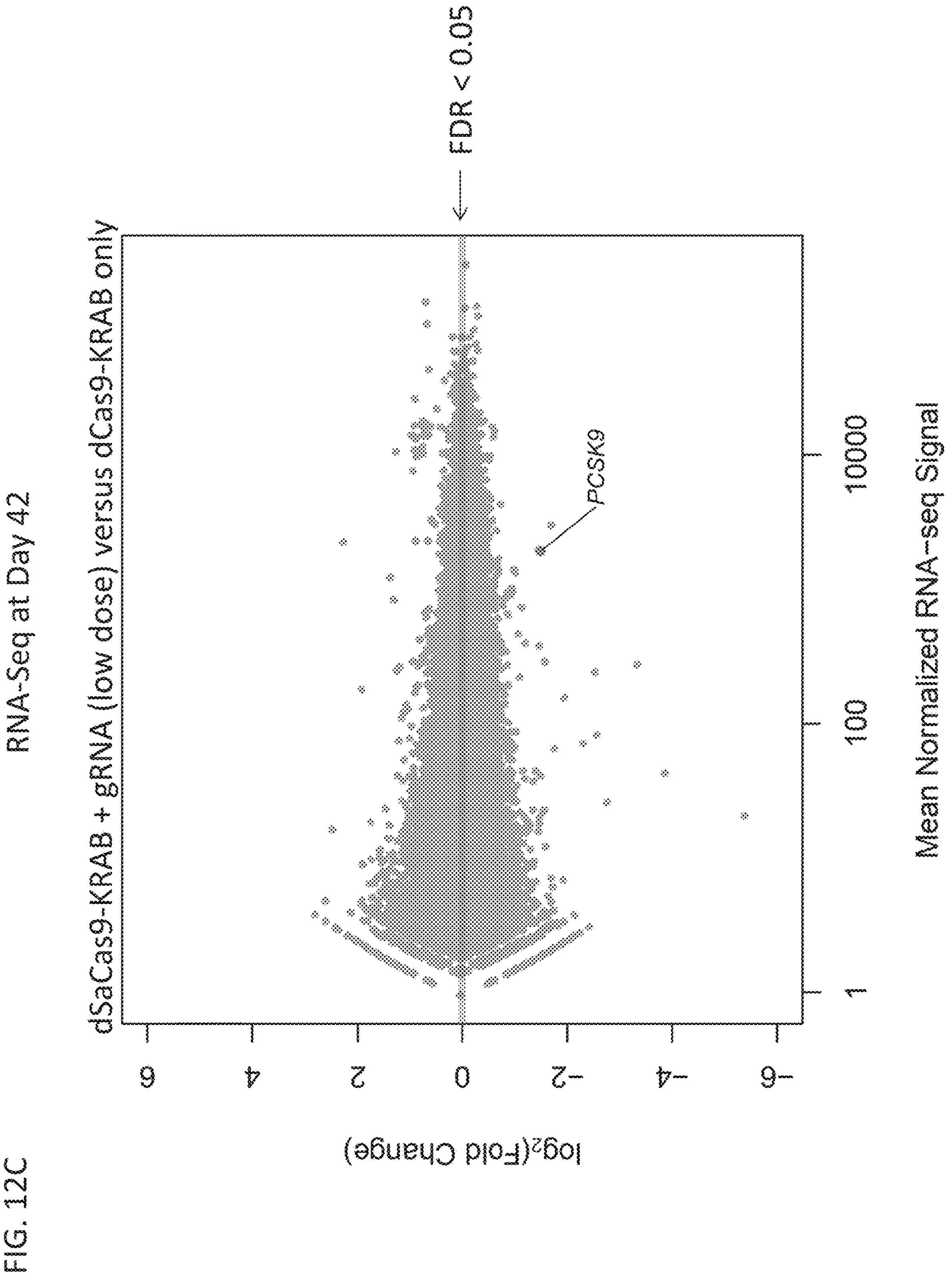
Figure 12E:
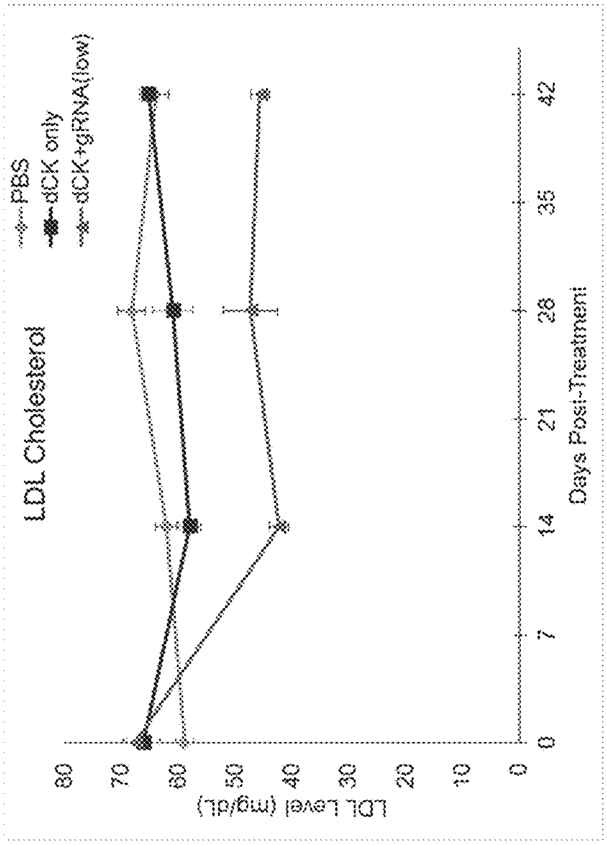
Figure 12D:
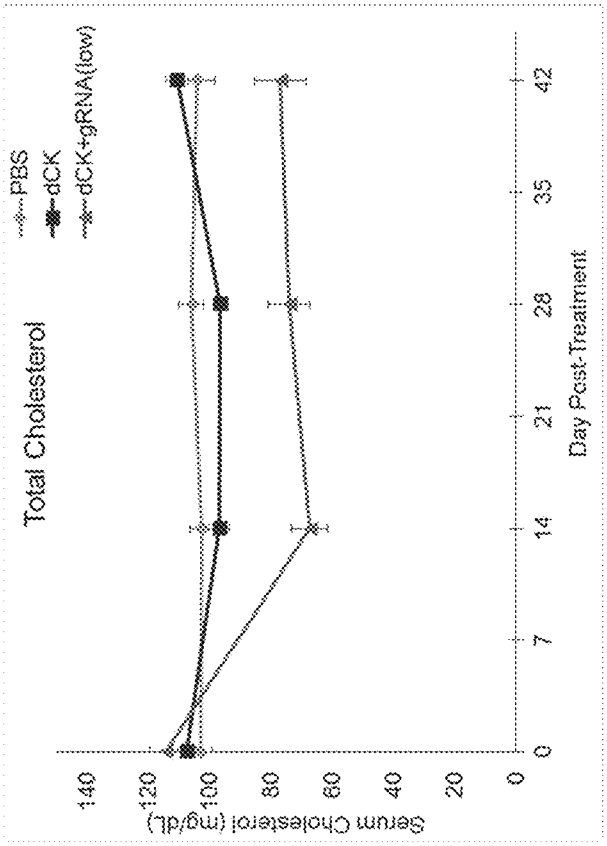

In the first study, mice were administered with PBS, AAV-dSaCas9-KRAB alone ($1\times10^{12}$ total genomes/vector/mouse), or a low-dose 1:1 mixture of AAV-dSaCas9-KRAB and AAV-U6 PCSK9 gRNA ($4\times10^{11}$ viral genomes/vector/mouse). Four mice were tested in each treatment group and followed for 6 weeks. As shown in FIG. 12A, low dose treatment with dSaCas9-KRAB and PCSK9 gRNA effectively lowered the serum levels of PCSK9 as measured by ELISA for at least 42 days post-treatment. Treatment with dSaCas9-KRAB alone did not reduce the serum levels of PCSK9 (FIG. 12A). Consistent with the reduction of PCSK9 protein levels, a reduction of PCSK9 mRNA levels in the liver was also observed in a qRT-PCR analysis (FIG. 12B) as well as a RNA-seq analysis (FIG. 12C). Total cholesterol and LDL cholesterol levels in the serum were measured using a colorimetric assay. As shown in FIGS. 12D and 12E, both the total and LDL cholesterol levels were reduced over the course of 42 days by the low-dose treatment with dSaCas9-KRAB and PCSK9 gRNA, compared to the PBS treatment or the treatment with dSaCas9-KRAB alone.

Figure 13A:
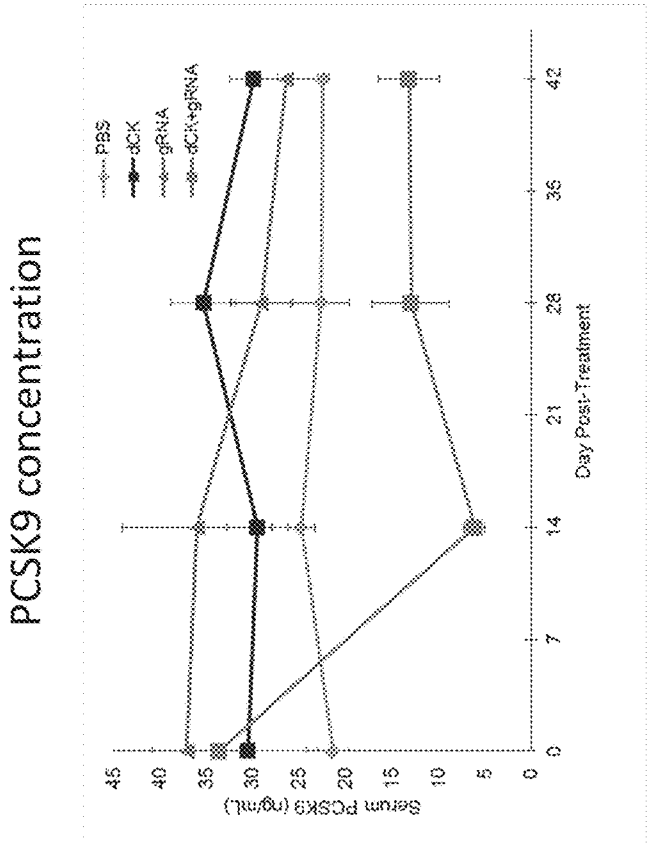
FIGS. 13A-13F are graphs showing results from a study in which mice were intravenously administered with PBS, or AAV vectors encoding dSaCas9-KRAB (dCK) alone, PCSK9 guide RNA (gRNA) alone, or moderate-dose dSaCas9-KRAB (dCK) and PCSK9 guide RNA (gRNA).
Figure 13B:
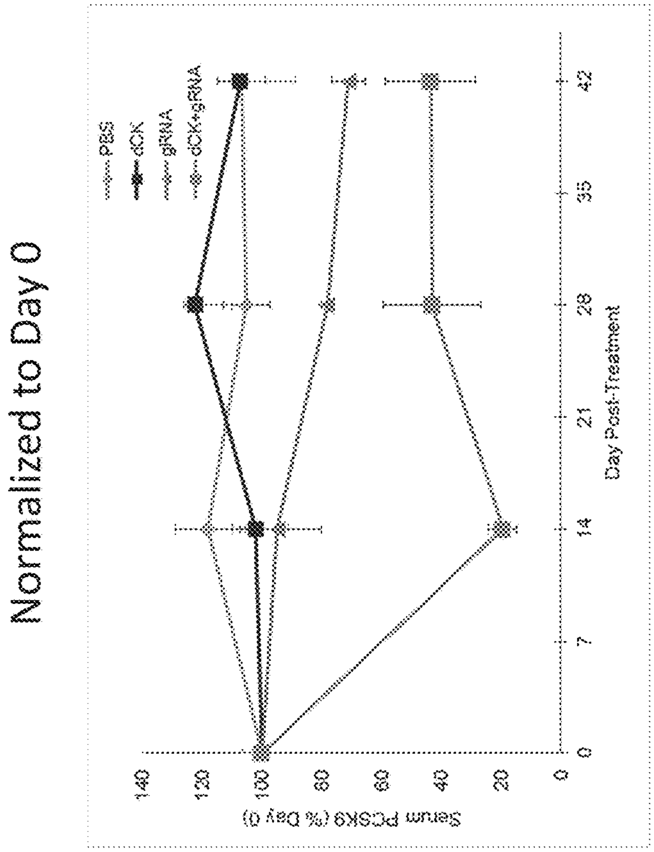
Figure 13C:
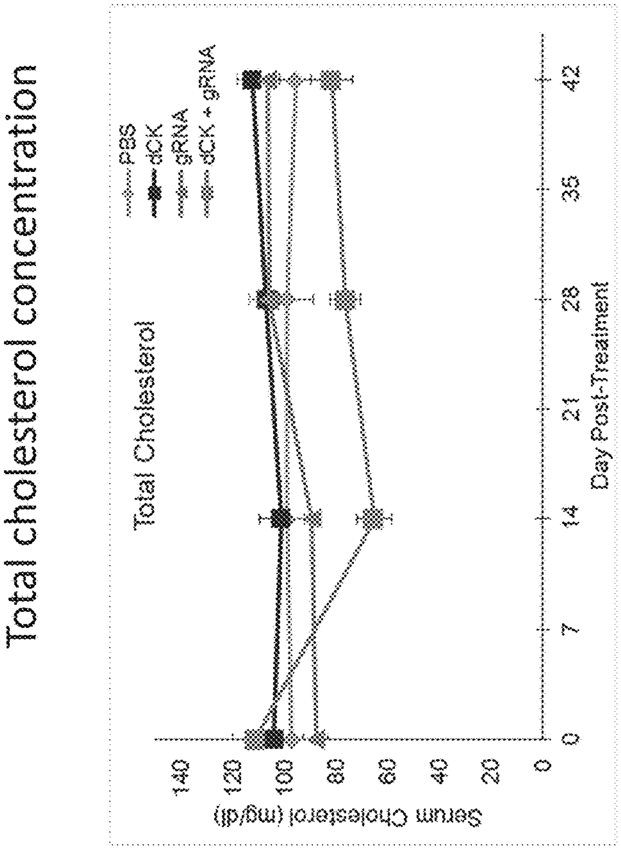
Figure 13D:
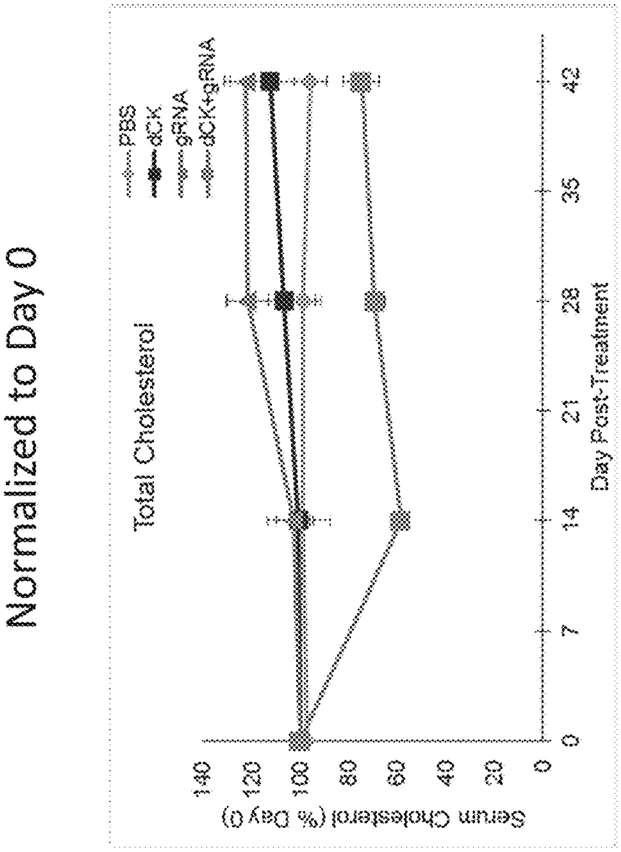
Figure 13F:
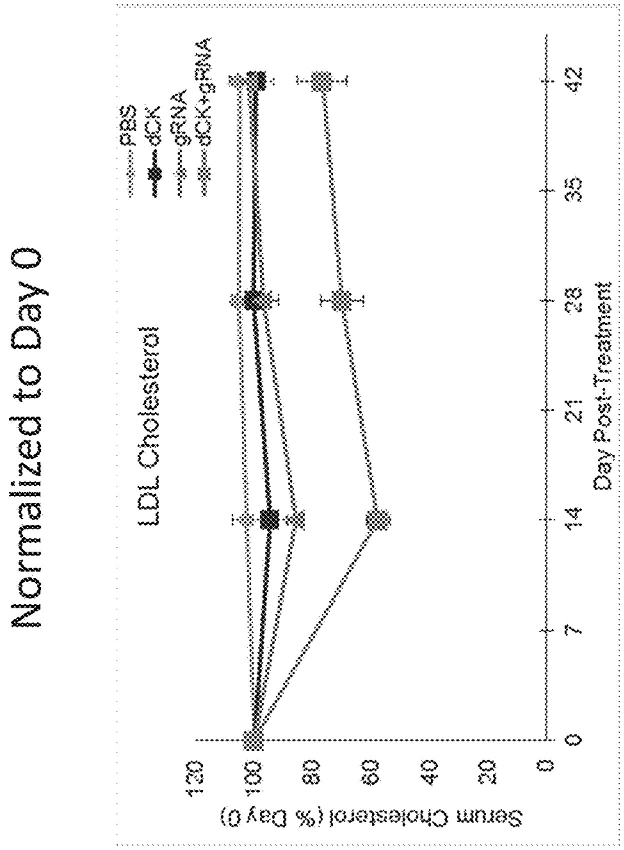
Figure 13E:
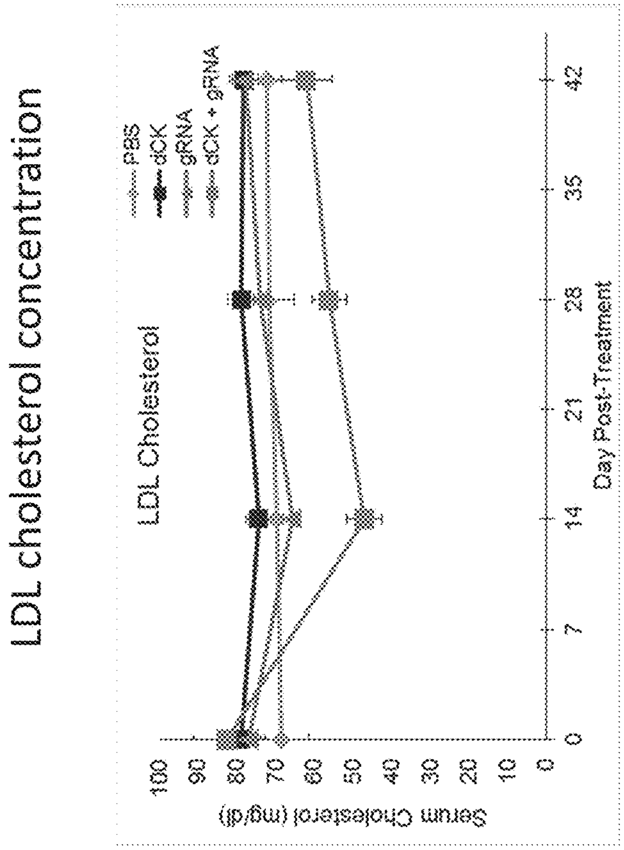

In the second study, mice were administered with PBS, AAV-dSaCas9-KRAB alone ($4\times10^{11}$ total genomes/vector/mouse), AAV-U6 PCSK9 gRNA alone ($4\times10^{11}$ total genomes/vector/mouse), or a moderate-dose 1:1 mixture of AAV-dSaCas9-KRAB and AAV-U6 PCSK9 gRNA ($8\times10^{11}$ viral genomes/vector/mouse). Four mice were tested in each treatment group and followed for 6 weeks. Consistent with results from the low-dose study described above, treatment with a moderate dose of dSaCas9-KRAB and PCSK9 gRNA also reduced PCSK9 protein levels (FIGS. 13A and 13B), as well as total cholesterol levels (FIGS. 13C and 13D) and LDL cholesterol levels (FIGS. 13E and 13F) in the serum.

Figure 14A:
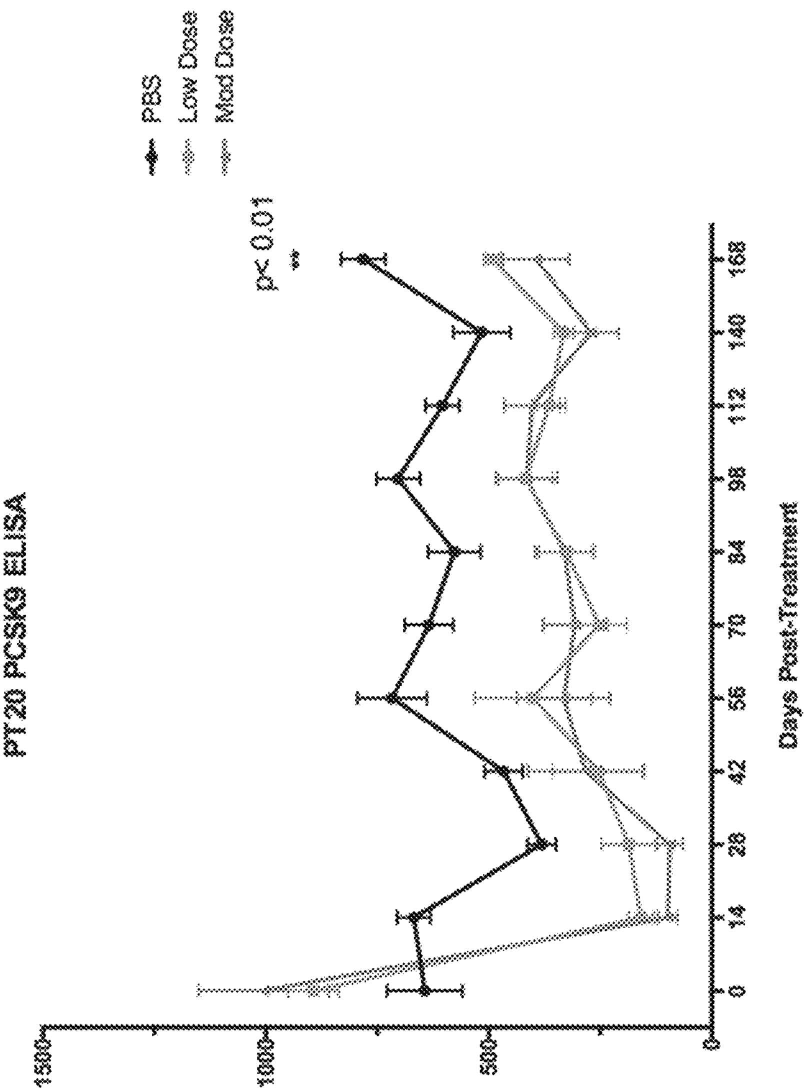
FIGS. 14A-14C are graphs showing results from a study in which mice were intravenously administered with PBS, moderate-dose, or high-dose of AAV vectors encoding dSaCas9-KRAB and PCSK9 gRNA.
Figure 14C:
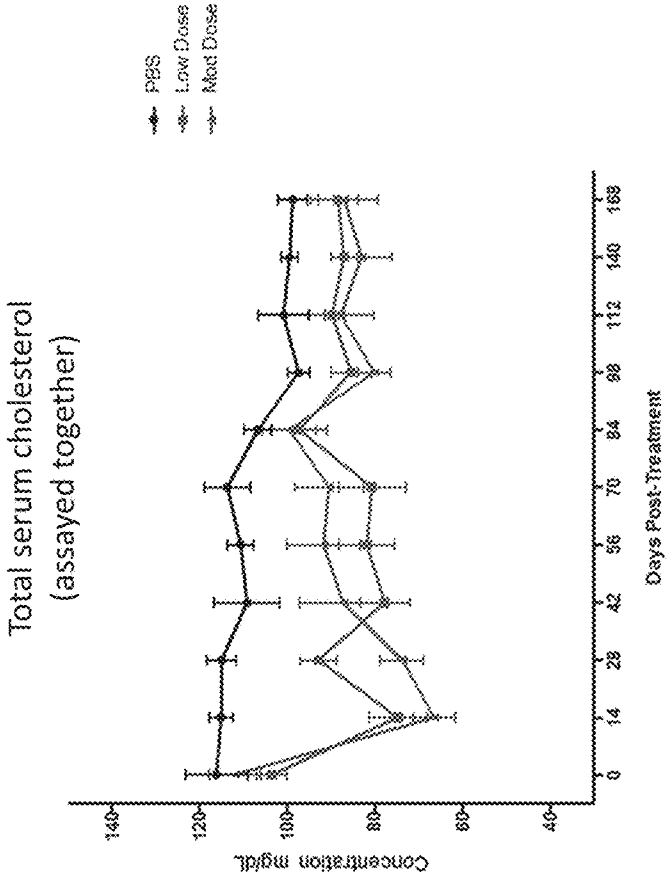
Figure 14B:
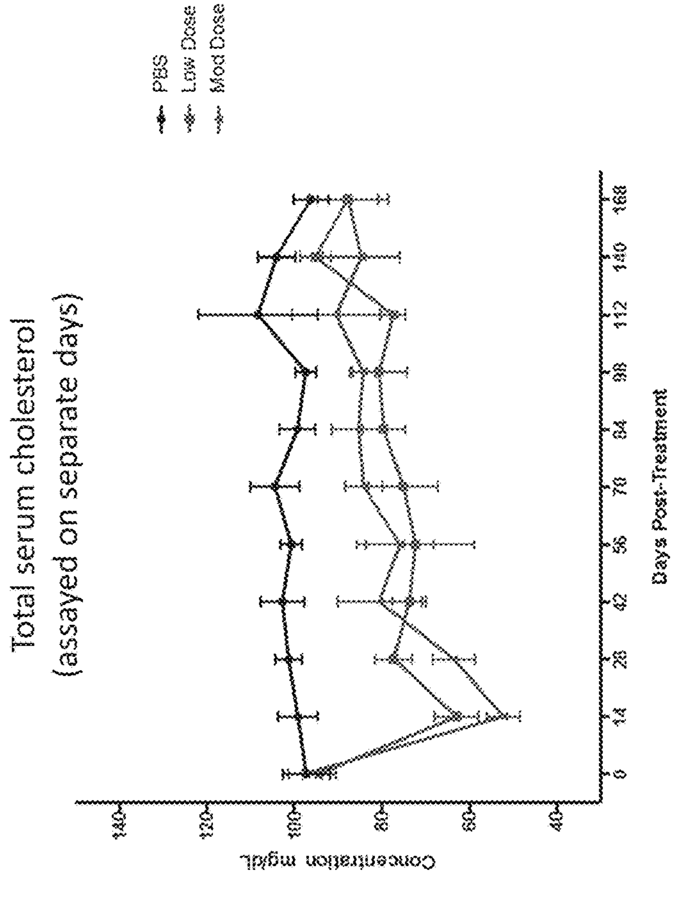
Figure 14D:
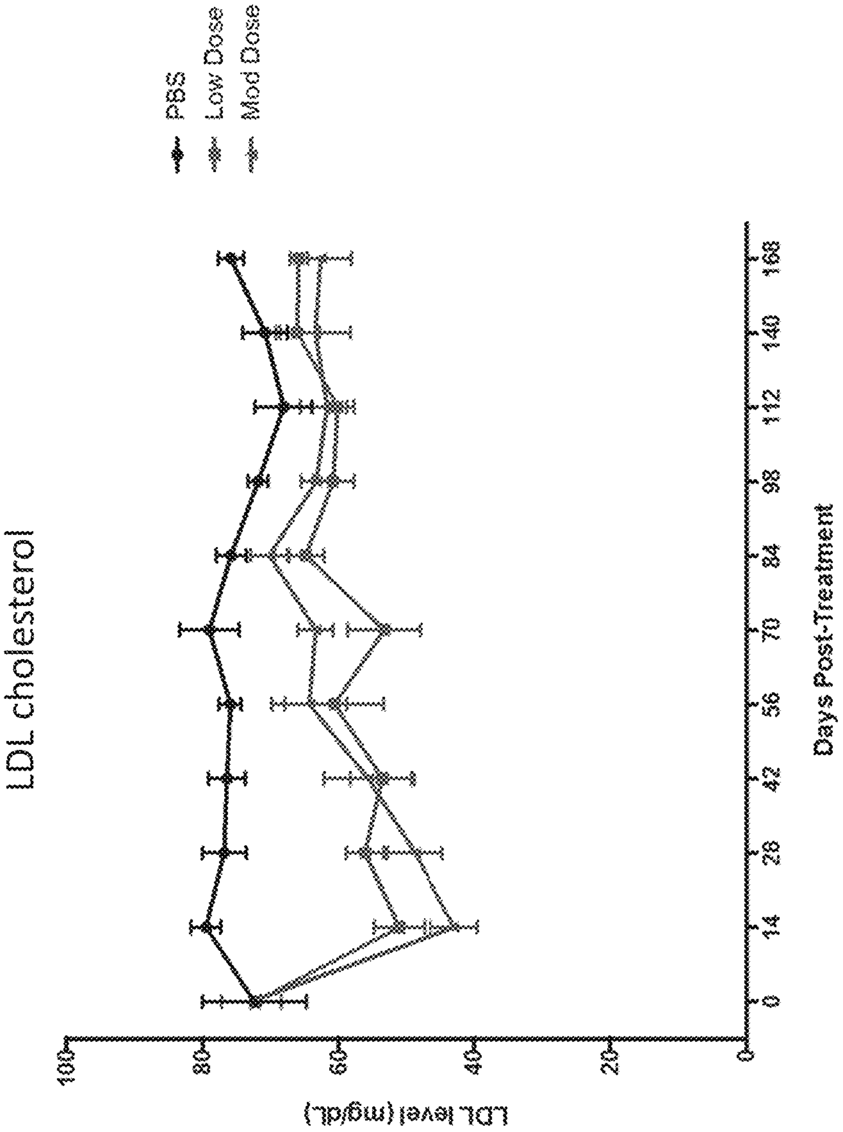
FIG. 14D is a graph showing LDL cholesterol levels in the serum.

In the third study, mice were administered with PBS, a low-dose 1:1 mixture of AAV-dSaCas9-KRAB and AAV-U6 PCSK9 gRNA ($4\times10^{11}$ viral genomes/vector/mouse), or a moderate-dose 1:1 mixture of AAV-dSaCas9-KRAB and AAV-U6 PCSK9 gRNA ($8\times10^{11}$ viral genomes/vector/mouse). Four mice were tested in each group and followed for 24 weeks. As shown in FIG. 14A, both the low-dose and moderate-dose treatments with dSaCas9-KRAB and PCSK9 gRNA significantly lowered the serum PCSK9 levels for at least 168 days post-treatment. Both treatments also reduced total (FIGS. 14B and 14C) and LDL (FIG. 14D) cholesterol levels in the serum.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control. One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method of modulating gene expression, in vivo, in a subject, the method comprising administering to the subject:

(a) a nucleic acid that encodes a fusion molecule comprising a dead Cas9 (dCas9) molecule fused to a modulator of gene expression, wherein the dCas9 molecule comprises an amino acid sequence having at least 90% or greater identity to SEQ ID NO: 24 in which is present the amino acid mutations D10A and H840A, and wherein the modulator of gene expression comprises a Krüppel associated box (KRAB) molecule and a DNA methyltransferase, and wherein the DNA methyltransferase is DNMT3a-DNMT3L; and (b) a nucleic acid that encodes a gRNA that targets the fusion molecule to the promoter region of a PCSK9 gene, in an amount sufficient to modulate expression of the PCSK9 gene.

2. The method of claim 1, wherein the modulator of gene expression is fused to the C-terminus, N-terminus, or both, of the dCas9 molecule.

3. The method of claim 1, wherein the fusion molecule further comprises a nuclear localization sequence (NLS).

4. The method of claim 3, wherein the NLS comprises an amino acid sequence having at least 98% or greater identity to SEQ ID NO: 37 or 38.

5. The method of claim 3, wherein the NLS comprises the amino acid sequence of SEQ ID NO: 38.

6. The method of claim 1, wherein the dCas9 molecule comprises an amino acid sequence having at least 95% or greater identity to SEQ ID NO: 24 in which is present the amino acid mutations D10A and H840A.

7. The method of claim 1, wherein the dCas9 molecule comprises an amino acid sequence having at least 98% or greater identity to SEQ ID NO: 24 in which is present the amino acid mutations D10A and H840A.

8. The method of claim 1, wherein the nucleic acid of (a) and (b) are administered using a viral vector.

9. The method of claim 1, wherein the nucleic acid of (a) and (b) are administered using a non-viral delivery system.

10. The method of claim 6, wherein the fusion molecule further comprises a nuclear localization sequence (NLS).

11. The method of claim 6, wherein the modulator of gene expression is fused to the C-terminus, N-terminus, or both, of the dCas9 molecule.

12. The method of claim 10, wherein the NLS comprises an amino acid sequence having at least 98% or greater identity to SEQ ID NO: 37 or 38.

13. The method of claim 10, wherein the NLS comprises the amino acid sequence of SEQ ID NO: 38.

14. The method of claim 8, wherein the dCas9 molecule comprises an amino acid sequence having at least 95% or greater identity to SEQ ID NO: 24 in which is present the amino acid mutations D10A and H840A.

15. The method of claim 8, wherein the dCas9 molecule comprises an amino acid sequence having at least 98% or greater identity to SEQ ID NO: 24 in which is present the amino acid mutations D10A and H840A.

16. The method of claim 6, wherein the nucleic acid of (a) and (b) are administered using a viral vector.

17. The method of claim 6, wherein the nucleic acid of (a) and (b) are administered using a non-viral delivery system.

18. The method of claim 9, wherein the dCas9 molecule comprises an amino acid sequence having at least 95% or greater identity to SEQ ID NO: 24 in which is present the amino acid mutations D10A and H840A.

19. The method of claim 9, wherein the dCas9 molecule comprises an amino acid sequence having at least 98% or greater identity to SEQ ID NO: 24 in which is present the amino acid mutations D10A and H840A.

* * * * *

SEQUENCE LISTING

```
Sequence total quantity: 42
SEQ ID NO: 1           moltype =   length =
SEQUENCE: 1
000

SEQ ID NO: 2           moltype = DNA  length = 14048
FEATURE                Location/Qualifiers
misc_feature           1..14048
                       note = AAV Vector Construct
source                 1..14048
```

-continued

```
                         mol_type = other DNA
                         organism = synthetic construct
SEQUENCE: 2
gtcgacggat cgggagatct cccgatcccc tatggtgcac tctcagtaca atctgctctg  60
atgccgcata gttaagccag tatctgctcc ctgcttgtgt gttggaggtc gctgagtagt  120
gcgcgagcaa aatttaagct acaacaaggc aaggcttgac cgacaattgc atgaagaatc  180
tgcttagggt taggcgtttt gcgctgcttc gcgatgtacg ggccagatat acgcgttgac  240
attgattatt gactagttat taatagtaat caattacggg gtcattagtt catagcccat  300
atatggagtt ccgcgttaca taacttacgg taaatggccc gcctggctga ccgcccaacg  360
acccccgccc attgacgtca ataatgacgt atgttcccat agtaacgcca atagggactt  420
tccattgacg tcaatgggtg gagtatttac ggtaaactgc ccacttggca gtacatcaag  480
tgtatcatat gccaagtacg ccccctattg acgtcaatga cggtaaatgg cccgcctggc  540
attatgccca gtacatgacc ttatgggact ttcctacttg gcagtacatc tacgtattag  600
tcatcgctat taccatggtg atgcggtttt ggcagtacat caatgggcgt ggatagcggt  660
ttgactcacg gggatttcca agtctccacc ccattgacgt caatgggagt ttgttttggc  720
accaaaatca acgggacttt ccaaaatgtc gtaacaactc cgccccattg acgcaaatgg  780
gcggtaggcg tgtacggtgg gaggtctata taagcagcgc gttttgcctg tactgggtct  840
ctctggttag accagatctg agcctgggag ctctctggct aactagggaa cccactgctt  900
aagcctcaat aaagcttgcc ttgagtgctt caagtagtgt gtgcccgtct gttgtgtgac  960
tctggtaact agagatccct cagacccttt tagtcagtgt ggaaaatctc tagcagtggc  1020
gcccgaacag ggacttgaaa gcgaaaggga aaccagagga gctctctcga cgcaggactc  1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga agaacttaga tcattatata atacagtagc aaccctctat tgtgtgcatc  1440
aaaggataga gataaaagac accaaggaag ctttagacaa gatagaggaa gagcaaaaca  1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gagaagagtg gtgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtggaaaga tacctaaagg atcaacagct cctggggatt  1920
tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
acaaattggc tgtggtatat aaaattattc ataatgatag taggaggctt ggtaggttta  2220
agaatagttt ttgctgtact ttctatagtg aatagagtta ggcagggata ttcaccatta  2280
tcgtttcaga cccacctccc aaccccgagg ggacccgaca ggcccgaagg aatagaagaa  2340
gaaggtggag agagagacag agacagatcc attcgattag tgaacggatc ggcactgcgt  2400
gcgccaattc tgcagacaaa tggcagtatt catccacaat tttaaaagaa aaggggggat  2460
tggggggtac agtgcagggg aaagaatagt agacataata gcaacagaca tacaaactaa  2520
agaattacaa aaacaaatta caaaaattca aaattttcgg gtttattaca gggacagcag  2580
agatccagtt tggttaatta aataacttcg tatagcatac attatacgaa gttatgataa  2640
gagacggtgg tggcgccgct acagggcgcg tcccattcgc cattcaggct gcgcaactgt  2700
tgggaagggc gatcggtgcg ggcctcttcg ctattacgcc agctggcgaa aggggggatgt  2760
gctgcaaggc gattaagttg ggtaacgcca gggttttccc agtcacgacg ttgtaaaacg  2820
acggccagtg agcgcgcgta atacgactca ctatagggcg aattgggtac cgggcccccc  2880
ctcgaggtcc tccagctttt gttcccttta gtgagggtta attgcgcgct tggcgtaatc  2940
atggtcatag ctgtttcctg tgtgaaattg ttatccgctc acaattccac acaacatacg  3000
agccggaagc ataaagtgta aagcctgggg tgcctaatga gtgagctaac tcacattaat  3060
tgcgttgcgc tcactgcccg ctttccactg catgacgtct ccacaattaa ttaagggtgc  3120
agcggcctcc gcgccgggtt ttggcgcctc ccgcgggcgc ccccctcctc acggcgagcg  3180
ctgccacgtc agacgaaggg cgcaggagcg ttcctgatcc ttccgcccgg acgctcagga  3240
cagcggcccg ctgctcataa gactcggcct tagaacccca gtatcagcag aaggacattt  3300
taggacggga cttgggtgac tctagggcac tggttttctt tccagagagc ggaacaggcg  3360
aggaaaagta gtcccttctc ggcgattctg cggagggatc tccgtggggc ggtgaacgcc  3420
gatgattata taaggacgcg ccgggtgtgg cacagctagt tccgtcgcag ccgggatttg  3480
ggtcgcggtt cttgtttgtg gatcgctgtg atcgtcactt ggtgagttgc gggctgctgg  3540
gctggccggg gctttcgtgg ccgccgggcc gctcggtggg acggaagcgt gtggagagac  3600
cgccaagggc tgtagtctgg gtccgcgagc aaggttgccc tgaactgggg gttgggggga  3660
gcgcacaaaa tggcggctgt tcccgagtct tgaatggaag acgcttgtaa ggcgggctgt  3720
gaggtcgttg aaacaaggtg gggggcatgg tgggcggcaa gaacccaagg tcttgaggcc  3780
ttcgctaatg cgggaaagct cttattcggg tgagatgggc tggggcacca tctggggacc  3840
ctgacgtgaa gtttgtcact gactggagaa ctcgggtttg tcgtctggtt gcgggggcgg  3900
cagttatgcg gtgccgttgg gcagtgcacc cgtacctttg ggagcgcgcg cctcgtcgtg  3960
tcgtgacgtc acccgttctg ttggcttata atgcagggtg gggccacctg ccggtaggtg  4020
tgcggtaggc ttttctccgt cgcaggacgc agggttcggg cctagggtag gctctcctga  4080
atcgacaggc gccggacctc tggtgagggg agggataagt gaggcgtcag tttctttggt  4140
cggttttatg tacctatctt cttaagtagc tgaagctccg gttttgaact atgcgctcgg  4200
ggttggcgag tgtgttttgt gaagtttttt aggcaccttt tgaaatgtaa tcatttgggt  4260
caatatgtaa ttttcagtgt tagactagta aattgtccgc taaattctgg ccgtttttgg  4320
cttttttgtt agacgaagct tgggctgcag gtcgactcta gagccaccat gtacccatac  4380
gatgttccag attacgctat ggccccaaag aagaagcgga aggtcggtat ccacggagtc  4440
ccagcagcca agcggaacta catcctgggc ctggccatcg gcatcaccag cgtgggctac  4500
ggcatcatcg actacgagac acgggacgtg atcgatgccg gcgtgcggct gttcaaagag  4560
```

-continued

```
gccaacgtgg aaaacaacga gggcaggcgg agcaagagag gcgccagaag gctgaagcgg  4620
cggaggcggc atagaatcca gagagtgaag aagctgctgt tcgactacaa cctgctgacc  4680
gaccacagcg agctgagcgg catcaacccc tacgaggcca gagtgaaggg cctgagccag  4740
aagctgagcg aggaagagtt ctctgccgcc ctgctgcacc tggccaagag aagaggcgtg  4800
cacaacgtga acgaggtgga agaggacacc ggcaacgagc tgtccaccaa agagcagatc  4860
agccggaaca gcaaggccct ggaagagaaa tacgtggccg aactgcagct ggaacggctg  4920
aagaaagacg gcgaagtgcg gggcagcatc aacagattca agaccagcga ctacgtgaaa  4980
gaagccaaac agctgctgaa ggtgcagaag gcctaccacc agctggacca gagcttcatc  5040
gacacctaca tcgacctgct ggaaacccgg cggacctact atgagggacc tggcgagggc  5100
agccccttcg gctggaagga catcaaagaa tggtacgaga tgctgatggg ccactgcacc  5160
tacttccccg aggaactgcg gagcgtgaag tacgcctaca acgccgacct gtacaacgcc  5220
ctgaacgacc tgaacaatct cgtgatcacc agggacgaga acgagaagct ggaatattac  5280
gagaagttcc agatcatcga gaacgtgttc aagcagaaga agaagcccac cctgaagcag  5340
atcgccaaag aaatcctcgt gaacgaagag gatattaagg gctacagagt gaccagcacc  5400
ggcaagcccg agttcaccaa cctgaaggtg taccacgaca tcaaggacat taccgcccgg  5460
aaagagatta ttgagaacgc cgagctgctg gatcagattg ccaagatcct gaccatctac  5520
cagagcagcg aggacatcca ggaagaactg accaatctga actccgagct gacccaggaa  5580
gagatcgagc agatctctaa tctgaagggc tataccggca cccacaacct gagcctgaag  5640
gccatcaacc tgatcctgga cgagctgtgg cacaccaacg acaaccagat cgctatcttc  5700
aaccggctga agctggtgcc caagaaggtg gacctgtccc agcagaaaga gatccccacc  5760
accctggtgg acgacttcat cctgagcccc gtcgtgaaga gaagcttcat ccagagcatc  5820
aaagtgatca acgccatcat caagaagtac ggcctgccca acgacatcat tatcgagctg  5880
gcccgcgaga agaactccaa ggacgcccag aaaatgatca acgagatgca gaagcggaac  5940
cggcagacca acgagcggat cgaggaaatc atccggacca ccggcaaaga gaacgccaag  6000
tacctgatcg agaagatcaa gctgcacgac atgcaggaag gcaagtgcct gtacagcctg  6060
gaagccatcc ctctggaaga tctgctgaac aaccccttca actatgaggt ggaccacatc  6120
atccccagaa gcgtgtcctt cgacaacagc ttcaacaaca aggtgctcgt gaagcaggaa  6180
gaagccagca agaagggcaa ccggaccccc ttccagtacc tgagcagcag cgacagcaag  6240
atcagctacg aaaccttcaa gaagcacatc ctgaatctgg ccaagggcaa gggcagaatc  6300
agcaagacca agaaagagta tctgctggaa gaacgggaca tcaacaggtt ctccgtgcag  6360
aaagacttca tcaaccggaa cctggtggat accagatacg ccaccagagg cctgatgaac  6420
ctgctgcgga gctacttcag agtgaacaac ctggacgtga aagtgaagtc catcaatggc  6480
ggcttcacca gctttctgcg gcggaagtgg aagtttaaga aagagcggaa caaggggtac  6540
aagcaccacg ccgaggacgc cctgatcatt gccaacgccg atttcatctt caaagagtgg  6600
aagaaactgg acaaggccaa aaaagtgatg gaaaaccaga tgttcgagga aaagcaggcc  6660
gagagcatgc ccgagatcga aaccgagcag gagtacaaag agatcttcat cacccccac  6720
cagatcaagc acattaagga cttcaaggac tacaagtaca gccaccgggt ggacaagaag  6780
cctaatagag agctgattaa cgacaccctg tactccaccc ggaaggacga caagggcaac  6840
accctgatcg tgaacaatct gaacggcctg tacgacaagg acaatgacaa gctgaaaaag  6900
ctgatcaaca agagccccga aaagctgctg atgtaccacc acgaccccca gacctaccag  6960
aaactgaagc tgattatgga acagtacggc gacgagaaga atcccctgta caagtactac  7020
gaggaaaccg ggaactacct gaccaagtac tccaaaaagg acaacggccc cgtgatcaag  7080
aagattaagt attacggcaa caaactgaac gcccatctgg acatcaccga cgactacccc  7140
aacagcagaa acaaggtcgt gaagctgtcc ctgaagccct acagattcga cgtgtacctg  7200
gacaatggcg tgtacaagtt cgtgaccgtg aagaatctgg atgtgatcaa aaaagaaaac  7260
tactacgaag tgaatagcaa gtgctatgag gaagctaaga agctgaagaa gatcagcaac  7320
caggccgagt ttatcgcctc cttctacaac aacgatctga tcaagatcaa cggcgagctg  7380
tatagagtga tcggcgtgaa caacgacctg ctgaaccgga tcgaagtgaa catgatcgac  7440
atcacctacc gcgagtacct ggaaaacatg aacgacaaga ggcccccccag gatcattaag  7500
acaatcgcct ccaagaccca gagcattaag aagtacagca cagacattct gggcaacctg  7560
tatgaagtga aatctaagaa gcaccctcag atcatcaaaa agggcaaaag gccggcggcc  7620
acgaaaaagg ccggccaggc aaaaaagaaa aagggatccg atgctaagtc actgactgcc  7680
tggtcccgga cactggtgac cttcaaggat gtgtttgtgg acttcaccag ggaggagtgg  7740
aagctgctgg acactgctca gcagatcctg tacagaaatg tgatgctgga gaactataag  7800
aacctggttt ccttgggtta tcagcttact aagccagatg tgatcctccg gttggagaag  7860
ggagaagagc cctggctggt ggagagagaa attcaccaag agacccatcc tgattcagag  7920
actgcatttg aaatcaaatc atcagttccg aaaaagaaac gcaaagttgc tagcgagggc  7980
agaggaagtc ttctaacatg cggtgacgtg gaggagaatc ccggccctat gaccgagtac  8040
aagcccacgg tgcgcctcgc cacccgcgac gacgtcccca gggccgtacg caccctcgcc  8100
gccgcgttcg ccgactaccc cgccacgcgc cacaccgtcg atccggaccg ccacatcgag  8160
cgggtcaccg agctgcaaga actcttcctc acgcgcgtcg ggctcgacat cggcaaggtg  8220
tgggtcgcgg acgacggcgc cgcggtggcg gtctggacca cgccggagag cgtcgaagcg  8280
ggggcggtgt tcgccgagat cggcccgcgc atggccgagt tgagcggttc ccggctggcc  8340
gcgcagcaac agatggaagg cctcctggcg ccgcaccggc ccaaggagcc cgcgtggttc  8400
ctggccaccg tcggcgtgtc gcccgaccac cagggcaagg gtctgggcag cgccgtcgtg  8460
ctccccggag tggaggcggc cgagcgcgcc ggggtgcccg ccttcctgga gacctccgcg  8520
ccccgcaacc tccccttcta cgagcggctc ggcttcaccg tcaccgccga cgtcgaggtg  8580
cccgaaggac cgcgcacctg gtgcatgacc cgcaagcccg gtgcctgacc agcacactgg  8640
cggccgttac tagcttctgc agcacgaccg gttgataata gataacttcg tatagcatac  8700
attatacgaa gttatgaatt cgatatcaag cttatcgata atcaacctct ggattacaaa  8760
atttgtgaaa gattgactgg tattcttaac tatgttgctc cttttacgct atgtggatac  8820
gctgctttaa tgcctttgta tcatgctatt gcttcccgta tggctttcat tttctcctcc  8880
ttgtataaat cctggttgct gtctctttat gaggagttgt ggcccgttgt caggcaacgt  8940
ggcgtggtgt gcactgtgtt tgctgacgca acccccactg gttggggcat tgccaccacc  9000
tgtcagctcc tttccgggac tttcgctttc cccctcccta ttgccacggc ggaactcatc  9060
gccgcctgcc ttgcccgctg ctggacaggg gctcggctgt tgggcactga caattccgtg  9120
gtgttgtcgg ggaaatcatc gtcctttcct tggctgctcg cctgtgttgc cacctggatt  9180
ctgcgcggga cgtccttctg ctacgtccct tcggccctca atccagcgga ccttccttcc  9240
cgcggcctgc tgccggctct gcggcctctt ccgcgtcttc gccttcgccc tcagacgagt  9300
```

-continued

```
cggatctccc tttgggccgc ctccccgcat cgataccgtc gacctcgaga cctagaaaaa  9360
catggagcaa tcacaagtag caatacagca gctaccaatg ctgattgtgc ctggctagaa  9420
gcacaagagg aggaggaggt gggttttcca gtcacacctc aggtaccttt aagaccaatg  9480
acttacaagg cagctgtaga tcttagccac tttttaaaag aaaagggggg actggaaggg  9540
ctaattcact cccaacgaag acaagatatc cttgatctgt ggatctacca cacacaaggc  9600
tacttccctg attggcagaa ctacacacca gggccaggga tcagatatcc actgaccttt  9660
ggatggtgct acaagctagt accagttgag caagagaagg tagaagaagc caatgaagga  9720
gagaacaccc gcttgttaca ccctgtgagc ctgcatggga tggatgaccc ggagagagaa  9780
gtattagagt ggaggtttga cagccgccta gcatttcatc acatggcccg agagctgcat  9840
ccggactgta ctgggtctct ctggttagac cagatctgag cctgggagct ctctggctaa  9900
ctagggaacc cactgcttaa gcctcaataa agcttgcctt gagtgcttca agtagtgtgt  9960
gcccgtctgt tgtgtgactc tggtaactag agatccctca gacccttta gtcagtgtgg  10020
aaaatctcta gcagggcccg tttaaacccg ctgatcagcc tcgactgtgc cttctagttg  10080
ccagccatct gttgtttgcc cctcccccgt gccttccttg accctggaag gtgccactcc  10140
cactgtcctt tcctaataaa atgaggaaat tgcatcgcat tgtctgagta ggtgtcattc  10200
tattctgggg ggtggggtgg ggcaggacag caagggggag gattgggaag acaatagcag  10260
gcatgctggg gatgcggtgg gctctatggc ttctgaggcg gaaagaacca gctggggctc  10320
tagggggtat ccccacgcgc cctgtagcgg cgcattaagc gcggcgggtg tggtggttac  10380
gcgcagcgtg accgctacac ttgccagcgc cctagcgccc gctcctttcg ctttcttccc  10440
ttcctttctc gccacgttcg ccggctttcc ccgtcaagct ctaaatcggg ggctcccttt  10500
agggttccga tttagtgctt tacggcacct cgaccccaaa aaacttgatt agggtgatgg  10560
ttcacgtagt gggccatcgc cctgatagac ggtttttcgc cctttgacgt tggagtccac  10620
gttctttaat agtggactct tgttccaaac tggaacaaca ctcaacccta tctcggtcta  10680
ttcttttgat ttataaggga ttttgccgat ttcggcctat tggttaaaaa atgagctgat  10740
ttaacaaaaa tttaacgcga attaattctg tggaatgtgt gtcagttagg gtgtggaaag  10800
tccccaggct ccccagcagg cagaagtatg caaagcatgc atctcaatta gtcagcaacc  10860
aggtgtggaa agtccccagg ctccccagca ggcagaagta tgcaaagcat gcatctcaat  10920
tagtcagcaa ccatagtccc gcccctaact ccgcccatcc cgcccctaac tccgcccagt  10980
tccgcccatt ctccgcccca tggctgacta atttttttta tttatgcaga ggccgaggcc  11040
gcctctgcct ctgagctatt ccagaagtag tgaggaggct tttttggagg cctaggcttt  11100
tgcaaaaagc tcccgggagc ttgtatatcc attttcggat ctgatcagca cgtgttgaca  11160
attaatcatc ggcatagtat atcggcatag tataatacga caaggtgagg aactaaacca  11220
tggccaagtt gaccagtgcc gttccggtgc tcaccgcgcg cgacgtcgcc ggagcggtcg  11280
agttctggac cgaccggctc gggttctccc gggacttcgt ggaggacgac ttcgccggtg  11340
tggtccggga cgacgtgacc ctgttcatca gcgcggtcca ggaccaggtg gtgccggaca  11400
acaccctggc ctgggtgtgg gtgcgcggcc tggacgagct gtacgccgag tggtcggagg  11460
tcgtgtccac gaacttccgg gacgcctccg ggccggccat gaccgagatc ggcgagcagc  11520
cgtgggggcg ggagttcgcc ctgcgcgacc cggccggcaa ctgcgtgcac ttcgtggccg  11580
aggagcagga ctgacacgtg ctacgagatt tcgattccac cgccgccttc tatgaaaggt  11640
tgggcttcgg aatcgttttc cgggacgccg gctggatgat cctccagcgc ggggatctca  11700
tgctggagtt cttcgcccac cccaacttgt ttattgcagc ttataatggt tacaaataaa  11760
gcaatagcat cacaaatttc acaaataaag cattttttc actgcattct agttgtggtt  11820
tgtccaaact catcaatgta tcttatcatg tctgtatacc gtcgacctct agctagagct  11880
tggcgtaatc atggtcatag ctgtttcctg tgtgaaattg ttatccgctc acaattccac  11940
acaacatacg agccggaagc ataaagtgta aagcctgggg tgcctaatga gtgagctaac  12000
tcacattaat tgcgttgcgc tcactgcccg ctttccagtc gggaaacctg tcgtgccagc  12060
tgcattaatg aatcggccaa cgcgcgggga gaggcggttt gcgtattggg cgctcttccg  12120
cttcctcgct cactgactcg ctgcgctcgg tcgttcggct gcggcgagcg gtatcagctc  12180
actcaaaggc ggtaatacgg ttatccacag aatcagggga taacgcagga aagaacatgt  12240
gagcaaaagg ccagcaaaag gccaggaacc gtaaaaaggc cgcgttgctg gcgtttttcc  12300
ataggctccg cccccctgac gagcatcaca aaaatcgacg ctcaagtcag aggtggcgaa  12360
acccgacagg actataaaga taccaggcgt ttccccctgg aagctccctc gtgcgctctc  12420
ctgttccgac cctgccgctt accggatacc tgtccgcctt tctcccttcg ggaagcgtgg  12480
cgctttctca tagctcacgc tgtaggtatc tcagttcggt gtaggtcgtt cgctccaagc  12540
tgggctgtgt gcacgaaccc cccgttcagc ccgaccgctg cgccttatcc ggtaactatc  12600
gtcttgagtc caacccggta agacacgact tatcgccact ggcagcagcc actggtaaca  12660
ggattagcag agcgaggtat gtaggcggtg ctacagagtt cttgaagtgg tggcctaact  12720
acggctacac tagaagaaca gtatttggta tctgcgctct gctgaagcca gttaccttcg  12780
gaaaaagagt tggtagctct tgatccggca aacaaaccac cgctggtagc ggtggttttt  12840
ttgtttgcaa gcagcagatt acgcgcagaa aaaaaggatc tcaagaagat cctttgatct  12900
tttctacggg gtctgacgct cagtggaacg aaaactcacg ttaagggatt ttggtcatga  12960
gattatcaaa aaggatcttc acctagatcc ttttaaatta aaaatgaagt tttaaatcaa  13020
tctaaagtat atatgagtaa acttggtctg acagttacca atgcttaatc agtgaggcac  13080
ctatctcagc gatctgtcta tttcgttcat ccatagttgc ctgactcccc gtcgtgtaga  13140
taactacgat acgggagggc ttaccatctg gccccagtgc tgcaatgata ccgcgagacc  13200
cacgctcacc ggctccagat ttatcagcaa taaaccagcc agccggaagg gccgagcgca  13260
gaagtggtcc tgcaacttta tccgcctcca tccagtctat taattgttgc cgggaagcta  13320
gagtaagtag ttcgccagtt aatagtttgc gcaacgttgt tgccattgct acaggcatcg  13380
tggtgtcacg ctcgtcgttt ggtatggctt cattcagctc cggttcccaa cgatcaaggc  13440
gagttacatg atcccccatg ttgtgcaaaa aagcggttag ctccttcggt cctccgatcg  13500
ttgtcagaag taagttggcc gcagtgttat cactcatggt tatggcagca ctgcataatt  13560
ctcttactgt catgccatcc gtaagatgct tttctgtgac tggtgagtac tcaaccaagt  13620
cattctgaga atagtgtatg cggcgaccga gttgctcttg cccggcgtca atacgggata  13680
ataccgcgcc acatagcaga actttaaaag tgctcatcat tggaaaacgt tcttcggggc  13740
gaaaactctc aaggatctta ccgctgttga gatccagttc gatgtaaccc actcgtgcac  13800
ccaactgatc ttcagcatct tttactttca ccagcgtttc tgggtgagca aaaacaggaa  13860
ggcaaaatgc cgcaaaaaag ggaataaggg cgacacggaa atgttgaata ctcatactct  13920
tcctttttca atattattga agcatttatc agggttattg tctcatgagc ggatacatat  13980
ttgaatgtat ttagaaaaat aaacaaatag gggttccgcg cacatttccc cgaaaagtgc  14040
```

```
cacctgac                                                          14048

SEQ ID NO: 3            moltype = DNA  length = 7340
FEATURE                 Location/Qualifiers
misc_feature            1..7340
                        note = AAV Vector Construct
source                  1..7340
                        mol_type = other DNA
                        organism = synthetic construct
SEQUENCE: 3
gcaggaaccc ctagtgatgg agttggccac tccctctctg cgcgctcgct cgctcactga  60
ggccgggcga ccaaaggtcg cccgacgccc gggctttgcc cgggcggcct cagtgagcga  120
gcgagcgcgc agctgcctgc aggggcgcct gatgcggtat tttctcctta cgcatctgtg  180
cggtatttca caccgcatac gtcaaagcaa ccatagtacg cgccctgtag cggcgcatta  240
agcgcggcgg gtgtggtggt tacgcgcagc gtgaccgcta cacttgccag cgccctagcg  300
cccgctcctt tcgctttctt cccttccttt ctcgccacgt tcgccggctt tccccgtcaa  360
gctctaaatc gggggctccc tttagggttc cgatttagtg ctttacggca cctcgacccc  420
aaaaaacttg atttgggtga tggttcacgt agtgggccat cgccctgata gacggttttt  480
cgccctttga cgttggagtc cacgttcttt aatagtggac tcttgttcca aactggaaca  540
acactcaacc ctatctcggg ctattctttt gatttataag ggattttgcc gatttcggcc  600
tattggttaa aaaatgagct gatttaacaa aaatttaacg cgaattttaa caaaatatta  660
acgtttacaa ttttatggtg cactctcagt acaatctgct ctgatgccgc atagttaagc  720
cagccccgac acccgccaac acccgctgac gcgccctgac gggcttgtct gctcccggca  780
tccgcttaca gacaagctgt gaccgtctcc gggagctgca tgtgtcagag gttttcaccg  840
tcatcaccga aacgcgcgag acgaaagggc ctcgtgatac gcctattttt ataggttaat  900
gtcatgataa taatggtttc ttagacgtca ggtggcactt ttcggggaaa tgtgcgcgga  960
acccctattt gtttattttt ctaaatacat tcaaatatgt atccgctcat gagacaataa  1020
ccctgataaa tgcttcaata atattgaaaa aggaagagta tgagtattca acatttccgt  1080
gtcgccctta ttcccttttt tgcggcattt tgccttcctg tttttgctca cccagaaacg  1140
ctggtgaaag taaaagatgc tgaagatcag ttgggtgcac gagtgggtta catcgaactg  1200
gatctcaaca gcggtaagat ccttgagagt tttcgccccg aagaacgttt tccaatgatg  1260
agcactttta aagttctgct atgtggcgcg gtattatccc gtattgacgc cgggcaagag  1320
caactcggtc gccgcataca ctattctcag aatgacttgg ttgagtactc accagtcaca  1380
gaaaagcatc ttacggatgg catgacagta agagaattat gcagtgctgc cataaccatg  1440
agtgataaca ctgcggccaa cttacttctg acaacgatcg gaggaccgaa ggagctaacc  1500
gcttttttgc acaacatggg ggatcatgta actcgccttg atcgttggga accggagctg  1560
aatgaagcca taccaaacga cgagcgtgac accacgatgc ctgtagcaat ggcaacaacg  1620
ttgcgcaaac tattaactgg cgaactactt actctagctt cccggcaaca attaatagac  1680
tggatggagg cggataaagt tgcaggacca cttctgcgct cggcccttcc ggctggctgg  1740
tttattgctg ataaatctgg agccggtgag cgtggaagcc gcggtatcat tgcagcactg  1800
gggccagatg gtaagccctc ccgtatcgta gttatctaca cgacggggag tcaggcaact  1860
atggatgaac gaaatagaca gatcgctgag ataggtgcct cactgattaa gcattggtaa  1920
ctgtcagacc aagtttactc atatatactt tagattgatt taaaacttca tttttaattt  1980
aaaaggatct aggtgaagat cctttttgat aatctcatga ccaaaatccc ttaacgtgag  2040
ttttcgttcc actgagcgtc agaccccgta gaaaagatca aaggatcttc ttgagatcct  2100
ttttttctgc gcgtaatctg ctgcttgcaa acaaaaaaac caccgctacc agcggtggtt  2160
tgtttgccgg atcaagagct accaactctt tttccgaagg taactggctt cagcagagcg  2220
cagataccaa atactgtcct tctagtgtag ccgtagttag gccaccactt caagaactct  2280
gtagcaccgc ctacatacct cgctctgcta atcctgttac cagtggctgc tgccagtggc  2340
gataagtcgt gtcttaccgg gttggactca agacgatagt taccggataa ggcgcagcgg  2400
tcgggctgaa cggggggttc gtgcacacag cccagcttgg agcgaacgac ctacaccgaa  2460
ctgagatacc tacagcgtga gctatgagaa agcgccacgc ttcccgaagg gagaaaggcg  2520
gacaggtatc cggtaagcgg cagggtcgga acaggagagc gcacgaggga gcttccaggg  2580
ggaaacgcct ggtatcttta tagtcctgtc gggtttcgcc acctctgact tgagcgtcga  2640
tttttgtgat gctcgtcagg ggggcggagc ctatggaaaa acgccagcaa cgcggccttt  2700
ttacggttcc tggccttttg ctggcctttt gctcacatgt cctgcaggca gctgcgcgct  2760
cgctcgctca ctgaggccgc ccgggcgtcg ggcgaccttt ggtcgcccgg cctcagtgag  2820
cgagcgagcg cgcagagagg gagtggccaa ctccatcact aggggttcct gcggcctcta  2880
gactcgaggc gttgacattg attattgact agttattaat agtaatcaat tacggggtca  2940
ttagttcata gcccatatat ggagttccgc gttacataac ttacggtaaa tggcccgcct  3000
ggctgaccgc ccaacgaccc ccgcccattg acgtcaataa tgacgtatgt tcccatagta  3060
acgccaatag ggactttcca ttgacgtcaa tgggtggagt atttacggta aactgcccac  3120
ttggcagtac atcaagtgta tcatatgcca agtacgcccc ctattgacgt caatgacggt  3180
aaatggcccg cctggcatta tgcccagtac atgaccttat gggactttcc tacttggcag  3240
tacatctacg tattagtcat cgctattacc atggtgatgc ggttttggca gtacatcaat  3300
gggcgtggat agcggtttga ctcacgggga tttccaagtc tccaccccat tgacgtcaat  3360
gggagtttgt tttggcacca aaatcaacgg gactttccaa aatgtcgtaa caactccgcc  3420
ccattgacgc aaatgggcgg taggcgtgta cggtgggagg tctatataag cagagctctc  3480
tggctaacta ccggtgccac catgtaccca tacgatgttc cagattacgc tgccccaaag  3540
aagaagcgga aggtcggtat ccacggagtc ccagcagcca agcggaacta catcctgggc  3600
ctggccatcg gcatcaccag cgtgggctac ggcatcatcg actacgagac acgggacgtg  3660
atcgatgccg gcgtgcggct gttcaaagag gccaacgtgg aaaacaacga gggcaggcgg  3720
agcaagagag gcgccagaag gctgaagcgg cggaggcggc atagaatcca gagagtgaag  3780
aagctgctgt tcgactacaa cctgctgacc gaccacagcg agctgagcgg catcaacccc  3840
tacgaggcca gagtgaaggg cctgagccag aagctgagcg aggaagagtt ctctgccgcc  3900
ctgctgcacc tggccaagag aagaggcgtg cacaacgtga acgaggtgga agaggacacc  3960
ggcaacgagc tgtccaccaa agagcagatc agccggaaca gcaaggccct ggaagagaaa  4020
tacgtggccg aactgcagct ggaacggctg aagaaagacg gcgaagtgcg gggcagcatc  4080
aacagattca agaccagcga ctacgtgaaa gaagccaaac agctgctgaa ggtgcagaag  4140
```

```
gcctaccacc agctggacca gagcttcatc gacacctaca tcgacctgct ggaaacccgg  4200
cggacctact atgagggacc tggcgagggc agccccttcg gctggaagga catcaaagaa  4260
tggtacgaga tgctgatggg ccactgcacc tacttccccg aggaactgcg gagcgtgaag  4320
tacgcctaca acgccgacct gtacaacgcc ctgaacgacc tgaacaatct cgtgatcacc  4380
agggacgaga acgagaagct ggaatattac gagaagttcc agatcatcga gaacgtgttc  4440
aagcagaaga agaagcccac cctgaagcag atcgccaaag aaatcctcgt gaacgaagag  4500
gatattaagg gctacagagt gaccagcacc ggcaagcccg agttcaccaa cctgaaggtg  4560
taccacgaca tcaaggacat taccgcccgg aaagagatta ttgagaacgc cgagctgctg  4620
gatcagattg ccaagatcct gaccatctac cagagcagcg aggacatcca ggaagaactg  4680
accaatctga actccgagct gacccaggaa gagatcgagc agatctctaa tctgaagggc  4740
tataccggca cccacaacct gagcctgaag gccatcaacc tgatcctgga cgagctgtgg  4800
cacaccaacg acaaccagat cgctatcttc aaccggctga agctggtgcc caagaaggtg  4860
gacctgtccc agcagaaaga gatccccacc accctggtgg acgacttcat cctgagcccc  4920
gtcgtgaaga gaagcttcat ccagagcatc aaagtgatca acgccatcat caagaagtac  4980
ggcctgccca acgacatcat tatcgagctg gcccgcgaga agaactccaa ggacgcccag  5040
aaaatgatca acgagatgca gaagcggaac cggcagacca acgagcggat cgaggaaatc  5100
atccggacca ccggcaaaga gaacgccaag tacctgatcg agaagatcaa gctgcacgac  5160
atgcaggaag gcaagtgcct gtacagcctg gaagccatcc ctctggaaga tctgctgaac  5220
aacccettca actatgaggt ggaccacatc atccccagaa gcgtgtcctt cgacaacagc  5280
ttcaacaaca aggtgctcgt gaagcaggaa gaagccagca agaagggcaa ccggacccca  5340
ttccagtacc tgagcagcag cgacagcaag atcagctacg aaaccttcaa gaagcacatc  5400
ctgaatctgg ccaagggcaa gggcagaatc agcaagacca agaaagagta tctgctggaa  5460
gaacgggaca tcaacaggtt ctccgtgcag aaagacttca tcaaccggaa cctggtggat  5520
accagatacg ccaccagagg cctgatgaac ctgctgcgga gctacttcag agtgaacaac  5580
ctggacgtga aagtgaagtc catcaatggc ggcttcacca gctttctgcg gcggaagtgg  5640
aagtttaaga aagagcggaa caaggggtac aagcaccacg ccgaggacgc cctgatcatt  5700
gccaacgccg atttcatctt caaagagtgg aagaaactgg acaaggccaa aaaagtgatg  5760
gaaaaccaga tgttcgagga aaagcaggcc gagagcatgc ccgagatcga aaccgagcag  5820
gagtacaaag agatcttcat cacccccac cagatcaagc acattaagga cttcaaggac  5880
tacaagtaca gccaccgggt ggacaagaag cctaatagag agctgattaa cgacaccctg  5940
tactccaccc ggaaggacga caagggcaac accctgatcg tgaacaatct gaacggcctg  6000
tacgacaagg acaatgacaa gctgaaaaag ctgatcaaca agagccccga aaagctgctg  6060
atgtaccacc acgaccccca gacctaccag aaactgaagc tgattatgga acagtacggc  6120
gacgagaaga atcccctgta caagtactac gaggaaaccg ggaactacct gaccaagtac  6180
tccaaaaagg acaacggccc cgtgatcaag aagattaagt attacggcaa caaactgaac  6240
gcccatctgg acatcaccga cgactacccc aacagcagaa acaaggtcgt gaagctgtcc  6300
ctgaagccct acagattcga cgtgtacctg gacaatggcg tgtacaagtt cgtgaccgtg  6360
aagaatctgg atgtgatcaa aaaagaaaac tactacgaag tgaatagcaa gtgctatgag  6420
gaagctaaga agctgaagaa gatcagcaac caggccgagt ttatcgcctc cttctacaac  6480
aacgatctga tcaagatcaa cggcgagctg tatagagtga tcggcgtgaa caacgacctg  6540
ctgaaccgga tcgaagtgaa catgatcgac atcacctacc gcgagtacct ggaaaacatg  6600
aacgacaaga ggcccccag gatcattaag acaatcgcct ccaagaccca gagcattaag  6660
aagtacagca cagacattct gggcaacctg tatgaagtga aatctaagaa gcaccctcag  6720
atcatcaaaa agggcaaaag gccggcggcc acgaaaaagg ccggccaggc aaaaaagaaa  6780
aagggatccg atgctaagtc actgactgcc tggtcccgga cactggtgac cttcaaggat  6840
gtgtttgtgg acttcaccag ggaggagtgg aagctgctgg acactgctca gcagatcctg  6900
tacagaaatg tgatgctgga gaactataag aacctggttt ccttgggtta tcagcttact  6960
aagccagatg tgatcctccg gttggagaag ggagaagagc cctggctggt ggagagagaa  7020
attcaccaag agacccatcc tgattcagag actgcatttg aaatcaaatc atcagttccg  7080
aaaaagaaac gcaaagttta agaattccta gagctcgctg atcagcctcg actgtgcctt  7140
ctagttgcca gccatctgtt gtttgcccct cccccgtgcc ttccttgacc ctggaaggtg  7200
ccactcccac tgtcctttcc taataaaatg aggaaattgc atcgcattgt ctgagtaggt  7260
gtcattctat tctggggggt ggggtggggc aggacagcaa gggggaggat tgggaagaga  7320
atagcaggca tgctggggag                                              7340
```

```
SEQ ID NO: 4           moltype = DNA  length = 6095
FEATURE                Location/Qualifiers
misc_feature           1..6095
                       note = AAV Vector Construct
source                 1..6095
                       mol_type = other DNA
                       organism = synthetic construct
SEQUENCE: 4
gggggggggg gggggggtt ggccactccc tctctgcgcg ctcgctcgct cactgaggcc  60
gggcgaccaa aggtcgcccg acgcccgggc tttgcccggg cggcctcagt gagcgagcga  120
gcgcgcagag agggagtggc caactccatc actaggggtt cctagatctg aattcggtac  180
cagatctagg aacctagggc ctatttccca tgattccttc atatttgcat atacgataca  240
aggctgttag agagataatt ggaattaatt tgactgtaaa cacaaagata ttagtacaaa  300
atacgtgacg tagaaagtaa taatttcttg ggtagtttgc agttttaaaa ttatgtttta  360
aaatggacta tcatatgctt accgtaactt gaaagtattt cgatttcttg gctttatata  420
tcttgtggaa aggacgaaac accgagcgcg ccccgcctag cccgttttag tactctggaa  480
acagaatcta ctaaaacaag gcaaaatgcc gtgtttatct cgtcaacttg ttggcgagat  540
ttttttgcgg ccgcccgcgg tggagctcca gcttttgttc cctttagtga gggttaattc  600
tagaggatcc ggtactcgag gaactgaaaa accagaaagt taactggtaa gtttagtctt  660
tttgtctttt atttcaggtc ccggatccgg tggtggtgca aatcaaagaa ctgctcctca  720
gtggatgttg cctttacttc taggcctgta cggaagtgtt acttctgctc taaaagctgc  780
ggaattgtac ccgcggcccg ggatccaccg gtcgccacca tggtgagcaa gggcgaggag  840
ctgttcaccg ggtggtgcc catcctggtc gagctggacg gcgacgtaaa cggccacaag  900
ttcagcgtgt ccggcgaggg cgagggcgat gccacctacg gcaagctgac cctgaagttc  960
```

-continued

```
atctgcacca ccggcaagct gcccgtgccc tggcccaccc tcgtgaccac cctgacctac  1020
ggcgtgcagt gcttcagccg ctaccccgac cacatgaagc agcacgactt cttcaagtcc  1080
gccatgcccg aaggctacgt ccaggagcgc accatcttct tcaaggacga cggcaactac  1140
aagacccgcg ccgaggtgaa gttcgagggc gacaccctgg tgaaccgcat cgagctgaag  1200
ggcatcgact tcaaggagga cggcaacatc ctggggcaca agctggagta caactacaac  1260
agccacaacg tctatatcat ggccgacaag cagaagaacg gcatcaaggt gaacttcaag  1320
atccgccaca acatcgagga cggcagcgtg cagctcgccg accactacca gcagaacacc  1380
cccatcggcg acggccccgt gctgctgccc gacaaccact acctgagcac ccagtccgcc  1440
ctgagcaaag accccaacga gaagcgcgat cacatggtcc tgctggagtt cgtgaccgcc  1500
gccgggatca ctctcggcat ggacgagctg tacaagtaaa gcggccgcgg ggatccagac  1560
atgataagat acattgatga gtttggacaa accacaacta gaatgcagtg aaaaaaatgc  1620
tttatttgtg aaatttgtga tgctattgct ttatttgtaa ccattataag ctgcaataaa  1680
caagttaaca acaacaattg cattcatttt atgtttcagg ttcaggggga ggtgtgggag  1740
gtttttagt cgacctcgag cagtgtggtt ttgcaagagg aagcaaaaag cctctccacc  1800
caggcctgga atgtttccac ccaagtcgaa ggcagtgtgg ttttgcaaga ggaagcaaaa  1860
agcctctcca cccaggcctg gaatgtttcc acccaatgtc gagcaacccc gcccagcgtc  1920
ttgtcattgg cgaattcgaa cacgcagatg cagtcggggc ggcgcggtcc caggtccact  1980
tcgcatatta aggtgacgcg tgtggcctcg aacaccgagc gaccctgcag ccaatatggg  2040
atcggccatt gaacaagatg gattgcacgc aggttctccg gccgcttggg tggagaggct  2100
attcggctat gactgggcac aacagacaat cggctgctct gatgccgccg tgttccggct  2160
gtcagcgcag gggcgcccgg ttctttttgt caagaccgac ctgtccggtg ccctgaatga  2220
actgcaggac gaggcagcgc ggctatcgtg gctggccacg acgggcgttc cttgcgcagc  2280
tgtgctcgac gttgtcactg aagcgggaag ggactggctg ctattgggcg aagtgccggg  2340
gcaggatctc ctgtcatctc accttgctcc tgccgagaaa gtatccatca tggctgatgc  2400
aatgcggcgg ctgcatacgc ttgatccggc tacctgccca ttcgaccacc aagcgaaaca  2460
tcgcatcgag cgagcacgta ctcggatgga agccggtctt gtcgatcagg atgatctgga  2520
cgaagagcat caggggctcg cgccagccga actgttcgcc aggctcaagg cgcgcatgcc  2580
cgacggcgag gatctcgtcg tgacccatgg cgatgcctgc ttgccgaata tcatggtgga  2640
aaatggccgc ttttctggat tcatcgactg tggccggctg ggtgtggcgg accgctatca  2700
ggacatagcg ttggctaccc gtgatattgc tgaagagctt ggcggcgaat gggctgaccg  2760
cttcctcgtg ctttacggta tcgccgctcc cgattcgcag cgcatcgcct tctatcgcct  2820
tcttgacgag ttcttctgag gggatccgtc gactagagct cgctgatcag cctcgactgt  2880
gccttctagt tgccagccat ctgttgtttg cccctccccc gtgccttcct tgaccctgga  2940
aggtgccact cccactgtcc tttcctaata aaatgaggaa attgcatcgc attgtctgag  3000
taggtgtcat tctattctgg ggggtggggt ggggcaggac agcaaggggg aggattggga  3060
agacaatagc aggcatgctg gggagagatc taggaacccc tagtgatgga gttggccact  3120
ccctctctgc gcgctcgctc gctcactgag gccgcccggg caaagcccgg gcgtcgggcg  3180
acctttggtc gcccggcctc agtgagcgag cgagcgcgca gagagggagt ggccaacccc  3240
cccccccccc cccctgcagc ccagctgcat taatgaatcg gccaacgcgc ggggagaggc  3300
ggtttgcgta ttgggcgctc ttccgcttcc tcgctcactg actcgctgcg ctcggtcgtt  3360
cggctgcggc gagcggtatc agctcactca aaggcggtaa tacggttatc cacagaatca  3420
ggggataacg caggaaagaa catgtgagca aaaggccagc aaaaggccag gaaccgtaaa  3480
aaggccgcgt tgctggcgtt tttccatagg ctccgccccc ctgacgagca tcacaaaaat  3540
cgacgctcaa gtcagaggtg gcgaaacccg acaggactat aaagatacca ggcgtttccc  3600
cctggaagct ccctcgtgcg ctctcctgtt ccgaccctgc cgcttaccgg atacctgtcc  3660
gcctttctcc cttcgggaag cgtggcgctt tctcaatgct cacgctgtag gtatctcagt  3720
tcggtgtagg tcgttcgctc caagctgggc tgtgtgcacg aaccccccgt tcagcccgac  3780
cgctgcgcct tatccggtaa ctatcgtctt gagtccaacc cggtaagaca cgacttatcg  3840
ccactggcag cagccactgg taacaggatt agcagagcga ggtatgtagg cggtgctaca  3900
gagttcttga agtggtggcc taactacggc tacactagaa ggacagtatt tggtatctgc  3960
gctctgctga agccagttac cttcggaaaa agagttggta gctcttgatc cggcaaacaa  4020
accaccgctg gtagcggtgg tttttttgtt tgcaagcagc agattacgcg cagaaaaaaa  4080
ggatctcaag aagatccttt gatcttttct acggggtctg acgctcagtg gaacgaaaac  4140
tcacgttaag ggattttggt catgagatta tcaaaaagga tcttcaccta gatcctttta  4200
aattaaaaat gaagttttaa atcaatctaa agtatatatg agtaaacttg gtctgacagt  4260
taccaatgct taatcagtga ggcacctatc tcagcgatct gtctatttcg ttcatccata  4320
gttgcctgac tccccgtcgt gtagataact acgatacggg agggcttacc atctggcccc  4380
agtgctgcaa tgataccgcg agacccacgc tcaccggctc cagatttatc agcaataaac  4440
cagccagccg gaagggccga gcgcagaagt ggtcctgcaa ctttatccgc ctccatccag  4500
tctattaatt gttgccggga agctagagta agtagttcgc cagttaatag tttgcgcaac  4560
gttgttgcca ttgctacagg catcgtggtg tcacgctcgt cgtttggtat ggcttcattc  4620
agctccggtt cccaacgatc aaggcgagtt acatgatccc ccatgttgtg caaaaaagcg  4680
gttagctcct tcggtcctcc gatcgttgtc agaagtaagt tggccgcagt gttatcactc  4740
atggttatgg cagcactgca taattctctt actgtcatgc catccgtaag atgcttttct  4800
gtgactggtg agtactcaac caagtcattc tgagaatagt gtatgcggcg accgagttgc  4860
tcttgcccgg cgtcaatacg ggataatacc gcgccacata gcagaacttt aaaagtgctc  4920
atcattggaa aacgttcttc ggggcgaaaa ctctcaagga tcttaccgct gttgagatcc  4980
agttcgatgt aacccactcg tgcacccaac tgatcttcag catcttttac tttcaccagc  5040
gtttctgggt gagcaaaaac aggaaggcaa aatgccgcaa aaaagggaat aagggcgaca  5100
cggaaatgtt gaatactcat actcttcctt tttcaatatt attgaagcat ttatcagggt  5160
tattgtctca tgagcggata catatttgaa tgtatttaga aaaataaaca aataggggtt  5220
ccgcgcacat ttccccgaaa agtgccacct gacgtctaag aaaccattat tatcatgaca  5280
ttaacctata aaaataggcg tatcacgagg ccctttcgtc tcgcgcgttt cggtgatgac  5340
ggtgaaaacc tctgacacat gcagctcccg gagacggtca cagcttgtct gtaagcggat  5400
gccgggagca gacaagcccg tcagggcgcg tcagcgggtg ttggcgggtg tcggggctgg  5460
cttaactatg cggcatcaga gcagattgta ctgagagtgc accatatgcg gtgtgaaata  5520
ccgcacagat gcgtaaggag aaaataccgc atcaggaaat tgtaaacgtt aatattttgt  5580
taaaattcgc gttaaatttt tgttaaatca gctcattttt taaccaatag gccgaaatcg  5640
gcaaaatccc ttataaatca aaagaataga ccgagatagg gttgagtgtt gttccagttt  5700
```

-continued

```
ggaacaagag tccactatta aagaacgtgg actccaacgt caaagggcga aaaaccgtct  5760
atcagggcga tggcccacta cgtgaaccat caccctaatc aagttttttg gggtcgaggt  5820
gccgtaaagc actaaatcgg aaccctaaag ggagcccccg atttagagct tgacggggaa  5880
agccggcgaa cgtggcgaga aaggaaggga agaaagcgaa aggagcgggc gctagggcgc  5940
tggcaagtgt agcggtcacg ctgcgcgtaa ccaccacacc cgccgcgctt aatgcgccgc  6000
tacagggcgc gtcgcgccat tcgccattca ggctacgcaa ctgttgggaa gggcgatcgg  6060
tgcgggcctc ttcgctatta cgccagctgg ctgca                            6095

SEQ ID NO: 5            moltype = DNA  length = 7025
FEATURE                 Location/Qualifiers
misc_feature            1..7025
                        note = AAV Vector Construct
source                  1..7025
                        mol_type = other DNA
                        organism = synthetic construct
SEQUENCE: 5
gggggggggg gggggggggtt ggccactccc tctctgcgcg ctcgctcgct cactgaggcc  60
gggcgaccaa aggtcgcccg acgcccgggc tttgcccggg cggcctcagt gagcgagcga  120
gcgcgcagag agggagtggc caactccatc actaggggtt cctagatctg aattcggtac  180
caagcttgcc tatttcccat gattccttca tatttgcata tacgatacaa ggctgttaga  240
gagataattg gaattaattt gactgtaaac acaaagatat tagtacaaaa tacgtgacgt  300
agaaagtaat aatttcttgg gtagtttgca gttttaaaat tatgttttaa aatggactat  360
catatgctta ccgtaacttg aaagtatttc gatttcttgg ctttatatat cttgtggaaa  420
ggacgaaaca ccgggtcttc gagaagacct gttttagtac tctggaaaca gaatctacta  480
aaacaaggca aaatgccgtg tttatctcgt caacttgttg gcgagatttt tttgcggccg  540
cccgcggtgg agctccagct tttgttccct ttagtgaggg ttaattctag agagacgtac  600
aaaaaagagc aagaagctaa aaaagattta aaaattattt ttagcgcagt taatggaaca  660
ggaactaaat ttaccccaaa aatattacgt gaatcaggat ataacgttat tgaggttgaa  720
gagcatgcat ttgaagatga aacatttaaa aatgttgtaa atccaaatcc agaatttgat  780
cctgcatgaa aaataccgct tgaatatggt attaaacatg atgcagatat tattattatg  840
aatgacccag atgctgacag atttggaatg gcaataaaac atgatggtca ttttgtaaga  900
ttagatggaa atcaaacagg accaatttta attgattgaa aattatcaaa tctaaaacgc  960
ttaaatagca ttccaaaaaa tccggctcta tattcaagtt ttgtaacaag tgatttgggt  1020
gatagaatcg ctcatgaaaa atatggagtt aatattgtaa aaactttaac tggatttaaa  1080
tgaatgggta gagaaattgc taaagaagaa gataacggat taaattttgt ttttgcttat  1140
gaagaaagtt atggatatgt aattgatgac tcagctagag ataaagatgg aatacaagct  1200
tctatattaa tagcagaggc tgcttgattt tataaaaaac aaaataaaac attagtagac  1260
tatttagaag atttatttaa agaaatgggt gcatattaca ctttcacttt aaacttgaat  1320
tttaaaccag aagaaaagaa attaaaaatt gaaccattaa tgaaatcatt gagagcaaca  1380
cccttaactc aaattgctgg acttaaagtt gttaatgttg aagactacat cgatggaatg  1440
tataatatgc caggacaaga cttactaaaa ttttatttag aagataagtc atgatttgct  1500
gttcgcccaa gtggaactga acctaaacta aaaatttatt ttataggtgt tggtgaatct  1560
gttcaaaacg ctaaagttaa agtagacgaa attattaaag aattaaaatt aaaaatgaat  1620
atataggaga aaaaatgaaa ctaaacaaat atatagatca cacattatta aaacaagatg  1680
ctacgaaagc tgaaattaaa caattatgtg atgaagcaat tgaatttgat tttgcaacag  1740
tttgtgttaa ttcatattga acaagctatt gtaaagaatt attaaaaggc acaaatgtag  1800
gaataacaaa tgttgtaggt tttcctctag gtgcatgcac aacagctaca aaagcattcg  1860
aagtttctga agcaattaaa gatggtgcaa cagaaattga tatggtatta aatattggtg  1920
cattaaaaga caaaaattat gaattagttt tagaagacat gaaagctgta aaaaaagcag  1980
ctggatcaca tgttgttaaa tgtattatgg aaaattgttt attaacaaaa gaagaaatca  2040
tgaaagcttg tgaaatagct gttgaagctg gattagaatt tgttaaaaca tcaacaggat  2100
tttcaaaatc aggtgcaaca tttgaagatg ttaaactaat gaagtcagtt gttaaagaca  2160
atgctttagt taaagcagct ggtggagtta gaacatttga agatgctcaa aaaatgattg  2220
aagcaggagc tgaccgctta ggaacaagtg gtggagtagc tattattaaa ggtgaagaaa  2280
acaacgcgag ttactaaaac tagcgttttt ttattttgct catttttatt aaaagtttgc  2340
aaaaaggaac ataaaaattc taattattga tactaaagtt attaaaaaga agattttggt  2400
tgattttata aaggtcatag aatataatat tttagcatgt gtattttgtg tgctcattta  2460
caaccgtctc gcggccgcgg ggatccagac atgataagat acattgatga gtttggacaa  2520
accacaacta gaatgcagtg aaaaaaatgc tttatttgtg aaatttgtga tgctattgct  2580
ttatttgtaa ccattataag ctgcaataaa caagttaaca acaacaattg cattcatttt  2640
atgtttcagg ttcaggggga ggtgtgggag gtttttttagt cgacctcgag cagtgtggtt  2700
ttgcaagagg aagcaaaaag cctctccacc caggcctgga atgtttccac ccaagtcgaa  2760
ggcagtgtgg ttttgcaaga ggaagcaaaa agcctctcca cccaggcctg gaatgtttcc  2820
acccaatgtc gagcaacccc gcccagcgtc ttgtcattgg cgaattcgaa cacgcagatg  2880
cagtcggggc ggcgcggtcc caggtccact tcgcatatta aggtgacgcg tgtggcctcg  2940
aacaccgagc gaccctgcag ccaatatggg atcggccatt gaacaagatg gattgcacgc  3000
aggttctccg gccgcttggg tggagaggct attcggctat gactgggcac aacagacaat  3060
cggctgctct gatgccgccg tgttccggct gtcagcgcag gggcgcccgg ttcttttttgt  3120
caagaccgac ctgtccggtg ccctgaatga actgcaggac gaggcagcgc ggctatcgtg  3180
gctggccacg acgggcgttc cttgcgcagc tgtgctcgac gttgtcactg aagcgggaag  3240
ggactggctg ctattgggcg aagtgccggg gcaggatctc ctgtcatctc accttgctcc  3300
tgccgagaaa gtatccatca tggctgatgc aatgcggcgg ctgcatacgc ttgatccggc  3360
tacctgccca ttcgaccacc aagcgaaaca tcgcatcgag cgagcacgta ctcggatgga  3420
agccggtctt gtcgatcagg atgatctgga cgaagagcat caggggctcg cgccagccga  3480
actgttcgcc aggctcaagg cgcgcatgcc cgacggcgag gatctcgtcg tgacccatgg  3540
cgatgcctgc ttgccgaata tcatggtgga aaatggccgc ttttctggat tcatcgactg  3600
tggccggctg ggtgtggcgg accgctatca ggacatagcg ttggctaccc gtgatattgc  3660
tgaagagctt ggcggcgaat gggctgaccg cttcctcgtg ctttacggta tcgccgctcc  3720
cgattcgcag cgcatcgcct tctatcgcct tcttgacgag ttcttctgag ggatccgtc  3780
```

-continued

```
gactagagct cgctgatcag cctcgactgt gccttctagt tgccagccat ctgttgtttg  3840
cccctccccc gtgccttcct tgaccctgga aggtgccact cccactgtcc tttcctaata  3900
aaatgaggaa attgcatcgc attgtctgag taggtgtcat tctattctgg ggggtggggt  3960
ggggcaggac agcaaggggg aggattggga agacaatagc aggcatgctg gggagagatc  4020
taggaacccc tagtgatgga gttggccact ccctctctgc gcgctcgctc gctcactgag  4080
gccgcccggg caaagcccgg gcgtcgggcg acctttggtc gcccggcctc agtgagcgag  4140
cgagcgcgca gagagggagt ggccaacccc cccccccccc cccctgcagc ccagctgcat  4200
taatgaatcg gccaacgcgc ggggagaggc ggtttgcgta ttgggcgctc ttccgcttcc  4260
tcgctcactg actcgctgcg ctcggtcgtt cggctgcggc gagcggtatc agctcactca  4320
aaggcggtaa tacggttatc cacagaatca ggggataacg caggaaagaa catgtgagca  4380
aaaggccagc aaaaggccag gaaccgtaaa aaggccgcgt tgctggcgtt tttccatagg  4440
ctccgccccc ctgacgagca tcacaaaaat cgacgctcaa gtcagaggtg gcgaaacccg  4500
acaggactat aaagatacca ggcgtttccc cctggaagct ccctcgtgcg ctctcctgtt  4560
ccgaccctgc cgcttaccgg atacctgtcc gcctttctcc cttcgggaag cgtggcgctt  4620
tctcaatgct cacgctgtag gtatctcagt tcggtgtagg tcgttcgctc caagctgggc  4680
tgtgtgcacg aaccccccgt tcagcccgac cgctgcgcct tatccggtaa ctatcgtctt  4740
gagtccaacc cggtaagaca cgacttatcg ccactggcag cagccactgg taacaggatt  4800
agcagagcga ggtatgtagg cggtgctaca gagttcttga agtggtggcc taactacggc  4860
tacactagaa ggacagtatt tggtatctgc gctctgctga agccagttac cttcggaaaa  4920
agagttggta gctcttgatc cggcaaacaa accaccgctg gtagcggtgg tttttttgtt  4980
tgcaagcagc agattacgcg cagaaaaaaa ggatctcaag aagatccttt gatcttttct  5040
acggggtctg acgctcagtg gaacgaaaac tcacgttaag ggattttggt catgagatta  5100
tcaaaaagga tcttcaccta gatcctttta aattaaaaat gaagttttaa atcaatctaa  5160
agtatatatg agtaaacttg gtctgacagt taccaatgct taatcagtga ggcacctatc  5220
tcagcgatct gtctatttcg ttcatccata gttgcctgac tccccgtcgt gtagataact  5280
acgatacggg agggcttacc atctggcccc agtgctgcaa tgataccgcg agacccacgc  5340
tcaccggctc cagatttatc agcaataaac cagccagccg gaagggccga gcgcagaagt  5400
ggtcctgcaa ctttatccgc ctccatccag tctattaatt gttgccggga agctagagta  5460
agtagttcgc cagttaatag tttgcgcaac gttgttgcca ttgctacagg catcgtggtg  5520
tcacgctcgt cgtttggtat ggcttcattc agctccggtt cccaacgatc aaggcgagtt  5580
acatgatccc ccatgttgtg caaaaaagcg gttagctcct tcggtcctcc gatcgttgtc  5640
agaagtaagt tggccgcagt gttatcactc atggttatgg cagcactgca taattctctt  5700
actgtcatgc catccgtaag atgcttttct gtgactggtg agtactcaac caagtcattc  5760
tgagaatagt gtatgcggcg accgagttgc tcttgcccgg cgtcaatacg ggataatacc  5820
gcgccacata gcagaacttt aaaagtgctc atcattggaa aacgttcttc ggggcgaaaa  5880
ctctcaagga tcttaccgct gttgagatcc agttcgatgt aacccactcg tgcacccaac  5940
tgatcttcag catcttttac tttcaccagc gtttctgggt gagcaaaaac aggaaggcaa  6000
aatgccgcaa aaaagggaat aagggcgaca cggaaatgtt gaatactcat actcttcctt  6060
tttcaatatt attgaagcat ttatcagggt tattgtctca tgagcggata catatttgaa  6120
tgtatttaga aaaataaaca aataggggtt ccgcgcacat ttccccgaaa agtgccacct  6180
gacgtctaag aaaccattat tatcatgaca ttaacctata aaaataggcg tatcacgagg  6240
ccctttcgtc tcgcgcgttt cggtgatgac ggtgaaaacc tctgacacat gcagctcccg  6300
gagacggtca cagcttgtct gtaagcggat gccgggagca gacaagcccg tcagggcgcg  6360
tcagcgggtg ttggcgggtg tcggggctgg cttaactatg cggcatcaga gcagattgta  6420
ctgagagtgc accatatgcg gtgtgaaata ccgcacagat gcgtaaggag aaaataccgc  6480
atcaggaaat tgtaaacgtt aatattttgt taaaattcgc gttaaatttt tgttaaatca  6540
gctcattttt taaccaatag gccgaaatcg gcaaaatccc ttataaatca aaagaataga  6600
ccgagatagg gttgagtgtt gttccagttt ggaacaagag tccactatta aagaacgtgg  6660
actccaacgt caaagggcga aaaaccgtct atcagggcga tggcccacta cgtgaaccat  6720
caccctaatc aagttttttg gggtcgaggt gccgtaaagc actaaatcgg aaccctaaag  6780
ggagcccccg atttagagct tgacggggaa agccggcgaa cgtggcgaga aaggaaggga  6840
agaaagcgaa aggagcgggc gctagggcgc tggcaagtgt agcggtcacg ctgcgcgtaa  6900
ccaccacacc cgccgcgctt aatgcgccgc tacagggcgc gtcgcgccat tcgccattca  6960
ggctacgcaa ctgttgggaa gggcgatcgg tgcgggcctc ttcgctatta cgccagctgg  7020
ctgca                                                              7025

SEQ ID NO: 6           moltype = DNA  length = 22
FEATURE                Location/Qualifiers
misc_feature           1..22
                       note = protospace sequence for CAG Luciferase gRNAs
source                 1..22
                       mol_type = other DNA
                       organism = synthetic construct
SEQUENCE: 6
gtcattattg acgtcaatgg gc                                           22

SEQ ID NO: 7           moltype = DNA  length = 20
FEATURE                Location/Qualifiers
misc_feature           1..20
                       note = protospace sequence for CAG Luciferase gRNAs
source                 1..20
                       mol_type = other DNA
                       organism = synthetic construct
SEQUENCE: 7
gtgctcagca actcggggag                                              20

SEQ ID NO: 8           moltype = DNA  length = 20
FEATURE                Location/Qualifiers
misc_feature           1..20
```

-continued

```
                      note = protospace sequence for CAG Luciferase gRNAs
source                1..20
                      mol_type = other DNA
                      organism = synthetic construct
SEQUENCE: 8
ctcggggagg ggggtgcagg                                                 20

SEQ ID NO: 9          moltype = DNA  length = 22
FEATURE               Location/Qualifiers
misc_feature          1..22
                      note = protospace sequence for CAG Luciferase gRNAs
source                1..22
                      mol_type = other DNA
                      organism = synthetic construct
SEQUENCE: 9
actttccatt gacgtcaatg gg                                              22

SEQ ID NO: 10         moltype = DNA  length = 22
FEATURE               Location/Qualifiers
misc_feature          1..22
                      note = protospace sequence for CAG Luciferase gRNAs
source                1..22
                      mol_type = other DNA
                      organism = synthetic construct
SEQUENCE: 10
cttcgggggg gacggggcag gg                                              22

SEQ ID NO: 11         moltype = DNA  length = 21
FEATURE               Location/Qualifiers
misc_feature          1..21
                      note = protospace sequence for CAG Luciferase gRNAs
source                1..21
                      mol_type = other DNA
                      organism = synthetic construct
SEQUENCE: 11
cttcgccccg cgcccgctag a                                               21

SEQ ID NO: 12         moltype = DNA  length = 19
FEATURE               Location/Qualifiers
misc_feature          1..19
                      note = protospace sequence for CAG Luciferase gRNAs
source                1..19
                      mol_type = other DNA
                      organism = synthetic construct
SEQUENCE: 12
tcggggaggg gggtgcagg                                                  19

SEQ ID NO: 13         moltype = DNA  length = 19
FEATURE               Location/Qualifiers
misc_feature          1..19
                      note = protospace sequence for CAG Luciferase gRNAs
source                1..19
                      mol_type = other DNA
                      organism = synthetic construct
SEQUENCE: 13
tgctcagcaa ctcggggag                                                  19

SEQ ID NO: 14         moltype = DNA  length = 19
FEATURE               Location/Qualifiers
misc_feature          1..19
                      note = protospace sequence for CAG Luciferase gRNAs
source                1..19
                      mol_type = other DNA
                      organism = synthetic construct
SEQUENCE: 14
gcggggggtg gcggcaggt                                                  19

SEQ ID NO: 15         moltype = DNA  length = 19
FEATURE               Location/Qualifiers
misc_feature          1..19
                      note = protospace sequence for Mouse Acvr2b gRNAs
source                1..19
                      mol_type = other DNA
                      organism = synthetic construct
SEQUENCE: 15
gctcctctgg gacccctga                                                  19

SEQ ID NO: 16         moltype = DNA  length = 19
FEATURE               Location/Qualifiers
```

-continued

```
misc_feature          1..19
                      note = protospace sequence for Mouse Acvr2b gRNAs
source                1..19
                      mol_type = other DNA
                      organism = synthetic construct
SEQUENCE: 16
tgctatggag cccacgcta                                               19

SEQ ID NO: 17         moltype = DNA  length = 19
FEATURE               Location/Qualifiers
misc_feature          1..19
                      note = protospace sequence for Mouse Acvr2b gRNAs
source                1..19
                      mol_type = other DNA
                      organism = synthetic construct
SEQUENCE: 17
ggcgcgctct ccgagctgg                                               19

SEQ ID NO: 18         moltype = DNA  length = 19
FEATURE               Location/Qualifiers
misc_feature          1..19
                      note = protospace sequence for Mouse Acvr2b gRNAs
source                1..19
                      mol_type = other DNA
                      organism = synthetic construct
SEQUENCE: 18
agcgcgcccc gcctagccc                                               19

SEQ ID NO: 19         moltype = DNA  length = 19
FEATURE               Location/Qualifiers
misc_feature          1..19
                      note = protospace sequence for Mouse Acvr2b gRNAs
source                1..19
                      mol_type = other DNA
                      organism = synthetic construct
SEQUENCE: 19
gcctctttgt atccaacat                                               19

SEQ ID NO: 20         moltype = DNA  length = 23
FEATURE               Location/Qualifiers
misc_feature          1..23
                      note = protospace sequence for Mouse Acvr2b gRNAs
source                1..23
                      mol_type = other DNA
                      organism = synthetic construct
SEQUENCE: 20
gcacgctcct ctgggacccc tga                                          23

SEQ ID NO: 21         moltype = DNA  length = 19
FEATURE               Location/Qualifiers
misc_feature          1..19
                      note = protospace sequence for Mouse Acvr2b gRNAs
source                1..19
                      mol_type = other DNA
                      organism = synthetic construct
SEQUENCE: 21
gtgggggagg ggacctgaa                                               19

SEQ ID NO: 22         moltype = DNA  length = 19
FEATURE               Location/Qualifiers
misc_feature          1..19
                      note = protospace sequence for Mouse Acvr2b gRNAs
source                1..19
                      mol_type = other DNA
                      organism = synthetic construct
SEQUENCE: 22
gaggggccat gaacggggg                                               19

SEQ ID NO: 23         moltype = DNA  length = 3600
FEATURE               Location/Qualifiers
misc_feature          1..3600
                      note = HA-NLS-dSaCas9-NLS-KRAB
source                1..3600
                      mol_type = other DNA
                      organism = synthetic construct
SEQUENCE: 23
atgtacccat acgatgttcc agattacgct gccccaaaga agaagcggaa ggtcggtatc  60
cacggagtcc cagcagccaa gcggaactac atcctgggcc tggccatcgg catcaccagc  120
gtgggctacg gcatcatcga ctacgagaca cgggacgtga tcgatgccgg cgtgcggctg  180
```

-continued

```
ttcaaagagg ccaacgtgga aaacaacgag ggcaggcgga gcaagagagg cgccagaagg  240
ctgaagcggc ggaggcggca tagaatccag agagtgaaga agctgctgtt cgactacaac  300
ctgctgaccg accacagcga gctgagcggc atcaacccct acgaggccag agtgaagggc  360
ctgagccaga agctgagcga ggaagagttc tctgccgccc tgctgcacct ggccaagaga  420
agaggcgtgc acaacgtgaa cgaggtggaa gaggacaccg gcaacgagct gtccaccaaa  480
gagcagatca gccggaacag caaggccctg gaagagaaat acgtggccga actgcagctg  540
gaacggctga agaaagacgg cgaagtgcgg ggcagcatca acagattcaa gaccagcgac  600
tacgtgaaag aagccaaaca gctgctgaag gtgcagaagg cctaccacca gctggaccag  660
agcttcatcg acacctacat cgacctgctg gaaacccggc ggacctacta tgagggacct  720
ggcgagggca gccccttcgg ctggaaggac atcaaagaat ggtacgagat gctgatgggc  780
cactgcacct acttccccga ggaactgcgg agcgtgaagt acgcctacaa cgccgacctg  840
tacaacgccc tgaacgacct gaacaatctc gtgatcacca gggacgagaa cgagaagctg  900
gaatattacg agaagttcca gatcatcgag aacgtgttca agcagaagaa gaagcccacc  960
ctgaagcaga tcgccaaaga aatcctcgtg aacgaagagg atattaaggg ctacagagtg  1020
accagcaccg gcaagcccga gttcaccaac ctgaaggtgt accacgacat caaggacatt  1080
accgccccgga aagagattat tgagaacgcc gagctgctgg atcagattgc caagatcctg  1140
accatctacc agagcagcga ggacatccag gaagaactga ccaatctgaa ctccgagctg  1200
acccaggaag agatcgagca gatctctaat ctgaagggct ataccggcac ccacaacctg  1260
agcctgaagg ccatcaacct gatcctggac gagctgtggc acaccaacga caaccagatc  1320
gctatcttca accggctgaa gctggtgccc aagaaggtgg acctgtccca gcagaaagag  1380
atccccacca ccctggtgga cgacttcatc ctgagccccg tcgtgaagag aagcttcatc  1440
cagagcatca aagtgatcaa cgccatcatc aagaagtacg gcctgcccaa cgacatcatt  1500
atcgagctgg cccgcgagaa gaactccaag gacgcccaga aaatgatcaa cgagatgcag  1560
aagcggaacc ggcagaccaa cgagcggatc gaggaaatca tccggaccac cggcaaagag  1620
aacgccaagt acctgatcga gaagatcaag ctgcacgaca tgcaggaagg caagtgcctg  1680
tacagcctgg aagccatccc tctggaagat ctgctgaaca accccttcaa ctatgaggtg  1740
gaccacatca tccccagaag cgtgtccttc gacaacagct tcaacaacaa ggtgctcgtg  1800
aagcaggaag aagccagcaa gaagggcaac cggacccccat tccagtacct gagcagcagc  1860
gacagcaaga tcagctacga aaccttcaag aagcacatcc tgaatctggc caagggcaag  1920
ggcagaatca gcaagaccaa gaaagagtat ctgctggaag aacgggacat caacaggttc  1980
tccgtgcaga aagacttcat caaccggaac ctggtggata ccagatacgc caccagaggc  2040
ctgatgaacc tgctgcggag ctacttcaga gtgaacaacc tggacgtgaa agtgaagtcc  2100
atcaatggcg gcttcaccag ctttctgcgg cggaagtgga agtttaagaa agagcggaac  2160
aaggggtaca agcaccacgc cgaggacgcc ctgatcattg ccaacgccga tttcatcttc  2220
aaagagtgga agaaactgga caaggccaaa aaagtgatgg aaaaccagat gttcgaggaa  2280
aagcaggccg agagcatgcc cgagatcgaa accgagcagg agtacaaaga gatcttcatc  2340
accccccacc agatcaagca cattaaggac ttcaaggact acaagtacag ccaccgggtg  2400
gacaagaagc ctaatagaga gctgattaac gacaccctgt actccacccg gaaggacgac  2460
aagggcaaca ccctgatcgt gaacaatctg aacggcctgt acgacaagga caatgacaag  2520
ctgaaaaagc tgatcaacaa gagccccgaa aagctgctga tgtaccacca cgacccccag  2580
acctaccaga aactgaagct gattatggaa cagtacggcg acgagaagaa tcccctgtac  2640
aagtactacg aggaaaccgg gaactacctg accaagtact ccaaaaagga caacggcccc  2700
gtgatcaaga agattaagta ttacggcaac aaactgaacg cccatctgga catcaccgac  2760
gactacccca acagcagaaa caaggtcgtg aagctgtccc tgaagcccta cagattcgac  2820
gtgtacctgg acaatggcgt gtacaagttc gtgaccgtga agaatctgga tgtgatcaaa  2880
aaagaaaact actacgaagt gaatagcaag tgctatgagg aagctaagaa gctgaagaag  2940
atcagcaacc aggccgagtt tatcgcctcc ttctacaaca acgatctgat caagatcaac  3000
ggcgagctgt atagagtgat cggcgtgaac aacgacctgc tgaaccggat cgaagtgaac  3060
atgatcgaca tcacctaccg cgagtacctg gaaaacatga acgacaagag gccccccagg  3120
atcattaaga caatcgcctc caagacccag agcattaaga agtacagcac agacattctg  3180
ggcaacctgt atgaagtgaa atctaagaag caccctcaga tcatcaaaaa gggcaaaagg  3240
ccggcggcca cgaaaaaggc cggccaggca aaaaagaaaa agggatccga tgctaagtca  3300
ctgactgcct ggtcccggac actggtgacc ttcaaggatg tgtttgtgga cttcaccagg  3360
gaggagtgga agctgctgga cactgctcag cagatcctgt acagaaatgt gatgctggag  3420
aactataaga acctggtttc cttgggttat cagcttacta agccagatgt gatcctccgg  3480
ttggagaagg gagaagagcc ctggctggtg gagagagaaa ttcaccaaga gacccatcct  3540
gattcagaga ctgcatttga aatcaaatca tcagttccga aaaagaaacg caaagtttaa  3600
```

```
SEQ ID NO: 24          moltype = AA  length = 1368
FEATURE                Location/Qualifiers
source                 1..1368
                       mol_type = protein
                       organism = Streptococcus pyogenes
SEQUENCE: 24
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
```

-continued

```
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 25          moltype = AA  length = 1053
FEATURE                Location/Qualifiers
source                 1..1053
                       mol_type = protein
                       organism = Staphylococcus aureus
SEQUENCE: 25
MKRNYILGLD IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEN SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                               1053

SEQ ID NO: 26          moltype = AA  length = 1107
FEATURE                Location/Qualifiers
source                 1..1107
                       mol_type = protein
                       organism = Eubacterium ventriosum
SEQUENCE: 26
MGYTVGLDIG VASVGVAVLD ENDNIVEAVS NIFDEADTSN NKVRRTLREG RRTKRRQKTR  60
IEDFKQLWET SGYIIPHKLH LNIIELRNKG LTELLSLDEL YCVLLSMLKH RGISYLEDAD  120
DGEKGNAYKK GLAFNEKQLK EKMPCEIQLE RMKKYGKYHG EFIIEINDEK EYQSNVFTTK  180
AYKKELEKIF ETQRCNGNKI NTKFIKKYME IYERKREYYI GPGNEKSRTD YGIYTTRTDE  240
EGNFIDEKNI FGKLIGKCSV YPEEYRASSA SYTAQEFNLL NDLNNLKINN EKLTEFQKKE  300
IVEIIKDASS VNMRKIIKKV IDEDIEQYSG ARIDKKGKEI YHTFEIYRKL KKELKTINVD  360
IDSFTREELD KTMDILTLNT ERESIVKAFD EQKFVYEENL IKKLIEFRKN NQRLFSGWHS  420
FSYKAMLQLI PVMYKEPKEQ MQLLTEMNVF KSKKEKYVNY KYIPENEVVK EIYNPVVVKS  480
IRTTVKILNA LIKKYGYPES VVIEMPRDKN SDDEKEKIDM NQKKNQEEYE KILNKIYDEK  540
GIEITNKDYK KQKKLVLKLK LWNEQEGLCL YSGKKIAIED LLNHPEFFEI DHIIPKSISL  600
DDSRSNKVLV YKTENSIKEN DTPYHYLTRI NGKWGFDEYK ANVLELRRRG KIDDKKVNNL  660
LCMEDITKID VVKGFINRNL NDTRYASRVV LNEMQSFFES RKYCNTKVKV IRGSLTYQMR  720
QDLHLKKNRE ESYSHHAVDA MLIAFSQKGY EAYRKIQKDC YDFETGEILD KEKWNKYIDD  780
DEFDDILYKE RMNEIRKKII EAEEKVKYNY KIDKKCNRGL CNQTIYGTRE KDGKIHKISS  840
YNIYDDKECN SLKKMINSGK GSDLLMYNND PKTYRDMLKI LETYSSEKNP FVAYNKETGD  900
YFRKYSKNHN GPKVEKVKYY SGQINSCIDI SHKYGHAKNS KKVVLVSLNP YRTDVYYDND  960
TGKYYLVGVK YNHIKCVGNK YVIDSETYNE LLRKEGVLNS DENLEDLNSK NITYKFSLYK  1020
NDIIQYEKGG EYYTERFLSR IKEQKNLIET KPINKPNFQR KNKKGEWENT RNQIALAKTK  1080
YVGKLVTDVL GNCYIVNMEK FSLVVDK                                      1107

SEQ ID NO: 27          moltype = AA  length = 1168
FEATURE                Location/Qualifiers
source                 1..1168
                       mol_type = protein
                       organism = Azospirillum sp.
SEQUENCE: 27
MARPAFRAPR REHVNGWTPD PHRISKPFFI LVSWHLLSRV VIDSSSGCFP GTSRDHTDKF  60
AEWECAVQPY RLSFDLGTNS IGWGLLNLDR QGKPREIRAL GSRIFSDGRD PQDKASLAVA  120
RRLARQMRRR RDRYLTRRTR LMGALVRFGL MPADPAARKR LEVAVDPYLA RERATRERLE  180
PFEIGRALFH LNQRRGYKPV RTATKPDEEA GKVKEAVERL EAAIAAAGAP TLGAWFAWRK  240
TRGETLRARL AGKGKEAAYP FYPARRMLEA EFDTLWAEQA RHHPDLLTAE AREILRHRIF  300
HQRPLKPPPV GRCTLYPDDG RAPRALPSAQ RLRLFQELAS LRVIHLDLSE RPLTPAERDR  360
IVAFVQGRPP KAGRKPGKVQ KSVPFEKLRG LLELPPGTGF SLESDKRPEL LGDETGARIA  420
PAFGPGWTAL PLEEQDALVE LLLTEAEPER AIAALTARWA LDEATAAKLA GATLPDFHGR  480
YGRRAVAELL PVLERETRGD PDGRVRPIRL DEAVKLLRGG KDHSDFSREG ALLDALPYYG  540
AVLERHVAFG TGNPADPEEK RVGRVANPTV HIALNQLRHL VNAILARHGR PEEIVIELAR  600
DLKRSAEDRR REDKRQADNQ KRNEERKRLI LSLGERPTPR NLLKLRLWEE QGPVENRRCP  660
YSGETISMRM LLSEQVDIDH ILPFSVSLDD SAANKVVCLR EANRIKRNRS PWEAFGHDSE  720
RWAGILARAE ALPKNKRWRF APDALEKLEG EGGLRARHLN DTRHLSRLAV EYLRCVCPKV  780
```

-continued

RVSPGRLTAL LRRRWGIDAI LAEADGPPPE VPAETLDPSP AEKNRADHRH HALDAVVIGC 840
IDRSMVQRVQ LAAASAEREA AAREDNIRRV LEGFKEEPWD GFRAELERRA RTIVVSHRPE 900
HGIGGALHKE TAYGPVDPPE EGFNLVVRKP IDGLSKDEIN SVRDPRLRRA LIDRLAIRRR 960
DANDPATALA KAAEDLAAQP ASRGIRRVRV LKKESNPIRV EHGGNPSGPR SGGPFHKLLL 1020
AGEVHHVDVA LRADGRRWVG HWVTLFEAHG GRGADGAAAP PRLGDGERFL MRLHKGDCLK 1080
LEHKGRVRVM QVVKLEPSSN SVVVVEPHQV KTDRSKHVKI SCDQLRARGA RRVTVDPLGR 1140
VRVHAPGARV GIGGDAGRTA MEPAEDIS 1168

SEQ ID NO: 28 moltype = AA length = 1050
FEATURE Location/Qualifiers
source 1..1050
mol_type = protein
organism = Gluconacetobacter diazotrophicus
SEQUENCE: 28
MGENMIDESL TFGIDLGIGS CGWAVLRRPS AFGRKGVIEG MGSWCFDVPE TSKERTPTNQ 60
IRRSNRLLRR VIRRRRNRMA AIRRLLHAAG LLPSTDSDAL KRPGHDPWEL RARGLDKPLK 120
PVEFAVVLGH IAKRRGFKSA AKRKATNISS DDKKMLTALE ATRERLGRYR TVGEMFARDP 180
DFASRRRNRE GKYDRTTARD DLEHEVHALF AAQRRLGQGF ASPELEEAFT ASAFHQRPMQ 240
DSERLVGFCP FERTEKRAAK LTPSFERFRL LARLLNLRIT TPDGERPLTV DEIALVTRDL 300
GKTAKLSIKR VRTLIGLEDN QRFTTIRPED EDRDIVARTG GAMTGTATLR KALGEALWTD 360
MQERPEQLDA IVQVLSFFEA NETITEKLRE IGLTLAVLDV LLTALDAGVF AKFKGAAHIS 420
TKAARNLLPH LEQGRRYDEA CTMAGYDHAA SRLSHHGQIV AKTQFNALVT EIGESIANPI 480
ARKALIEGLK QIWAMRNHWG LPGSIHVELA RDVGNSIEKR REIEKHIEKN TALRARERRE 540
VHDLLDLEDV NGDTLLRYRL WKEQGGKCLY TGKAIHIRQI AATDNSVQVD HILPWSRFGD 600
DSFNNKTLCL ASANQQKKRS TPYEWLSGQT GDAWNAFVQR IETNKELRGF KKRNYLLKNA 660
KEAEEKFRSR NLNDTRYAAR LFAEAVKLLY AFGERQEKGG NRRVFTRPGA LTAALRQAWG 720
VESLKKQDGK RINDDRHHAL DALTVAAVDE AEIQRLTKSF HEWEQQGLGR PLRRVEPPWE 780
SFRADVEATY PEVFVARPER RRARGEGHAA TIRQVKEREC TPIVFERKAV SSLKEADLER 840
IKDGERNEAI VEAIRSWIAT GRPADAPPRS PRGDIITKIR LATTIKAAVP VRGGTAGRGE 900
MVRADVFSKP NRRGKDEWYL VPVYPHQIMN RKAWPKPPMR SIVANKDEDE WTEVGPEHQF 960
RFSLYPRSNI EIIRPSGEVI EGYFVGLHRN TGALTISAHN DPKSIHSGIG TKTLLAISKY 1020
QVDRFGRKSP VRKEVRTWHG EACISPTPPG 1050

SEQ ID NO: 29 moltype = AA length = 1082
FEATURE Location/Qualifiers
source 1..1082
mol_type = protein
organism = Neisseria cinerea
SEQUENCE: 29
MAAFKPNPMN YILGLDIGIA SVGWAIVEID EEENPIRLID LGVRVFERAE VPKTGDSLAA 60
ARRLARSVRR LTRRRAHRLL RARRLLKREG VLQAADFDEN GLIKSLPNTP WQLRAAALDR 120
KLTPLEWSAV LLHLIKHRGY LSQRKNEGET ADKELGALLK GVADNTHALQ TGDFRTPAEL 180
ALNKFEKESG HIRNQRGDYS HTFNRKDLQA ELNLLFEKQK EFGNPHVSDG LKEGIETLLM 240
TQRPALSGDA VQKMLGHCTF EPTEPKAAKN TYTAERFVWL TKLNNLRILE QGSERPLTDT 300
ERATLMDEPY RKSKLTYAQA RKLLDLDDTA FFKGLRYGKD NAEASTLMEM KAYHAISRAL 360
EKEGLKDKKS PLNLSPELQD EIGTAFSLFK TDEDITGRLK DRVQPEILEA LLKHISFDKF 420
VQISLKALRR IVPLMEQGNR YDEACTEIYG DHYGKKNTEE KIYLPPIPAD EIRNPVVLRA 480
LSQARKVING VVRRYGSPAR IHIETAREVG KSFKDRKEIE KRQEENRKDR EKSAAKFREY 540
FPNFVGEPKS KDILKLRLYE QQHGKCLYSG KEINLGRLNE KGYVEIDHAL PFSRTWDDSF 600
NNKVLALGSE NQNKGNQTPY EYFNGKDNSR EWQEFKARVE TSRFPRSKKQ RILLQKFDED 660
GFKERNLNDT RYINRFLCQF VADHMLLTGK GKRRVFASNG QITNLLRGFW GLRKVRAEND 720
RHHALDAVVV ACSTIAMQQK ITRFVRYKEM NAFDGKTIDK ETGEVLHQKA HFPQPWEFFA 780
QEVMIRVFGK PDGKPEFEEA DTPEKLRTLL AEKLSSRPEA VHKYVTPLFI SRAPNRKMSG 840
QGHMETVKSA KRLDEGISVL RVPLTQLKLK DLEKMVNRER EPKLYEALKA RLEAHKDDPA 900
KAFAEPFYKY DKAGNRTQQV KAVRVEQVQK TGVWVHNHNG IADNATIVRV DVFEKGGKYY 960
LVPIYSWQVA KGILPDRAVV QGKDEEDWTV MDDSFEFKFV LYANDLIKLT AKKNEFLGYF 1020
VSLNRATGAI DIRTHDTDST KGKNGIFQSV GVKTALSFQK YQIDELGKEI RPCRLKKRPP 1080
VR 1082

SEQ ID NO: 30 moltype = AA length = 1140
FEATURE Location/Qualifiers
source 1..1140
mol_type = protein
organism = Roseburia intestinalis
SEQUENCE: 30
MRENGSDERR RNMDEKMDYR IGLDIGIASV GWAVLQNNSD DEPVRIVDLG VRIFDTAEIP 60
KTGESLAGPR RAARTTRRRL RRRKHRLDRI KWLFENQGLI NIDDFLKRYN MAGLPDVYQL 120
RYEALDRKLT DEELAQVLLH IAKHRGFRST RKAETAAKEN GAVLKATDEN QKRMQEKGYR 180
TVGEMIYLDE AFRTGCSWSE KGYILTPRNK AENYQHTMLR AMLVEEVKEI FSSQRRLGNE 240
KATEELEEKY LEIMTSQRSF DLGPGMQPDG KPSPYAMEGF SDRVGKCTFL GDQGELRGAK 300
GTYTAEYFVA LQKINHTKLV NQDGETRNFT EEERRALTLL LFTQKEVKYA AVRKKLGLPE 360
DILFYNLNYK KAATKEEQQK ENQNTEKAKF IGMPYYHDYK KCLEERVKYL TENEVRDLFD 420
EIGMILTCYK NDDSRTERLA KLGLVPIEME GLLAYTPTKF QHLSMKAMRN IIPFLEKGMT 480
YDKACEEAGY DFKADSKGTK QKLLTGENVN QTINEITNPV VKRSVSQTVK VINAIIRTYG 540
SPQAINIELA REMSKTFEER RKIKGDMEKR QKNNEDVKKQ IQELGKLSPT GQDILKYRLW 600
QEQQGICMYS GKTIPLEELF KPGYDIDHIL PYSITFDDSF RNKVLVTSQE NRQKGNRTPY 660
EYMGNDEQRW NEFETRVKTT IRDYKKQQKL LKKHFSEEER SEFKERNLTD TKYITTVIYN 720
MIRQNLEMAP LNRPEKKKQV RAVNGAITAY LRKRWGLPQK NRETDTHHAM DAVVIACCTD 780
GMIQKISRYT KVRERCYSKG TEFVDAETGE IFRPEDYSRA EWDEIFGVHI PKPWETFRAE 840

-continued

```
LDVRMGDDPK GFLDTHSDVA LELDYPEYIY ENLRPIFVSR MPNHKVTGAA HADTIRSPRH  900
FKDEGIVLTK TALTDLKLDK DGEIDGYYNP QSDLLLYEAL KKQLLLYGND AKKAFAQDFH  960
KPKADGTEGP VVRKVKIQKK QTMGVFVDSG NGIAENGGMV RIDVFRVNGK YYFVPVYTAD  1020
VVKKVLPNRA STAHKPYGEW KVMEDKDFLF SLYSRDLIHI KSKKDIPIKM VNGGMEGIKE  1080
TYAYYIGADI SAANIQGIAH DSRYKFRGLG IQSLDVLEKC QIDVLGHVSV VRSEKRMGFS  1140

SEQ ID NO: 31          moltype = AA  length = 1037
FEATURE                Location/Qualifiers
source                 1..1037
                       mol_type = protein
                       organism = Parvibaculum lavamentivorans
SEQUENCE: 31
MERIFGFDIG TTSIGFSVID YSSTQSAGNI QRLGVRIFPE ARDPDGTPLN QQRRQKRMMR  60
RQLRRRRIRR KALNETLHEA GFLPAYGSAD WPVVMADEPY ELRRRGLEEG LSAYEFGRAI  120
YHLAQHRHFK GRELEESDTP DPDVDDEKEA ANERAATLKA LKNEQTTLGA WLARRPPSDR  180
KRGIHAHRNV VAEEFERLWE VQSKFHPALK SEEMRARISD TIFAQRPVFW RKNTLGECRF  240
MPGEPLCPKG SWLSQQRRML EKLNNLAIAG GNARPLDAEE RDAILSKLQQ QASMSWPGVR  300
SALKALYKQR GEPGAEKSLK FNLELGGESK LLGNALEAKL ADMFGPDWPA HPRKQEIRHA  360
VHERLWAADY GETPDKKRVI ILSEKDRKAH REAAANSFVA DFGITGEQAA QLQALKLPTG  420
WEPYSIPALN LFLAELEKGE RFGALVNGPD WEGWRRTNFP HRNQPTGEIL DKLPSPASKE  480
ERERISQLRN PTVVRTQNEL RKVVNNLIGL YGKPDRIRIE VGRDVGKSKR EREEIQSGIR  540
RNEKQRKKAT EDLIKNGIAN PSRDDVEKWI LWKEGQERCP YTGDQIGFNA LFREGRYEVE  600
HIWPRSRSFD NSPRNKTLCR KDVNIEKGNR MPFEAFGHDE DRWSAIQIRL QGMVSAKGGT  660
GMSPGKVKRF LAKTMPEDFA ARQLNDTRYA AKQILAQLKR LWPDMGPEAP VKVEAVTGQV  720
TAQLRKLWTL NNILADDGEK TRADHRHHAI DALTVACTHP GMTNKLSRYW QLRDDPRAEK  780
PALTPPWDTI RADAEKAVSE IVVSHRVRKK VSGPLHKETT YGDTGTDIKT KSGTYRQFVT  840
RKKIESLSKG ELDEIRDPRI KEIVAAHVAG RGGDPKKAFP PYPCVSPGGP EIRKVRLTSK  900
QQLNLMAQTG NGYADLGSNH HIAIYRLPDG KADFEIVSLF DASRRLAQRN PIVQRTRADG  960
ASFVMSLAAG EAIMIPEGSK KGIWIVQGVW ASGQVVLERD TDADHSTTTR PMPNPILKDD  1020
AKKVSIDPIG RVRPSND                                                 1037

SEQ ID NO: 32          moltype = AA  length = 1132
FEATURE                Location/Qualifiers
source                 1..1132
                       mol_type = protein
                       organism = Nitratifractor salsuginis
SEQUENCE: 32
MKKILGVDLG ITSFGYAILQ ETGKDLYRCL DNSVVMRNNP YDEKSGESSQ SIRSTQKSMR  60
RLIEKRKKRI RCVAQTMERY GILDYSETMK INDPKNNPIK NRWQLRAVDA WKRPLSPQEL  120
FAIFAHMAKH RGYKSIATED LIYELELELG LNDPEKESEK KADERRQVYN ALRHLEELRK  180
KYGGETIAQT IHRAVEAGDL RSYRNHDDYE KMIRREDIEE EIEKVLLRQA ELGALGLPEE  240
QVSELIDELK ACITDQEMPT IDESLFGKCT FYKDELAAPA YSYLYDLYRL YKKLADLNID  300
GYEVTQEDRE KVIEWVEKKI AQGKNLKKIT HKDLRKILGL APEQKIFGVE DERIVKGKKE  360
PRTFVPFFFL ADIAKFKELF ASIQKHPDAL QIFRELAEIL QRSKTPQEAL DRLRALMAGK  420
GIDTDDRELL ELFKNKRSGT RELSHRYILE ALPLFLEGYD EKEVQRILGF DDREDYSRYP  480
KSLRHLHLRE GNLFEKEENP INNHAVKSLA SWALGLIADL SWRYGPFDEI ILETTRDALP  540
EKIRKEIDKA MREREKALDK IIGKYKKEFP SIDKRLARKI QLWERQKGLD LYSGKVINLS  600
QLLDGSADIE HIVPQSLGGL STDYNTIVTL KSVNAAKGNR LPGDWLAGNP DYRERIGMLS  660
EKGLIDWKKR KNLLAQSLDE IYTENTHSKG IRATSYLEAL VAQVLKRYYP FPDPELRKNG  720
IGVRMIPGKV TSKTRSLLGI KSKSRETNFH HAEDALILST LTRGWQNRLH RMLRDNYGKS  780
EAELKELWKK YMPHIEGLTL ADYIDEAFRR FMSKGEESLF YRDMFDTIRS ISYWVDKKPL  840
SASSHKETVY SSRHEVPTLR KNILEAFDSL NVIKDRHKLT TEEFMKRYDK EIRQKLWLHR  900
IGNTNDESYR AVEERATQIA QILTRYQLMD AQNDKEIDEK FQQALKELIT SPIEVTGKLL  960
RKMRFVYDKL NAMQIDRGLV ETDKNMLGIH ISKGPNEKLI FRRMDVNNAH ELQKERSGIL  1020
CYLNEMLFIF NKKGLIHYGC LRSYLEKGQG SKYIALFNPR FPANPKAQPS KFTSDSKIKQ  1080
VGIGSATGII KAHLDLDGHV RSYEVFGTLP EGSIEWFKEE SGYGRVEDDP HH           1132

SEQ ID NO: 33          moltype = AA  length = 1003
FEATURE                Location/Qualifiers
source                 1..1003
                       mol_type = protein
                       organism = Campylobacter lari
SEQUENCE: 33
MRILGFDIGI NSIGWAFVEN DELKDCGVRI FTKAENPKNK ESLALPRRNA RSSRRRLKRR  60
KARLIAIKRI LAKELKLNYK DYVAADGELP KAYEGSLASV YELRYKALTQ NLETKDLARV  120
ILHIAKHRGY MNKNEKKSND AKKGKILSAL KNNALKLENY QSVGEYFYKE FFQKYKKNTK  180
NFIKIRNTKD NYNNCVLSSD LEKELKLILE KQKEFGYNYS EDFINEILKV AFFQRPLKDF  240
SHLVGACTFF EEEKRACKNS YSAWEFVALT KIINEIKSLE KISGEIVPTQ TINEVLNLIL  300
DKGSITYKKF RSCINLHESI SFKSLKYDKE NAENAKLIDF RKLVEFKKAL GVHSLSRQEL  360
DQISTHITLI KDNVKLKTVL EKYNLSNEQI NNLLEIEFND YINLSFKALG MILPLMREGK  420
RYDEACEIAN LKPKTVDEKK DFLPAFCDSI FAHELSNPVV NRAISEYRKV LNALLKKYGK  480
VHKIHLELAR DVGLSKKARE KIEKEQKENQ AVNAWALKEC ENIGLKASAK NILKLKLWKE  540
QKEICIYSGN KISIEHLKDE KALEVDHIYP YSRSFDDSFI NKVLVFTKEN QEKLNKTPFE  600
AFGKNIEKWS KIQTLAQNLP YKKKNKILDE NFKDKQQEDF ISRNLNDTRY IATLIAKYTK  660
EYLNFLLLSE NENANLKSGE KGSKIHVQTI SGMLTSVLRH TWGFDKKDRN NHLHHALDAI  720
IVAYSTNSII KAFSDFRKNQ ELLKARFYAK ELTSDNYKHQ VKFFEPFKSF REKILSKIDE  780
IFVSKPPRKR ARRALHKDTF HSENKIIDKC SYNSKEGLQI ALSCGRVRKI GTKYVENDTI  840
VRVDIFKKQN KFYAIPIYAM DFALGILPNK IVITGKDKNN NPKQWQTIDE SYEFCFSLYK  900
NDLILLQKKN MQEPEFAYYN DFSISTSSIC VEKHDNKFEN LTSNQKLLFS NAKEGSVKVE  960
```

```
SLGIQNLKVF EKYIITPLGD KIKADFQPRE NISLKTSKKY GLR                    1003

SEQ ID NO: 34           moltype = AA  length = 103
FEATURE                 Location/Qualifiers
REGION                  1..103
                        note = exemplary KRAB
source                  1..103
                        mol_type = protein
                        organism = synthetic construct
SEQUENCE: 34
DAKSLTAWSR TLVTFKDVFV DFTREEWKLL DTAQQILYRN VMLENYKNLV SLGYQLTKPD  60
VILRLEKGEE PWLVEREIHQ ETHPDSETAF EIKSSVPKKK RKV                    103

SEQ ID NO: 35           moltype = AA  length = 1052
FEATURE                 Location/Qualifiers
REGION                  1..1052
                        note = exemplary KRAB
source                  1..1052
                        mol_type = protein
                        organism = synthetic construct
SEQUENCE: 35
KRNYILGLAI GITSVGYGII DYETRDVIDA GVRLFKEANV ENNEGRRSKR GARRLKRRRR  60
HRIQRVKKLL FDYNLLTDHS ELSGINPYEA RVKGLSQKLS EEEFSAALLH LAKRRGVHNV  120
NEVEEDTGNE LSTKEQISRN SKALEEKYVA ELQLERLKKD GEVRGSINRF KTSDYVKEAK  180
QLLKVQKAYH QLDQSFIDTY IDLLETRRTY YEGPGEGSPF GWKDIKEWYE MLMGHCTYFP  240
EELRSVKYAY NADLYNALND LNNLVITRDE NEKLEYYEKF QIIENVFKQK KKPTLKQIAK  300
EILVNEEDIK GYRVTSTGKP EFTNLKVYHD IKDITARKEI IENAELLDQI AKILTIYQSS  360
EDIQEELTNL NSELTQEEIE QISNLKGYTG THNLSLKAIN LILDELWHTN DNQIAIFNRL  420
KLVPKKVDLS QQKEIPTTLV DDFILSPVVK RSFIQSIKVI NAIIKKYGLP NDIIIELARE  480
KNSKDAQKMI NEMQKRNRQT NERIEEIIRT TGKENAKYLI EKIKLHDMQE GKCLYSLEAI  540
PLEDLLNNPF NYEVDHIIPR SVSFDNSFNN KVLVKQEEAS KKGNRTPFQY LSSSDSKISY  600
ETFKKHILNL AKGKGRISKT KKEYLLEERD INRFSVQKDF INRNLVDTRY ATRGLMNLLR  660
SYFRVNNLDV KVKSINGGFT SFLRRKWKFK KERNKGYKHH AEDALIIANA DFIFKEWKKL  720
DKAKKVMENQ MFEEKQAESM PEIETEQEYK EIFITPHQIK HIKDFKDYKY SHRVDKKPNR  780
ELINDTLYST RKDDKGNTLI VNNLNGLYDK DNDKLKKLIN KSPEKLLMYH HDPQTYQKLK  840
LIMEQYGDEK NPLYKYYEET GNYLTKYSKK DNGPVIKKIK YYGNKLNAHL DITDDYPNSR  900
NKVVKLSLKP YRFDVYLDNG VYKFVTVKNL DVIKKENYYE VNSKCYEEAK KLKKISNQAE  960
FIASFYNNDL IKINGELYRV IGVNNDLLNR IEVNMIDITY REYLENMNDK RPPRIIKTIA  1020
SKTQSIKKYS TDILGNLYEV KSKKHPQIIK KG                                1052

SEQ ID NO: 36           moltype = AA  length = 1053
FEATURE                 Location/Qualifiers
REGION                  1..1053
                        note = dCas9 sequence
source                  1..1053
                        mol_type = protein
                        organism = synthetic construct
SEQUENCE: 36
MKRNYILGLA IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEA SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                               1053

SEQ ID NO: 37           moltype = AA  length = 16
FEATURE                 Location/Qualifiers
REGION                  1..16
                        note = exemplary nuclear localization sequence
source                  1..16
                        mol_type = protein
                        organism = synthetic construct
SEQUENCE: 37
APKKKRKVGI HGVPAA                                                  16

SEQ ID NO: 38           moltype = AA  length = 16
FEATURE                 Location/Qualifiers
```

```
REGION              1..16
                    note = exemplary nuclear localization sequence
source              1..16
                    mol_type = protein
                    organism = synthetic construct
SEQUENCE: 38
KRPAATKKAG QAKKKK                                               16

SEQ ID NO: 39       moltype = AA  length = 1199
FEATURE             Location/Qualifiers
REGION              1..1199
                    note = exemplary HA-NLS-dSaCas9-NLS-KRAB sequence
source              1..1199
                    mol_type = protein
                    organism = synthetic construct
SEQUENCE: 39
MYPYDVPDYA APKKKRKVGI HGVPAAKRNY ILGLAIGITS VGYGIIDYET RDVIDAGVRL  60
FKEANVENNE GRRSKRGARR LKRRRRHRIQ RVKKLLFDYN LLTDHSELSG INPYEARVKG  120
LSQKLSEEEF SAALLHLAKR RGVHNVNEVE EDTGNELSTK EQISRNSKAL EEKYVAELQL  180
ERLKKDGEVR GSINRFKTSD YVKEAKQLLK VQKAYHQLDQ SFIDTYIDLL ETRRTYYEGP  240
GEGSPFGWKD IKEWYEMLMG HCTYFPEELR SVKYAYNADL YNALNDLNNL VITRDENEKL  300
EYYEKFQIIE NVFKQKKKPT LKQIAKEILV NEEDIKGYRV TSTGKPEFTN LKVYHDIKDI  360
TARKEIIENA ELLDQIAKIL TIYQSSEDIQ EELTNLNSEL TQEEIEQISN LKGYTGTHNL  420
SLKAINLILD ELWHTNDNQI AIFNRLKLVP KKVDLSQQKE IPTTLVDDFI LSPVVKRSFI  480
QSIKVINAII KKYGLPNDII IELAREKNSK DAQKMINEMQ KRNRQTNERI EEIIRTTGKE  540
NAKYLIEKIK LHDMQEGKCL YSLEAIPLED LLNNPFNYEV DHIIPRSVSF DNSFNNKVLV  600
KQEEASKKGN RTPFQYLSSS DSKISYETFK KHILNLAKGK GRISKTKKEY LLEERDINRF  660
SVQKDFINRN LVDTRYATRG LMNLLRSYFR VNNLDVKVKS INGGFTSFLR RKWKFKKERN  720
KGYKHHAEDA LIIANADFIF KEWKKLDKAK KVMENQMFEE KQAESMPEIE TEQEYKEIFI  780
TPHQIKHIKD FKDYKYSHRV DKKPNRELIN DTLYSTRKDD KGNTLIVNNL NGLYDKDNDK  840
LKKLINKSPE KLLMYHHDPQ TYQKLKLIME QYGDEKNPLY KYYEETGNYL TKYSKKDNGP  900
VIKKIKYYGN KLNAHLDITD DYPNSRNKVV KLSLKPYRFD VYLDNGVYKF VTVKNLDVIK  960
KENYYEVNSK CYEEAKKLKK ISNQAEFIAS FYNNDLIKIN GELYRVIGVN NDLLNRIEVN  1020
MIDITYREYL ENMNDKRPPR IIKTIASKTQ SIKKYSTDIL GNLYEVKSKK HPQIIKKGKR  1080
PAATKKAGQA KKKKGSDAKS LTAWSRTLVT FKDVFVDFTR EEWKLLDTAQ QILYRNVMLE  1140
NYKNLVSLGY QLTKPDVILR LEKGEEPWLV EREIHQETHP DSETAFEIKS SVPKKKRKV   1199

SEQ ID NO: 40       moltype = AA  length = 1198
FEATURE             Location/Qualifiers
REGION              1..1198
                    note = exemplary HA-NLS-dSaCas9-NLS-KRAB sequence
source              1..1198
                    mol_type = protein
                    organism = synthetic construct
SEQUENCE: 40
YPYDVPDYAA PKKKRKVGIH GVPAAKRNYI LGLAIGITSV GYGIIDYETR DVIDAGVRLF  60
KEANVENNEG RRSKRGARRL KRRRRHRIQR VKKLLFDYNL LTDHSELSGI NPYEARVKGL  120
SQKLSEEEFS AALLHLAKRR GVHNVNEVEE DTGNELSTKE QISRNSKALE EKYVAELQLE  180
RLKKDGEVRG SINRFKTSDY VKEAKQLLKV QKAYHQLDQS FIDTYIDLLE TRRTYYEGPG  240
EGSPFGWKDI KEWYEMLMGH CTYFPEELRS VKYAYNADLY NALNDLNNLV ITRDENEKLE  300
YYEKFQIIEN VFKQKKKPTL KQIAKEILVN EEDIKGYRVT STGKPEFTNL KVYHDIKDIT  360
ARKEIIENAE LLDQIAKILT IYQSSEDIQE ELTNLNSELT QEEIEQISNL KGYTGTHNLS  420
LKAINLILDE LWHTNDNQIA IFNRLKLVPK KVDLSQQKEI PTTLVDDFIL SPVVKRSFIQ  480
SIKVINAIIK KYGLPNDIII ELAREKNSKD AQKMINEMQK RNRQTNERIE EIIRTTGKEN  540
AKYLIEKIKL HDMQEGKCLY SLEAIPLEDL LNNPFNYEVD HIIPRSVSFD NSFNNKVLVK  600
QEEASKKGNR TPFQYLSSSD SKISYETFKK HILNLAKGKG RISKTKKEYL LEERDINRFS  660
VQKDFINRNL VDTRYATRGL MNLLRSYFRV NNLDVKVKSI NGGFTSFLRR KWKFKKERNK  720
GYKHHAEDAL IIANADFIFK EWKKLDKAKK VMENQMFEEK QAESMPEIET EQEYKEIFIT  780
PHQIKHIKDF KDYKYSHRVD KKPNRELIND TLYSTRKDDK GNTLIVNNLN GLYDKDNDKL  840
KKLINKSPEK LLMYHHDPQT YQKLKLIMEQ YGDEKNPLYK YYEETGNYLT KYSKKDNGPV  900
IKKIKYYGNK LNAHLDITDD YPNSRNKVVK LSLKPYRFDV YLDNGVYKFV TVKNLDVIKK  960
ENYYEVNSKC YEEAKKLKKI SNQAEFIASF YNNDLIKING ELYRVIGVNN DLLNRIEVNM  1020
IDITYREYLE NMNDKRPPRI IKTIASKTQS IKKYSTDILG NLYEVKSKKH PQIIKKGKRP  1080
AATKKAGQAK KKKGSDAKSL TAWSRTLVTF KDVFVDFTRE EWKLLDTAQQ ILYRNVMLEN  1140
YKNLVSLGYQ LTKPDVILRL EKGEEPWLVE REIHQETHPD SETAFEIKSS VPKKKRKV    1198

SEQ ID NO: 41       moltype = AA  length = 1189
FEATURE             Location/Qualifiers
REGION              1..1189
                    note = exemplary NLS-dSaCas9-NLS-KRAB
source              1..1189
                    mol_type = protein
                    organism = synthetic construct
SEQUENCE: 41
APKKKRKVGI HGVPAAKRNY ILGLAIGITS VGYGIIDYET RDVIDAGVRL FKEANVENNE  60
GRRSKRGARR LKRRRRHRIQ RVKKLLFDYN LLTDHSELSG INPYEARVKG LSQKLSEEEF  120
SAALLHLAKR RGVHNVNEVE EDTGNELSTK EQISRNSKAL EEKYVAELQL ERLKKDGEVR  180
GSINRFKTSD YVKEAKQLLK VQKAYHQLDQ SFIDTYIDLL ETRRTYYEGP GEGSPFGWKD  240
IKEWYEMLMG HCTYFPEELR SVKYAYNADL YNALNDLNNL VITRDENEKL EYYEKFQIIE  300
```

-continued

```
NVFKQKKKPT LKQIAKEILV NEEDIKGYRV TSTGKPEFTN LKVYHDIKDI TARKEIIENA  360
ELLDQIAKIL TIYQSSEDIQ EELTNLNSEL TQEEIEQISN LKGYTGTHNL SLKAINLILD  420
ELWHTNDNQI AIFNRLKLVP KKVDLSQQKE IPTTLVDDFI LSPVVKRSFI QSIKVINAII  480
KKYGLPNDII IELAREKNSK DAQKMINEMQ KRNRQTNERI EEIIRTTGKE NAKYLIEKIK  540
LHDMQEGKCL YSLEAIPLED LLNNPFNYEV DHIIPRSVSF DNSFNNKVLV KQEEASKKGN  600
RTPFQYLSSS DSKISYETFK KHILNLAKGK GRISKTKKEY LLEERDINRF SVQKDFINRN  660
LVDTRYATRG LMNLLRSYFR VNNLDVKVKS INGGFTSFLR RKWKFKKERN KGYKHHAEDA  720
LIIANADFIF KEWKKLDKAK KVMENQMFEE KQAESMPEIE TEQEYKEIFI TPHQIKHIKD  780
FKDYKYSHRV DKKPNRELIN DTLYSTRKDD KGNTLIVNNL NGLYDKDNDK LKKLINKSPE  840
KLLMYHHDPQ TYQKLKLIME QYGDEKNPLY KYYEETGNYL TKYSKKDNGP VIKKIKYYGN  900
KLNAHLDITD DYPNSRNKVV KLSLKPYRFD VYLDNGVYKF VTVKNLDVIK KENYYEVNSK  960
CYEEAKKLKK ISNQAEFIAS FYNNDLIKIN GELYRVIGVN NDLLNRIEVN MIDITYREYL  1020
ENMNDKRPPR IIKTIASKTQ SIKKYSTDIL GNLYEVKSKK HPQIIKKGKR PAATKKAGQA  1080
KKKKGSDAKS LTAWSRTLVT FKDVFVDFTR EEWKLLDTAQ QILYRNVMLE NYKNLVSLGY  1140
QLTKPDVILR LEKGEEPWLV EREIHQETHP DSETAFEIKS SVPKKKRKV             1189

SEQ ID NO: 42          moltype = DNA  length = 22
FEATURE                Location/Qualifiers
misc_feature           1..22
                       note = protospacer sequence
source                 1..22
                       mol_type = other DNA
                       organism = synthetic construct
SEQUENCE: 42
gagggaaggg atacaggctg ga                                          22
```